(12) United States Patent
Clasby et al.

(10) Patent No.: US 8,148,363 B2
(45) Date of Patent: Apr. 3, 2012

(54) HETEROCYCLIC COMPOUNDS AS FACTOR IXA INHIBITORS

(75) Inventors: Martin C. Clasby, Plainsboro, NJ (US); William J. Greenlee, Teaneck, NJ (US); Yan Xia, Edison, NJ (US); Tin-Yau Chan, Edison, NJ (US); Mariappan V. Chelliah, Edison, NJ (US); Samuel Chackalamannil, Califon, NJ (US); Haiyan Pu, Livingston, NJ (US); Keith A. Eagen, Long Valley, NJ (US); Henry Vaccaro, South Plainfield, NJ (US); Brian A. McKittrick, New Vernon, NJ (US); Liyuan Wang, Warren, NJ (US); Xiaobang Gao, Conshohocken, PA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/993,607

(22) PCT Filed: May 18, 2009

(86) PCT No.: PCT/US2009/044291
§ 371 (c)(1),
(2), (4) Date: Nov. 19, 2010

(87) PCT Pub. No.: WO2009/143039
PCT Pub. Date: Nov. 26, 2009

(65) Prior Publication Data
US 2011/0065682 A1  Mar. 17, 2011

Related U.S. Application Data

(60) Provisional application No. 61/054,310, filed on May 19, 2008.

(51) Int. Cl.
*A61K 31/55* (2006.01)
*A61K 31/4184* (2006.01)
*A61K 31/5377* (2006.01)
*A61K 31/4192* (2006.01)
*A61K 31/454* (2006.01)
*A61K 31/4439* (2006.01)
*A61K 31/422* (2006.01)
*A61K 31/506* (2006.01)
*A61K 31/496* (2006.01)
*A61P 7/02* (2006.01)
*C07D 403/14* (2006.01)
*C07D 413/14* (2006.01)
*C07D 403/04* (2006.01)
*C07D 401/14* (2006.01)

(52) U.S. Cl. ............. 514/212.08; 514/230.8; 514/234; 514/254.06; 514/256; 514/322; 514/338; 514/359; 514/376; 514/394; 540/524; 544/139; 544/333; 544/370; 546/199; 546/273.1; 548/229; 548/255; 548/302.1; 548/306.1

(58) Field of Classification Search .................. None
See application file for complete search history.

(56) References Cited

U.S. PATENT DOCUMENTS 7,968,683 B1 * 6/2011 Beyer et al. .................. 530/384

OTHER PUBLICATIONS

Celera et al., caplus an 2006:315166.*
Chawla et al., "Challenges in Polymorphism of Pharmaceuticals", CRIPS vol. 5, No. 1 , Jan.-Mar. 2004 (4 Pages.*
Newman et al., "Solid-state analysis of the active pharmaceutical ingredient in drug products", DDT vol. 8, No. 19, Oct. 2003, p. 898-905.*
Cohen et al., Circulation, 2010, 614-622, vol. 122.*
Vijaykumar,D. et al: "Discovery of Novel Hydroxy Pyrazole Based Factor IXa Inhibitor", Bioorganic & Medicinal Chemistry Letters, Pergamon, Elsevier Science, GB, vol. 16, No. 10, May 15, 2006, pp. 2796-2799, XP025106845; ISSN: 0960-894X [Retrieved on May 15, 2006] cited in the application table 1; compounds 2-4.
EPO International Search Report for PCT/US2009/044291; Performed on Sep. 23, 2009.

* cited by examiner

*Primary Examiner* — Sun Jae Loewe
(74) *Attorney, Agent, or Firm* — Richard S. Parr; Catherine D. Fitch

(57) ABSTRACT

The present invention relates to novel heterocyclic compounds of Formulae I-III; as disclosed herein or a pharmaceutically acceptable salt, solvate, ester, prodrug or stereoisomer thereof. Also disclosed are pharmaceutical compositions comprising said compounds, and methods for using said compounds for treating or preventing a thromboembolic disorder.

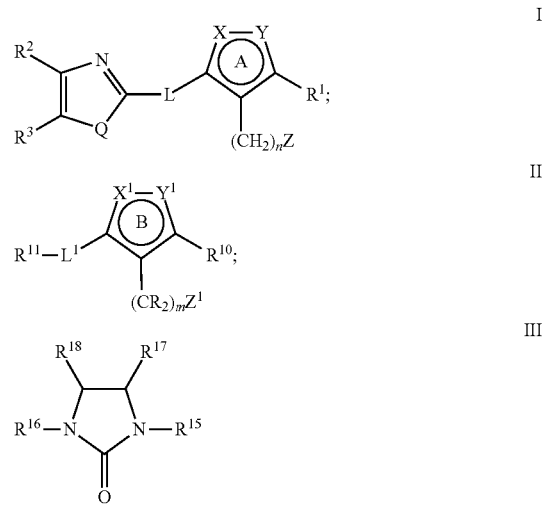

4 Claims, No Drawings

HETEROCYCLIC COMPOUNDS AS FACTOR IXA INHIBITORS

CROSS REFERENCE TO RELATED APPLICATIONS

This application is a U.S. National Phase application under 35 U.S.C. §371 of PCT Application No. PCT/US2009/044291 filed May 18, 2009, which claims priority under 35 U.S.C. §119(e) from U.S. Provisional Application No. 61/054,310, filed May 19, 2008.

FIELD OF THE INVENTION

The present invention relates to heterocyclic compounds useful as serine protease inhibitors, regulators or modulators, in particular, serine protease enzymes of the coagulation cascade and/or contact activation system; for example thrombin, factor XIa, factor Xa, factor IXa, factor VIIa, and/or plasma kallikrein. In particular, it relates to compounds that are selective factor IXa inhibitors, pharmaceutical compositions comprising the compounds, and methods of treatment using the compounds and compositions to treat various thromboembolic disorders, such as acute coronary syndrome, atrial fibrillation, myocardial infarction, and atherosclerosis.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation involves three distinct phases: initiation, priming and propagation.[1,2,3] Initiation involves binding of tissue factor (TF) to activated factor VII, a circulating coagulation factor. Blood, in general is not exposed to TF which is a transmembrane protein expressed on extravascular cells. Vascular injury causes the TF-bearing cells to be exposed to blood, and initiates the coagulation process.[1]

The TF/VIIa complex activates factors IX and X.[1,4] Factor IXa is relatively unstable in plasma and diffuses toward activated platelets. Factor Xa on the other hand, is unstable in plasma and is rapidly inhibited by TF pathway inhibitor and antithrombin III.[1,5,6] Factor Xa binds factor Va on the surface of TF-bearing cells.[1-7] In turn, the Xa/Va complex generates a small but sufficient amount of thrombin to cause platelet activation.[1,8,9]

Thrombin activates platelets and coagulation factors in the priming phase.[1,2] Thrombin binds and cleaves platelet protease-activated receptors (PAR1 and PAR4), triggering a signaling cascade that catalyzes platelet activation and release of factor V from platelet α granules. Thrombin also activates factors V, VIII, and XI.[1]

It is during the propagation phase that thrombin generation is maximized on the surface of platelets. The primed, activated platelets bind the IXa/VIIIa "tenase" complex. Additional IXa is generated by factor XIa on the platelet surface.[10] The IXa/VIIIa complex, in physical proximity to Va, recruits factor X to the platelet surface for activation. The Xa/Va complex on the platelet surface is protected from TF pathway inhibitor and antithrombin III.[11,12]

Enzymology studies have shown that activation of factor X by IXa/VIIIa is nearly 50× more efficient than activation by factor VIIa/TF.[13] The platelet Xa/Va complex generates a "burst" of thrombin, resulting in a stable fibrin-platelet clot.[1]

The cell-based model of coagulation highlights the importance of the IXa/VIIIa complex in clot formation. Factor IXa therefore represents an excellent target for anticoagulant therapy.[1] There is a need for effective inhibitors of factor IXa in order to treat or prevent thromboembolic disorders.

Vijaykumar et al., Biorganic & Medicinal Chemistry Letters (2006), 16 (10), 2796-2799, discloses hydroxy pyrazole based factor IXa inhibitors.

REFERENCES CITED

1. Howard, E L, Becker K C, Rusconi, C P, Becker R C. Factor IXa Inhibitors as Novel Anticoagulents. *Arterioscler Thromb Vasc Biol.* 2007; 27: 722-727.
2. Monroe D M, Hoffman M, Roberts H R. Platelets and thrombin generation. *Arterioscler Thromb Vasc Biol.* 2002; 22: 1381-1389.
3. Ahmad S S, London F S, Walsh P N. The assembly of the factor X-activating complex on activated human platelets. *J Thromb Haemost.* 2003; 1: 48-59.
4. Komiyama Y, Pedersen A H, Kisiel W. Proteolytic activation of human factors IX and X by recombinant human factor VIIa: effects of calcium, phospholipids, and tissue factor. *Biochemistry.* 1990; 29: 9418-9425.
5. Broze G J, Warren L A, Novotny W F, Higuchi D A, Girard J J, Miletich P J. The lipoprotein-associated coagulation inhibitor that inhibits the factor VII-tissue factor complex also inhibits factor Xa: insight into its possible mechanism of action. *Blood.* 1988; 71: 335-343.
6. Rapaport S I. The extrinsic pathway inhibitor: a regulator of tissue factor-dependent blood coagulation. *Thromb Haemost.* 1991; 66: 6-15.
7. Monkovic D D, Tracy P B. Activation of human factor V by factor Xa and thrombin. *Biochemistry.* 1990; 29: 1118-1128.
8. Hoffman M, Monroe D M, Oliver J A, Roberts H R. Factors IXa and Xa play distinct roles in tissue factor-dependent initiation of coagulation. *Blood.* 1995; 86: 1794-1801.
9. Monroe D M, Hoffman M, Roberts H R. Transmission of a procoagulant signal from tissue factor-bearing cells to platelets. *Blood Coagul Fibrinolysis.* 1996; 7: 459-464.
10. Walsh P N, Sinha D, Koshy A, Seaman F S, Bradford H. Functional characterization of platelet-bound factor XIa: retention of factor XIa activity on the platelet surface. *Blood.* 1986; 68: 225-230.
11. Franssen J, Salemink I, Willems G M, Wun T C, Hemker H C, Lindhout T. Prothrombinase is protected from inactivation by tissue factor pathway inhibitor: competition between prothrombin and inhibitor. *Biochem J.* 1997; 323: 33-37.
12. Rezaie A R. Prothrombin protects factor Xa in the prothrombinase complex from inhibition by the heparin-antithrombin complex. *Blood.* 2001; 97: 2308-2313.
13. Lawson J H, Mann K G. Cooperative activation of human factor IX by the human extrinsic pathway of blood coagulation. *J Biol. Chem.* 1991; 266: 11317-11327.

SUMMARY OF THE INVENTION

In its many embodiments, the present invention provides a novel class of heterocyclic compounds, pharmaceutical compositions comprising one or more said compounds, and methods for using said compounds for treating or preventing a thromboembolic disorder.

Accordingly, in one aspect, the present invention provides compounds of Formula (I):

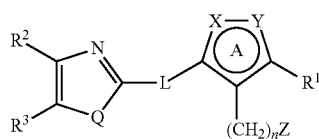

Formula I or a pharmaceutically acceptable salt, solvate or ester thereof; wherein:

ring A comprising ring atoms X and Y as shown is a heteroaryl ring;

X is N or NR;

Y is N, NR, O or S;

L is selected from the group consisting of a covalent bond, —C(=O)N(R)—, —N(R)—C(=O)—, —S(=O)$_2$NR— and —N(R)S(=O)$_2$—;

Q is NR, S or O;

each R independently is H, alkyl, cycloalkyl, heterocyclyl, aryl, heteroaryl, or —(CR$^5$R$^6$)$_n$W, wherein W is selected from the group consisting of cycloalkyl, heterocyclyl, aryl, heteroaryl, —C(=O)NR$^5$R$^6$, C(=O)OR$^4$, —OR$^4$, —NR$^5$R$^6$;

R$^1$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, cycloalkenyl, heterocyclyl, heterocyclenyl, aryl, or heteroaryl.

R$^2$ and R$^3$ are each independently selected from the group consisting of H, alkyl, cycloalkyl, cycloalkenyl, heterocyclyl, heterocyclenyl, aryl, heteroaryl, halo, hydroxy, alkoxy, haloalkyl, and aryloxy, wherein when each of said cycloalkyl, cycloalkenyl, heterocyclyl, heterocyclenyl, aryl, heteroaryl, or the "aryl" portion of aryloxy contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl; or R$^2$ and R$^3$ together with the carbon atoms to which they are shown attached form a five to six-membered cycloalkyl, cycloalkenyl, heterocyclyl, heterocyclenyl, aryl or heteroaryl ring, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring;

n is 0-2; and

Z is selected from the group consisting of H, halogen, alkyl, —OR$^4$, —NR$^5$R$^6$, —NR$^5$C(O)R$^6$, —NR$^5$C(O)OR$^6$, —NR$^5$C(O)NR$^5$R$^6$; —NR$^5$S(O)$_2$R$^6$, —NR$^5$S(O)$_2$N(R$^6$)$_2$;

each R$^4$ independently is selected from the group consisting of H, alkyl, —C(=O)-heterocyclyl, —C(=O)NHalkyl, and —C(=O)N(alkyl)$_2$;

each R$^5$ and R$^6$ is independently selected from the group consisting of H alkyl, and —C(=O)alkyl;

with the proviso that the compound of formula I is not

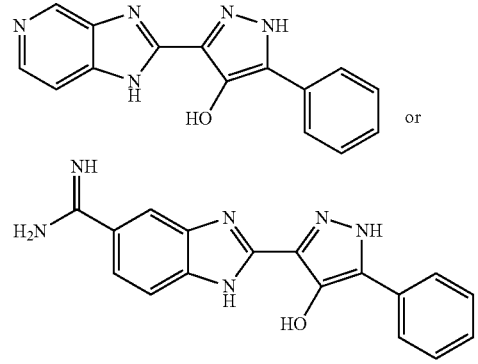

or

In another aspect, the present invention provides compounds of Formula (I):

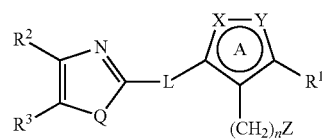

Formula I or a pharmaceutically acceptable salt, solvate or ester thereof; wherein:

ring A comprising ring atoms X and Y as shown is a heteroaryl ring;

X is N or NR;

Y is N, NR, O or S;

L is selected from the group consisting of a covalent bond, —C(=O)N(R)—, —N(R)—C(=O)—, —S(=O)$_2$NR— and —N(R)S(=O)$_2$—;

Q is NR, S or O;

each R independently is H, alkyl, cycloalkyl, heterocyclyl, aryl, heteroaryl, or —(CR$^5$R$^6$)$_n$W, wherein W is selected from the group consisting of cycloalkyl, heterocyclyl, aryl, heteroaryl, —C(=O)NR$^5$R$^6$, C(=O)OR$^4$, —NR$^5$R$^6$;

R$^1$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, cycloalkenyl, heterocyclyl, heterocyclenyl, aryl, or heteroaryl.

R$^2$ and R$^3$ are each independently selected from the group consisting of H, alkyl, cycloalkyl, cycloalkenyl, heterocyclyl, heterocyclenyl, aryl, heteroaryl, halo, hydroxy, alkoxy, haloalkyl, and aryloxy, wherein when each of said cycloalkyl, cycloalkenyl, heterocyclyl, heterocyclenyl, aryl, heteroaryl, or the "aryl" portion of aryloxy contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl; or R$^2$ and R$^3$ together with the carbon atoms to which they are shown attached form a five to six-membered cycloalkyl, cycloalkenyl, heterocyclyl, heterocyclenyl, aryl or heteroaryl ring, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring;

n is 0-2; and

Z is selected from the group consisting of —$OR^4$, —$NR^5R^6$, —$NR^5C(O)R^6$, —$NR^5C(O)OR^6$, —$NR^5C(O)NR^5R^6$; —$NR^5S(O)_2R^6$, —$NR^5S(O)_2N(R^6)_2$ each $R^4$ independently is H or alkyl;

each $R^5$ and $R^6$ is independently selected from the group consisting of H and alkyl;

with the proviso that the compound of formula I is not

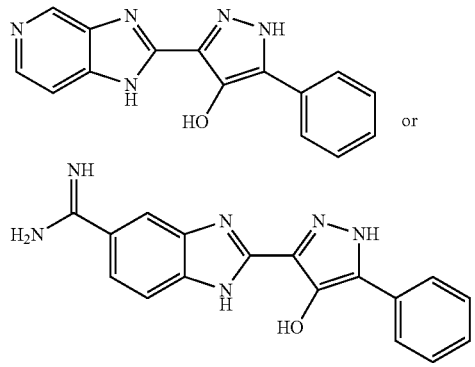

or

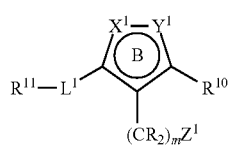

In another aspect, the present invention provides compounds of Formula (II):

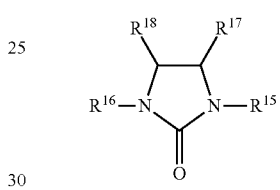

Formula II or a pharmaceutically acceptable salt, solvate or ester thereof; wherein:

ring B comprising ring atoms $X^1$ and $Y^1$ as shown is a heteroaryl ring;

$X^1$ is N or NR;

$Y^1$ is N, NR, O or S;

$L^1$ is selected from the group consisting of —C(=O)N(R)—, —N(R)—C(=O)—, —S(=O)$_2$NR— and —N(R)S(=O)$_2$—;

each R independently in H or alkyl;

$R^{10}$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

$R^{11}$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

m is 0-2;

$Z^1$ is selected from the group consisting of —$OR^4$, —$NR^5R^6$, —$NR^5C(O)R^6$, —$NR^5C(O)OR^6$, —$NR^5C(O)NR^5R^6$; —$NR^5S(O)_2R^6$, —$NR^5S(O)_2N(R^6)_2$ $R^4$ is H or alkyl; and each $R^5$ and $R^6$ is independently selected from the group consisting of H and alkyl;

with the proviso that: (i) when $R^{11}$ is phenyl, said phenyl is unsubstituted or substituted by groups other than —(C=NR)NR$_2$, and (ii) when $L^1$ is —N(R)C(=O)— which is linked to the B ring via the nitrogen atom, $R^{11}$ is other than unsubstituted phenyl.

In another aspect, the present invention provides compounds of Formula (III):

Formula III $$\begin{array}{c} R^{18} \quad R^{17} \\ R^{16}-N \quad N-R^{15} \\ \parallel \\ O \end{array}$$

or a pharmaceutically acceptable salt, solvate, or ester thereof;

wherein:

$R^{15}$ is aryl, wherein when said aryl contains two substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

$R^{16}$ is selected from the group consisting of a five- or six-membered heteroaryl which is fused to a benzene ring, a quinolin-2-one, and a phenyl which is fused to a five- or six-membered heteroaryl; with the proviso that when $R^{16}$ is phenyl fused to a pyridine ring, then $R^{15}$ is an unsubstituted aryl; and each of $R^{17}$ and $R^{18}$ independently is H or alkyl.

In another aspect, the compounds of any one of Formula I-Formula III, or a pharmaceutically acceptable salt, solvate or ester thereof can be useful for treating or preventing a disorder or disease mediated by factor IXa, or a thromboembolic disorder (each disorder being a "Condition").

In another aspect, the present invention provides pharmaceutical compositions comprising at least one compound of any one of Formulae I-III or a pharmaceutically acceptable salt, solvate or ester thereof, and a pharmaceutically acceptable carrier. The compositions can be useful for treating or preventing a Condition.

In still another aspect, the present invention provides methods for treating a Condition, the method comprising administering to a patient an effective amount of at least one compound of any one of Formulae I-III or a pharmaceutically acceptable salt, solvate or ester thereof.

DETAILED DESCRIPTION OF THE INVENTION

In an embodiment, the present invention provides compounds of any one of Formulae I-III and or pharmaceutically acceptable salts, solvates, esters and prodrugs thereof. The compounds of formula I can be useful for treating or preventing a Condition in a patient.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, heteroaryl, cyano, hydroxy, alkoxy, alkylthio, amino, —NH (alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, heteroaryl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

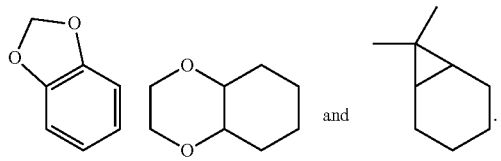

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

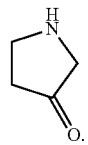

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

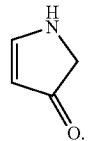

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

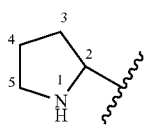

there is no —OH attached directly to carbons marked 2 and 5.

It should also be noted that tautomeric forms such as, for example, the moieties:

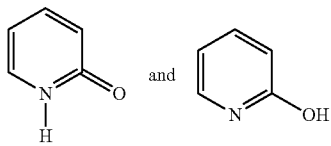

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)-group in which the aryl group is as previously described. The bond to the parent moiety is through the carbonyl. Non-limiting examples of suitable groups include benzoyl and 1-naphthoyl.

"Alkoxy" means an alkyl-O-group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O-group in which the aryl group is as previously described. Non-limiting examples of suitable aryloxy groups include phenoxy and naphthoxy. The bond to the parent moiety is through the ether oxygen.

"Aralkyloxy" means an aralkyl-O-group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S-group in which the alkyl group is as previously described. Non-limiting examples of suitable alkylthio groups include methylthio and ethylthio. The bond to the parent moiety is through the sulfur.

"Arylthio" means an aryl-S-group in which the aryl group is as previously described. Non-limiting examples of suitable arylthio groups include phenylthio and naphthylthio. The bond to the parent moiety is through the sulfur.

"Aralkylthio" means an aralkyl-S-group in which the aralkyl group is as previously described. Non-limiting example of a suitable aralkylthio group is benzylthio. The bond to the parent moiety is through the sulfur.

"Alkoxycarbonyl" means an alkyl-O—CO-group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)-group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)-group. Non-limiting example of a suitable aralkoxycarbonyl group is benzyloxycarbonyl. The bond to the parent moiety is through the carbonyl.

"Alkylsulfonyl" means an alkyl-S($O_2$)-group. Preferred groups are those in which the alkyl group is lower alkyl. The bond to the parent moiety is through the sulfonyl.

"Arylsulfonyl" means an aryl-S($O_2$)-group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis*, 4$^{th}$ edition (2007), Wiley, New York.

When any variable (e.g., aryl, heterocycle, $R^2$, etc.) occurs more than one time in any constituent or in Formula I-VI, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I-VI can form salts which are also within the scope of this invention. Reference to a compound of Formula I-VI herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I-VI contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I-VI may be formed, for example, by reacting a compound of Formula I-VI with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I-VI, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974

Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I-VI, and of the salts, solvates, esters and prodrugs of the compounds of Formula I, are intended to be included in the present invention.

Heterocyclic Compounds of the Invention

In one embodiment, the present invention provides a compound of Formula I:

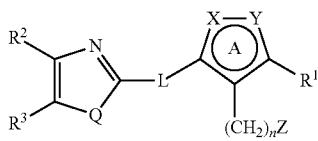

Formula I or a pharmaceutically acceptable salt, solvate or ester thereof; wherein:

ring A comprising ring atoms X and Y as shown is a heteroaryl ring;

X is N or NR;

Y is N, NR, O or S;

L is selected from the group consisting of a covalent bond, —C(=O)N(R)—, —N(R)—C(=O)—, —S(=O)$_2$NR— and —N(R)S(=O)$_2$—;

Q is NR, S or O;

each R independently is H, alkyl, haloalkyl, cycloalkyl, heterocyclyl, aryl, heteroaryl, or —(CR$^5$R$^6$)$_n$W, wherein W is selected from the group consisting of cycloalkyl, heterocyclyl, aryl, heteroaryl, —C(=O)NR$^5$R$^6$, —OR$^4$, —NR$^5$R$^6$;

R$^1$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, cycloalkenyl, heterocyclyl, heterocyclenyl, aryl, or heteroaryl.

R$^2$ and R$^3$ are each independently selected from the group consisting of H, alkyl, cycloalkyl, cycloalkenyl, heterocyclyl, heterocyclenyl, aryl, heteroaryl, halo, hydroxy, alkoxy, haloalkyl, and aryloxy, wherein when each of said cycloalkyl, cycloalkenyl, heterocyclyl, heterocyclenyl, aryl, heteroaryl, or the "aryl" portion of aryloxy contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl; or R$^2$ and R$^3$ together with the carbon atoms to which they are shown attached form a five to six-membered cycloalkyl, cycloalkenyl, heterocyclyl, heterocyclenyl, aryl or heteroaryl ring, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring;

n is 0-2; and

Z is selected from the group consisting of H, halogen, alkyl, —OR$^4$, NR$^5$R$^6$, —NR$^5$C(O)R$^6$, —NR$^5$C(O)OR$^6$, —NR$^5$C(O)NR$^5$R$^6$; —NR$^5$S(O)$_2$R$^6$, —NR$^5$S(O)$_2$N(R$^6$)$_2$;

each R$^4$ independently is selected from the group consisting of H, alkyl, —C(=O)-heterocyclyl, —C(=O)NHalkyl, and —C(=O)N(alkyl)$_2$;

each R$^5$ and R$^6$ is independently selected from the group consisting of H alkyl, —C(=O)alkyl, and —C(=O)Oalkyl;

with the proviso that the compound of formula I is not

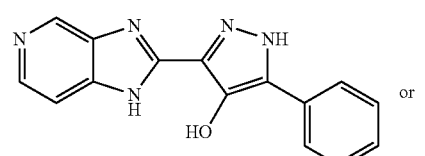

or

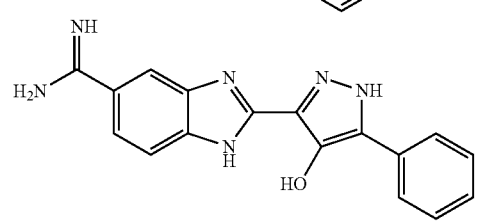

In another embodiment, the present invention provides a compound of Formula I:

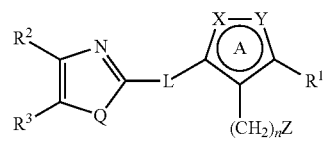

Formula I or a pharmaceutically acceptable salt, solvate, ester, prodrug, or stereoisomer thereof; wherein:

ring A comprising ring atoms X and Y as shown is a heteroaryl ring;

X is N or NR;

Y is N, NR, O or S;

L is selected from the group consisting of a covalent bond (i.e., Formula I corresponds to

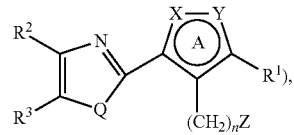

—C(=O)N(R)—, —N(R)—C(=O)—, —S(=O)$_2$NR— and —N(R)S(=O)$_2$—;

Q is NR, S or O;

each R independently is H, alkyl, cycloalkyl, heterocyclyl, aryl, heteroaryl, or —(CR$^5$R$^6$)$_n$W, wherein W is selected from the group consisting of cycloalkyl, heterocyclyl, aryl, heteroaryl, —C(=O)NR$^5$R$^6$, C(=O)OR$^4$, —NR$^5$R$^6$;

R$^1$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, cycloalkenyl, heterocyclyl, heterocyclenyl, aryl, or heteroaryl.

$R^2$ and $R^3$ are each independently selected from the group consisting of H, alkyl, cycloalkyl, cycloalkenyl, heterocyclyl, heterocyclenyl, aryl, heteroaryl, halo, hydroxy, alkoxy, haloalkyl, and aryloxy, wherein when each of said cycloalkyl, cycloalkenyl, heterocyclyl, heterocyclenyl, aryl, heteroaryl, or the "aryl" portion of aryloxy contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl; or $R^2$ and $R^3$ together with the carbon atoms to which they are shown attached form a five to six-membered cycloalkyl, cycloalkenyl, heterocyclyl, heterocyclenyl, aryl or heteroaryl ring, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring;

n is 0-2; and

Z is selected from the group consisting of H, halogen, alkyl, —$OR^4$, —$NR^5R^6$, —$NR^5C(O)R^6$, —$NR^5C(O)OR^6$, —$NR^5C(O)NR^5R^6$; —$NR^5S(O)_2R^6$, —$NR^5S(O)_2N(R^6)_2$;

each $R^4$ independently is H or alkyl;

each $R^5$ and $R^6$ is independently selected from the group consisting of H and alkyl;

with the proviso that the compound of formula I is not

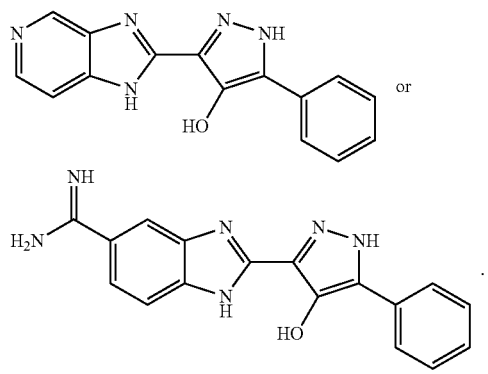

In one embodiment, in formula I, X is N and Y is NR.
In another embodiment, in formula I, X is NR and Y is N.
In another embodiment, in formula I, ring A is pyrazolyl.
In another embodiment, in formula I, Q is NR.
In another embodiment, in formula I, Q is O.
In another embodiment, in formula I, L is a covalent bond.
In another embodiment, in formula I, n is 0.
In another embodiment, in formula I, n is 1.
In another embodiment, in formula I, Z is selected from the group consisting of —$OR^4$, —$NR^5R^6$, —$NR^5C(O)R^6$, —$NR^5C(O)OR^6$, —$NR^5C(O)NR^5R^6$; —$NR^5S(O)_2R^6$, and —$NR^5S(O)_2N(R^6)_2$.
In another embodiment, in formula I, Z is $OR^4$.

In another embodiment, in formula I, X is N and Y is NR, wherein Y is selected from the group consisting of NH, N(methyl), N(ethyl), N(benzyl), and N(4-methoxybenzyl).
In another embodiment, in formula I, X is NR and Y is N, wherein X is selected from the group consisting of NH, N(methyl), N(ethyl), N(benzyl), and N(4-methoxybenzyl).
In another embodiment, in formula I, Z is $OR^4$, wherein Z is selected from the group consisting of OH, methoxy, ethoxy, 4-methoxybenzyloxy, benzyloxy, —OC(=O)—N(alkyl)$_2$, —OC(=O)-alkyl, and —OC(=O)-heterocyclyl.
In another embodiment, in formula I, Z is $OR^4$, wherein Z is selected from the group consisting of OH, methoxy, ethoxy, 4-methoxybenzyloxy, and benzyloxy.
In another embodiment, in formula I, R is selected from the group consisting of H, CH$_3$, —CH$_2$CH$_3$, —CH$_2$CH$_2$OCH$_3$, —CH$_2$CH$_2$CH$_2$OCH$_3$, —CH$_2$-phenyl, —CH$_2$-(2-fluorophenyl), —CH$_2$-(2-methoxyphenyl), —CH$_2$-(4-methoxyphenyl), and —CH$_2$-phenyl-phenyl, and —CH$_2$CF$_3$.
In another embodiment, in formula I, $R^1$ is aryl.
In another embodiment, in formula I, $R^1$ is aryl, wherein said $R^1$ aryl is phenyl which is optionally substituted with one to four substituents selected independently from the group consisting of cyano, halo, alkyl, alkenyl, -alkyl-aryl, aminoalkyl, -alkyl-NR$^5$C(=O)OR$^4$, -alkyl-S(=O)$_2$-aryl, -aryl-S(=O)$_2$-alkyl, —NR$^5$—C(=O)-alkyl, —NR$^5$S(=O)$_2$-aryl, -alkyl-NR$^5$S(=O)$_2$-alkyl, -alkyl-NR$^5$C(=O)NR$^5$-alkyl, -alkyl-NR$^5$C(=O)NR$^5$-aryl, -alkyl-heteraryl, -alkyl-heterocyclyl, —NR$^5$C(=O)NR$^6$aryl, -alkyl-NR$^5$C(=O)alkyl, -alkyl-NR$^5$C(=O)aryl, hydroxyalkyl, alkoxyalkyl, haloalkyl, alkoxy, haloalkoxy, aryl, heteroaryl, cycloalkyl, heterocycylyl, —NR$^5$R$^6$, —SR$^4$, and —C(O)NR$^5$R$^6$, wherein when each of said aryl, heteroaryl, cycloalkyl, and heterocycylyl substituents of said $R^1$ phenyl contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring.
In another embodiment, in formula I, $R^1$ is aryl, wherein said $R^1$ aryl is phenyl which is optionally substituted with one to four substituents selected independently from the group consisting of cyano, halo, alkyl, aminoalkyl, -alkyl-NR$^5$C(=O)OR$^4$, -alkyl-S(=O)$_2$-aryl, -alkyl-NR$^5$S(=O)$_2$-alkyl, -alkyl-NR$^5$C(=O)NR$^5$-alkyl, -alkyl-heteraryl, -alkyl-heterocyclyl, -alkyl-NR$^5$C(=O)alkyl, -alkyl-NR$^5$C(=O)aryl, hydroxyalkyl, alkoxyalkyl, haloalkyl, alkoxy, haloalkoxy, aryl, heteroaryl, cycloalkyl, heterocycylyl, —NR$^5$R$^6$, —SR$^4$, and —C(O)NR$^5$R$^6$.
In another embodiment, in formula I, $R^1$ aryl is phenyl wherein said phenyl is optionally substituted with one to four substituents selected independently from the group consisting of cyano, bromo, chloro, methoxy, —C(=O)NH$_2$, —CH$_2$OH, —CH$_2$OCH$_2$CH$_3$, —CH$_2$NH$_2$, —CH$_2$NHC(=O)OCH$_3$, —CH$_2$S(=O)$_2$-phenyl, —CH$_2$NHS(=O)$_2$CH$_3$, —CH$_2$NHC(=O)NH(ethyl), —CH$_2$-(1,2,3-triazole), —CH$_2$NHC(=O)CH$_3$, —CH$_2$NHC(=O)-phenyl, -(2-methoxy)pyridyl, fluorophenyl, pyridyl, and —CH$_2$-piperidine.
In another embodiment, in formula I, $R^1$ is aryl, wherein said $R^1$ aryl is phenyl which is optionally substituted with one to four substituents selected independently from the group consisting of cyano, bromo, chloro, methoxy, —NH$_2$, —NH—C(=O)—CH$_3$, —NHS(=O)$_2$-phenyl, —CH=CH$_2$, —C(H)(CH$_3$)(OH), —C(=O)NH$_2$, —CH$_2$OH, —CH$_2$OCH$_2$CH$_3$, —CH$_2$NH$_2$, —CH$_2$NHC(=O)OCH$_3$, —CH$_2$S(=O)$_2$-phenyl, —CH$_2$NHS(=O)$_2$CH$_3$, —CH$_2$NHC(=O)NH(ethyl), —NHC(=O)NH(phenyl), —CH$_2$NHC(=O)NH(phenyl), triazolyl, -(1,2,3- triazolyl), —CH₂-(1,2,3-triazolyl), —CH₂NHC(═O)CH₃, —CH₂NHC(═O)-phenyl, 2-methoxypyridyl-, pyrimidinyl, -pyridyl-C(═O)NHCH₃, -pyridyl-C(═O)NH₂, -pyridyl-CN, dimethoxypyridyl, 2-fluorophenyl, 3-fluorophenyl, 4-fluorophenyl, pyridyl, —CH₂-piperidine, phenyl, benzyl, cyclopropyl, —NHC(═O)CH₃, —CH₂-piperadinyl, methyl, ethyl, n-pentyl, n-butyl, n-propyl, cyclopenyl, cyclohexyl, 3-ethylphenyl, 3-methylphenyl-, 2-methoxyphenyl-, 3-methoxyphenyl-, 4-methoxyphenyl-, (3-aminomethyl)phenyl-, 3-trifluoromethylphenyl-, 3,5-dimethylphenyl-, 4-methylphenyl-, 3-chlorophenyl-, 4-chlorophenyl-, 2-cyanophenyl-, 3-cyanophenyl-, 4-cyanophenyl, 2-(C(═O)NH₂)phenyl-, 3-(C(═O)NH₂)phenyl-, 4-(C(═O)NH₂)phenyl-, 3-methylsulfonylphenyl-, 4-methylsulfonylphenyl-, 3-trifluoromethoxyphenyl-, 4-trifluoromethoxyphenyl-, 2-chlorophenyl-, 3,5-dichlorophenyl-, 3,5-dimethoxyphenyl-, 3,4-dihydroxyphenyl-, -phenyl-(4-(S(O)₂NH₂), -phenyl-(4-(S(O)₂NHCH₃), -phenyl-(4-(S(O)₂CH₃), -phenyl-(4-(S(O)₂N(CH₃)₂), -phenyl-(4-(C═O)NHCH₃), -phenyl-(4-(C═O)N(CH₃)₂), —CH₂-pyrazolyl, —CH₂-morpholinyl, —CH₂—N(CH₃)CH₂CH₂OCH₃, —CH₂-piperazinyl-C(═O)CH₃, —CH₂-piperazinyl-methyl, -phenyl-S(═O)₂—CH₃, —CH₂CH₂phenyl, N-piperidone, N-pyrrolidone,

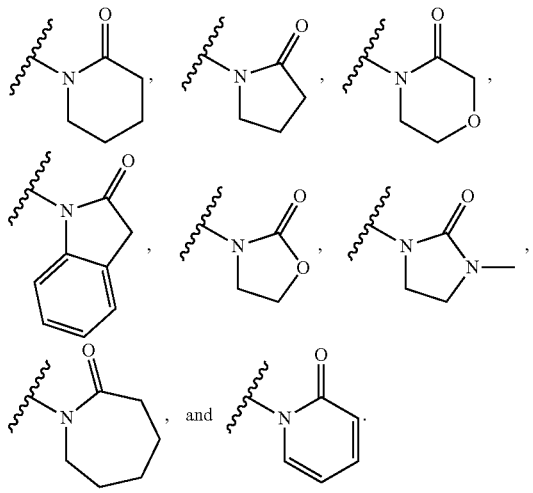

In another embodiment, in formula I, R¹ is heteroaryl.

In another embodiment, in formula I, R¹ is heteroaryl, wherein said heteroaryl is pyridyl which is optionally substituted with one to four substituents selected independently from the group consisting of cyano, halo, alkyl, hydroxyalkyl, alkoxyalkyl, haloalkyl, alkoxy, haloalkoxy, —C(O)NR⁵R⁶, —NR⁵R⁶, heterocyclyl, aryl, heteroaryl, cycloalkyl, —SR⁴, and -alkylaryl.

In another embodiment, in formula I, R¹ is heteroaryl, wherein said heteroaryl is pyridyl which is optionally substituted with one to four substituents selected independently from the group consisting of cyano, bromo, chloro, methoxy, phenyl, —C(═O)NH₂, —CH₂OH, and —CH₂OCH₂CH₃.

In another embodiment, in formula I, R¹ is heteroaryl, wherein said heteroaryl is pyridyl which is optionally substituted with one to four substituents selected independently from the group consisting of cyano, bromo, chloro, methoxy, —C(═O)NH₂, —CH₂OH, and —CH₂OCH₂CH₃.

In another embodiment, in formula I, R² and R³ together with the carbon atoms to which they are shown attached form a six membered aryl, wherein when said six-membered aryl contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring.

In another embodiment, in formula I, R² and R³ together with the carbon atoms to which they are shown attached form a six membered aryl, wherein said six-membered aryl is phenyl, wherein said phenyl contains substituents on adjacent carbon atoms, and wherein said substituents together with the carbon atoms to which they are attached form a five-membered heterocyclyl.

In another embodiment, in formula I, R² and R³ together with the carbon atoms to which they are shown attached form a six membered aryl, wherein said six-membered aryl is phenyl which is optionally substituted with one to four substituents independently selected from the group consisting of halo, alkyl, aminoalkyl, —CR⁵R⁶NR⁵R⁶, haloalkyl, alkoxy, haloalkoxy, cyano, hydroxy, hydroxyalkyl, —C(O)NR⁵R⁶, —C(═NR⁵)N(R⁶)₂ and —C(O)OR⁴.

In another embodiment, in formula I, R² and R³ together with the carbon atoms to which they are shown attached form a six membered aryl, wherein said six-membered aryl is phenyl which is optionally substituted with one to four substituents independently selected from the group consisting of methyl, —C(CH₃)₃, —CH₂NH₂, chloro, fluoro, bromo, hydroxy, methoxy, ethoxy, trifluoromethyl, trifluoromethoxy, cyano, —C(O)NH₂, —C(O)NHCH₃, —C(O)N(CH₃)₂, —C(═NH)NH₂, —C(O)OH, —C(O)OCH₂CH₃ and —C(O)OCH₃.

In another embodiment, in formula I, R² and R³ together with the carbon atoms to which they are shown attached form a six membered heteroaryl, wherein when said six-membered aryl contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl ring.

In another embodiment, in formula I, R² and R³ together with the carbon atoms to which they are shown attached form a six membered heteroaryl, wherein said six-membered heteroaryl is pyridyl which is optionally substituted with one to four substituents independently selected from the group consisting of halo, alkyl, aminoalkyl, haloalkyl, alkoxy, haloalkoxy, cyano, hydroxy, —C(O)NR⁵R⁶, —C(═NR⁵)N(R⁶)₂ and —C(O)OR⁴.

In another embodiment, in formula I, R² and R³ together with the carbon atoms to which they are shown attached form a six membered heteroaryl, wherein said six-membered aryl is pyridyl which is optionally substituted with one to four substituents independently selected from the group consisting of methyl, —C(CH₃)₃, chloro, fluoro, bromo, hydroxy, methoxy, ethoxy, trifluoromethyl, trifluoromethoxy, cyano, —CH₂NH₂, —C(O)NH₂, —C(O)NHCH₃, —C(O)N(CH₃)₂, —C(═NH)NH₂, —C(O)OH, —C(O)OCH₂CH₃ and —C(O)OCH₃.

In another embodiment, in formula I, R² and R³ together with the carbon atoms to which they are shown attached is

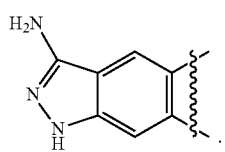

In another embodiment, in formula I, $R^2$ and $R^3$ together with the carbon atoms to which they are shown attached is

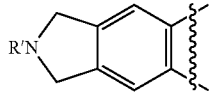

wherein R' is selected from the group consisting of H, alkyl, —C(=O)-alkyl, —C(=O)Oalkyl, —C(=O)alkyl-aryl, and —C(=O)aryl.

In another embodiment, in formula I, $R^2$ and $R^3$ together with the carbon atoms to which they are shown attached is

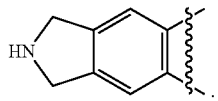

In another embodiment, in formula I, $R^2$ and $R^3$ together with the carbon atoms to which they are shown attached is

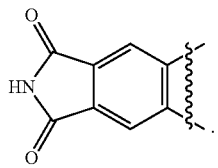

In another embodiment, in formula I, $R^2$ and $R^3$ together with the carbon atoms to which they are shown attached is

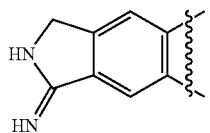

In another embodiment, in formula I, $R^2$ and $R^3$ together with the carbon atoms to which they are shown attached is

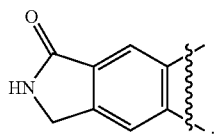

In another embodiment, in formula I, one of $R^2$ and $R^3$ is aryl, and the other is H.

In another embodiment, in formula I, one of $R^2$ and $R^3$ is aryl, and the other is H, wherein said $R^2$ or $R^3$ aryl is phenyl which is optionally substituted with a halo.

In another embodiment, in formula I, one of $R^2$ and $R^3$ is aryl, and the other is H, wherein said $R^2$ or $R^3$ aryl is phenyl which is optionally substituted with a chloro.

In another embodiment, the compound of formula I is selected from the group consisting of:

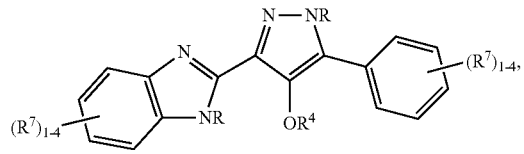
(IA)

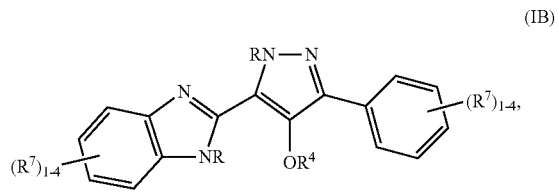
(IB)

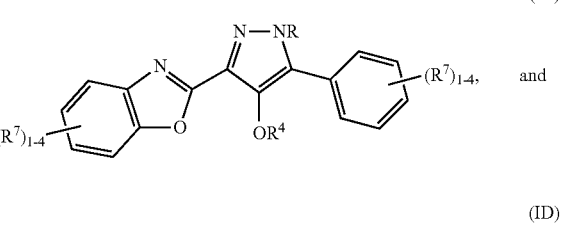
(IC)

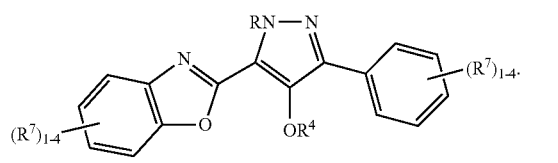
(ID)

or a pharmaceutically acceptable salt, solvate or ester thereof; wherein each $R^7$ is independently selected from the group consisting of hydrogen, halo, alkyl, aminoalkyl, hydroxyalkyl, haloalkyl, alkoxy, -alkyl-O-hydroxyalkyl, haloalkoxy, cyano, hydroxy, —C(O)$NR^5R^6$, —C(=$NR^5$)N($R^6$)$_2$ and —C(O)$OR^4$, -alkyl-$NR^5$C(=O)$OR^4$, -alkyl-S(=O)$_2$-aryl, -alkyl-$NR^5$S(=O)$_2$-alkyl, -alkyl-$NR^5$C(=O)$NR^5$-alkyl, -alkyl-heteraryl, -alkyl-heterocyclyl, -alkyl-$NR^5$C(=O)alkyl, -alkyl-$NR^5$C(=O)aryl, alkoxyalkyl, aryl, heteroaryl, cycloalkyl, heterocycylyl, —$NR^5R^6$, —$SR^4$, and —C(O)$NR^5R^6$.

In another embodiment, the compound of formula I is represented by the compound of formula (IE)

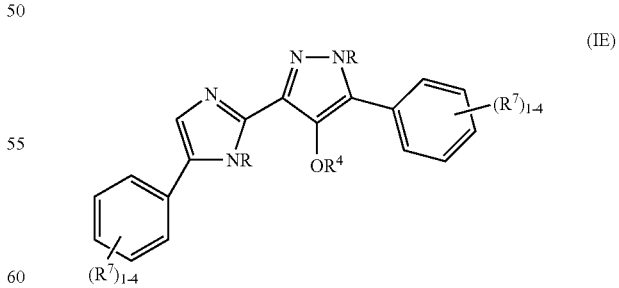
(IE)

or a pharmaceutically acceptable salt, solvate or ester thereof; wherein each $R^7$ is independently selected from the group consisting of hydrogen, halo, alkyl, aminoalkyl, hydroxyalkyl, haloalkyl, alkoxy, haloalkoxy, cyano, hydroxy, —C(O)$NR^5R^6$, and —C(O)$OR^4$.

In another embodiment, the compound of formula I is selected from the group consisting of:
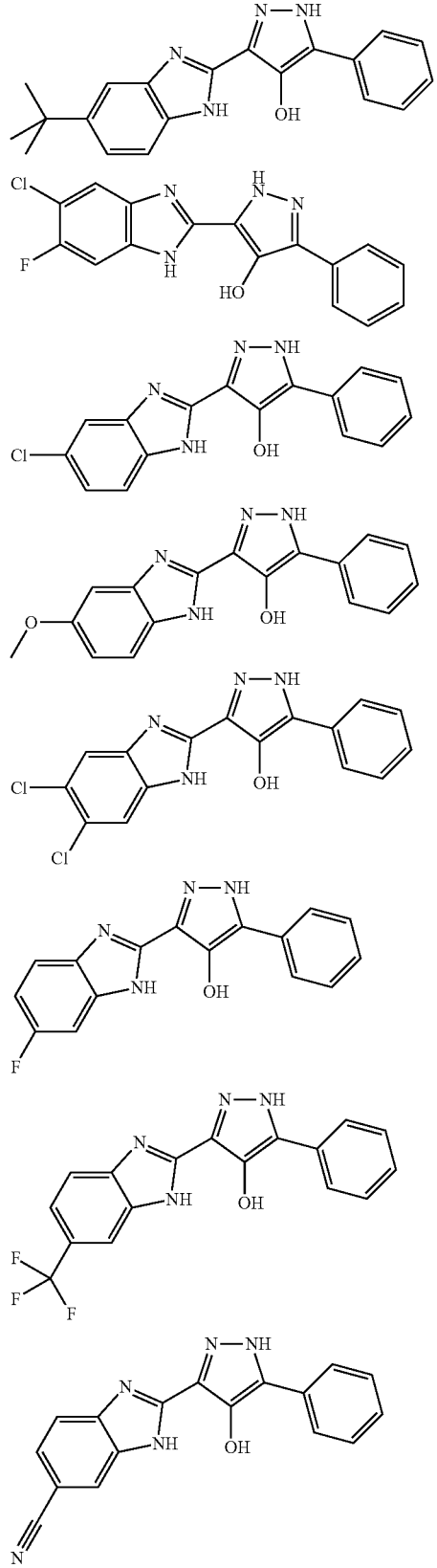
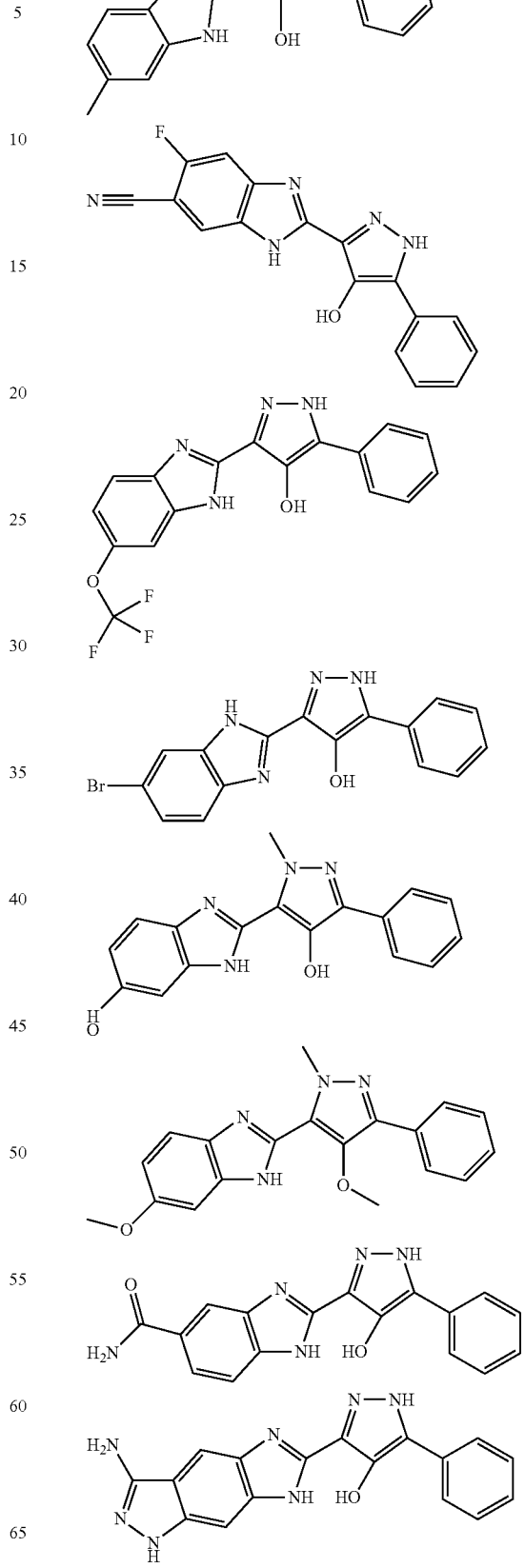

27
-continued
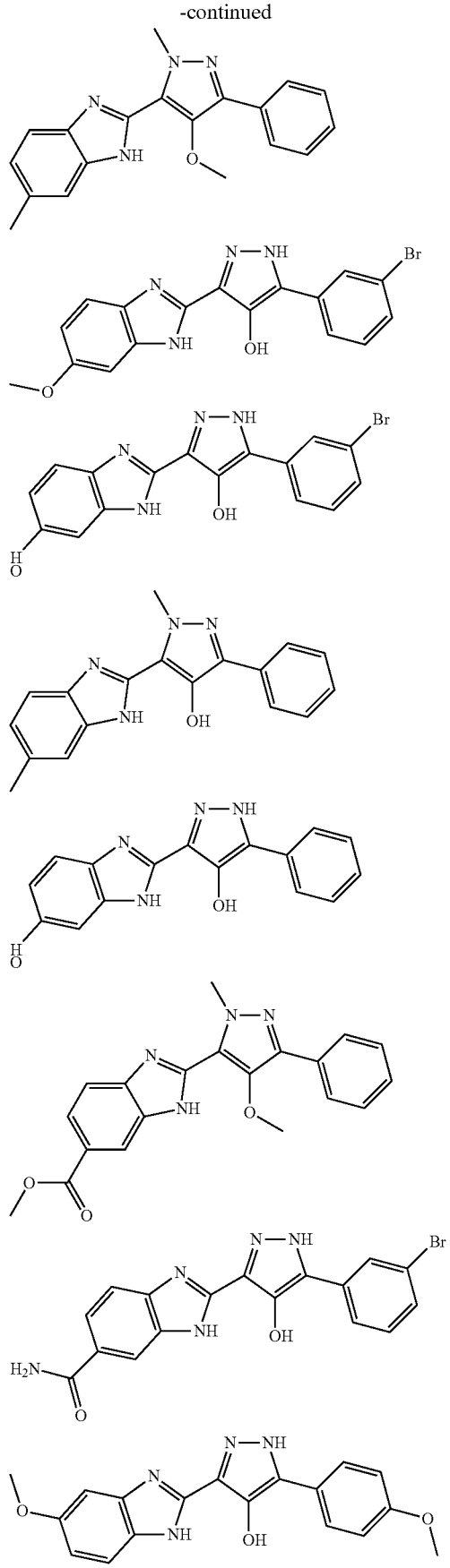
28
-continued
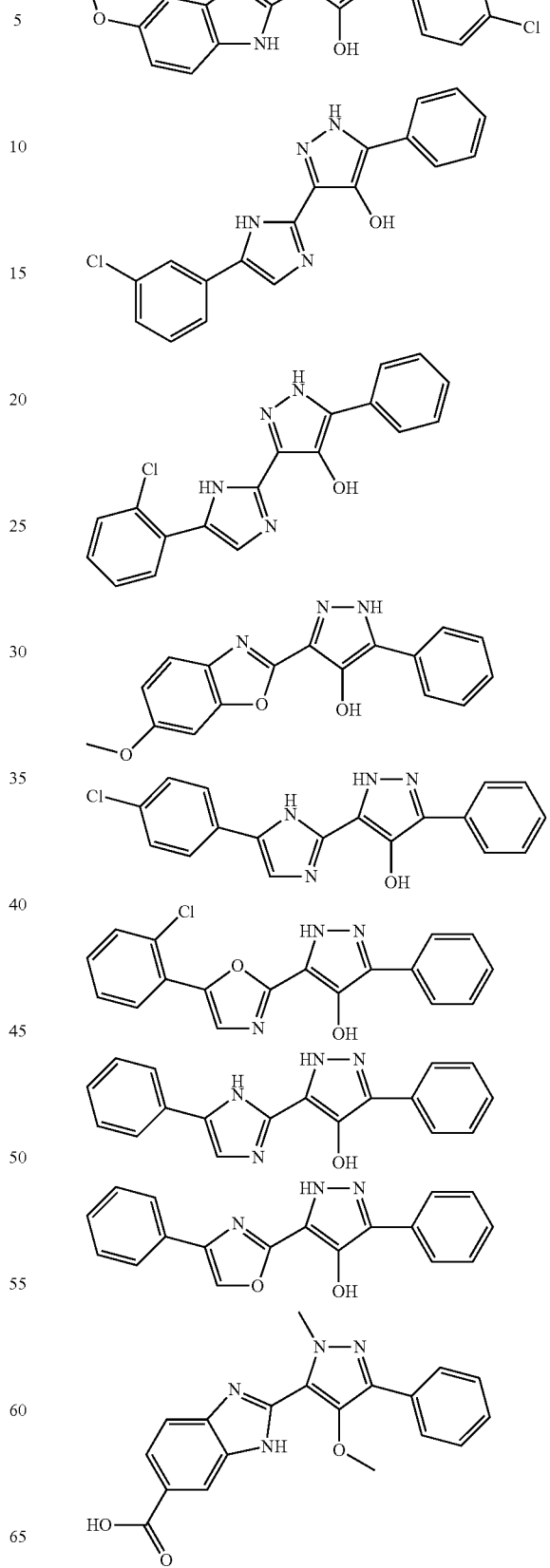

29
-continued
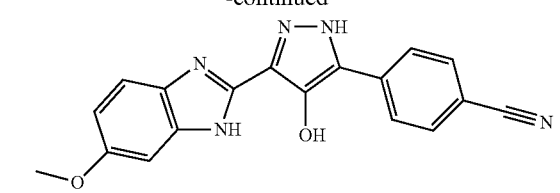
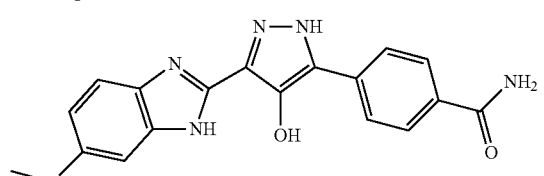
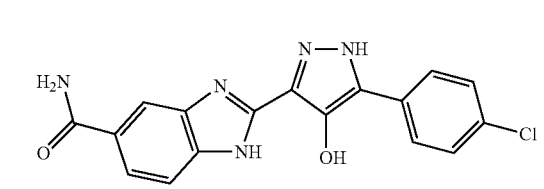
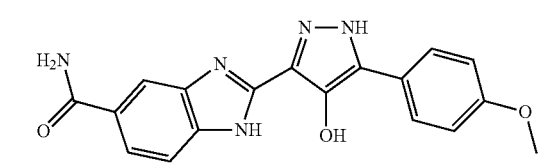
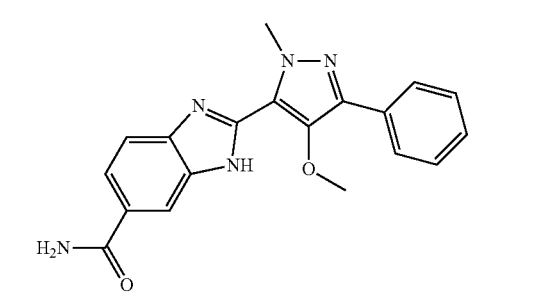
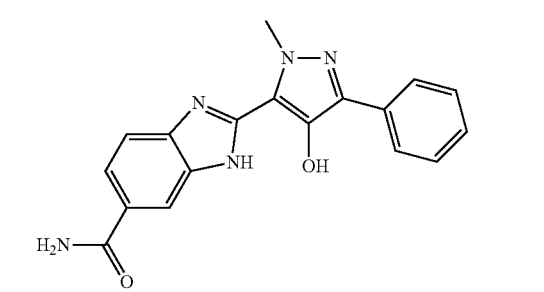
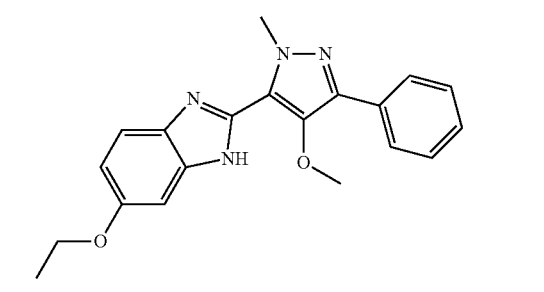
30
-continued
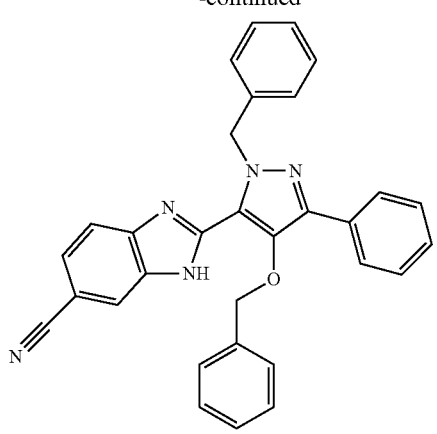
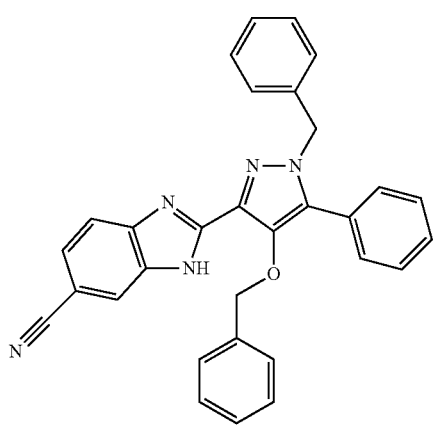
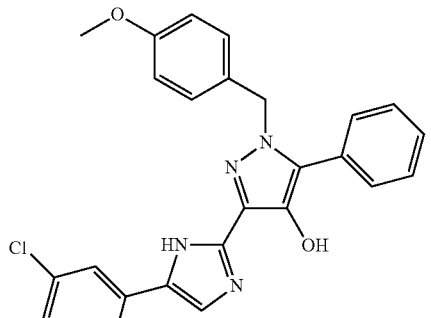
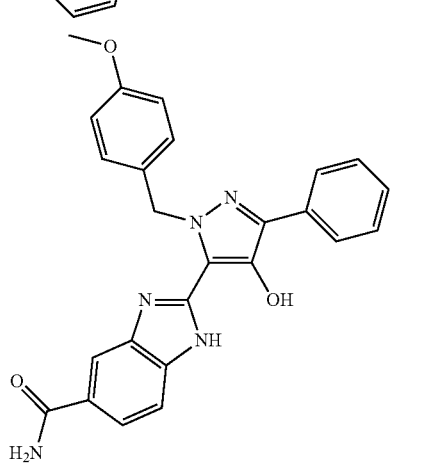

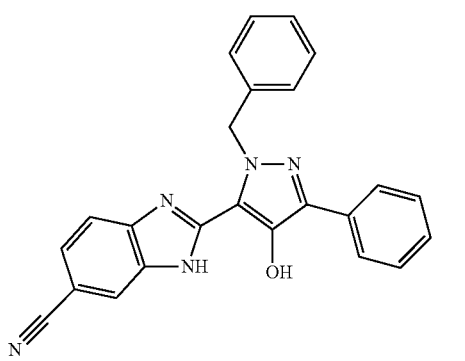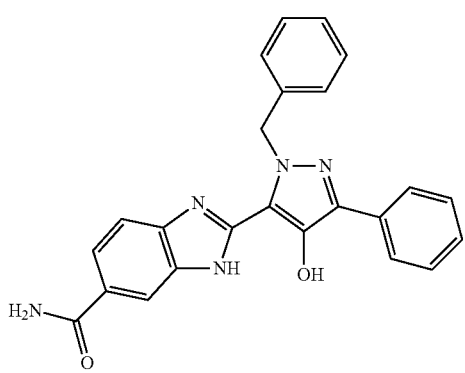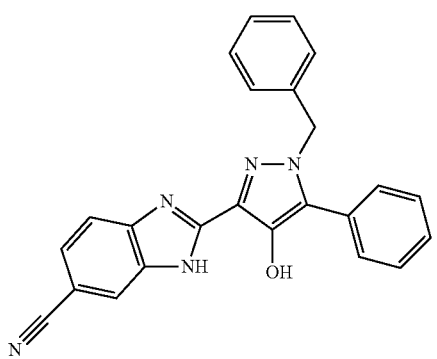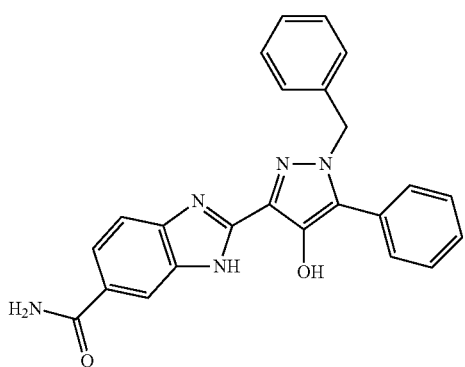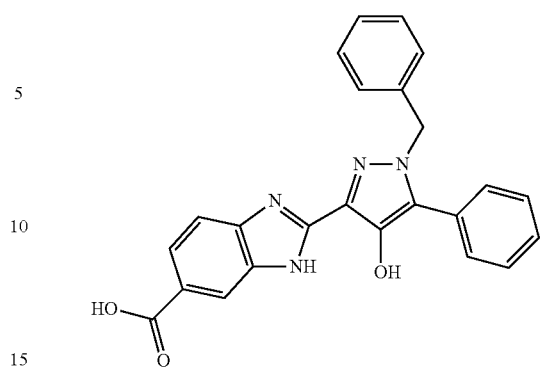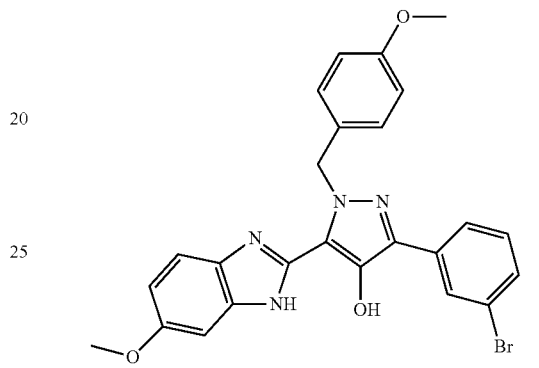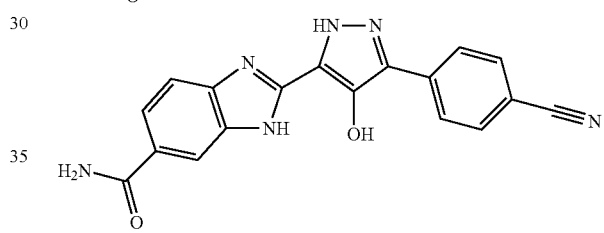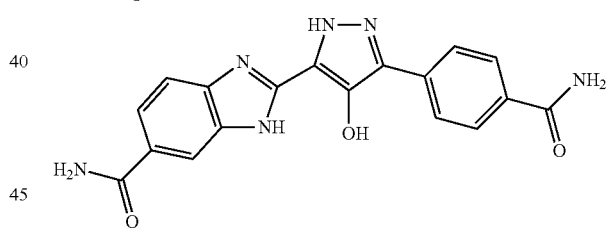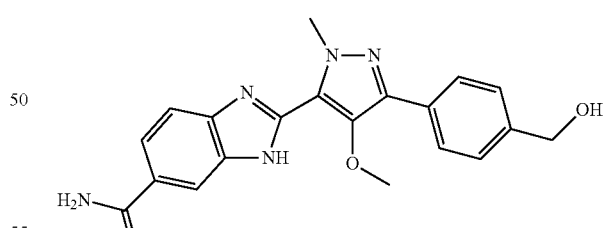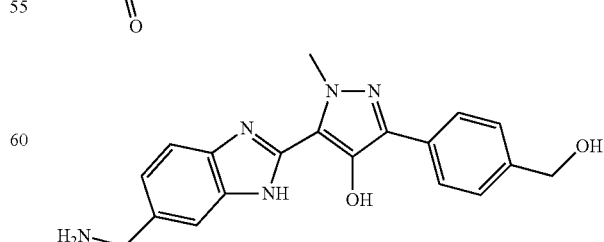

33
-continued
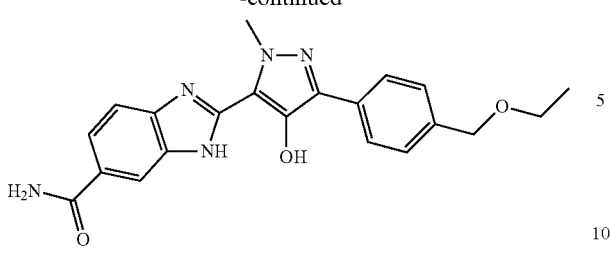
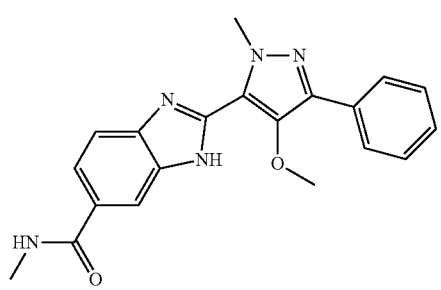
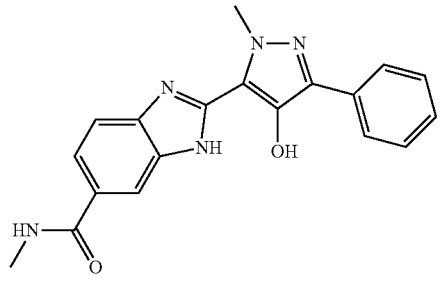
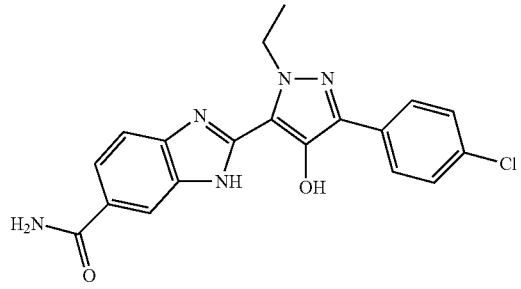
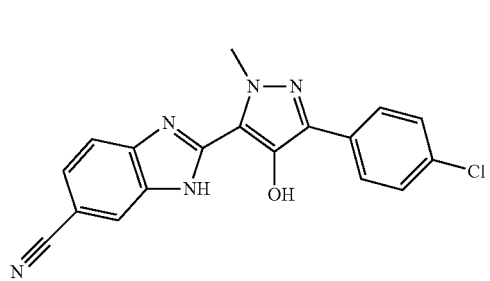
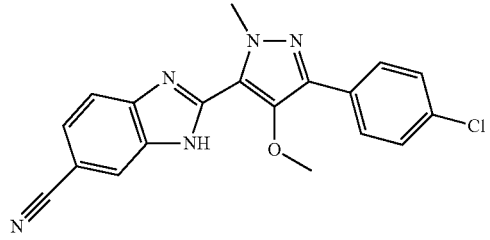
34
-continued
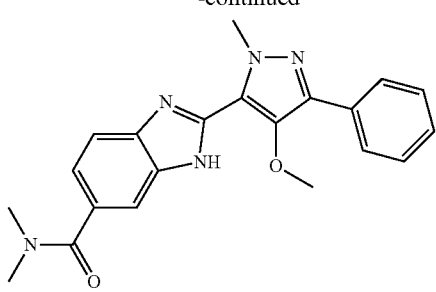
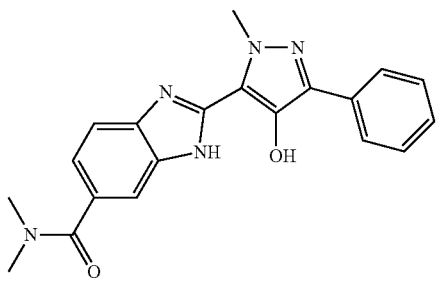
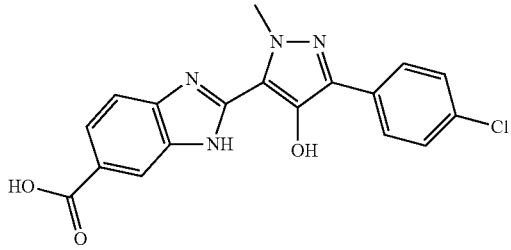
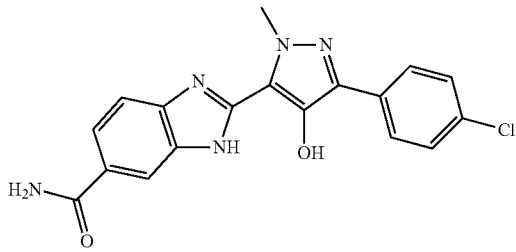
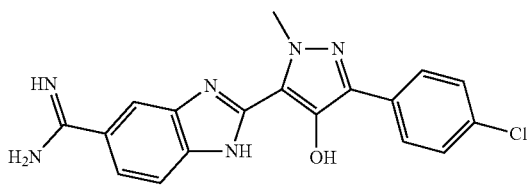
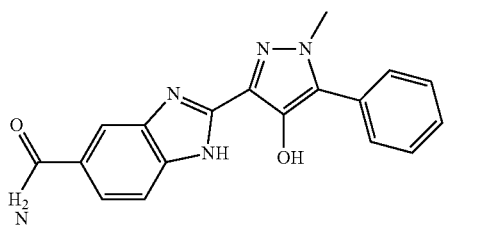

| 35 | 36 |
|---|---|
| -continued | -continued |
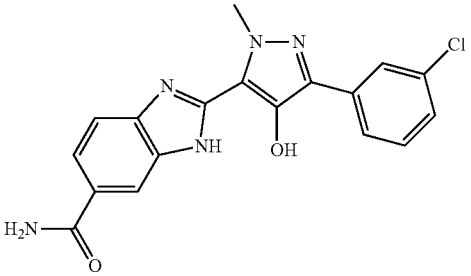
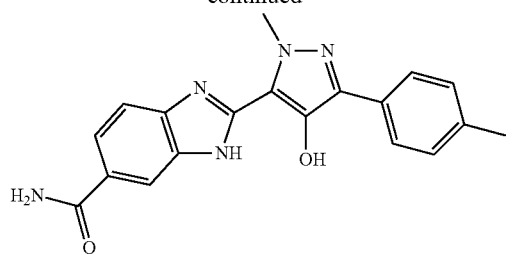
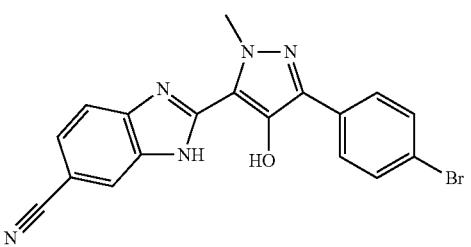
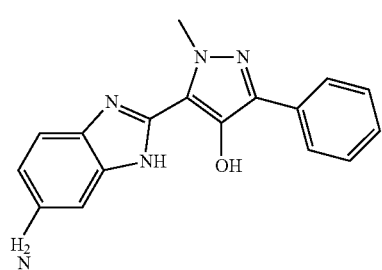
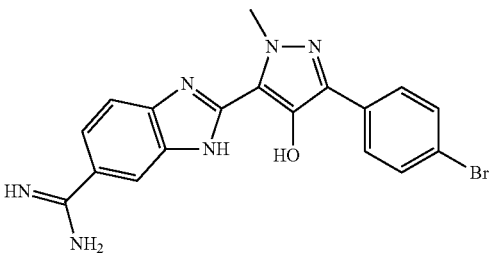
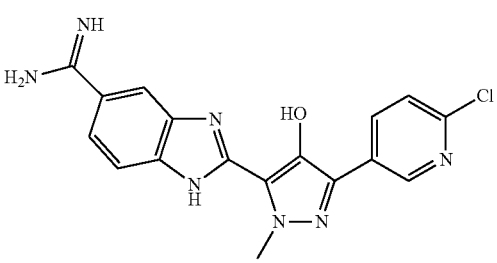
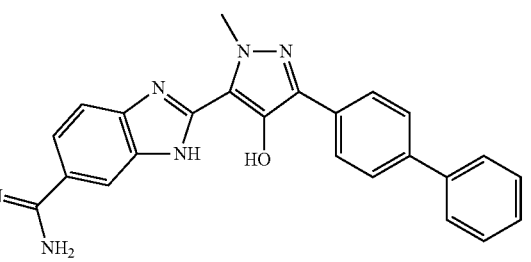
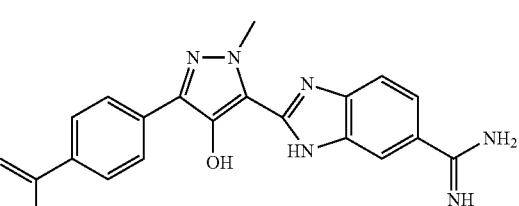
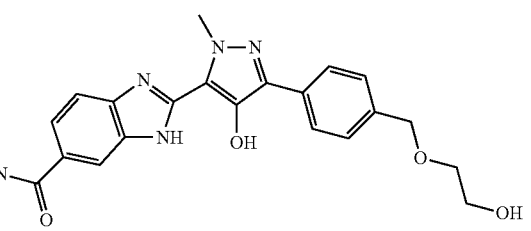
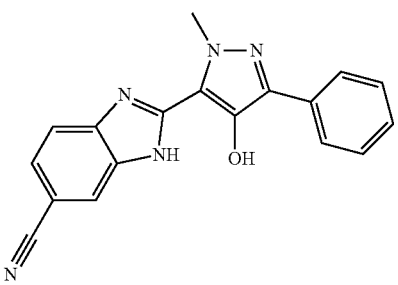
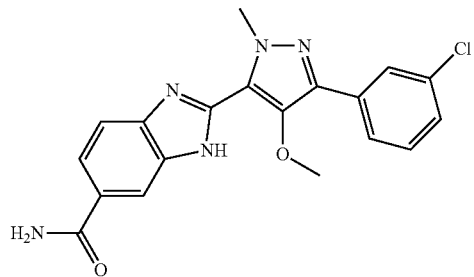

37
-continued
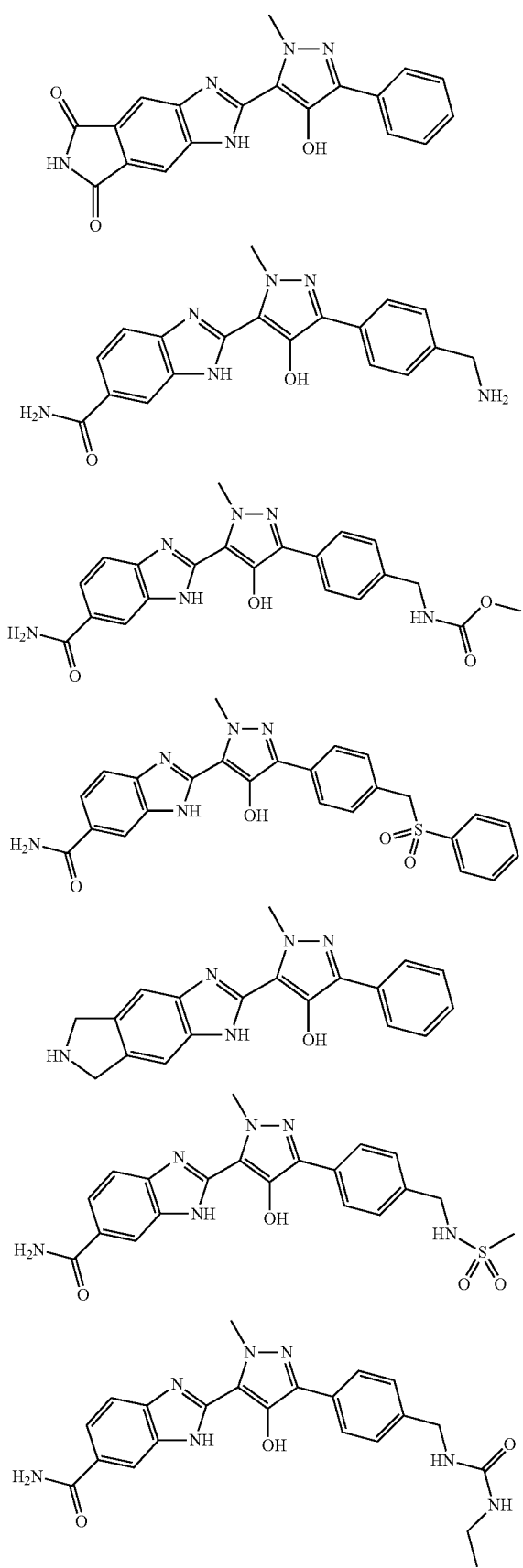
38
-continued
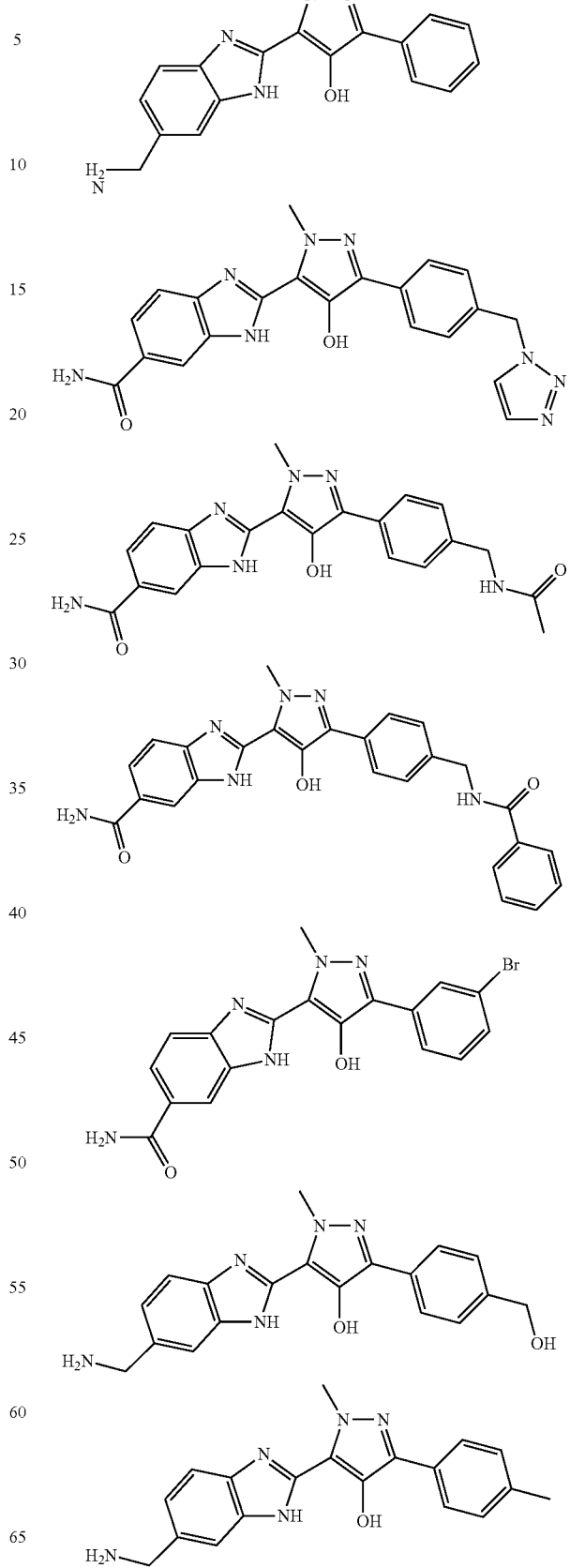

39
-continued
40
-continued
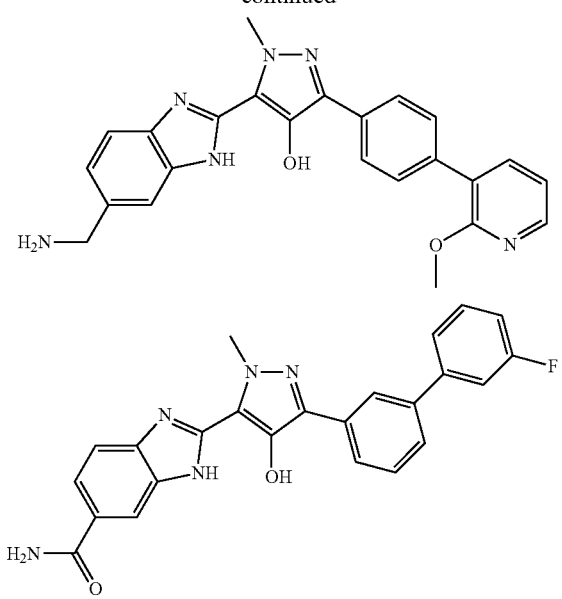
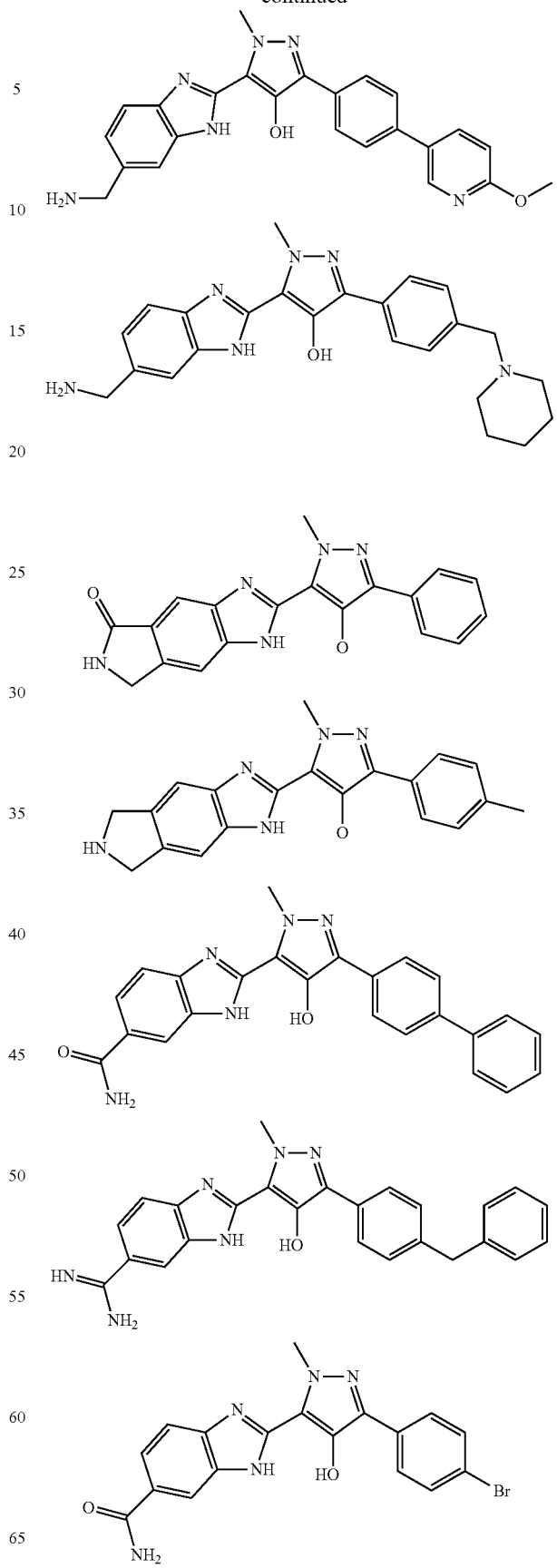

41
-continued
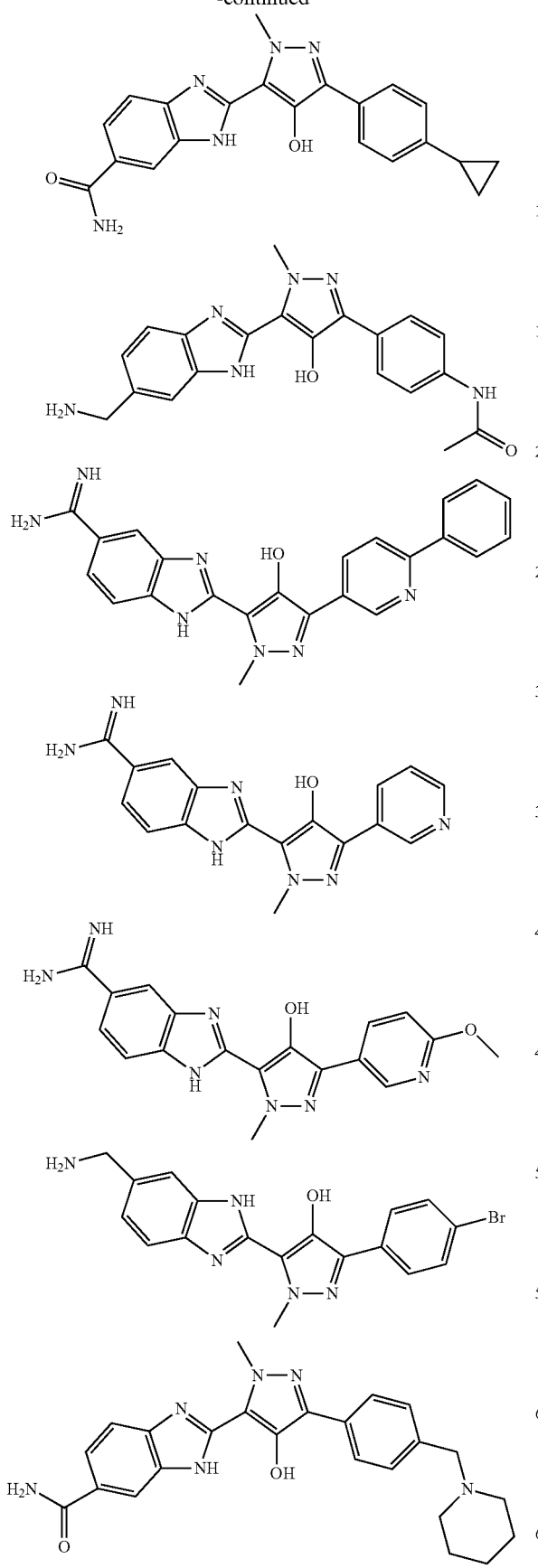
42
-continued
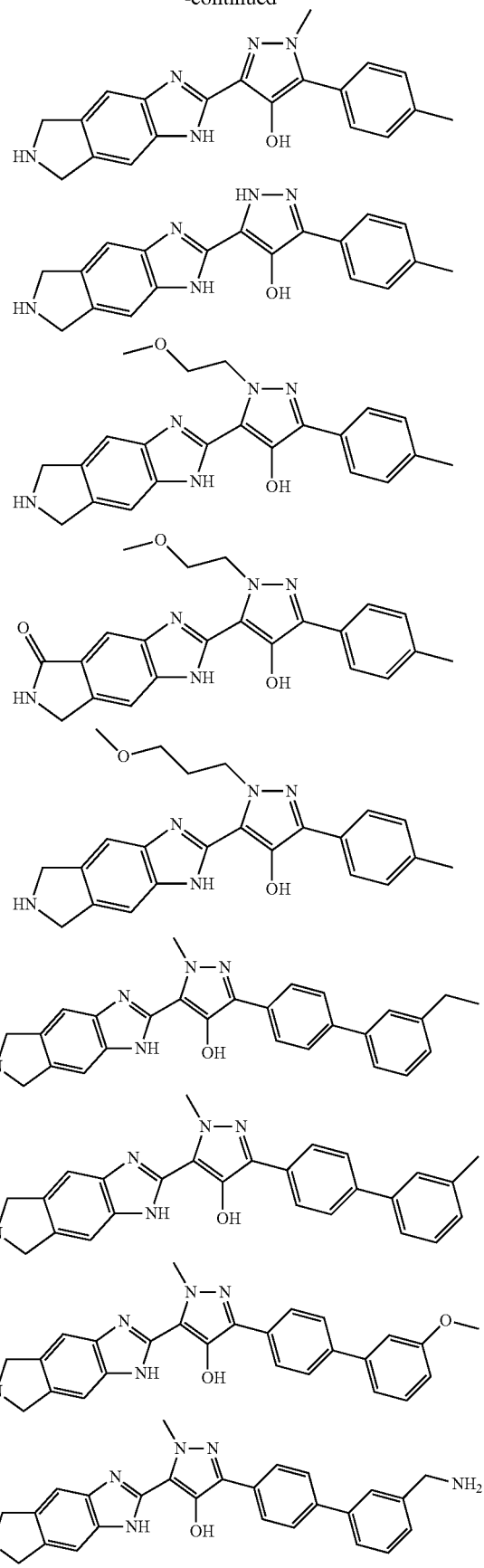

-continued

-continued
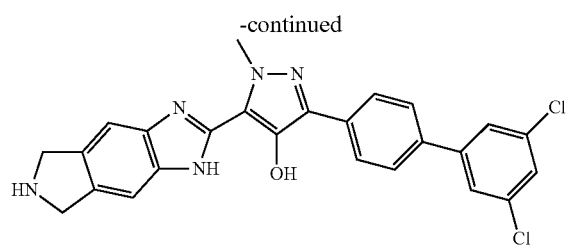
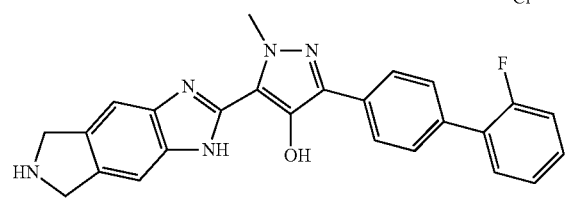
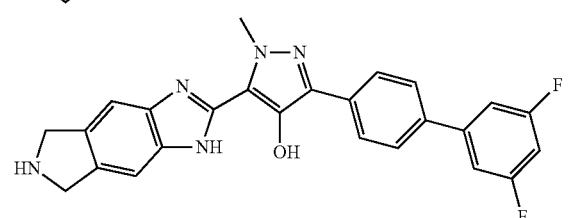
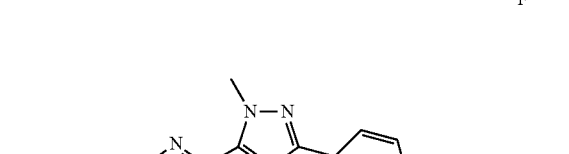
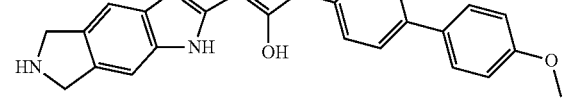
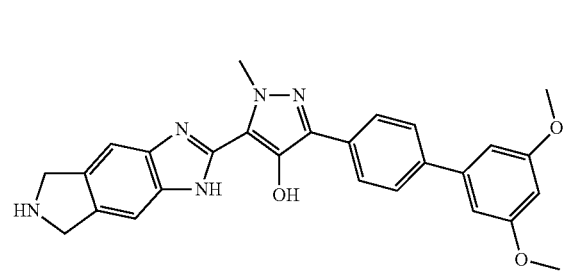
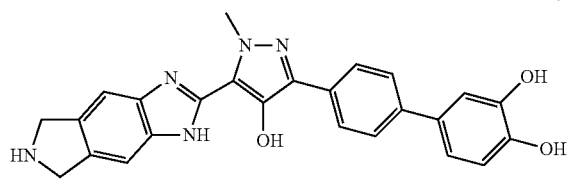
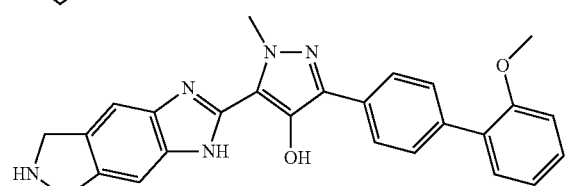
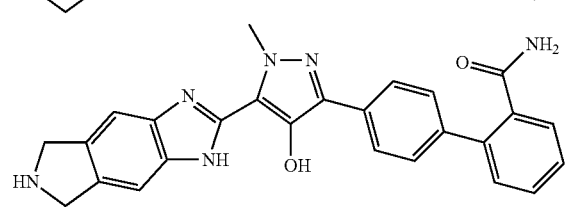
-continued
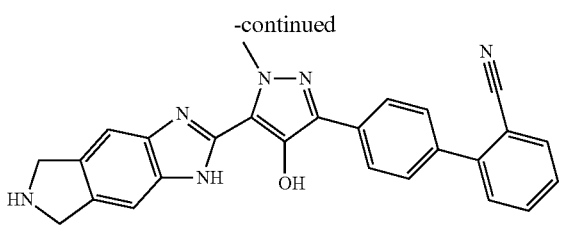
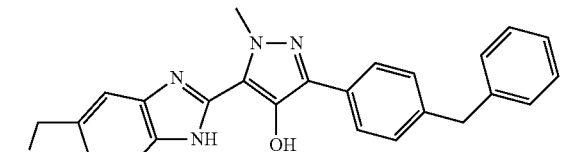
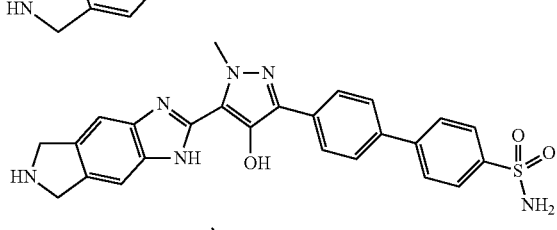
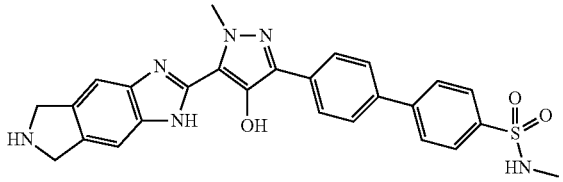
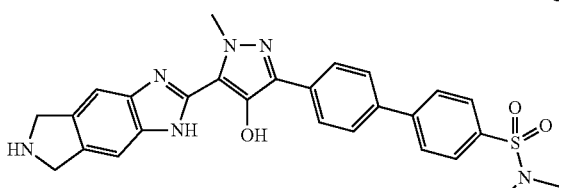
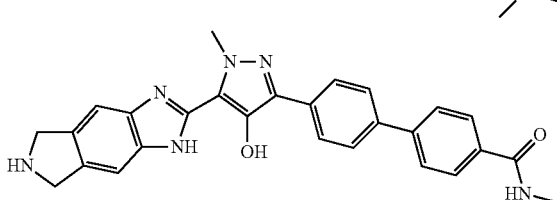
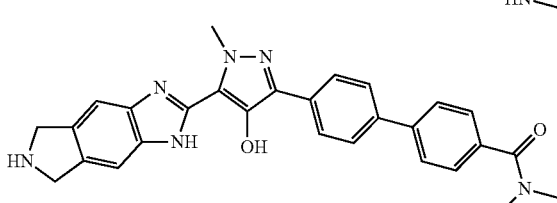
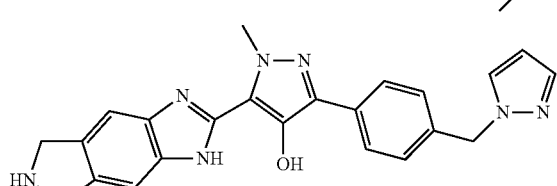
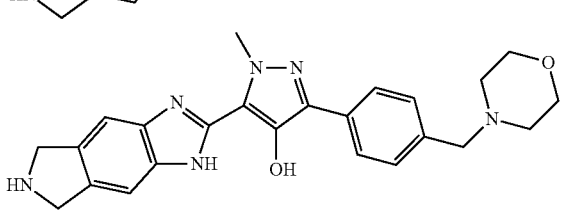

47
-continued
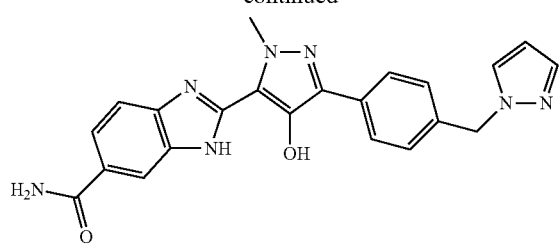
48
-continued
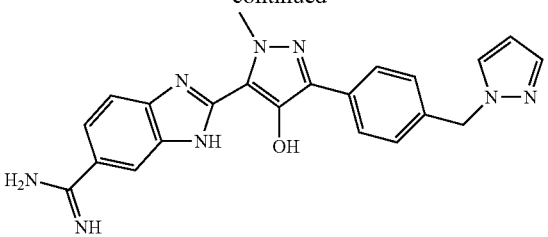
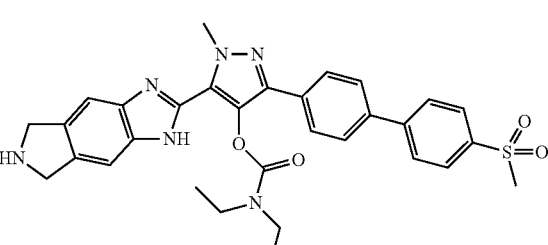
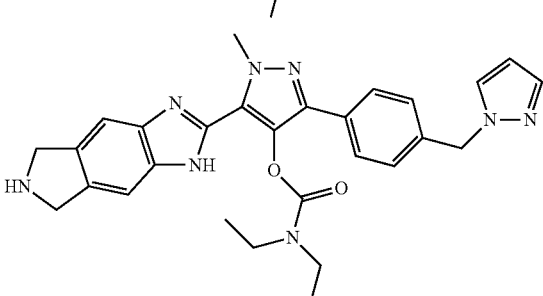
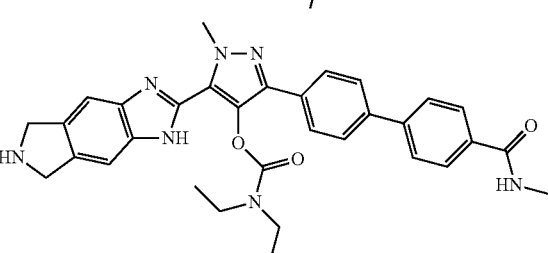
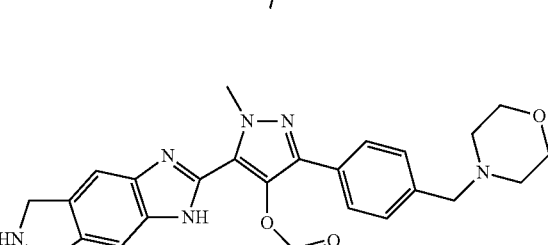
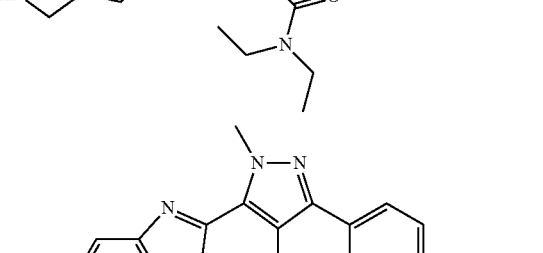
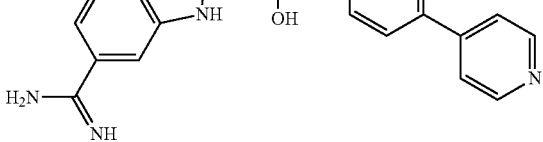

49
-continued
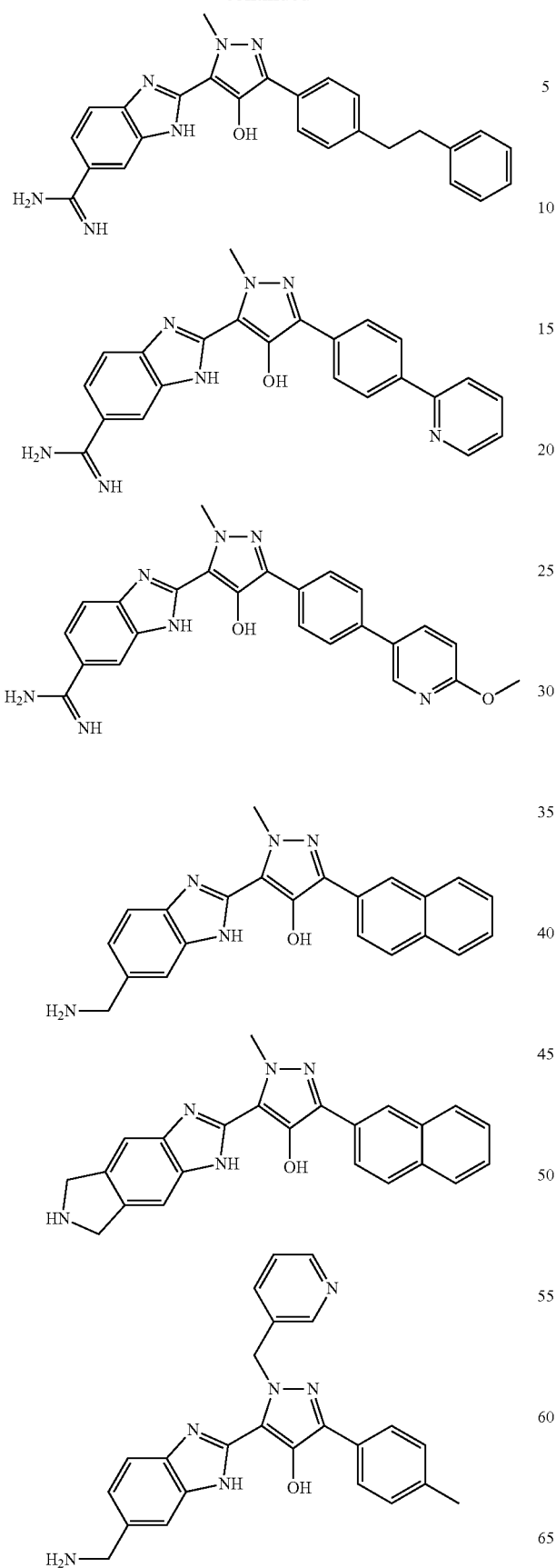
50
-continued
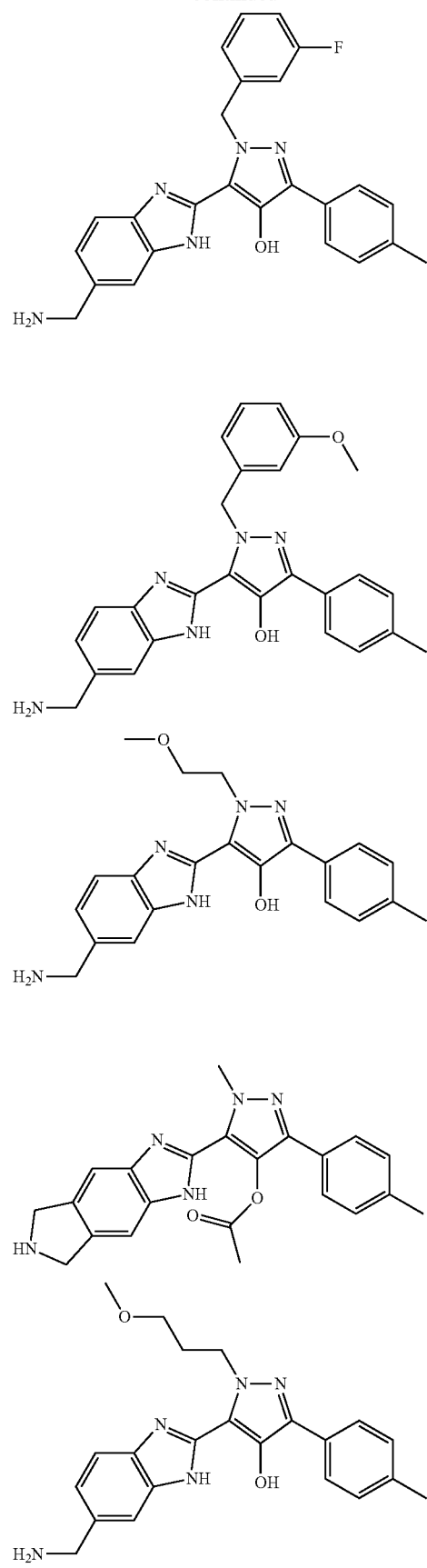

51
-continued
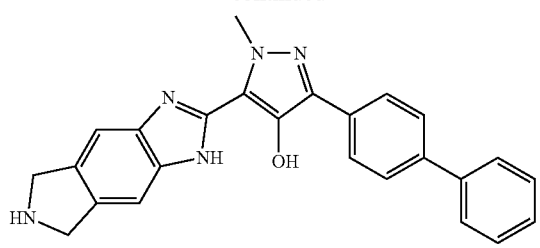
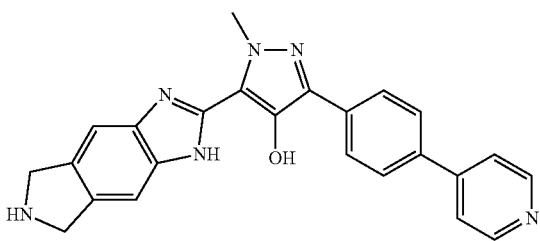
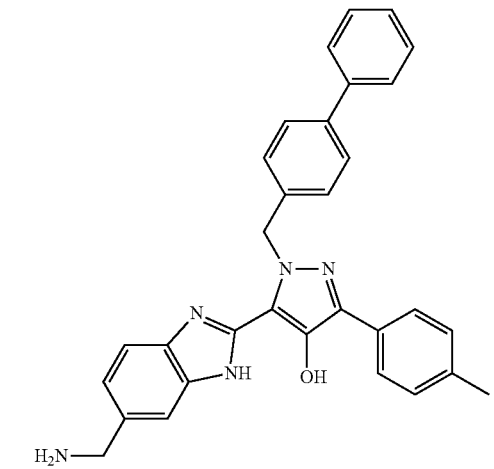
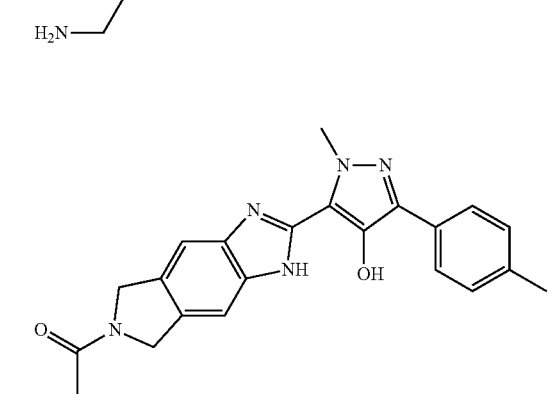
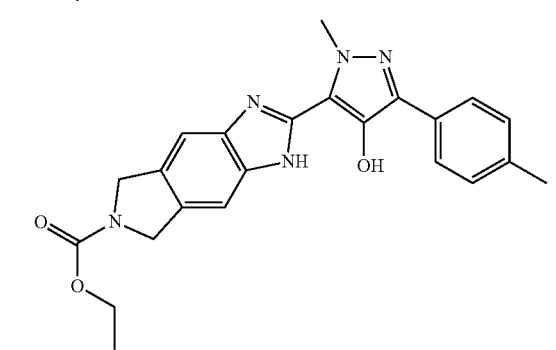
52
-continued
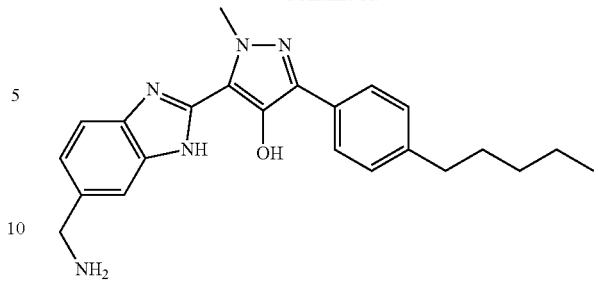
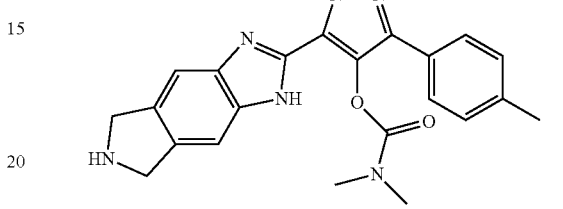
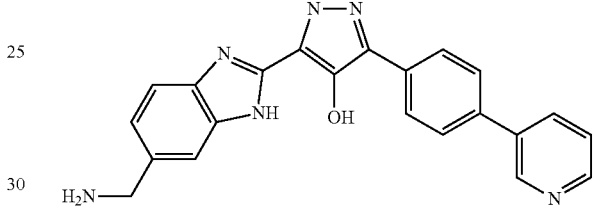
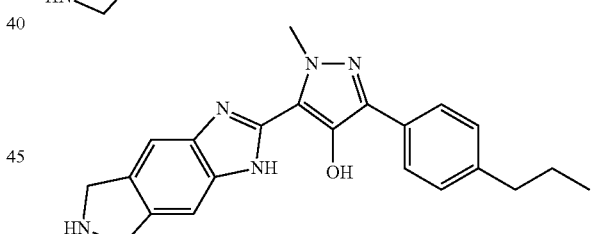
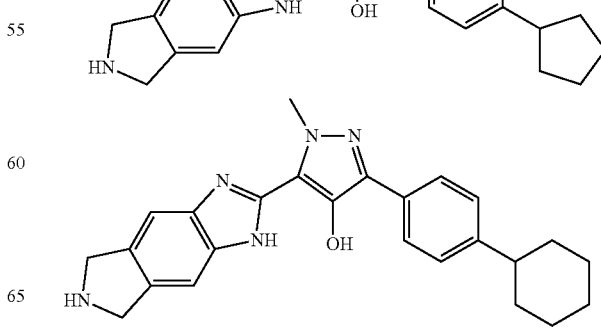

53
-continued
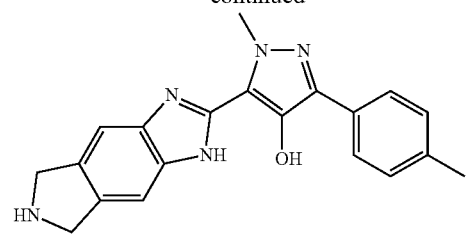
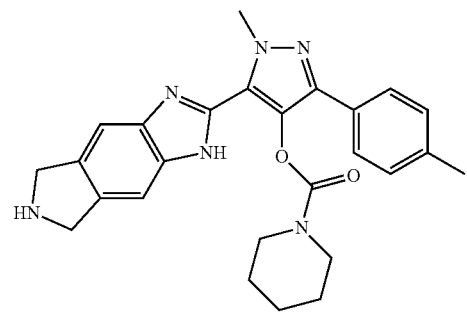
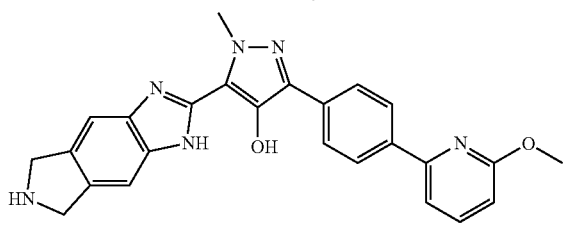
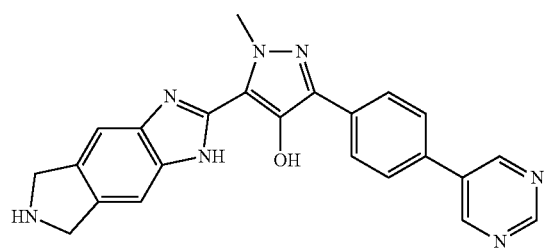
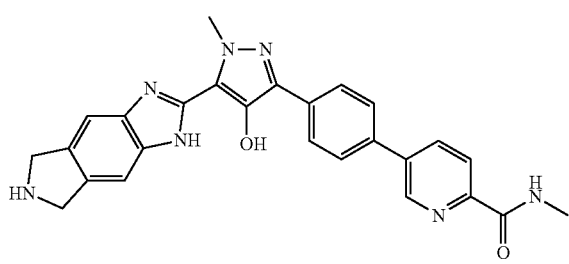
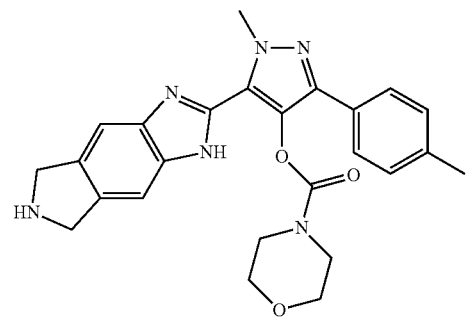
54
-continued
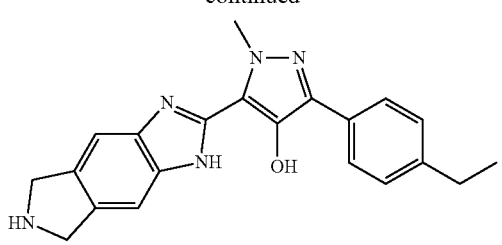
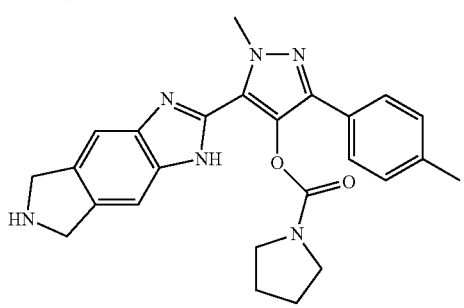
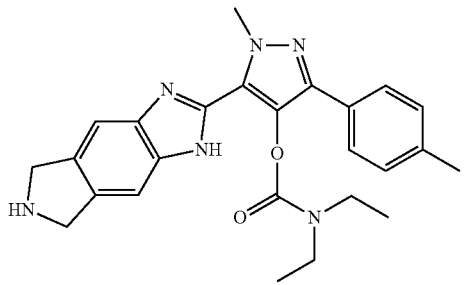
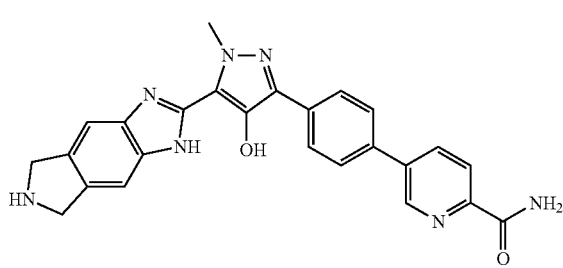
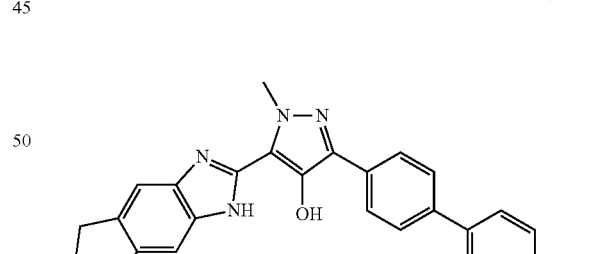
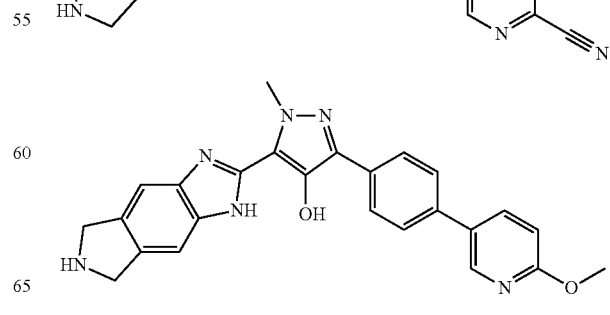

55
-continued
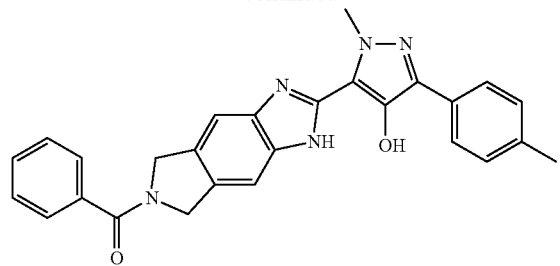
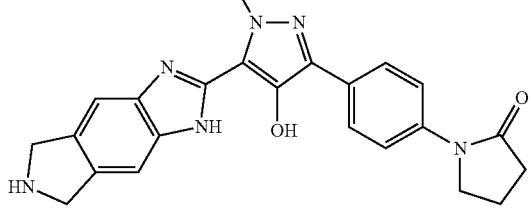
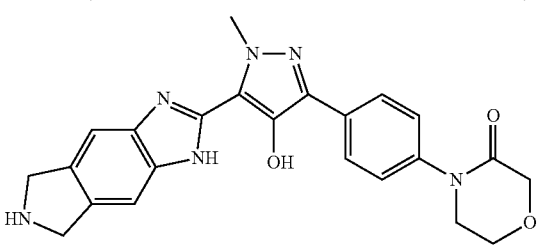
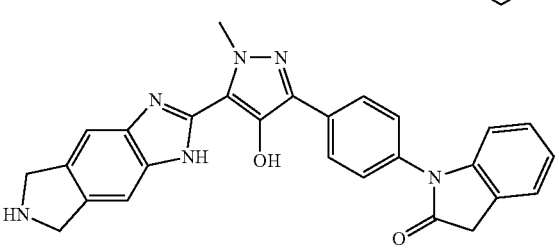
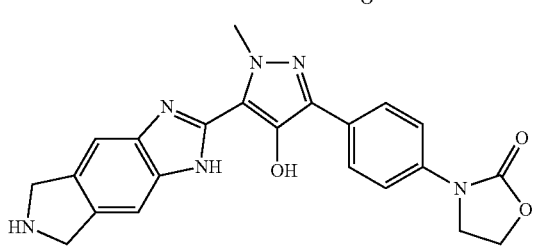
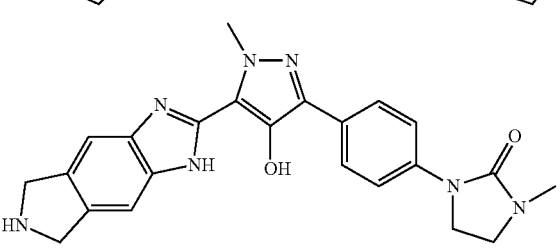
56
-continued
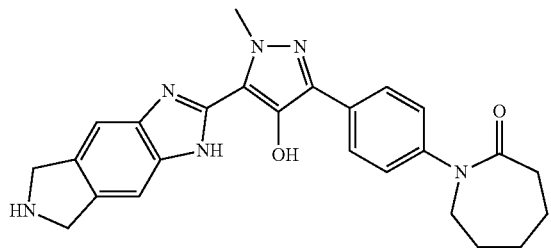

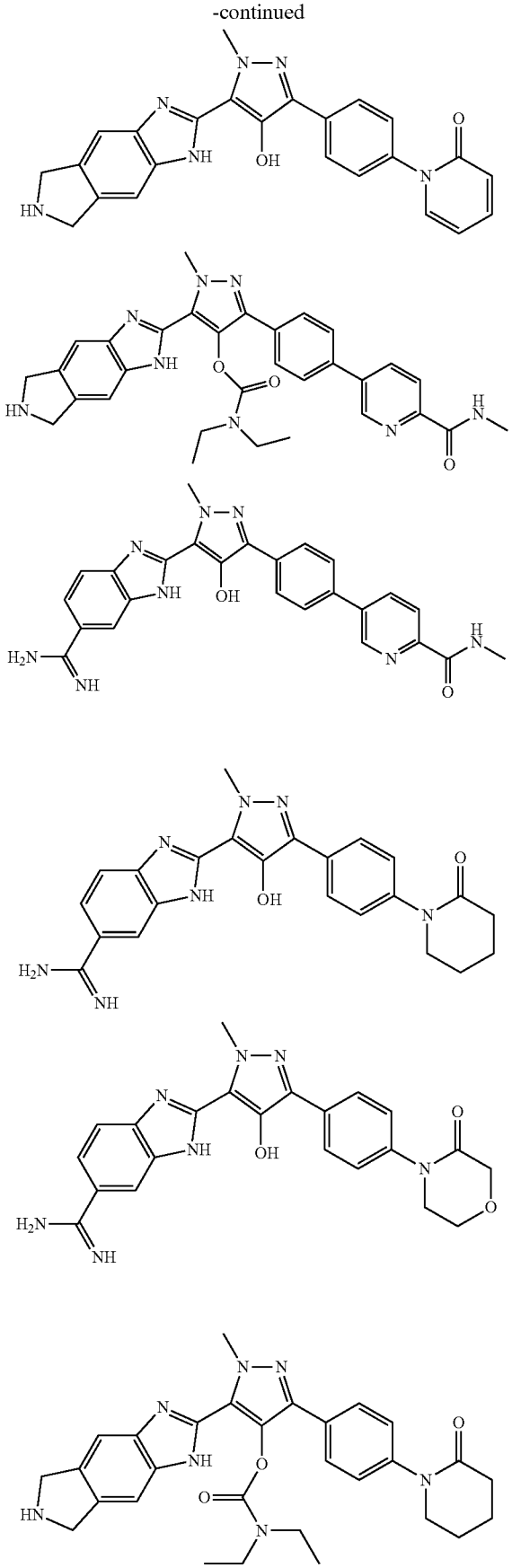
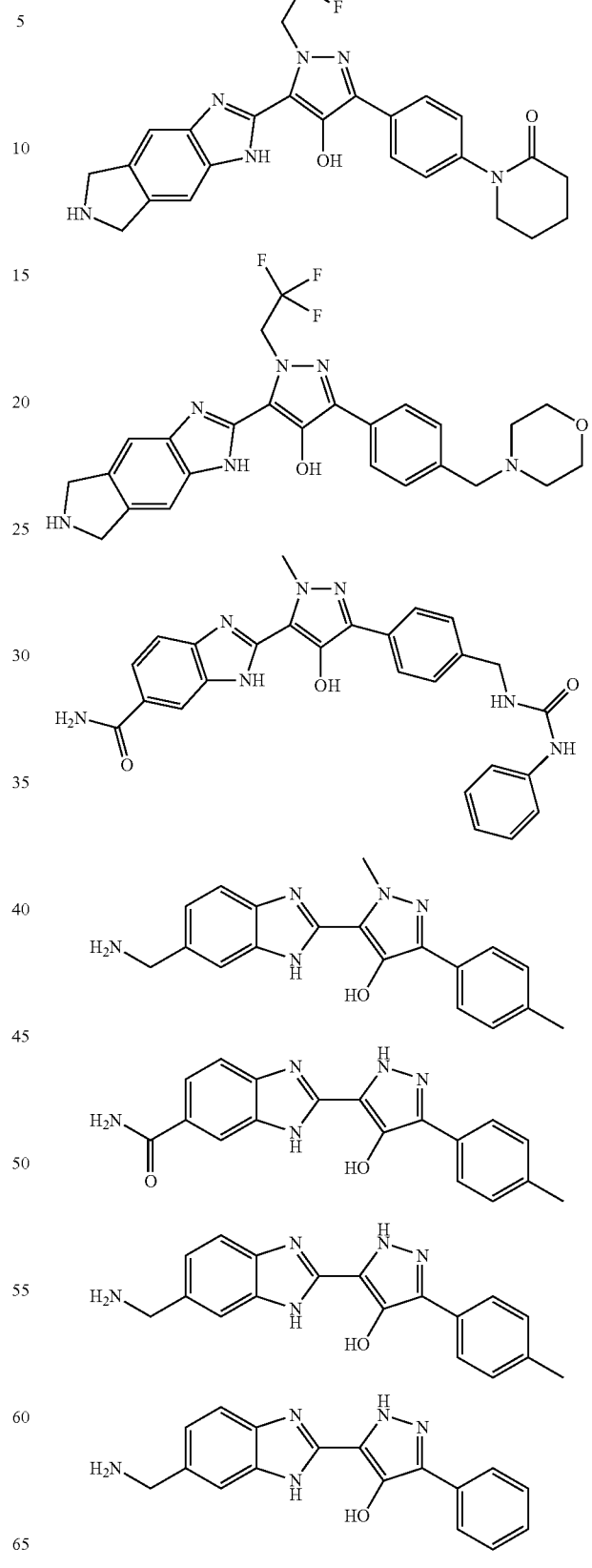

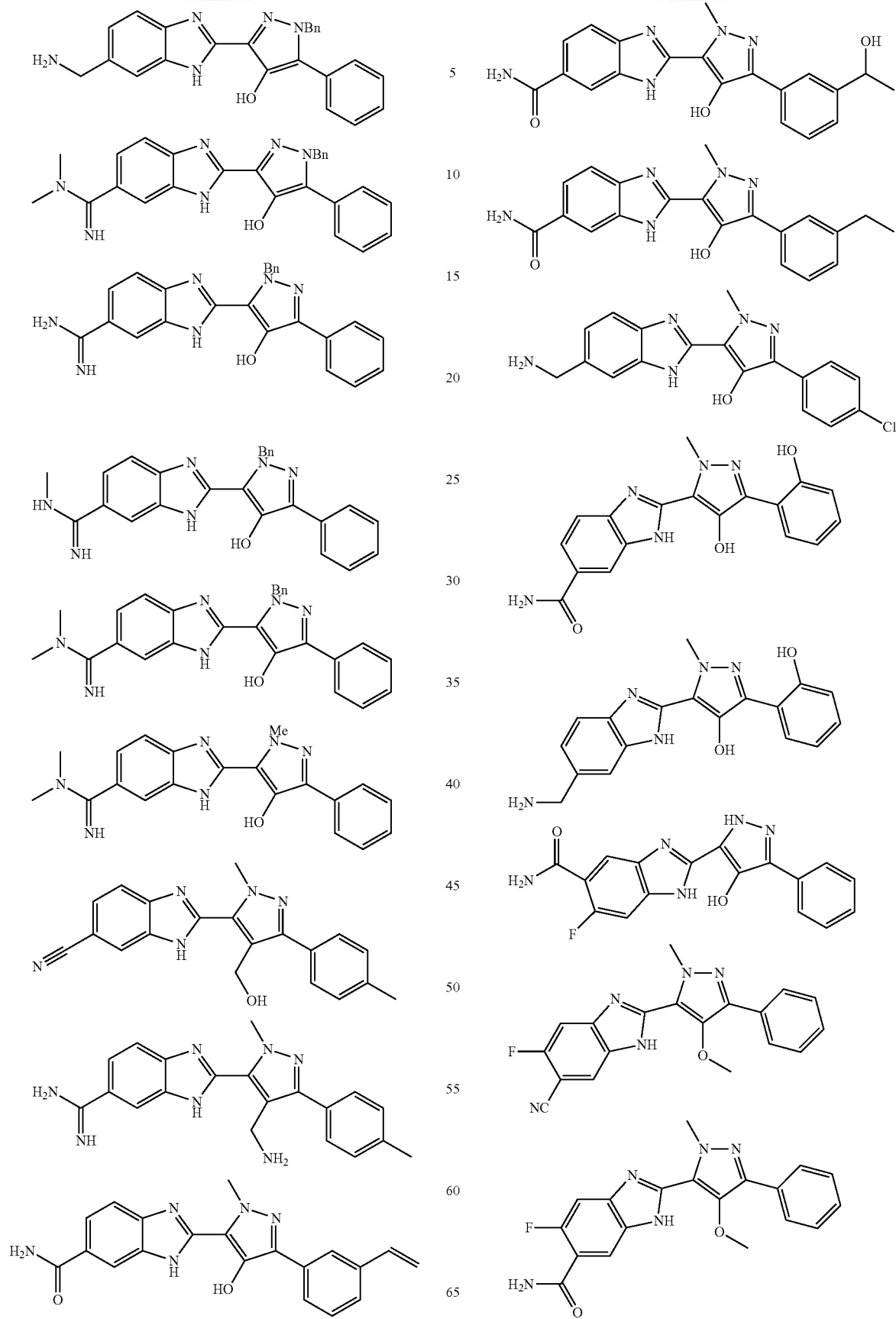

-continued
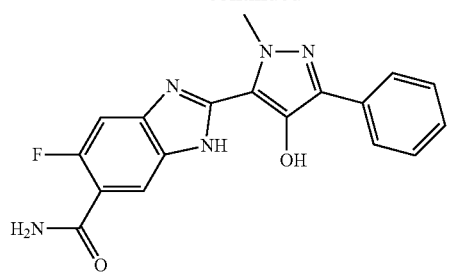
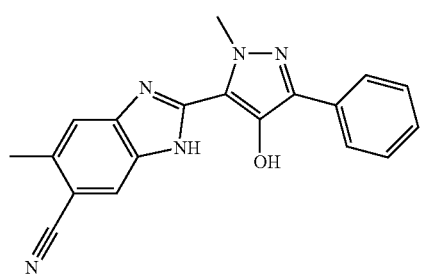
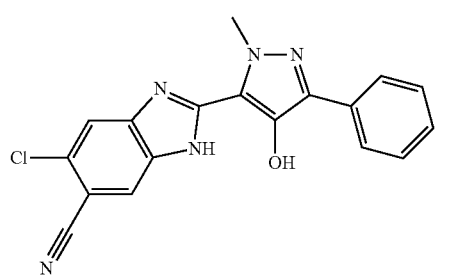
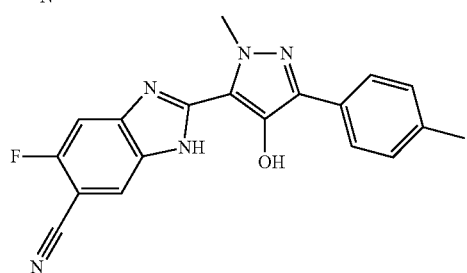
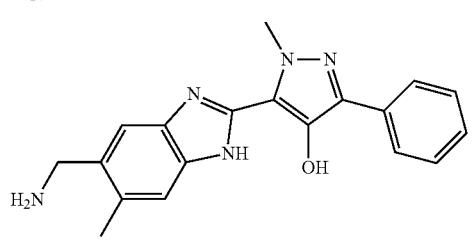
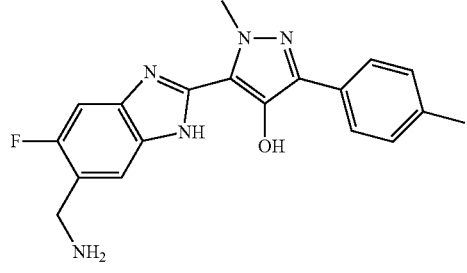
-continued
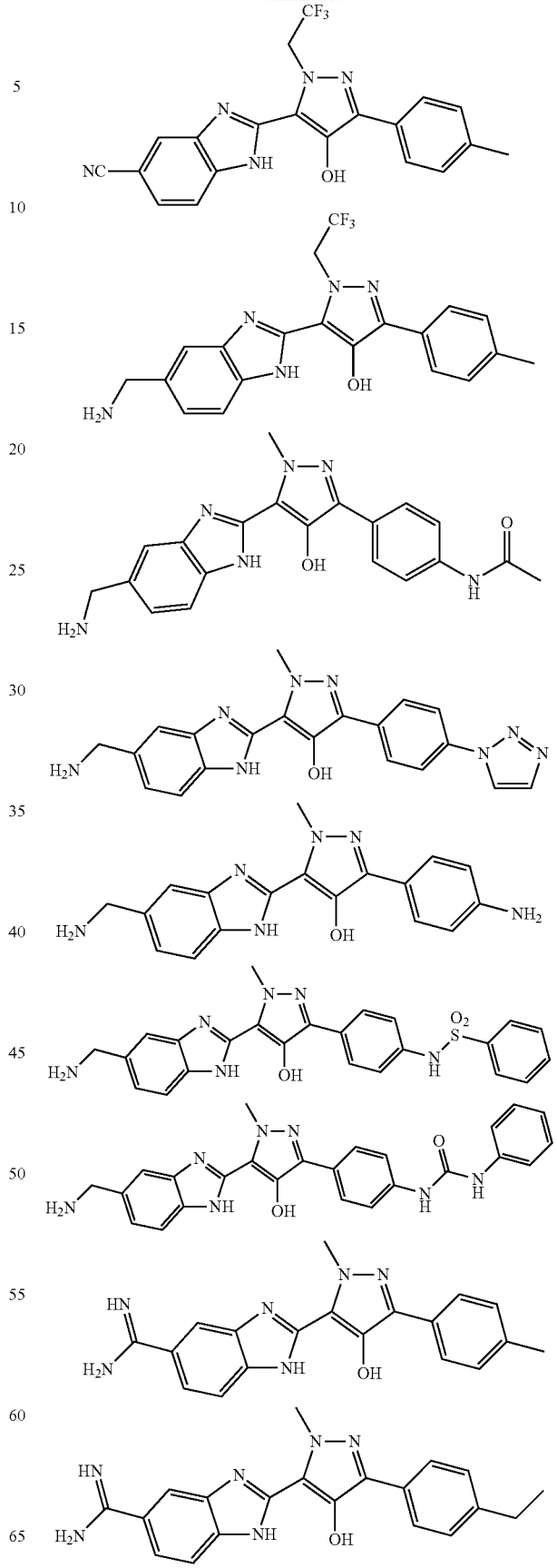

-continued
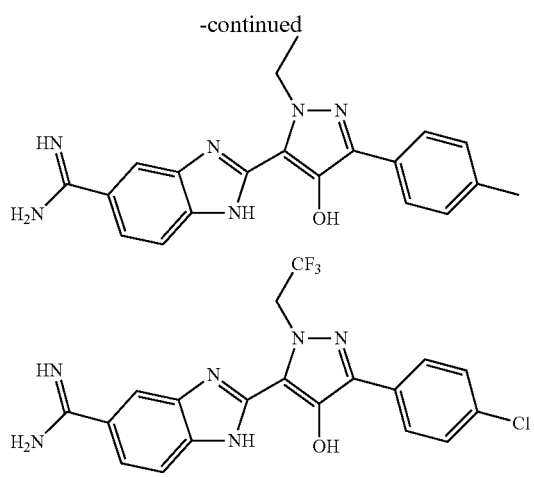
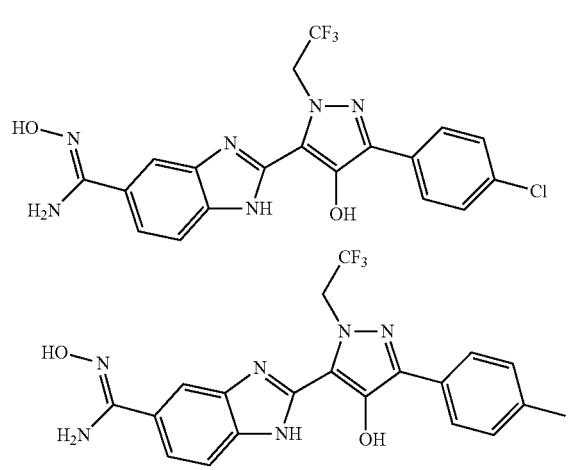
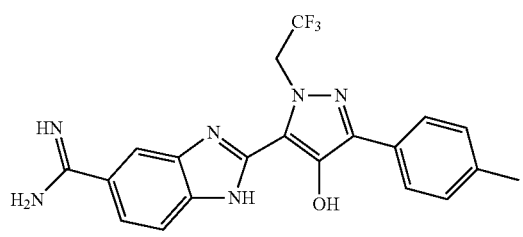
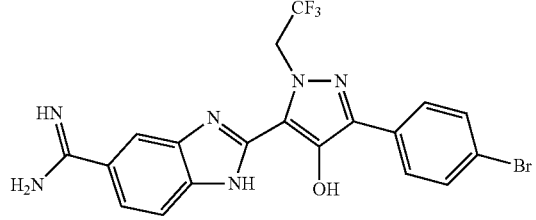
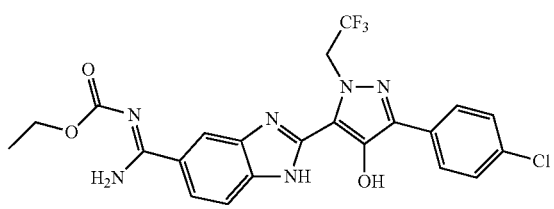
-continued
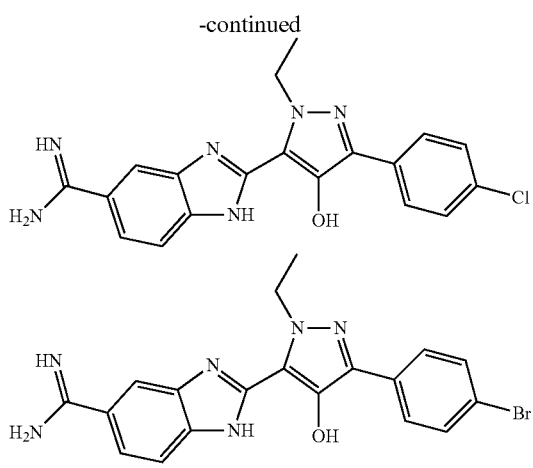
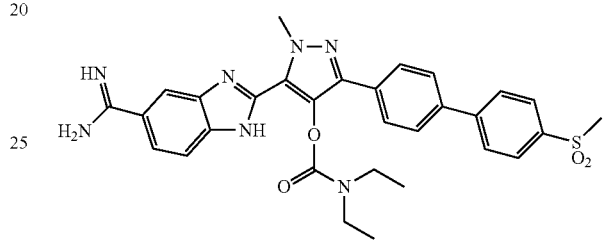
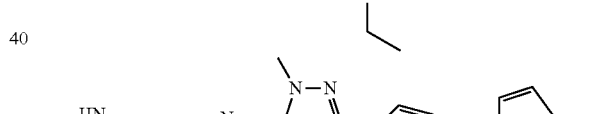
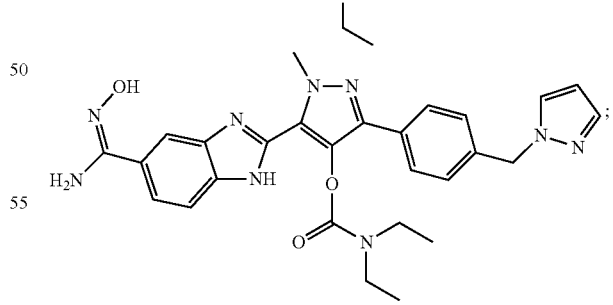
and
or a pharmaceutically acceptable salt, solvate, or ester thereof, wherein Bn=benzyl.
In another embodiment, the compound of formula I is in isolated and purified form.
In another embodiment, the present invention provides a compound of Formula II

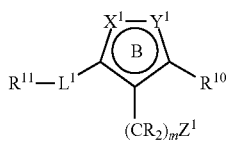

Formula II or a pharmaceutically acceptable salt, solvate or ester thereof; wherein:

ring B comprising ring atoms $X^1$ and $Y^1$ as shown is a heteroaryl ring;

$X^1$ is N or NR;

$Y^1$ is N, NR, O or S;

$L^1$ is selected from the group consisting of —C(=O)N(R)—, —N(R)—C(=O)—, —S(=O)$_2$NR— and —N(R)S(=O)$_2$—;

each R independently in H or alkyl;

$R^{10}$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

$R^{11}$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

m is 0-2;

$Z^1$ is selected from the group consisting of —OR$^4$, —NR$^5$R$^6$, —NR$^5$C(O)R$^6$, —NR$^5$C(O)OR$^6$, —NR$^5$C(O)NR$^5$R$^6$; —NR$^5$S(O)$_2$R$^6$, —NR$^5$S(O)$_2$N(R$^6$)$_2$ $R^4$ is H or alkyl; and each $R^5$ and $R^6$ is independently selected from the group consisting of H and alkyl;

with the proviso that: (i) when $R^{11}$ is phenyl, said phenyl is unsubstituted or substituted by groups other than —(C=NR)NR$_2$, and (ii) when $L^1$ is —N(R)C(=O)— which is linked to the B ring via the nitrogen atom, $R^{11}$ is other than unsubstituted phenyl.

In another embodiment, in formula II, $X^1$ is N and $Y^1$ is NR.

In another embodiment, in formula II, $X^1$ is NR and $Y^1$ is N.

In another embodiment, in formula II, $L^1$ is —N(R)C(=O)— or —C(=O)N(R)—.

In another embodiment, in formula II, $L^1$ is —N(R)C(=O)—.

In another embodiment, in formula II, $L^1$ is —NHC(=O)—.

In another embodiment, in formula II, $R^{10}$ is aryl.

In another embodiment, in formula II, $R^{10}$ is aryl, wherein said $R^{10}$ aryl is phenyl which is optionally substituted with one to four substituents selected from the group consisting of cyano, halo, alkyl, hydroxyalkyl, alkoxyalkyl, haloalkyl, alkoxy, haloalkoxy, and —C(O)NR$^5$R$^6$.

In another embodiment, in formula II, $R^{10}$ is aryl, wherein said $R^{10}$ aryl is phenyl which is optionally substituted with one to four substituents selected from the group consisting of chloro and methoxy.

In another embodiment, in formula II, $X^1$ is N and $Y^1$ is NR, wherein $Y^1$ is selected from the group consisting of NH, and N(benzyl).

In another embodiment, in formula II, $X^1$ is NR and $Y^1$ is N, wherein $X^1$ is selected from the group consisting of NH, N(methyl), N(ethyl), N(benzyl), and N(p-methoxybenzyl).

In another embodiment, in formula II, m is 0.

In another embodiment, in formula II, $Z^1$ is OR$^4$.

In another embodiment, in formula II, $Z^1$ is OR$^4$, wherein $Z^1$ is selected from the group consisting of OH, methoxy, ethoxy, 4-methoxybenzyloxy, and benzyloxy.

In another embodiment, in formula II, $R^{11}$ is aryl.

In another embodiment, in formula II, $R^{11}$ is aryl, wherein said $R^{11}$ aryl is phenyl which is optionally substituted with one to four substituents selected independently from the group consisting of cyano, —OR$^4$, —NR$^5$R$^6$, —NR$^5$C(O)R$^6$, —C(=O)NR$^5$R$^6$, —NR$^5$C(=O)aryl.

In another embodiment, in formula II, $R^{11}$ is aryl, wherein said $R^{11}$ aryl is phenyl which is optionally substituted with one to four substituents selected independently from the group consisting of cyano, hydroxy, methoxy, —NH$_2$, —NHC(=O)CF$_3$, —C(=O)NH$_2$, —NHC(=O)(pyrazolyl substituted with phenyl, benzyl and benzyloxy moieties), and —NHC(=O)CH$_3$.

In another embodiment, the compound of Formula II is a compound of Formula IIA:

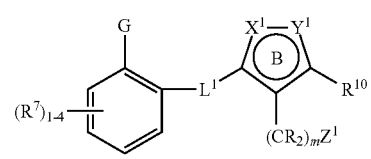

Formula IIA wherein:

ring B comprising ring atoms $X^1$ and $Y^1$ as shown is a heteroaryl ring;

$X^1$ is N or NR;

$Y^1$ is N, NR, O or S;

$L^1$ is selected from the group consisting of —C(=O)N(R)—, —N(R)—C(=O)—, —S(=O)$_2$NR— and —N(R)S(=O)$_2$—;

G is OR or NRR';

each R independently in H or alkyl;

R' is selected from the group consisting of H, alkyl, —C(=O)alkyl, —C(=O)haloalkyl, and —C(=O)heteroaryl;

each $R^7$ independently is selected from the group consisting of hydrogen, halo, alkyl, haloalkyl, alkoxy, haloalkoxy, cyano, hydroxy, —C(O)NR$^5$R$^6$, —C(=NR$^5$)N(R$^6$)$_2$ and —C(O)OR$^4$;

$R^{10}$ is selected from the group consisting of cycloalkyl, cycloalkenyl, heterocyclyl, heterocyclenyl, aryl, and heteroaryl, wherein when each of said cycloalkyl, cycloalkenyl, heterocyclyl, heterocyclenyl, aryl or heteroaryl ring contains substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

m is 0-2;

$Z^1$ is selected from the group consisting of —OR$^4$, —NR$^5$R$^6$, —NR$^5$C(O)R$^6$, —NR$^5$C(O)OR$^6$, —NR$^5$C(O)NR$^5$R$^6$; —NR$^5$S(O)$_2$R$^6$, —NR$^5$S(O)$_2$N(R$^6$)$_2$ $R^4$ is H or alkyl; and each of $R^5$ and $R^6$ is independently selected from the group consisting of H and alkyl.

In another embodiment, in formula IIA, L¹ is —N(R)C(=O)— which is linked to the B ring via the —C(=O)— of L¹.
In another embodiment, in formula IIA, each R⁷ independently is selected from the group consisting of methoxy, cyano, and —C(=O)NH₂.
In another embodiment, the compound of formula IIA is selected from the group consisting of
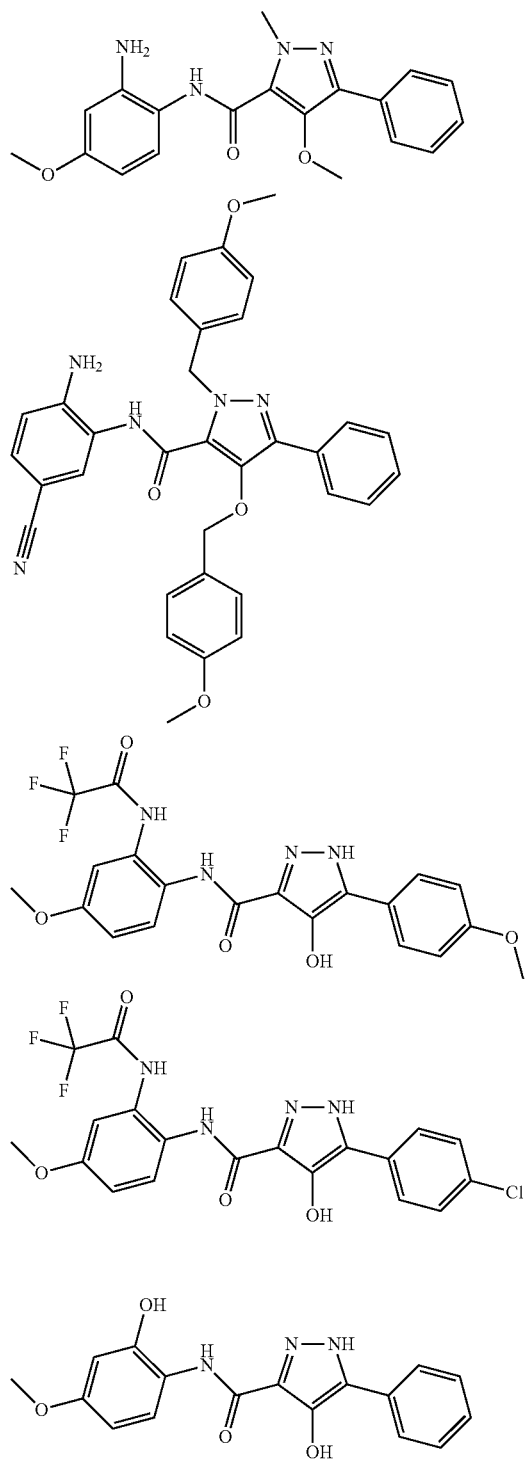
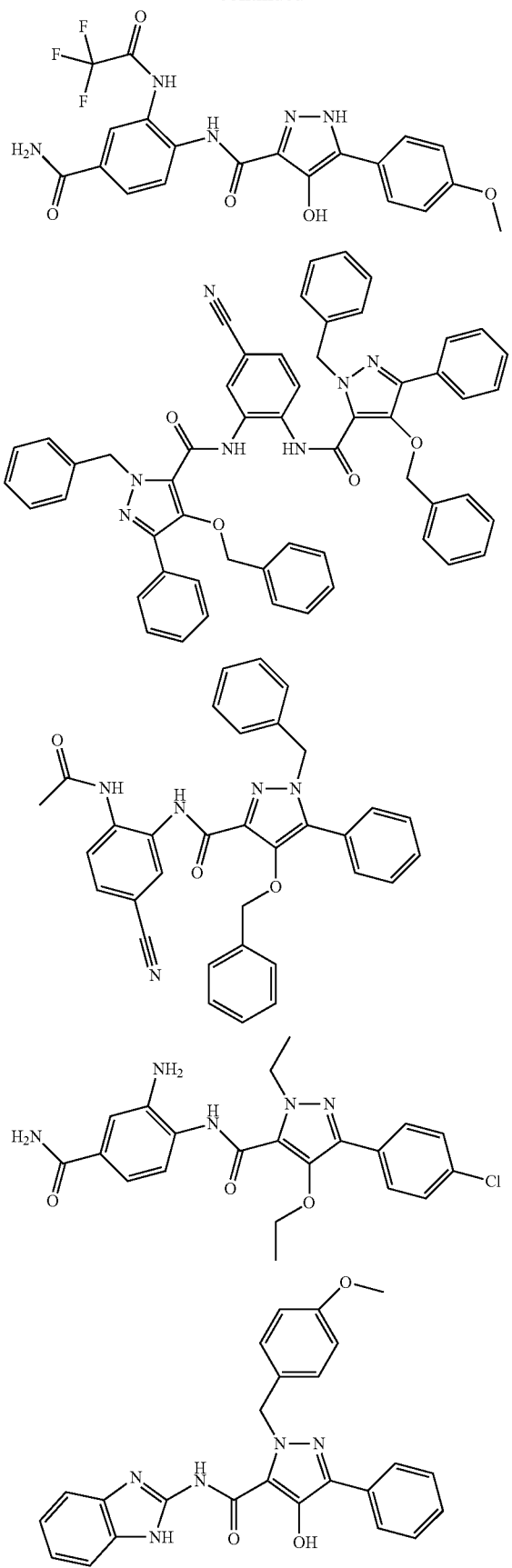
-continued

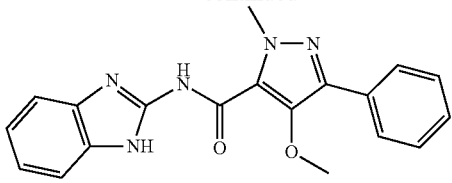

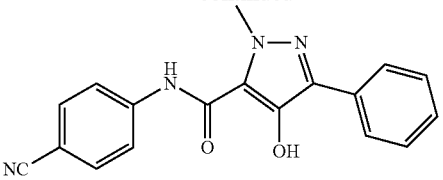
and

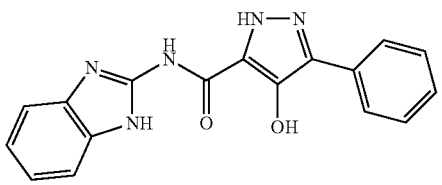

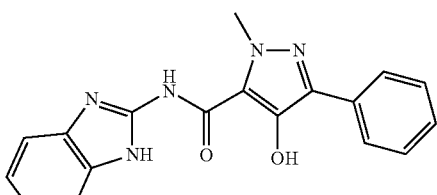

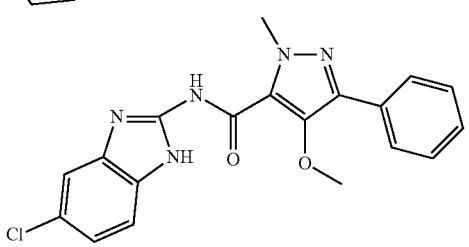

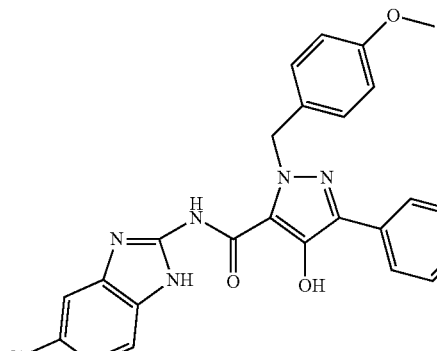

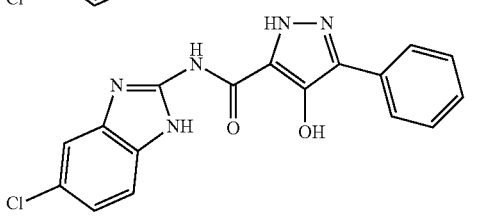

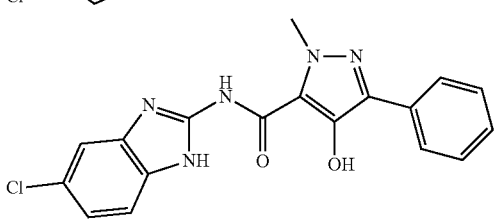
;

or a pharmaceutically acceptable salt, solvate, or ester thereof.

In another embodiment, the present invention provides a compound of Formula III

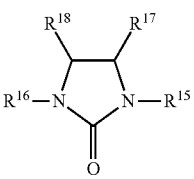

Formula III or a pharmaceutically acceptable salt, solvate, or ester thereof;

wherein:

$R^{15}$ is aryl, wherein when said aryl contains two substituents on adjacent carbon atoms, said substituents may optionally be taken together with the carbon atoms to which they are attached to form a five to six membered cycloalkyl, clycloalkenyl, heterocyclyl, heterocyclenyl, aryl, or heteroaryl;

$R^{16}$ is selected from the group consisting of a five- or six-membered heteroaryl which is fused to a benzene ring, a quinolin-2-one, and a phenyl which is fused to a five- or six-membered heteroaryl; with the proviso that when $R^{16}$ is phenyl fused to a pyridine ring, then $R^{15}$ is an unsubstituted aryl; and each of $R^{17}$ and $R^{18}$ independently is H or alkyl.

In another embodiment, in formula III, $R^{17}$ and $R^{18}$ are each H.

In another embodiment, in formula III, $R^{15}$ aryl is phenyl which is unsubstituted or substituted with one to four substituents selected from the group consisting of cyano, halo, alkyl, hydroxyalkyl, alkoxyalkyl, haloalkyl, alkoxy, haloalkoxy, and —C(O)NR$^5$R$^6$ wherein R$^5$ and R$^6$ independently are H or alkyl.

In another embodiment, in formula III, $R^{15}$ aryl is unsubstituted phenyl.

In another embodiment, in formula III, $R^{16}$ is a benzimidazolyl.

In another embodiment, in formula III, the compound of Formula III is a compound of Formula IIIA:

Formula IIIA

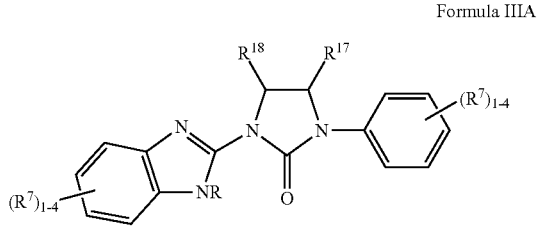

or a pharmaceutically acceptable salt, solvate or ester thereof; wherein:

R is H or alkyl;

each $R^7$ is independently selected from the group consisting of hydrogen, halo, alkyl, haloalkyl, alkoxy, haloalkoxy, cyano, hydroxy, —C(O)NR$^5$R$^6$, —C(=NR$^5$)N(R$^6$)$_2$ and —C(O)OR$^4$, wherein $R^4$ is H or alkyl, and $R^5$ and $R^6$ are each independently H or alkyl; and each of $R^{17}$ and $R^{18}$ independently is H or alkyl.

In another embodiment, in formula IIIA, each $R^7$ is independently selected from the group consisting of hydrogen, chloro, cyano, fluoro, trifluoromethyl, methoxy, —C(=O)NH$_2$, —C(=O)OCH$_2$CH$_3$, and —C(=NH)NH$_2$.

In another embodiment, the compound of Formula III is a compound of Formula IIIB:

Formula IIIB

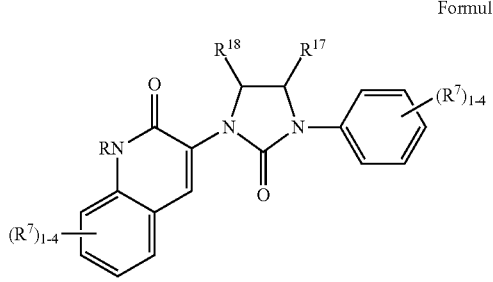

or a pharmaceutically acceptable salt, solvate or ester thereof; wherein:

R is H or alkyl;

each $R^7$ is independently selected from the group consisting of hydrogen, halo, alkyl, haloalkyl, alkoxy, haloalkoxy, cyano, hydroxy, —C(O)NR$^5$R$^6$, —C(=NR$^5$)N(R$^6$)$_2$ and —C(O)OR$^4$, wherein $R^4$ is H or alkyl, and $R^5$ and $R^6$ are each independently H or alkyl; and each of $R^{17}$ and $R^{18}$ independently is H or alkyl.

In another embodiment, the compound of Formula III is a compound of Formula IIIC:

Formula IIIC

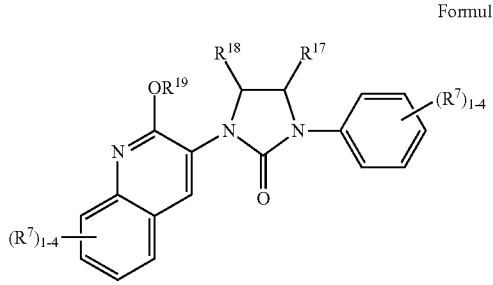

or a pharmaceutically acceptable salt, solvate or ester thereof; wherein:

R is H or alkyl;

each $R^7$ is independently selected from the group consisting of hydrogen, halo, alkyl, haloalkyl, alkoxy, haloalkoxy, cyano, hydroxy, —C(O)NR$^5$R$^6$, —C(=NR$^5$)N(R$^6$)$_2$ and —C(O)OR$^4$, wherein $R^4$ is H or alkyl, and $R^5$ and $R^6$ are each independently H or alkyl;

each of $R^{17}$ and $R^{18}$ independently is H or alkyl; and $R^{19}$ is alkyl.

In another embodiment, the compound of Formula III is a compound of Formula IIID:

Formula IIID

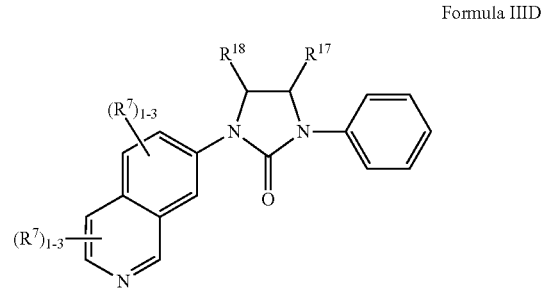

or a pharmaceutically acceptable salt, solvate or ester thereof; wherein:

each $R^7$ is independently selected from the group consisting of hydrogen, halo, alkyl, haloalkyl, alkoxy, haloalkoxy, cyano, hydroxy, —C(O)NR$^5$R$^6$, —C(=NR$^5$)N(R$^6$)$_2$ and —C(O)OR$^4$, wherein $R^4$ is H or alkyl, and $R^5$ and $R^6$ are each independently H or alkyl; and each of $R^{17}$ and $R^{18}$ independently is H or alkyl.

In another embodiment, the compound of formula III is selected from the group consisting of:

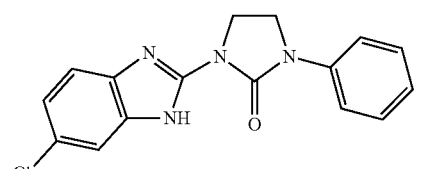

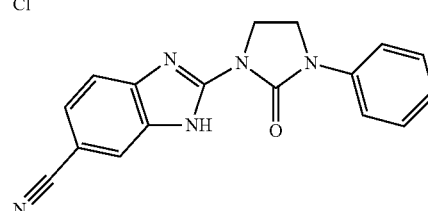

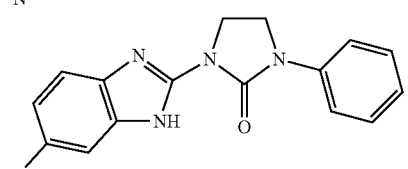

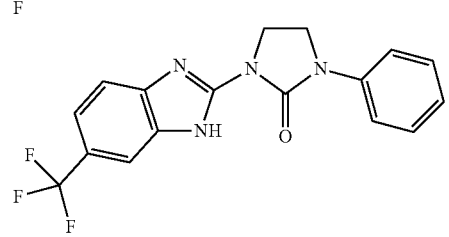

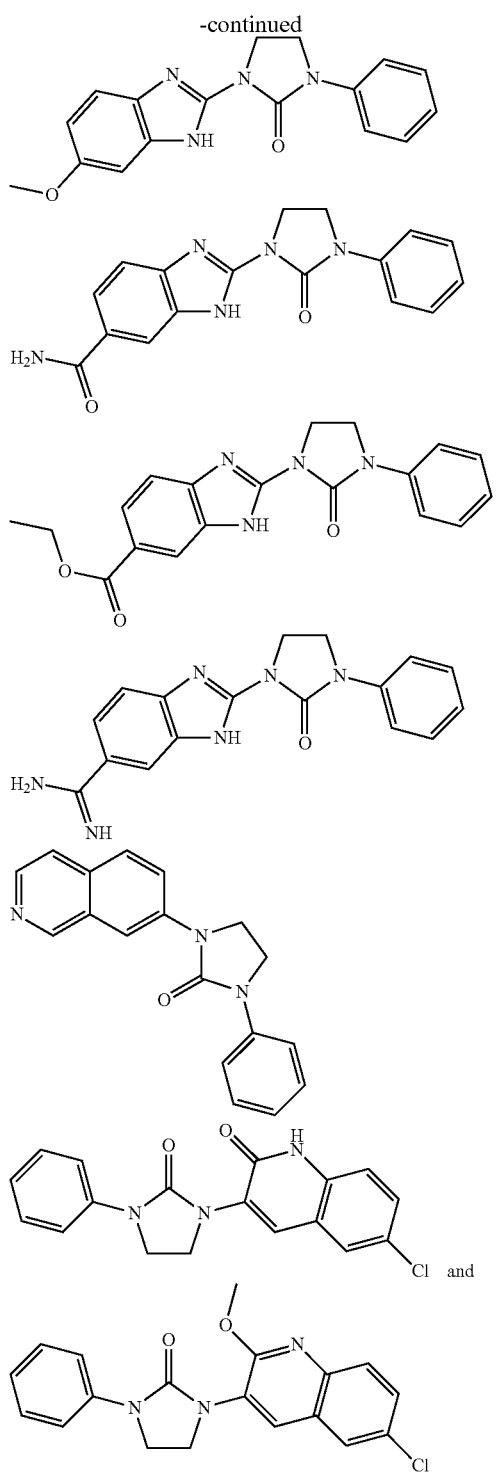

or a pharmaceutically acceptable salt, solvate or ester thereof.

Methods for Making the Compounds of Present Invention

General Methods
Abbreviations Used
μW microwave
10% Pd(C) 10% palladium on carbon
Ac acetyl
AcOH acetic acid
Ag$_2$CO$_3$ silver carbonate
BBr$_3$ borontribromide
BF$_3$.OEt$_2$ borontrifluoride etherate
BH$_3$.SMe$_2$ borane dimethylsulfide complex
n-BuOH n-butanol
t-BuOH tert-butanol
t-BuOK potassium tert-butoxide
CH$_2$Cl$_2$ or DCM methylene chloride
Cs$_2$CO$_3$ cesium carbonate
DIPEA N,N-diisopropylethylamine
DME 1,2-dimethoxyethane
DMAP dimethylaminopyridine
DMF N,N-dimethylfomamide
DMSO dimethylsulfoxide
DPPA diphenylphosphonyl azide
EDCI 1-ethyl-3-(3-dimethylaminopropyl)carbodiimide
Et ethyl
Et$_3$N triethylamine
EtOAc ethyl acetate
EtOH ethanol
H$_2$O water
HATU 2-(1H-7-azabenzotriazol-1-yl)-1,1,3,3-tetramethyluronium hexafluorophosphate
HCl hydrogen chloride
HPLC high performance liquid chromatography
hr or h hour
KOH potassium hydroxide
LiOH lithium hydroxide
Me methyl
MeCN acetonitrile
MeOH methanol
MeI iodomethane
MgSO$_4$ magnesium sulfate
NaHCO$_3$ sodium bicarbonate
NaH sodium hydride
NaN$_3$ sodium azide
NaOAc sodium acetate
Na$_2$CO$_3$ sodium carbonate
NaOEt sodium ethoxide
NH$_4$OAc ammonium acetate
NH$_3$ ammonia
NH$_4$Cl ammonium chloride
Pd$_2$(dba)$_3$ tris(dibenzylideneacetone)dipalladium(0))
PhSNa sodium thiophenolate
PMB para-methoxybenzyl
RT or rt room temperature
SGC silica gel chromatography
TBAF tetrabutylammonium fluoride
TBS tert-butyldimethylsilyl
TFA trifluoroacetic acid
THF tetrahydrofuran
TLC thin layer chromatography Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from Me$_4$Si with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH₃CN, 9 min-stop. MS data were obtained using Agilent Technologies LC/MSD SL or 1100 series LC/MSD mass spectrometer.

Methods useful for making the compounds of formula I-III are set forth below in various schemes

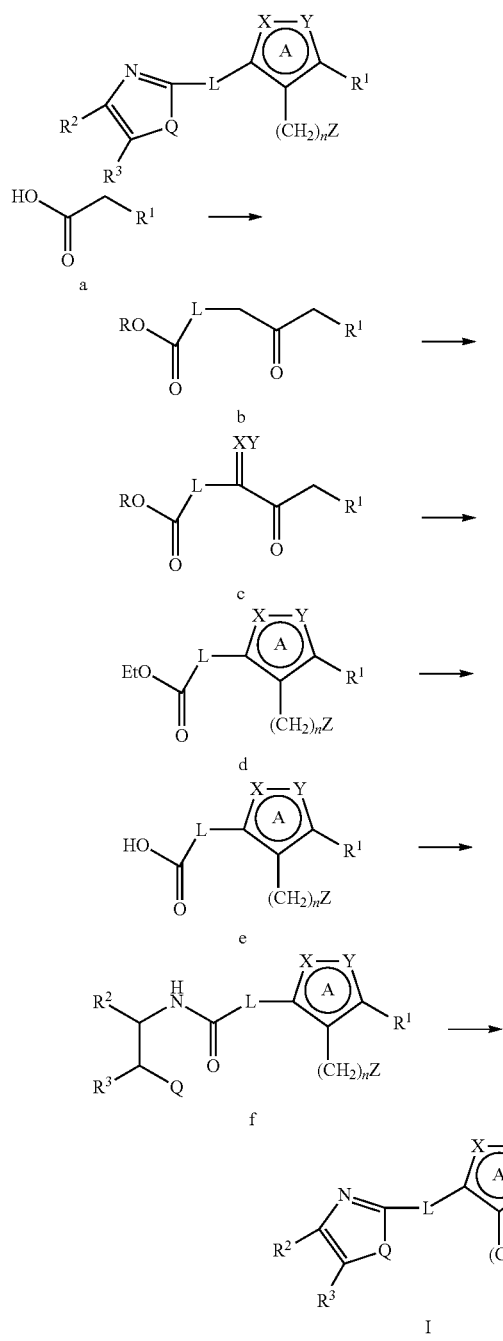

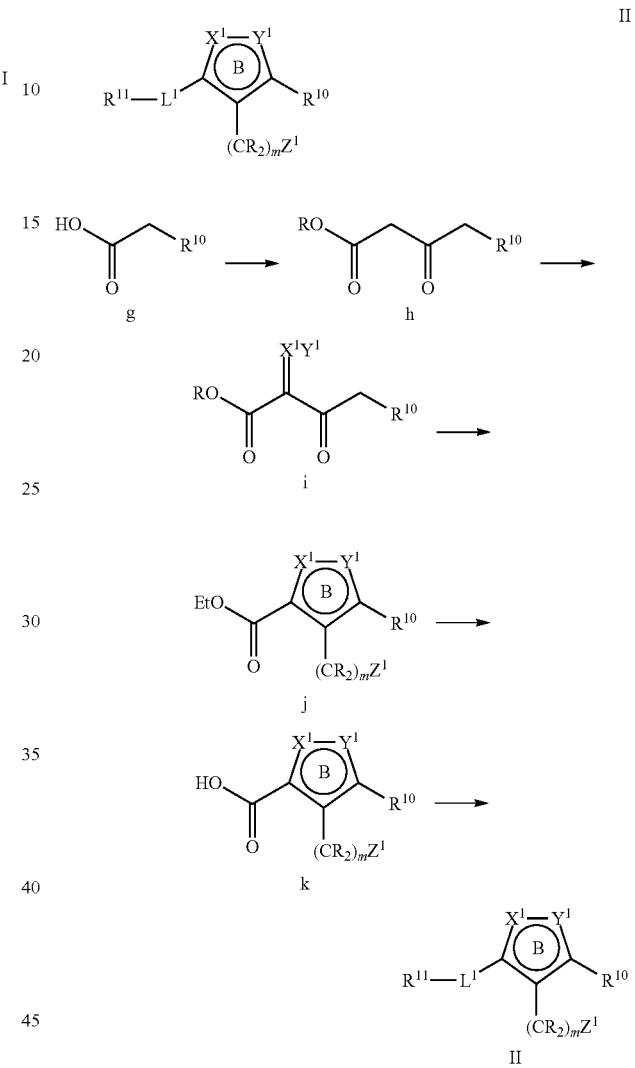

A compound of formula I can be synthesized from a via activation then condensation to give b. This compound is then further functionalized with an electrophilic heteroatom source to give c which is cyclized under standard conditions the give the heterocyclic core d. Compound type d is hydrolyzed and coupled under standard amide coupling conditions to give f. Compound type f is then cyclized under acidic conditions to give compounds of formula I.

A compound of formula II can be synthesized from g via activation then condensation to give h. This compound is then further functionalized with an electrophilic heteroatom source to give i which is cyclized under standard conditions the give the heterocyclic core j. Compound type j is hydrolyzed to give type k which is subjected to functional group manipulations to give compounds of formula II.

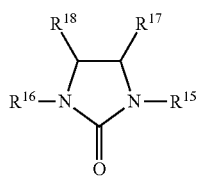

Formula III

77
-continued

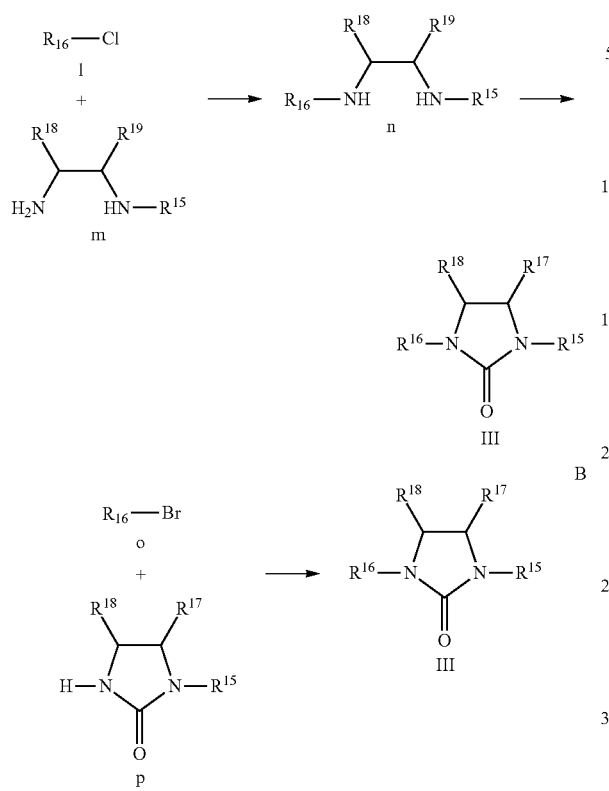

A compound of formula III can be synthesized from m via nucleophilic addition to 1 followed by treatment with a carbonyl source (not limited to carbonyl diimidazole) to give III. Similarly p can be alkylated with o to give compounds of the formula III.

Example 1

Step 1

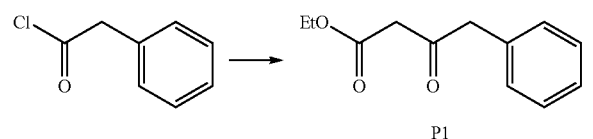

Pyridine (10.46 ml, 129.37 mmol, 2 eq) and 2,2-dimethyl-1,3-dioxane-4,6-dione (Meldrum's Acid) (9.3 g, 1 eq) were dissolved in CH$_2$Cl$_2$ (140 ml) at 0° C. 2-phenylacetyl chloride (10 g, 64.68 mmol) was added slowly; the mixture was allowed to warm to room temperature and stirred overnight. The mixture was washed with 10% HCl (2×100 ml), water (2×100 ml), dried (MgSO$_4$) and concentrated under reduced pressure. The residue was dissolved in EtOH and heated at reflux for 4 hours. After cooling to room temperature the volatiles were removed under reduced pressure and the residue purified by silica gel chromatography (SGC, 0-10% EtOAc in hexane) to give 6.4 g of product.

78

Step 2

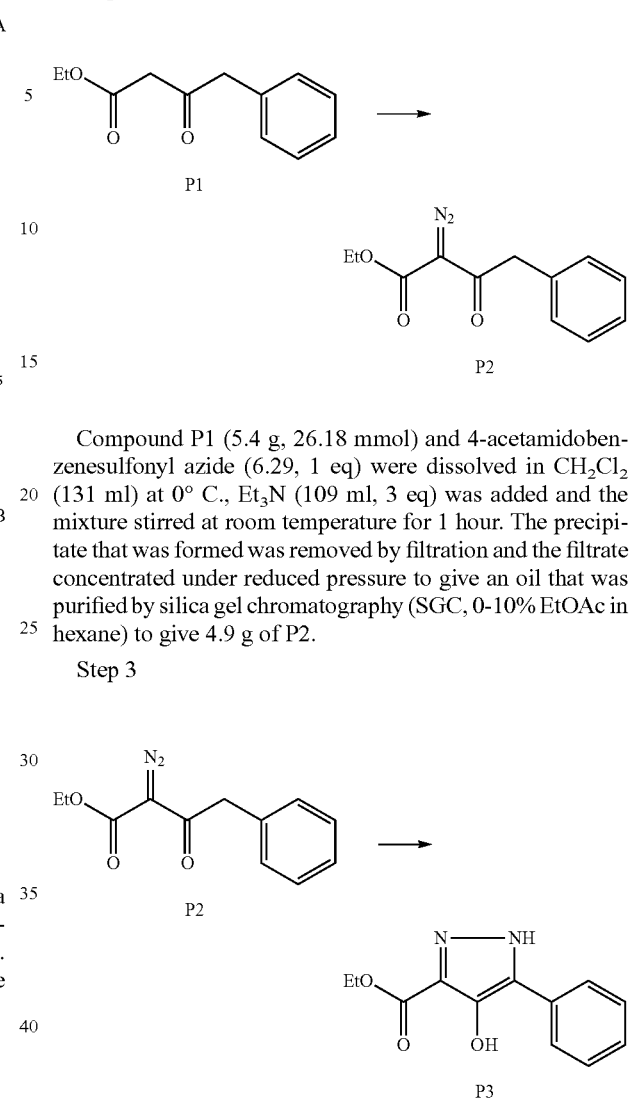

Compound P1 (5.4 g, 26.18 mmol) and 4-acetamidobenzenesulfonyl azide (6.29, 1 eq) were dissolved in CH$_2$Cl$_2$ (131 ml) at 0° C., Et$_3$N (109 ml, 3 eq) was added and the mixture stirred at room temperature for 1 hour. The precipitate that was formed was removed by filtration and the filtrate concentrated under reduced pressure to give an oil that was purified by silica gel chromatography (SGC, 0-10% EtOAc in hexane) to give 4.9 g of P2.

Step 3

Compound P2 (5 g, 21.53 mmol) in THF (54 ml) was slowly added to a suspension of NaH (4.3 g, 5 eq, 60% dispersion in mineral oil) in THF (54 ml) at 0° C. The mixture was allowed to warm to room temperature and stirred overnight. After cooling to 0° C., AcOH (4.1 ml, 3.3 eq)) was added, the mixture was concentrated and the residue taken up in water (100 ml). Additional AcOH was added to neutralize the solution and the resulting precipitate collected by filtration and dried to give 5 g of product. $^1$H NMR (CDCl$_3$) δ 1.438 (t, J=7 Hz, 3H), 4.46 (q, J=7 Hz, 2H), 7.34 (m, 1H), 7.45 (t, J=8 Hz, 1H), 7.89 (d, J=8.2 Hz, 1H)

Step 4

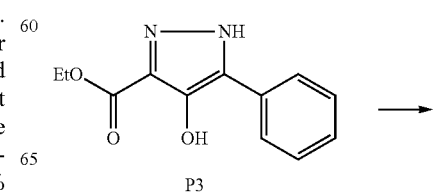

-continued

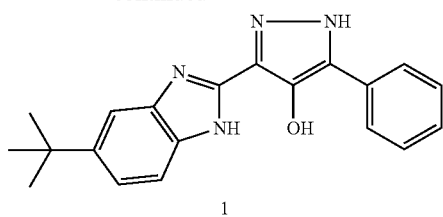

1

Compound P3 (50 mg, 0.22 mmol), 4-tert-butylbenzene-1,2-diamine (35 mg, 1 eq), and DMAP (26 mg, 1 eq) were mixed together in m-xylenes and heated at 200° C. overnight. After cooling to room temperature, the mixture was diluted with EtOAc, washed with $NH_4Cl$ (saturated), dried ($MgSO_4$) and concentrated under reduced pressure. The residue was purified by reverse-phase HPLC (C18 89.91:9.99:0.1 to 9.99:89.91:0.1 $H_2O$:MeCN:$HCO_2H$) to give 14 mg of compound 1. LCMS: $MH^+$=333.2.

Examples 2-11

The following were synthesized using an analogous procedure.

| Structure | Example | MS m/e (MH+) |
|---|---|---|
|  | 2 | 329 |
|  | 3 | 311 |
|  | 4 | 307 |
|  | 5 | 345 |
| 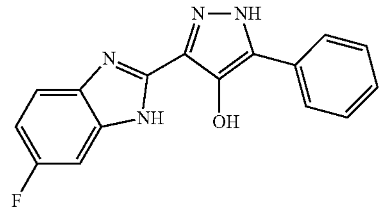 | 6 | 295 |
| 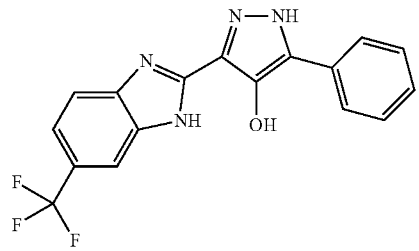 | 7 | 345 |
| 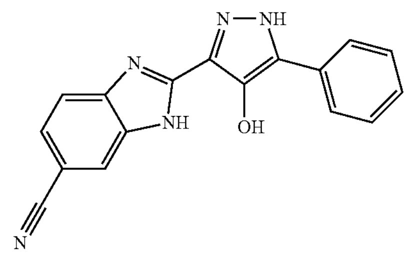 | 8 | 302 |
| 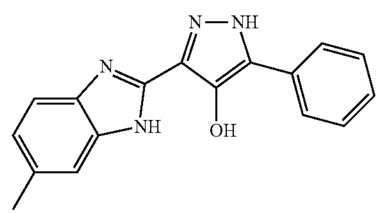 | 9 | 291 |
| 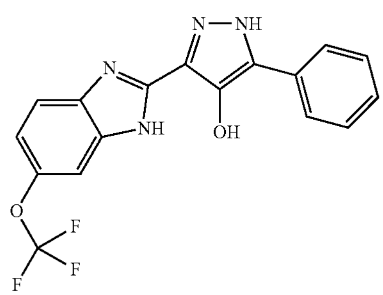 | 10 | 361 |
| 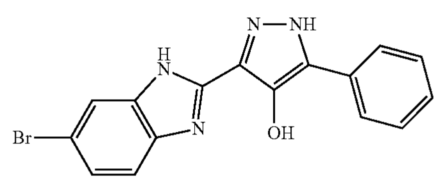 | 11 | 357 |

Example 12

Step 1

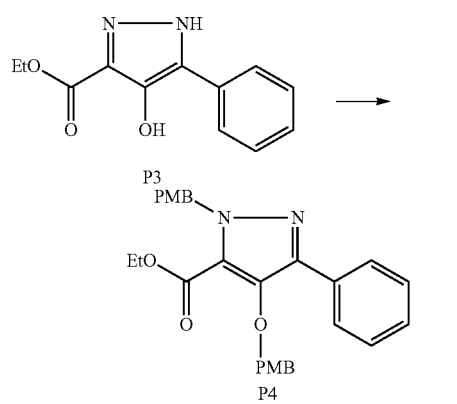

Compound P3 3 (5.3 g, 22.83 mmol) was dissolved in DMF, NaH (2.01 g of a 60% dispersion in mineral oil, 2.2 eq) was added. After stirring for 10 minutes 4-methoxy benzylbromide (7.21 ml, 2.2 eq) was added and the mixture stirred overnight. Saturated ammonium chloride was added and the mixture extracted with EtOAc. The extracts were washed with water, dried (MgSO$_4$), and purified by silica gel chromatography (SGC, 0-30% EtOAc in hexane) to give, in order of elution, P4 (5.87 g), and P5 (1.28 g)

Step 2

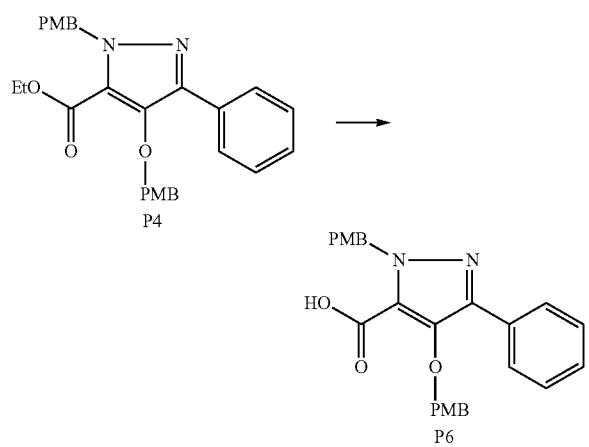

Product P4 from step 1 (4.3 g, 9.1 mmol) was dissolved in MeOH (45.5 ml), a 2M aqueous solution of KOH (16 ml, 3.5 eq) was added and the mixture stirred at 70° C. for 2 hours. Most of the MeOH was removed under reduced pressure and the aqueous residue acidified to PH1 with concentrated HCl in an ice-water bath. The mixture extracted with EtOAc, the extracts were washed with water, dried (MgSO$_4$), and concentrated under reduced pressure to give the 3.8 g of P6.

Step 3

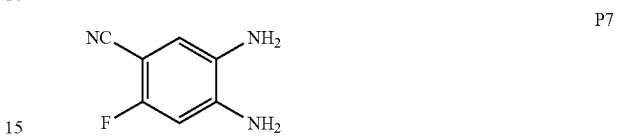

P7 was prepared using the procedures outlined in *Bioorganic and Medicinal Chemistry Letters* 2002, 12, 2019-2022.

Step 4

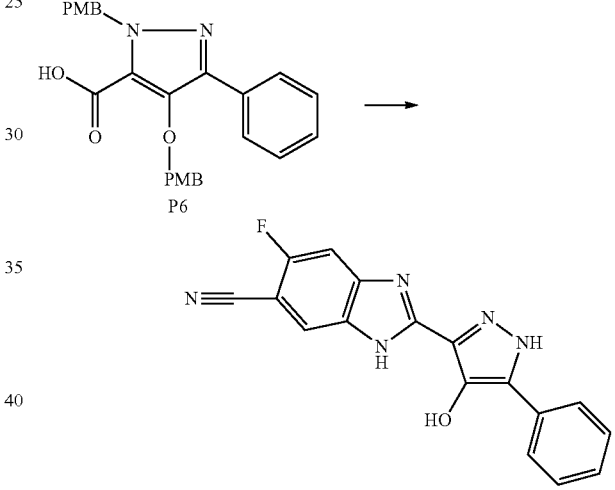

Compound P6 (1 g, 2.25 mmol) and the product from step 3 (P7) (340 mg, 1 eq) were dissolved in DMF (11.25 ml). HATU (1.28 g, 1.5 eq) followed by DIPEA (0.59 m, l, 1.5 eq) were added and the mixture stirred overnight. The mixture was diluted with EtOAc, washed with NH$_4$Cl$_{(sat)}$, dried (MgSO$_4$) and concentrated under reduced pressure. Purification by silica gel chromatography (SGC, 0-40% EtOAc in hexane) gave 942 mg of intermediate which was dissolved in TFA (20 ml) and heated at 90° C. overnight. After cooling to room temperature the solvent was removed under reduced pressure. The residue was treated with NaHCO$_{3(sat)}$ and extracted with EtOAc. The organic extracts were dried (MgSO$_4$) and concentrated under reduced pressure. Purification by silica gel chromatography (SGC, 0-100% EtOAc in hexane) gave 310 mg of 12. LCMS: MH$^+$=320.2.

Examples 13-22

The following examples were synthesized using an analogous procedure to example 12.

| Structure | Example | MS m/e (MH+) |
|---|---|---|
| 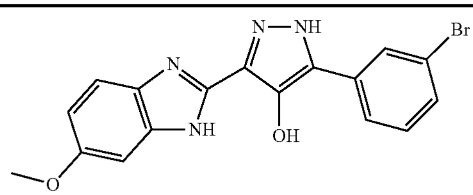 | 13 | 387.2 |
| 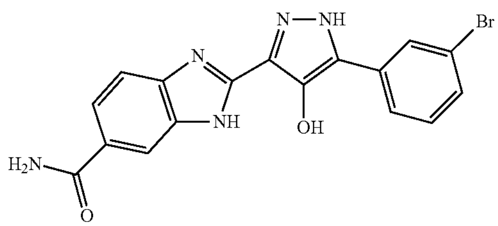 | 14 | 398.2 |
| 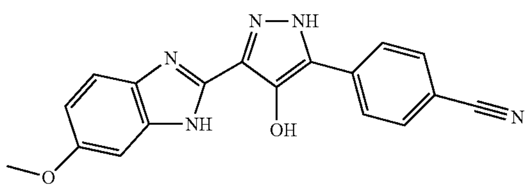 | 15 | 332.2 |
| 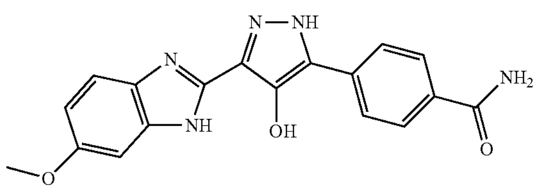 | 16 | 350.2 |
| 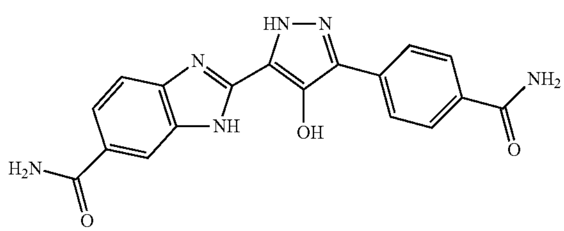 | 17 | 363.2 |
| 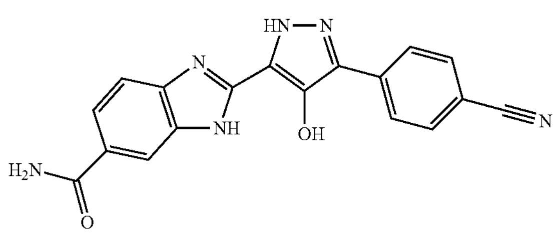 | 18 | 345.2 |
| 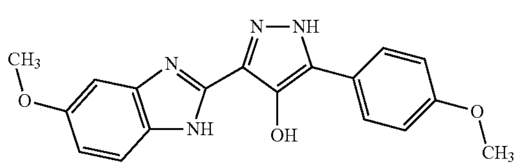 | 19 | 337.2 |
| 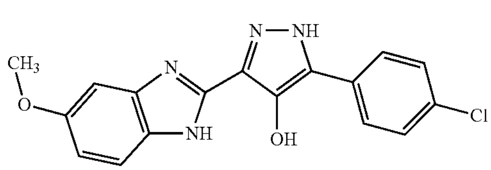 | 20 | 341.2 |

-continued

| Structure | Example | MS m/e (MH+) |
|---|---|---|
| 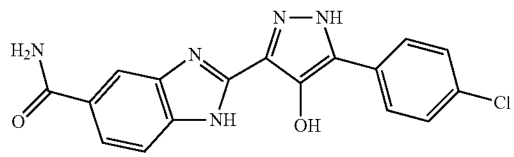 | 21 | 354.2 |
| 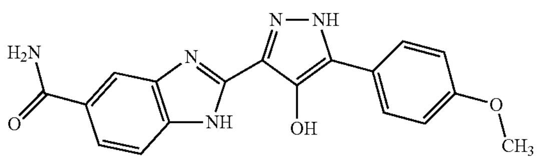 | 22 | 350.2 |
| 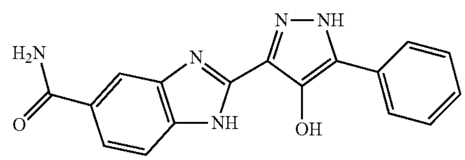 | 23 | 320 |

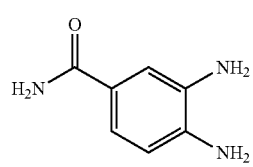

P8 was prepared using the procedures outlined in *J. Med. Chem.* 2005, 48, 1873-1885 and used in the synthesis of example 23.

Example 24

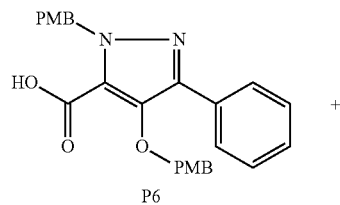

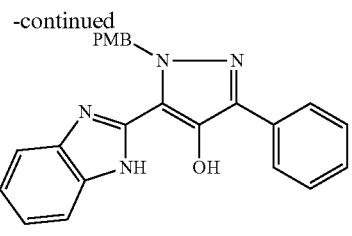

Compound P6 (0.35 g, 0.79 mmol) and P8 (119 mg, 1.2 eq) were dissolved in DMF (3.94 ml), HATU (449 mg, 1.5 eq) and DIPEA (0.21 ml, 1.5 eq) were added and the mixture stirred overnight. The mixture was diluted with EtOAc, washed with $NH_4Cl_{(sat)}$, dried ($MgSO_4$) and concentrated under reduced pressure. Purification by silica gel chromatography (SGC, 0-100% EtOAc in Hexanes) gave 458 mg of intermediate 348 mg of which was dissolved in AcOH (20 ml) and heated at 135° C. for 5 hours. After cooling to room temperature the mixture was then concentrated and purified by reverse-phase HPLC (C18 89.91:9.99:0.1 to 9.99:89.91: $0.1 H_2O:MeCN:HCO_2H$) to give 26 mg of 24. LCMS: $MH^+=440.2$.

Example 25

Step 1

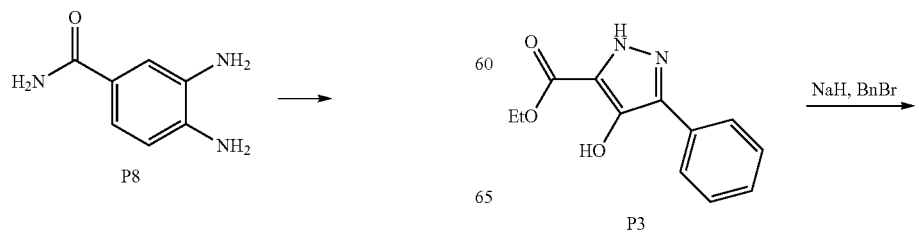

-continued

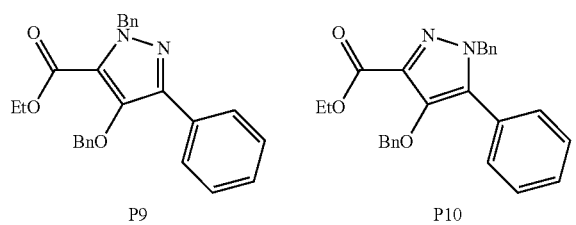

To a solution of P3 (2.5 g, 10.76 mmol), tetra-n-butylammonium iodide (800 mg, 2.17 mmol, 0.2 eq.) in 30 ml DMF at 0° C. was added a 60% dispersion of NaH in mineral oil (1.3 g, 32.50 mmol, 3 eq.). The mixture was stirred for 10 min, benzyl bromide was added (3.9 ml, 32.79 mmol, 3 eq.), stirred at 0° C. for 30 min and at rt for 1 hr. It was quenched by the addition of aq. NH$_4$Cl, extracted 3× with ethyl acetate, the combined organic layers was washed with brine and dried over MgSO$_4$. The crude product was purified column chromatography using 0% to 20% ethyl acetate in hexanes as eluent to provide 2.6 g of P9 and 0.54 g of P10. MS for P9: m/e=413.2 (MH$^+$) MS for P10: m/e=413.2 (MH$^+$)

Step 2

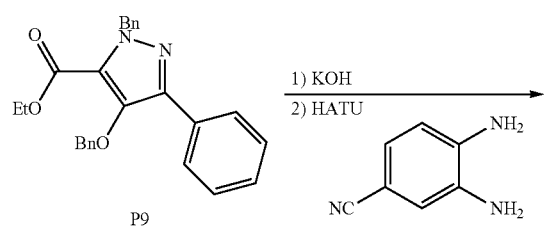

A solution of P9 (1.03 g, 2.50 mmol) and KOH (420 mg, 7.49 mmol) in 4 ml each of THF, methanol and water was heated at 70° C. for 2 hr. The solution was diluted with water, acidified with 1N HCl and extracted 3× with ethyl acetate. The combined organic layer was washed with water, brine, dried over MgSO$_4$, filtered and concentrated to provide 0.86 g of the acid. A solution of this acid (700 mg, 1.82 mmol) and 3,4-diaminobenzonitrile (270 mg, 2.03 mmol, 1.1 eq.) in 10 ml DMF at 0° C. was added HATU (760 mg, 2.00 mmol, 1.1 eq.) followed by triethyl amine (0.51 ml, 3.66 mmol, 2 eq.). The mixture was stirred overnight at rt and diluted with ethyl acetate. The mixture was washed 3× with water, brine, dried over MgSO$_4$, filtered and concentrated. The crude product was purified by chromatography using 0% to 50% ethyl acetate in hexane as eluent to provide 0.56 g of P11. MS: m/e=500.3 (MH$^+$)

Step 3

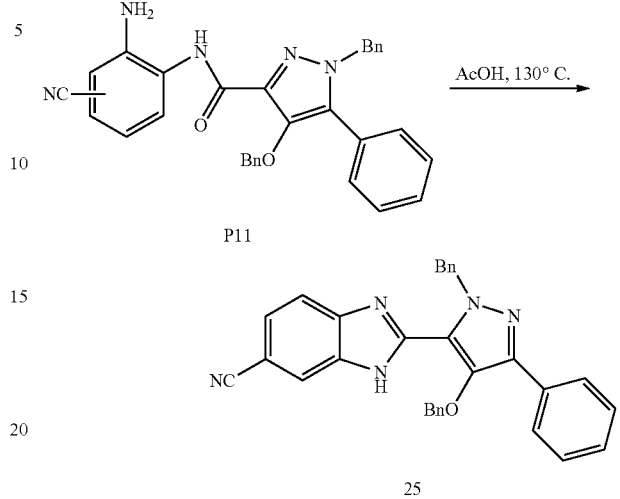

A solution of P11 (0.83 g, 1.66 mmol) in 20 ml of glacial acetic acid in a sealed tube was heated at 130° C. for 3 hr. The solvent was evaporated and the residue was suspended in aq. Na$_2$CO$_3$, extracted 4× with ethyl acetate. The combined organic layers was washed with brine, dried over MgSO$_4$, filtered and concentrated to give the crude product. Another batch of the reaction was carried-out using 200 mg of 5. Crude products from both batches were combined and taken as a suspension in diethyl ether. The solid was filtered off, rinsed with ether and dried in vacuum oven to provide 0.73 g of 25. MS: m/e=482.3 (MH$^+$)

Example 26

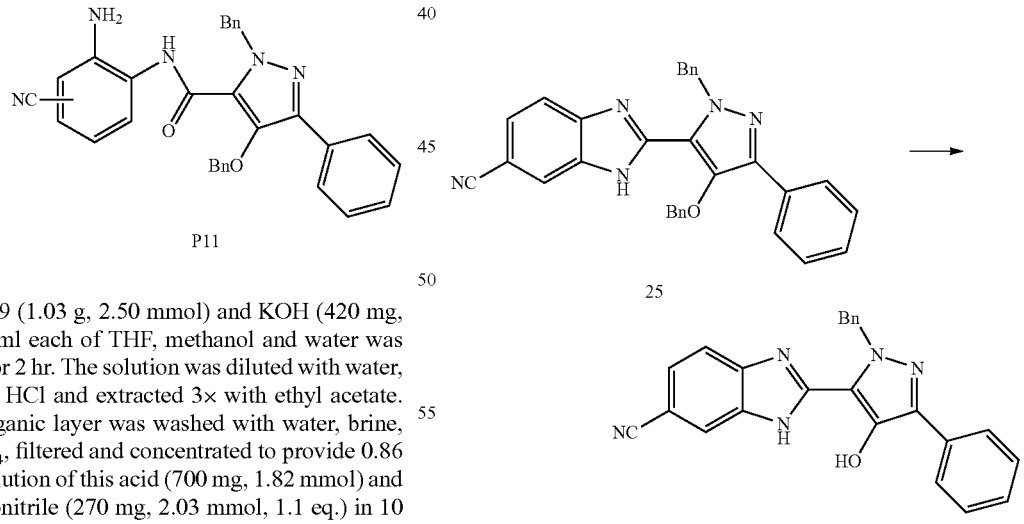

A mixture of 25 (105 mg, 0.218 mmol) and 10% Pd—C (20 mg) in 2 ml each of THF and methanol was stirred under a hydrogen balloon for 2 hr. It was filtered through a CELITE pad and evaporated to provide 85 mg of 26. MS: m/e=392.2 (MH$^+$)

Example 27

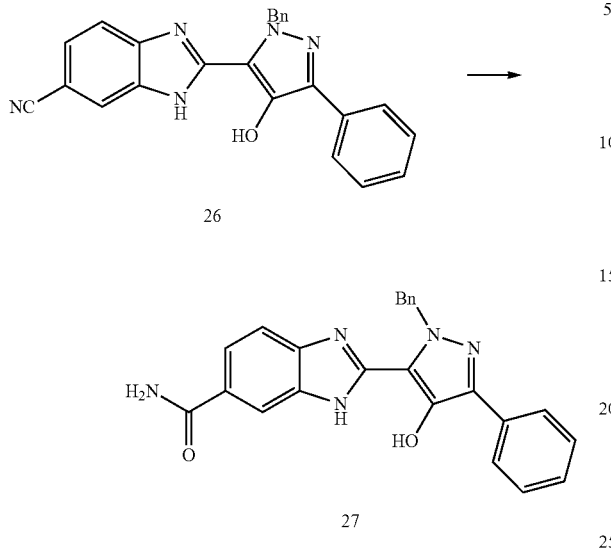

A mixture of 26 (65 mg, 0.166 mmol) and KOH (47 mg (0.838 mmol, 5 eq.) in 0.5 ml each of THF, methanol and water was heated in a sealed tube at 80° C. for 14 hr followed by heating at 100° C. for 4 hr. The mixture was diluted with water, acidified with 1N HCl and extracted 3× with ethyl acetate. The combined organic layer was washed with brine, dried over MgSO$_4$, filtered, concentrated and the residue was purified by preparative TLC using 10% methanol in dichloromethane as eluent to provide 19 mg of 27. MS: m/e=410.2 (MH$^+$)

Example 28

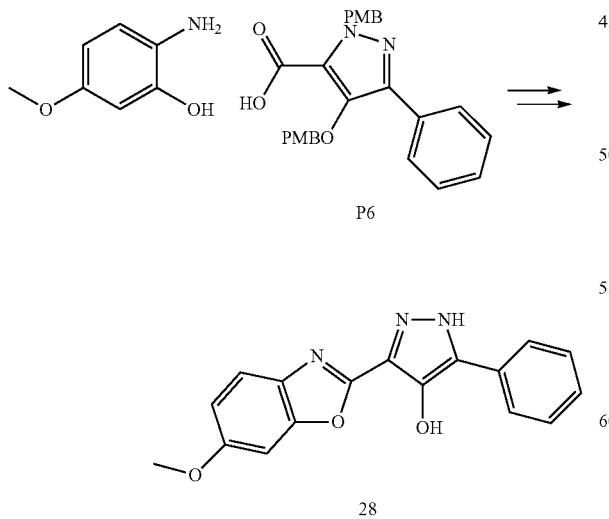

MS: 308.2 (MH$^+$)

Example 28 was prepared from P6 and 2-amino-5-methoxy-phenol using a similar procedure used for the preparation of 25.

Example 29

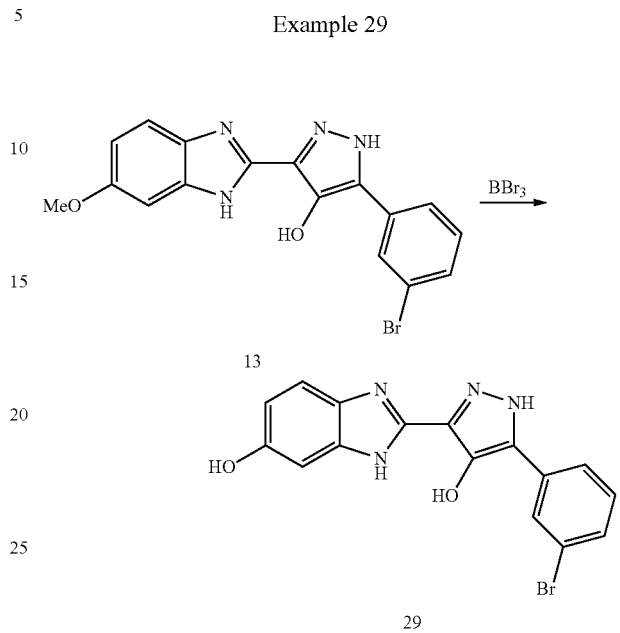

To a suspension of 13 (30 mg, 0.078 mmol) in 1 ml dichloromethane at rt was added neat BBr$_3$ (37 µl, 0.388 mmol, 5 eq) and the suspension immediately turned into a clear solution. After stirring for 2 hr at rt, the mixture was poured in aq. NaHCO$_3$ solution and extracted three times with ethyl acetate. The combined organic layer was washed with brine, dried over MgSO$_4$, filtered, concentrated and chromatographed with ethyl acetate to provide 27 mg of 29.

MS: 373.2 (MH$^+$)

Example 30

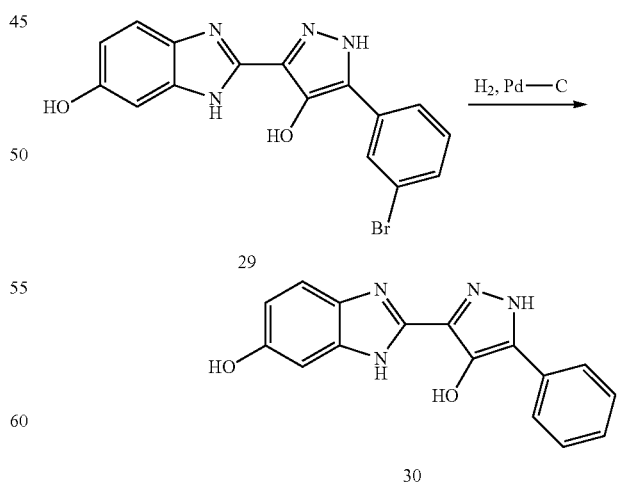

A suspension of 29 (40 mg) and 10% Pd—C (20 mg) in 1 ml each of ethyl acetate and methanol was stirred overnight under a hydrogen balloon. The mixture was filtered through a CELITE pad, concentrated and purified by chromatography using 10% of 7N ammonia-methanol in dichloromethane to provide 15 mg of 30.

MS: 293.2 (MH⁺)

Example 31

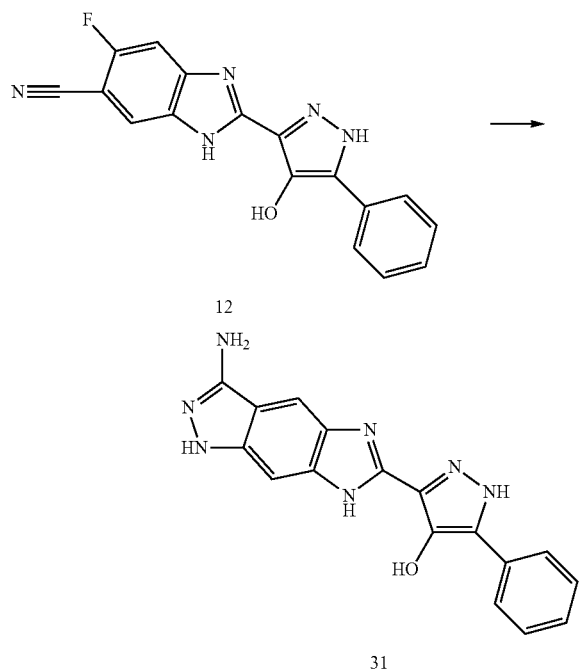

Example 12 (50 mg, 0.16 mmol) was dissolved in nBuOH (1.57 ml), hydrazine (0.49 ml, 100 eq) was added and the mixture stirred at 120° C. overnight. The mixture was cooled to room temperature, concentrated and the residue was purified by reverse-phase HPLC (C18 89.91:9.99:0.1 to 9.99: 89.91:0.1 H₂O:MeCN:HCO₂H) to give 8 mg of 31. LCMS: MH⁺=332.2.

Example 32

Step 1

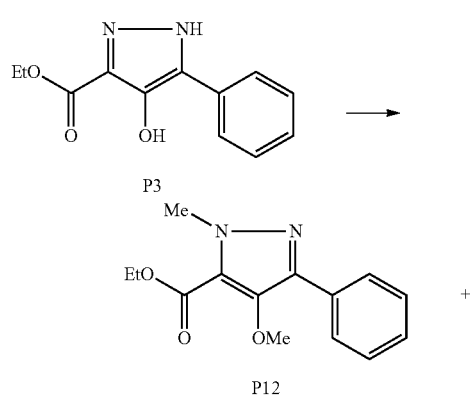

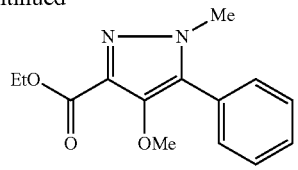

Compounds P12 and P13 were prepared in a similar manner to P4 and P5 substituting MeI for 4-methoxy benzylbromide.

Step 2

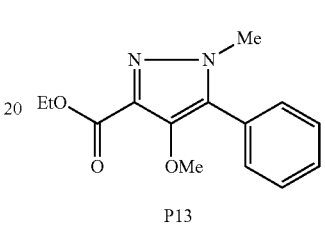

P14 was synthesized using a similar procedure to P6 from P13.

Step 3

Compounds P14 (0.1 g, 0.43 mmol) and P8 (78 mg, 1.2 eq) were dissolved in DMF (2.15 ml), HATU (246 mg, 1.5 eq) and DIPEA (0.11 ml, 1.5 eq) were added and the mixture stirred overnight. The mixture was diluted with EtOAc, washed with NH₄Cl$_{(sat)}$, dried (MgSO₄) and concentrated under reduced pressure. Purification by silica gel chromatography (SGC, 0-5% MeOH in EtOAc) gave 140 mg of intermediate which was dissolved in AcOH (4 ml) and heated in a microwave at 150° C. for 40 minutes. After cooling to room temperature the mixture was then concentrated and purified by reverse-phase HPLC (C18 89.91:9.99:0.1 to 9.99:89.91: 0.1H$_2$O:MeCN:HCO$_2$H) to give 84 mg of 32. LCMS: MH$^+$=348.2.

Example 33

Step 1

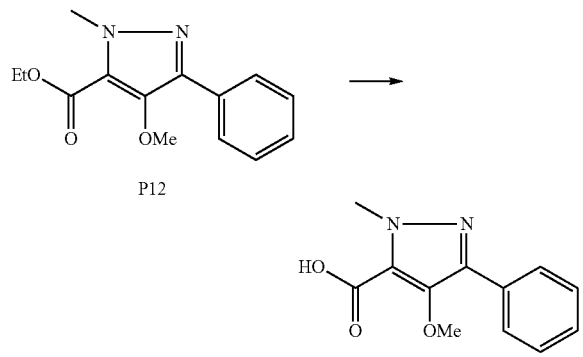

P15 was synthesized using a similar procedure to P6 from P12.

Step 2

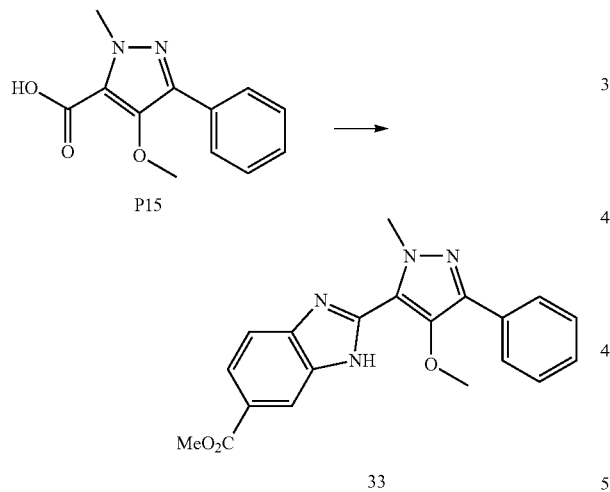

P15 (150 mg, 0.646 mmol) was dissolved in DMF, methyl 3,4-diaminobenzoate (161 mg, 1.5 equiv.), DIPEA (0.169 ml, 1.5 equiv.) and HATU (368 mg, 1.5 equiv.) were added. The mixture was stirred at RT overnight. The mixture was diluted with EtOAc, saturated NH$_4$Cl was added, and the mixture extracted with EtOAc. The extracts were washed with saturated NaHCO$_3$, brine, dried over MgSO$_4$ and purified by silica gel chromatography (SGC, 0-60% EtOAc in Hexane) to give the 205 mg of an intermediate that was suspended in AcOH (3.8 ml) and heated at 90° C. overnight. The suspension was cooled down to rt and diluted with EtOAc. Saturated NaHCO$_3$ was added slowly until pH ~7. The extracts were washed brine, dried over MgSO$_4$ and purified by silica gel chromatography (SGC, 0-60% EtOAc in Hexane) to give the 161 mg of 33. ESI-MS (m/z): 363 [M+H]$^+$ Example 34-36

The following compounds were synthesized using a similar procedure to 33 from P15 using the appropriate diaminobenzenes.

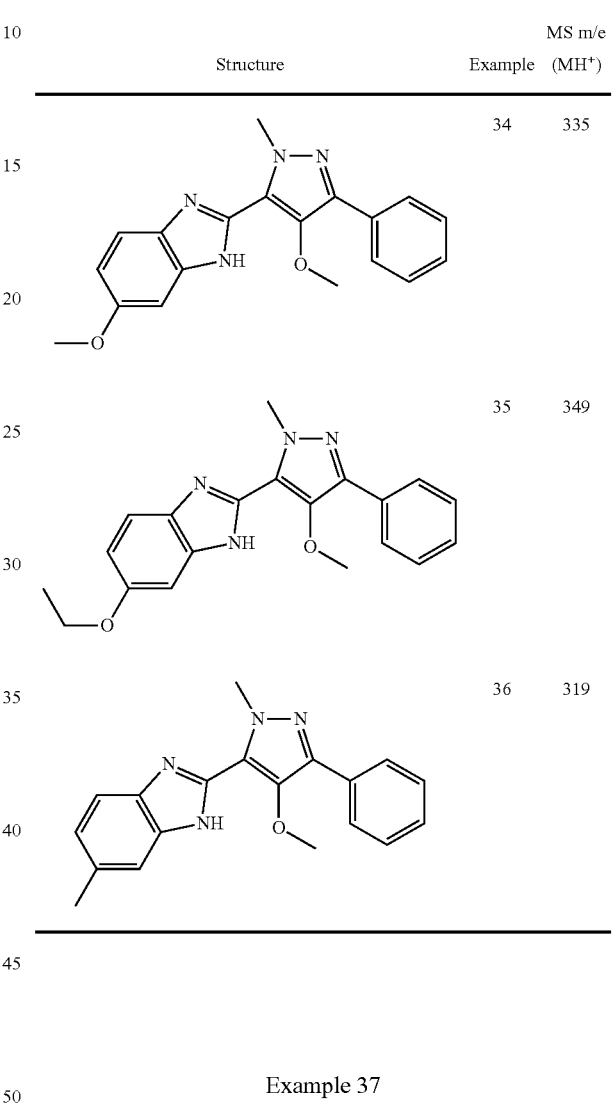

Example 37

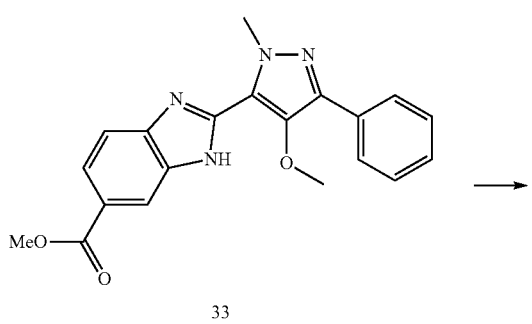

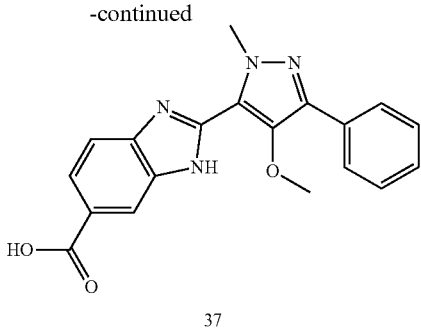

37

Example 33 (720 mg, 1.99 mmol) was dissolved in MeOH (8.0 ml), a 2.0 M aqueous solution of KOH (3.48 ml, 3.5 equiv.) was added and the mixture stirred at 80° C. overnight. Most of MeOH was removed under reduced pressure and the aqueous residue acidified to pH ~1 with 0.1 N HCl in an ice-water bath. The mixture was extracted with EtOAc, the extracts were washed with brine, dried over MgSO$_4$ and concentrated under reduced pressure to give 645 mg of 37. ESI-MS (m/z): 349 [M+H]$^+$ Example 38

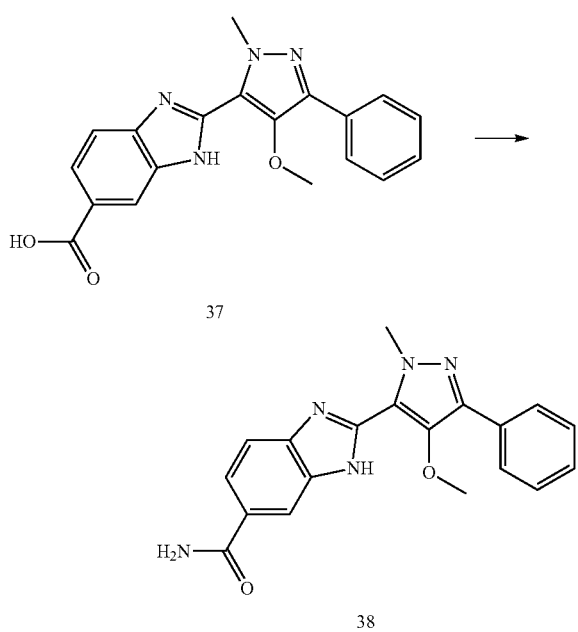

Example 37 (100 mg, 0.287 mmol) was dissolved in DMF, NH$_4$Cl (23 mg, 1.5 equiv.), DIPEA (0.125 ml, 2.5 equiv.) and HATU (164 mg, 1.5 equiv.) were added. The mixture was stirred at RT overnight. Dilute with EtOAc, saturated NH$_4$Cl was added and the mixture extracted with EtOAc. The extracts were washed with saturated NaHCO$_3$, brine, dried over MgSO$_4$ and purified by silica gel chromatography (SGC, 0-100% EtOAc in Hexane) to give the 82 mg of 38. ESI-MS (m/z): 348 [M+H]$^+$ The following examples were synthesized using a similar procedure to 38 from 37 using an appropriate amine hydrochloride.

| Structure | Example | MS m/e (MH$^+$) |
|---|---|---|
| 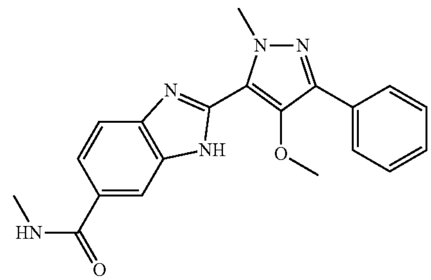 | 39 | 362 |
| 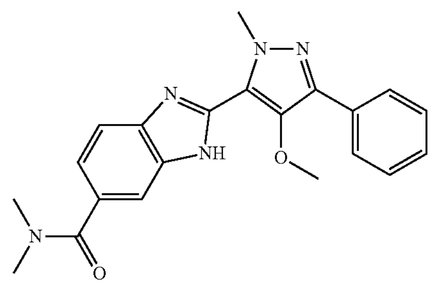 | 40 | 376 |

Example 41

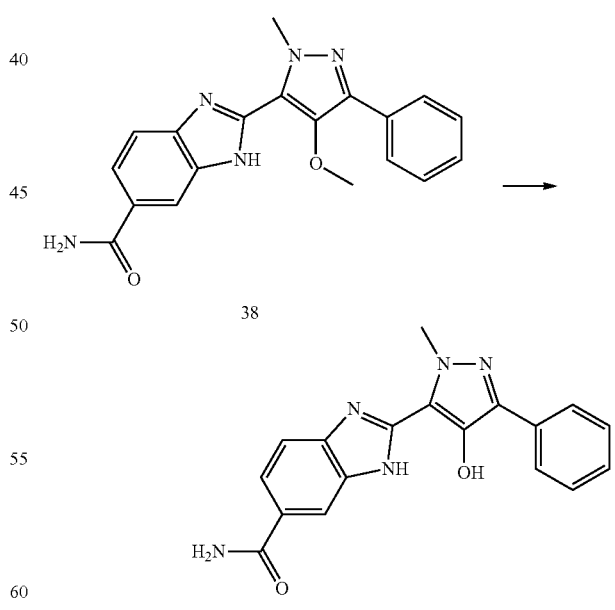

To example 38 (71 mg, 0.203 mmol) in CH$_2$Cl$_2$ at 0° C. was added BBr$_3$ (87 μl, 4.5 equiv.). After 4 hours, H$_2$O was added cautiously and the mixture stirred for 15 minutes. The mixture was extracted with EtOAc and the extracts were washed with brine, dried over MgSO$_4$ and purified by reverse phase HPLC (10:90-90:10 MeCN/H$_2$O) to give 11 mg of 41. ESI-MS (m/z): 334 [M+H]$^+$ Example 42

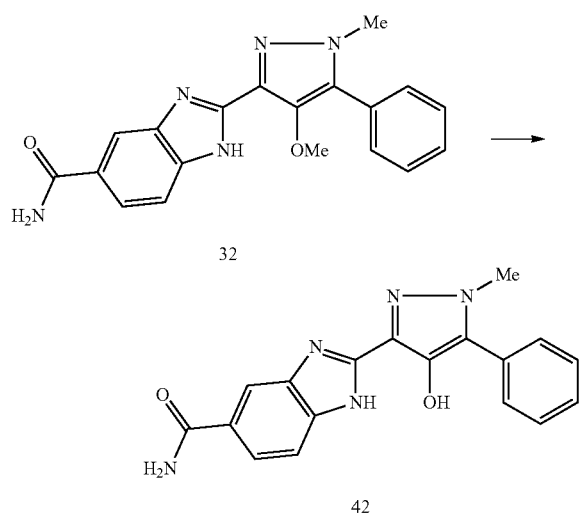

Example 32 (80 mg, 0.23 mmol) was dissolved in CH$_2$Cl$_2$ (9.21 ml) cooled to 0° C., BBr$_3$ (0.1 ml, 4.5 eq) was added and the mixture stirred at room temperature overnight. The mixture was treated with NaHCO$_{3(sat)}$, extracted with CH$_2$Cl$_2$, and concentrated under reduced pressure. Purification by reverse-phase HPLC (C18 89.91:9.99:0.1 to 9.99:89.91:0.1 H$_2$O:MeCN:HCO$_2$H) gave 43 mg of 42. LCMS: MH$^+$=334.2

Example 43

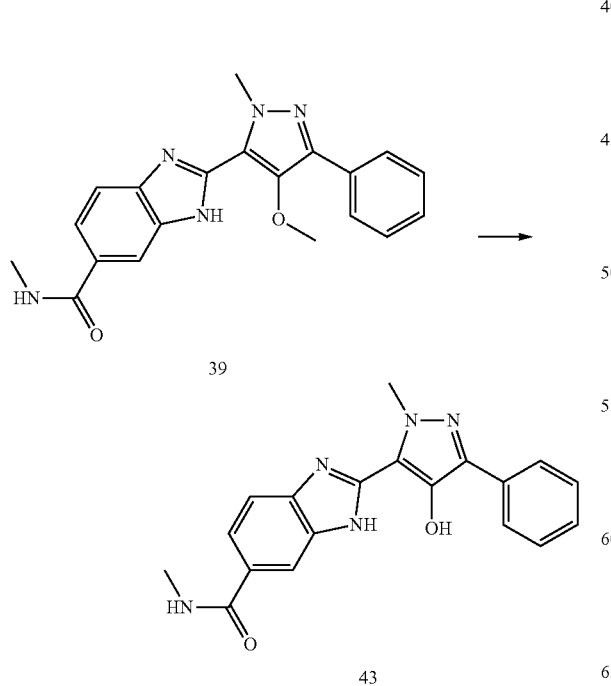

Example 43 was synthesized from example 39 in a similar manner to example 41. ESI-MS (m/z): 348 [M+H]$^+$ Example 44

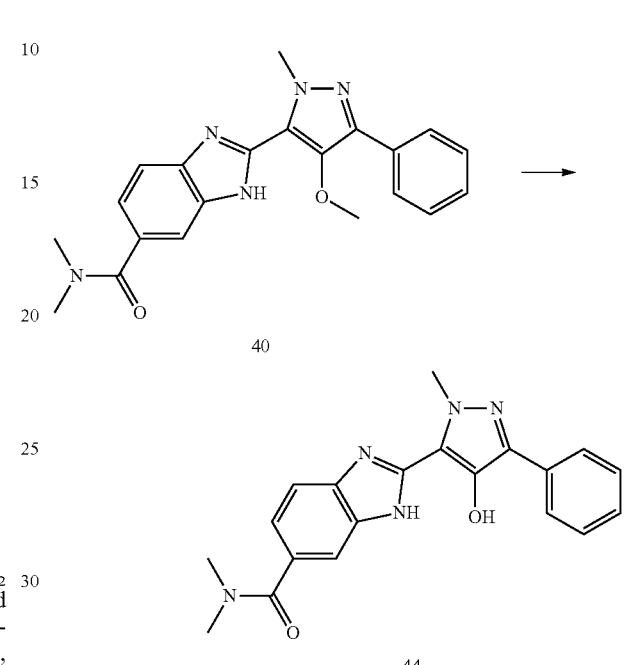

Example 44 was synthesized from example 40 in a similar manner to example 41. ESI-MS (m/z): 362 [M+H]$^+$ Example 45

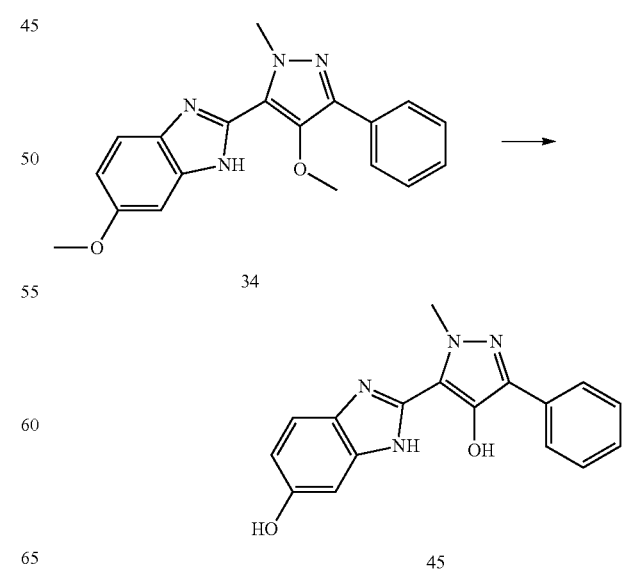

Example 45 was synthesized from example 34 in a similar manner to example 41. ESI-MS (m/z): 307 [M+H]+
Example 46
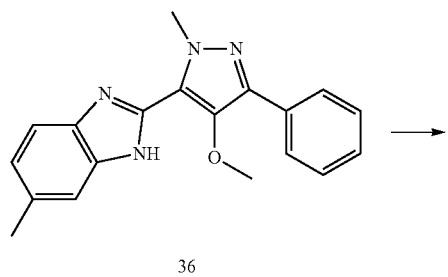
36
→
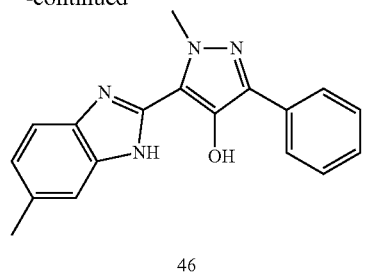
46
Example 46 was synthesized from example 36 in a similar manner to example 41. ESI-MS (m/z): 305 [M+H]+
Examples 47-57
The following compounds were prepared using procedures similar to those previously outlined.
| Structure | Example | MS m/e (MH+) |
|---|---|---|
| 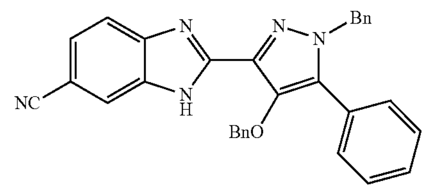 | 47 | 482.3 |
| 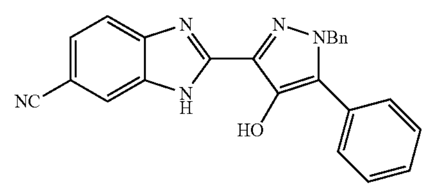 | 48 | 392.2 |
| 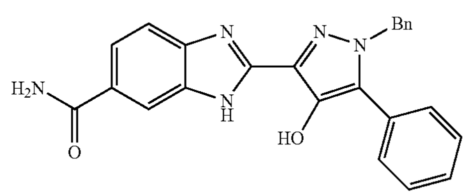 | 49 | 410.2 |
| 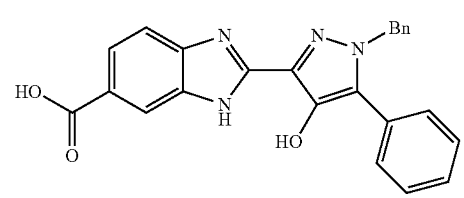 | 50 | 411.2 |
| 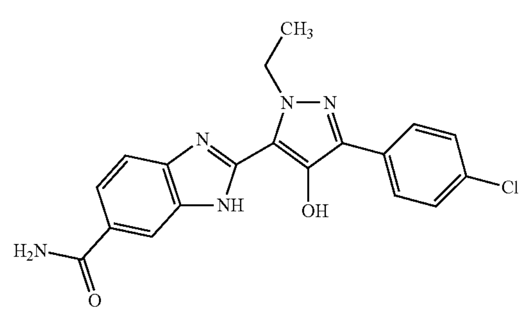 | 51 | 382.2 |

-continued

| Structure | Example | MS m/e (MH+) |
|---|---|---|
| (6-cyano-1H-benzimidazol-2-yl) 1-methyl-3-(4-chlorophenyl)-4-hydroxypyrazole | 52 | 350.2 |
| (6-cyano-1H-benzimidazol-2-yl) 1-methyl-3-(4-chlorophenyl)-4-methoxypyrazole | 53 | 364.2 |
| 2-[1-methyl-3-(4-chlorophenyl)-4-hydroxypyrazol-5-yl]-1H-benzimidazole-6-carboxylic acid | 54 | 369.2 |
| 2-[1-methyl-3-(4-chlorophenyl)-4-hydroxypyrazol-5-yl]-1H-benzimidazole-6-carboxamide | 55 | 368.2 |
| 2-[1-methyl-3-(3-chlorophenyl)-4-hydroxypyrazol-5-yl]-1H-benzimidazole-6-carboxamide | 56 | 368 |

| Structure | Example | MS m/e (MH+) |
|---|---|---|
| 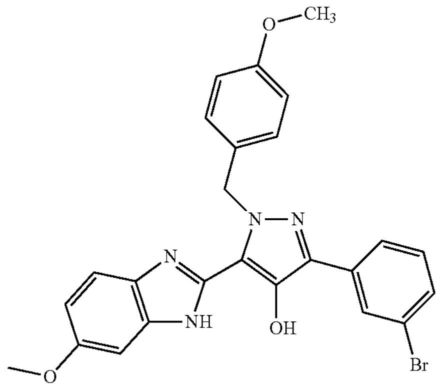 | 57 | 505.3 |

Example 58

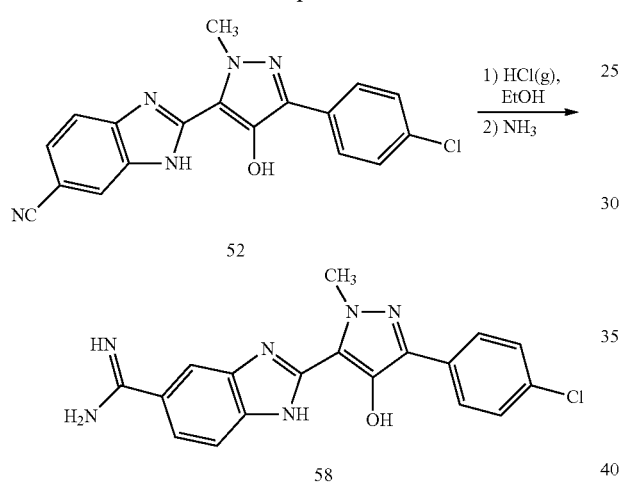

To 288 mg of 52 in 75 mL of ethanol at −78° C. was bubbled HCl gas for about 10 minutes. The flask was sealed with a rubber septum and allowed to warm to room temperature while stirring. After about 16 hours the reaction mixture was evaporated to dryness. To the residue was added 15 mL of 7N NH₃ in methanol and the flask sealed with a rubber septum and allowed to stir for about 16 hours. The reaction mixture was evaporated to dryness then the crude product purified by reversed phase HPLC yielding 30 mg of 58 MS: m/e=367.2 (MH+)

Example 59

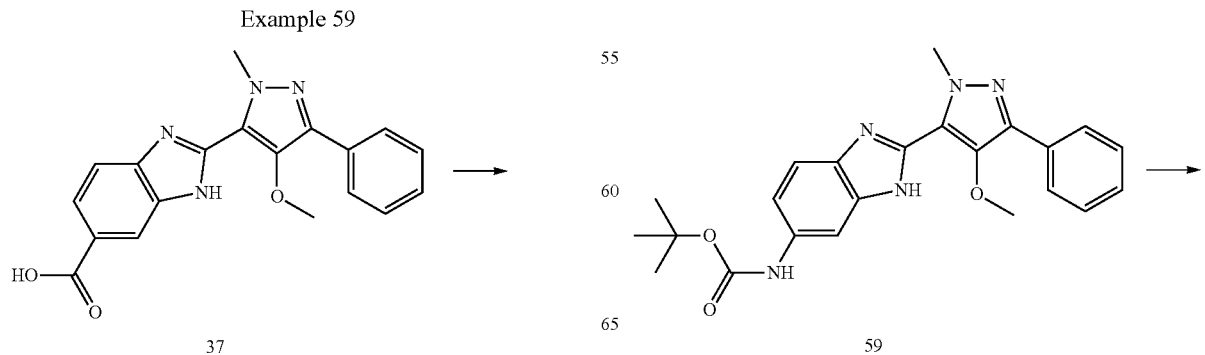

Example 37 (82 mg, 0.235 mmol) was suspended in ᵗBuOH/PhMe (1:1, 1.4 ml) and Et₃N (0.164 ml, 5 equiv.) was added with stirring at RT. To the resultant solution was added DPPA and the mixture stirred at RT for 30 minutes before warming to 100° C. overnight. The mixture was then allowed to cool and diluted with EtOAc, washed with brine and the aqueous phase extracted with EtOAc. The organic phase was dried over MgSO₄ and purified by silica gel chromatography (SGC, 0-100% EtOAc in Hexane) to give the 85 mg of 59. ESI-MS (m/z): 420 [M+H]+

Example 60

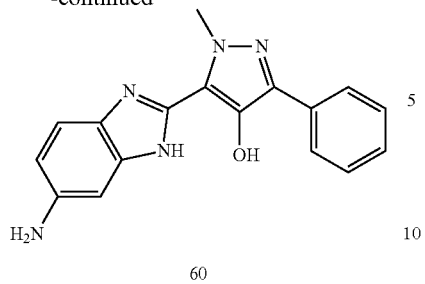

60

Example 60 was synthesized from example 59 in a similar manner to Example 41. ESI-MS (m/z): 306 [M+H]+

Example 61

Step 1

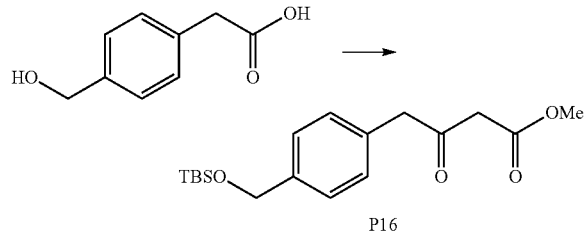

P16

To a solution of 4-(hydroxymethyl)phenylacetic acid (20 g, 0.12 mol) and imidazole (41 g, 0.602 mol, 5 eq.) in 500 ml DMF at rt was added tert-butyldimethylchlorosilane (45.5 g, 0.302 mol, 2.5 eq.). The mixture was stirred overnight at rt and quenched with aq. NH$_4$Cl solution. After stirring at rt for 1.5 hr, the pH was adjusted to ~3 using 1N HCl and extracted 3× with ethyl acetate. The combined organic layer was washed twice with 0.5N HCl, brine, dried over MgSO$_4$, filtered and concentrated. The residue was dried in a vacuum oven kept at 80° C. to give 36.4 g of oil. A solution of above product, 2,2-dimethyl-1,3-dioxane-4,6-dione (Meldrum's Acid, 17.3 g, 0.12 mol, 1 eq.) and DMAP (2.9 g, 0.024 mol, 0.2 eq.) in 400 ml of dichloromethane was cooled to 0° C., added EDCI (25.3 g, 0.132 mol, 1.1 eq) followed by triethyl amine (33.5 ml, 0.24 mol, 2 eq.). The mixture was stirred overnight at rt, diluted with dichloromethane and washed successively with 3×1N HCl, brine, dried over MgSO$_4$, filtered and concentrated to provide the Meldrum's acid ester. This was dissolved in 300 ml of methanol, heated at reflux for 4 hr, concentrated and purified by chromatography using 100% hexane to 50% ethyl acetate in hexanes as eluent to provide 13.8 g of P16. MS: m/e=205.1 (M-OTBS$^+$)

Step 2

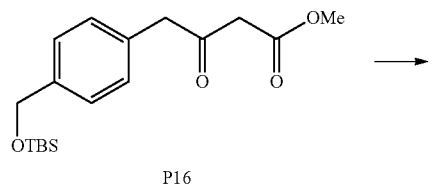

P16

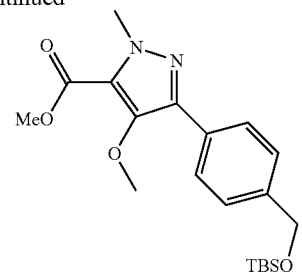

P17

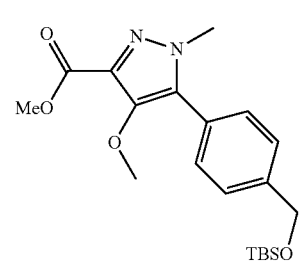

P18

Intermediate P16 was converted to P17 and P18 using analogous procedures described for the preparation of P12 and P13 above.

Step 3

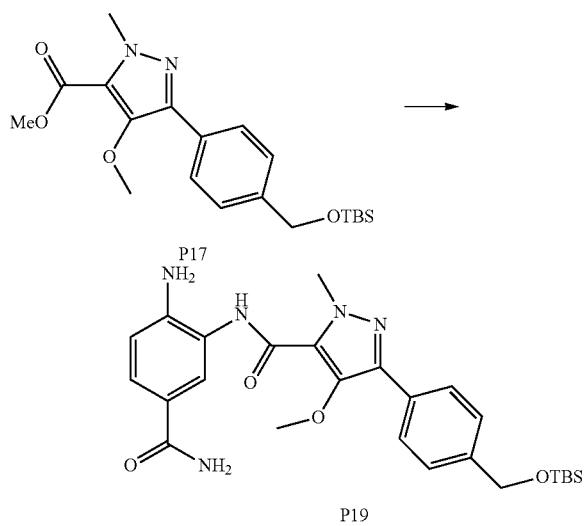

To a solution of P17 (1.85 g, 4.74 mmol) in 15 ml of methanol and 5 ml of water was added LiOH (230 mg, 9.58 mmol, 2 eq.) and heated at reflux for 1 hr at which point another 2 equivalent of LiOH was added and heated at reflux for another 1 hr. After cooling to rt, THF was evaporated, diluted with water, cooled in an ice-bath and acidified with 1N HCl. The slurry was extracted 3× with ethyl acetate, the combined organic layers was washed with brine, dried over MgSO$_4$, filtered and evaporated to dryness to provide 1.6 g of acid. To a solution of this acid (1.6 g, 4.25 mmol) and 3,4-diamino-benzamide (710 mg, 1.1 eq.) in 20 ml DMF at 0° C. was added HATU (1.8 g, 4.73 mmol, 1.1 eq.) followed by triethyl amine (1.2 ml, 8.61 mmol, 2 eq.). The mixture was stirred at rt for two days then diluted with ethyl acetate. It was washed 3× with water, brine, dried over MgSO$_4$, filtered and concentrated to provide the crude product. This was purified by chromatography using 100% dichloromethane to 10% methanol in dichloromethane as eluent to provide 1.29 g of P19 as a solid.

MS: 510.3 (MH⁺)

Step 4

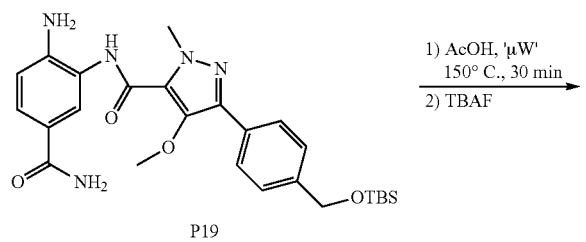

P19

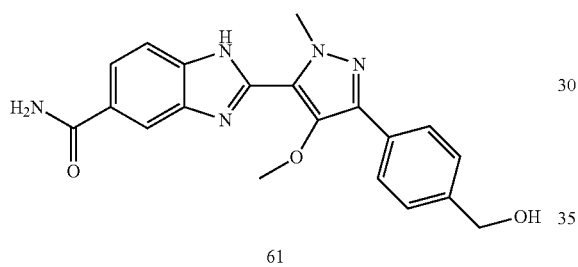

61

A solution of P19 (1.28 g, 2.51 mmol) in 15 ml glacial acetic acid was heated in a microwave reactor at 150° C. for 30 min. The mixture was evaporated to dryness, dissolved in 10 ml of THF and to this was added 5 ml of a 1M solution of TBAF in THF (2 eq.). The mixture was stirred overnight at rt, diluted with ethyl acetate, washed 3× with water, brine, dried over MgSO₄, filtered, concentrated and purified by chromatography using 0% to 10% methanol in dichloromethane as eluent to provide 503 mg of 61 as solid.

MS: 420.2 (MH⁺)

Example 62-63

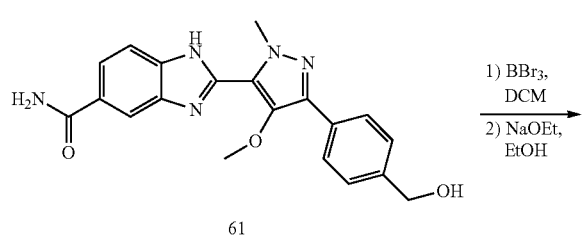

61

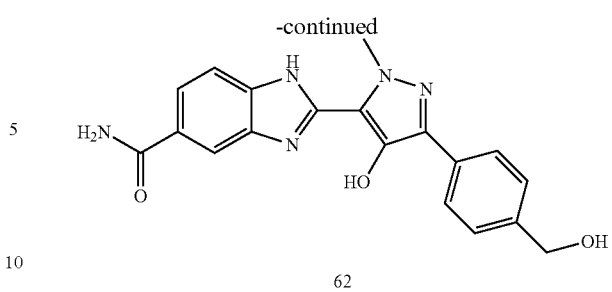

62

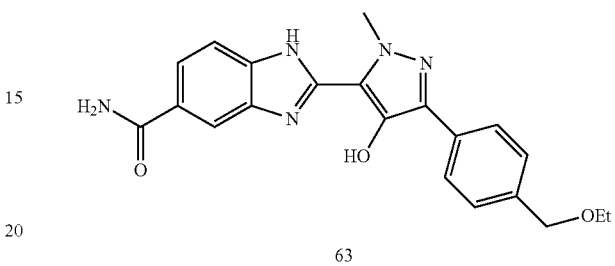

63

To a suspension of example 61 (90 mg, 0.238 mmol) in 3 ml dichloromethane at rt was added BBr₃ (115 µl, 1.22 mmol, 5 eq.) and the mixture was stirred for 3.5 hr at rt. It was quenched with water, solvent evaporated and the solid was filtered and dried. This was taken in 1.5 ml of ethanol, added 2 drops of a solution of sodium ethoxide in ethanol and heated in a microwave reactor at 100° C. for 10 min. The solvent was evaporated and the residue purified by reverse-phase HPLC to obtain 14 mg of 62 and 23 mg of 63. MS for 62: 364.2 (MH⁺) MS for 63: 392.2 (MH⁺)

Example 64

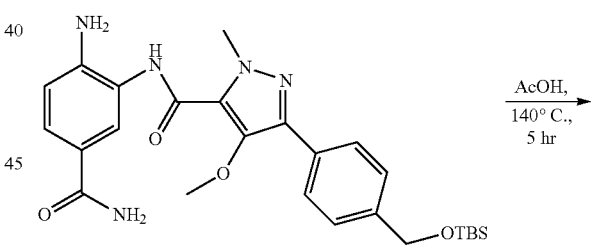

P19

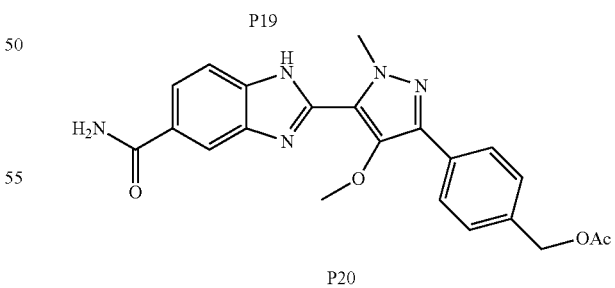

P20

A solution of P19 (~22.6 mmol) in 100 ml of glacial acetic acid was heated in a sealed tube at 140° C. for 5 hr. The solution was concentrated and purified by chromatography using 5% methanol in dichloromethane to provide 5.86 g of P20.

MS: 420.2 (MH⁺)

Example 65

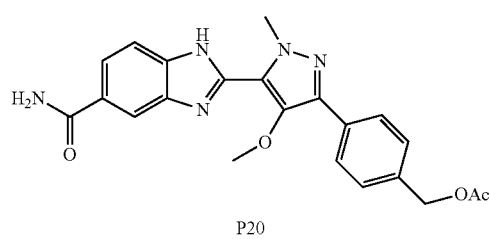

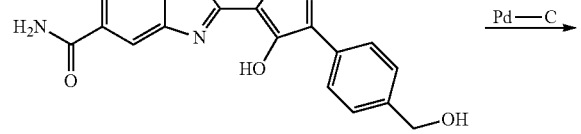

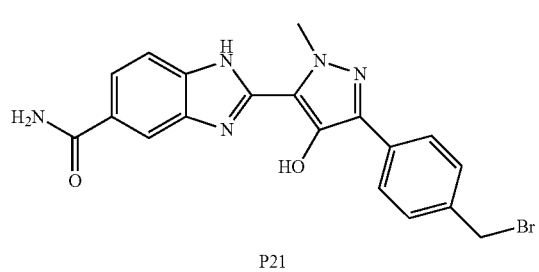

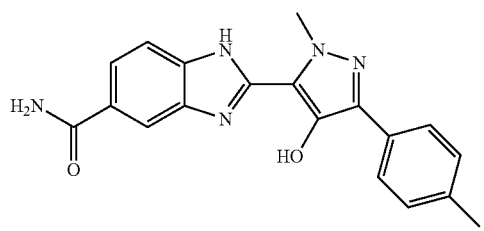

To a solution of P20 (1.15 g, 2.74 mmol) in 30 ml dichloromethane at 0° C. was added BBr$_3$ (1.3 ml, 13.75 mmol, 5 eq.). The resultant slurry was stirred at 0° C. for 1 hr followed by 4 hr at rt. It was quenched by the addition of water, the dichloromethane was evaporated and the precipitate was filtered and washed with water. The solid was dried overnight in a vacuum oven kept at ~40° C. to provide 1.19 g of P21.

A suspension of 62 (15 mg) and 10% Pd—C (15 mg) in 3 ml methanol was stirred under a H$_2$ balloon, filtered though a CELITE pad, concentrated and purified by preparative TLC using 10% methanol in dichloromethane to provide 1.5 mg of 65.

MS: m/e=348.2 (MH$^+$)

Example 66

Step 1

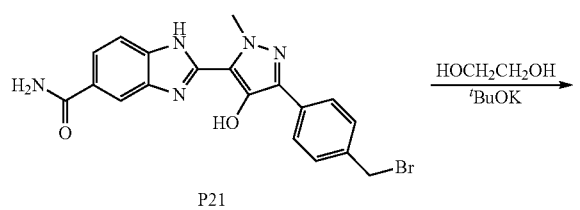

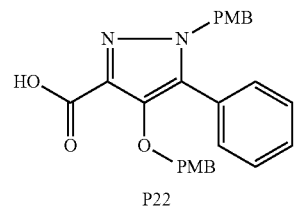

P22 was synthesized using a similar procedure to P6 from P5.

Step 2

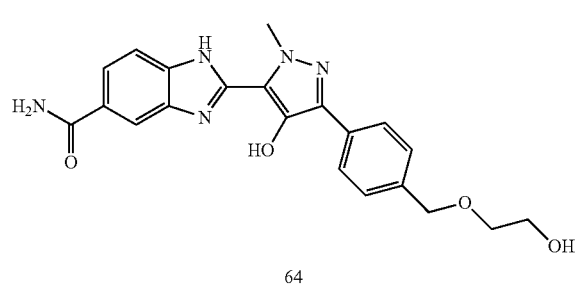

To a solution of P21 (45 mg) in 0.5 ml ethylene glycol was added tBuOK (10 mg) and the mixture was heated in a microwave reactor at 100° C. for 20 min. The mixture was purified by RPHPLC to provide 4 mg of 64.

MS: m/e=408.2 (MH+)

111

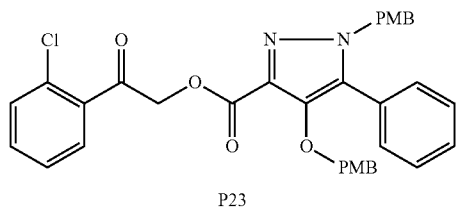

P23

Compound P22 (456 mg, 1.03 mmol) was suspended in EtOH (5 ml), Cs₂CO₃ (334 mg, 1 eq) was added and the mixture heated at 70° C. until it gave a clear solution. The EtOH was removed under reduced pressure, the residue taken up in DMF, and 2-bromo-1-(2-chlorophenyl)ethanone (240 mg, 1 eq) added. The resulting mixture was stirred overnight. The mixture was diluted with EtOAc, washed with water, dried (MgSO₄), and concentrated. The resulting residue was purified by silica gel chromatography (SGC, 0-40% EtOAc in hexanes) to give 271 mg of P23.

Step 3

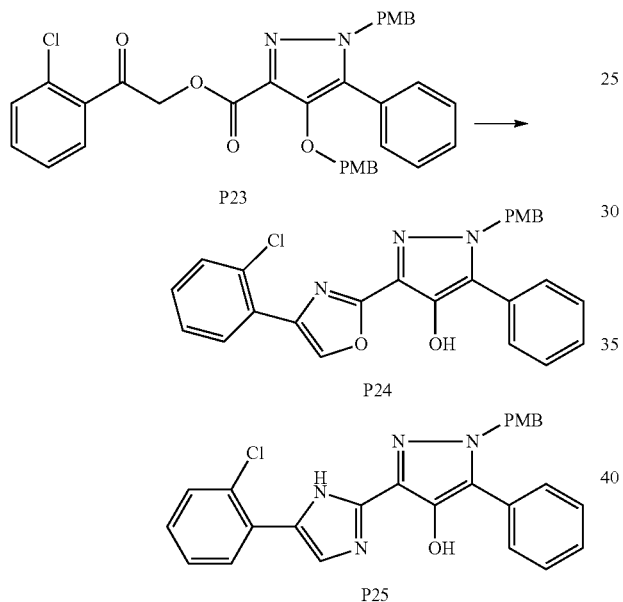

The product from step 2 (P23) (271 mg, 0.46 mmol) was dissolved in AcOH (14 ml), NH₄OAc (800 mg, 30 eq) was added and the mixture heated at 135° C. overnight. The mixture was cooled to room temperature, concentrated under reduced pressure, neutralized with NaHCO₃, and extracted with EtOAc. The organic extracts were dried (MgSO₄), concentrated under reduced pressure and the residue purified by silica gel chromatography (SGC, 0-40% EtOAc in hexanes) to give; in order of elution; P24 26 mg, and B P25 mg.

Step 4

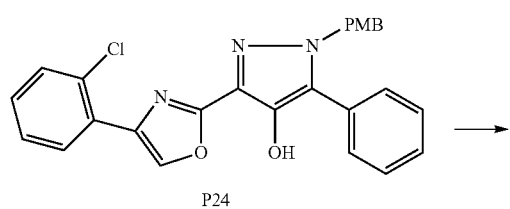

112

-continued

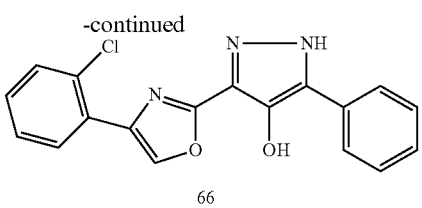

66

Product P24 (from step 2) (26 mg, 0.056 mmol) was dissolved in TFA (3 ml) and heated at 90° C. overnight. After cooling to room temperature the mixture was concentrated under reduced pressure, treated with NaHCO₃(sat), and extracted with EtOAc. Purification by silica gel chromatography (SGC, 0-30% EtOAc in hexanes) gave 4 mg of 66. LCMS: MH⁺=338.2

Example 67

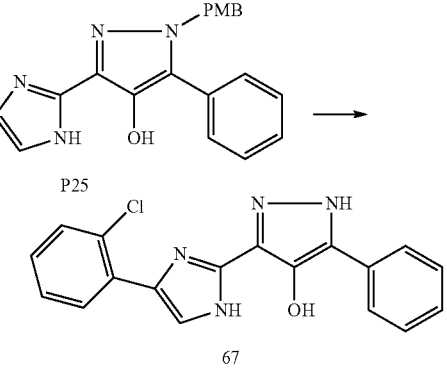

Example 67 was prepared from P25 using a similar procedure to example 66.

LCMS: MH⁺=337.2

Examples 68-72

The following were prepared using the procedures outlined for examples 66 and 67.

| Structure | Example | MS m/e (MH⁺) |
|---|---|---|
| 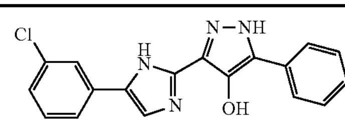 | 68 | 337 |
| 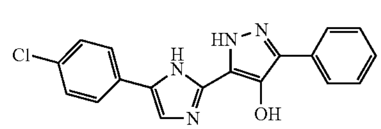 | 69 | 337 |
| 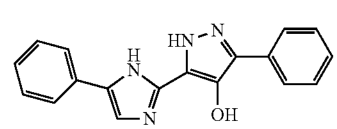 | 70 | 303 |

| Structure | Example | MS m/e (MH+) |
|---|---|---|
| 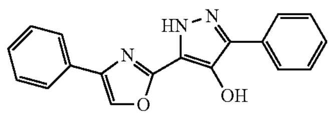 | 71 | 304 |
| 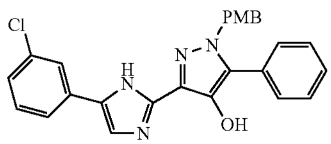 | 72 | 337 |

Example 73

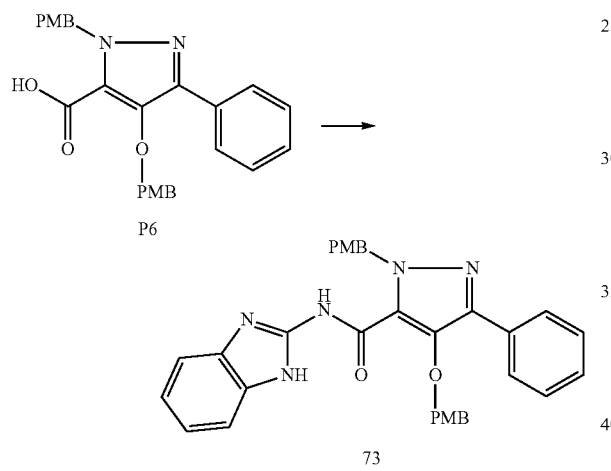

Compound P6 (0.3 g, 0.67 mmol) and 1H-benzo[d]imidazol-2-amine (108 mg, 0.81 mol, 1.2 eq) were dissolved in DMF (3.37 ml). HATU (385 mg, 1.5 eq) and DIPEA (0.18 ml, 1.5 eq) were added and the mixture stirred overnight. NH4Cl (sat) was added and the resulting solid, collected, and purified by silica gel chromatography (SGC, 0-100% EtOAc in hexane) to give 234 mg of 73.
LCMS: MH+=560.3.

Example 74

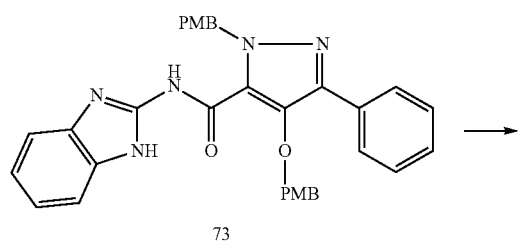

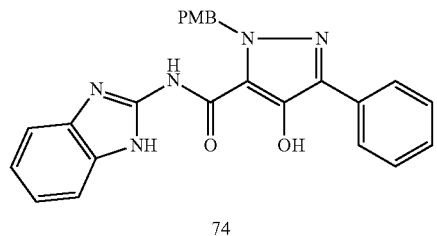

Example 73 (50 mg, 0.09 mmol) was dissolved in AcOH (5 ml) and heated at 90° C. overnight. After cooling to room temperature the mixture was concentrated and purified by reverse-phase HPLC (C18 89.91:9.99:0.1 to 9.99:89.91:0.1H2O:MeCN:HCO2H) to give 23 mg of 74. LCMS: MH+=440.2.

Example 75

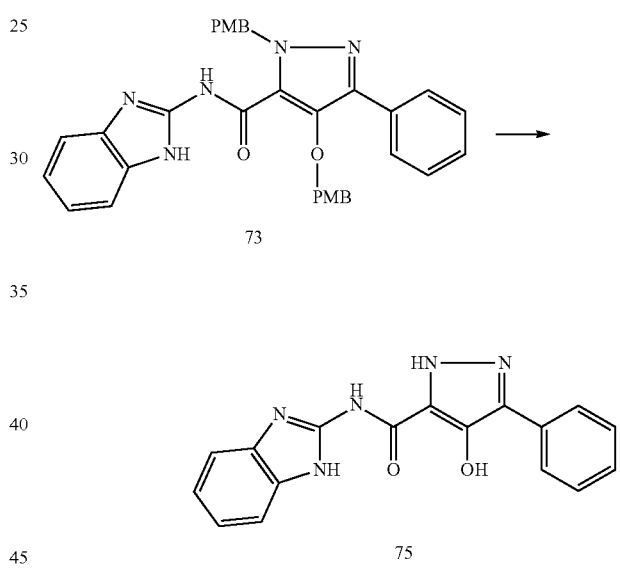

Example 73 (100 mg, 0.18 mmol) was dissolved in TFA (5 ml) and heated at 90° C. for 2 hours. After cooling to room temperature the mixture was concentrated and triturated with CH2Cl2 and the solid collected to give 21 mg of the 75.
LCMS: MH+=320.2.

Example 76

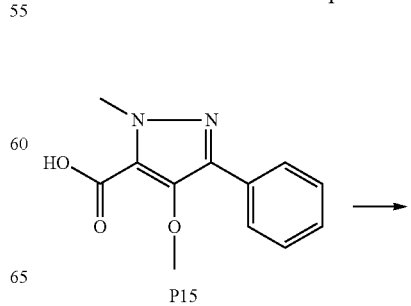

-continued

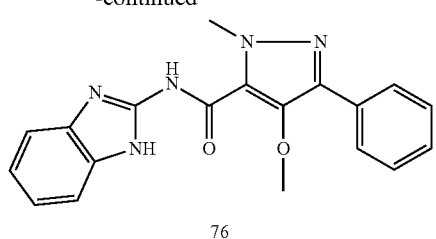

76

Example 76 was synthesized from P15 in a similar manner to example 73.
LCMS: MH⁺=348.2.

Example 77

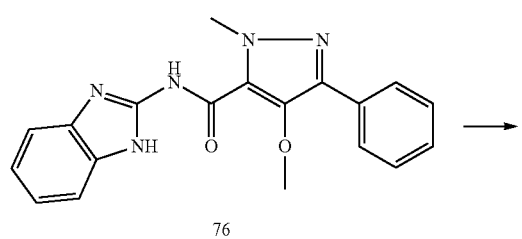

Example 77 was synthesized from example 76 in a similar manner to example 42. LCMS: MH⁺=334.2.

Example 78

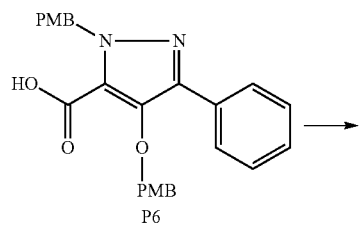
P6

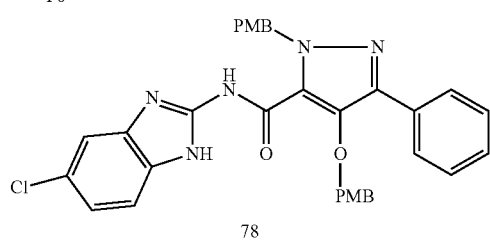
78

Example 78 was synthesized in the same manner as example 73 substituting 5-chloro-1H-benzo[d]imidazol-2-amine as the amine. LCMS: MH⁺=594.3.

Example 79

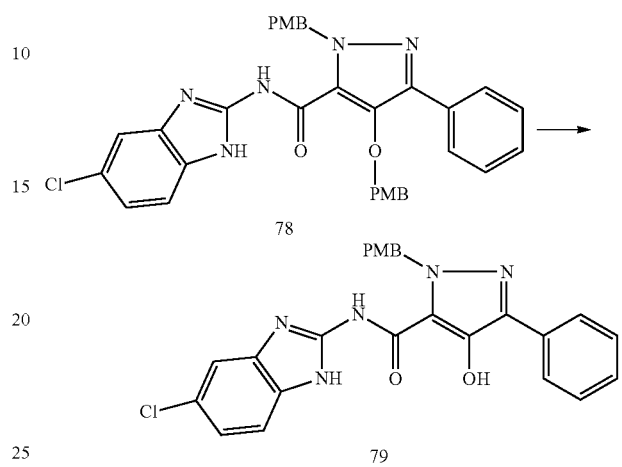

Example 79 was synthesized from example 78 in a similar manner to example 74. LCMS: MH⁺=474.3.

Example 80

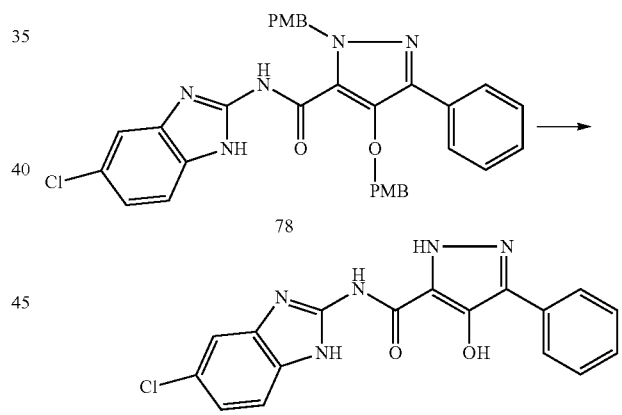

Example 80 was synthesized from example 78 in a similar manner to example 75. LCMS: MH⁺=354.2.

Example 81

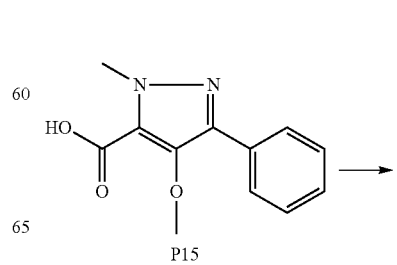
P15

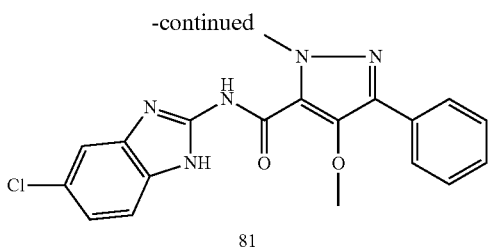

81

Example 81 was synthesized from P15 in a similar manner to example 76 substituting 5-chloro-1H-benzo[d]imidazol-2-amine as the amine. LCMS: MH+=382.2.

Example 82

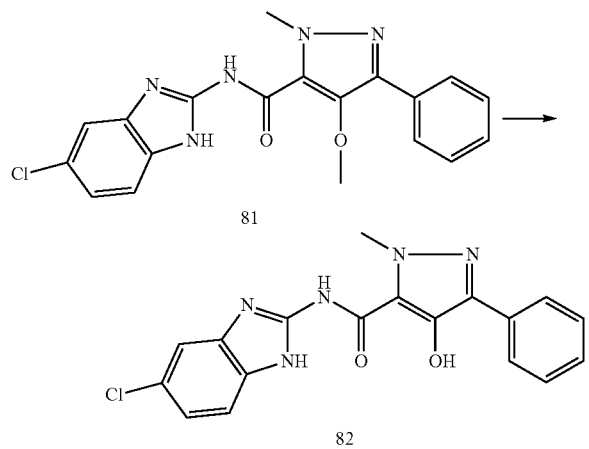

Example 82 was synthesized from example 81 in a similar manner to example 42 LCMS: MH+=368.2

Example 83

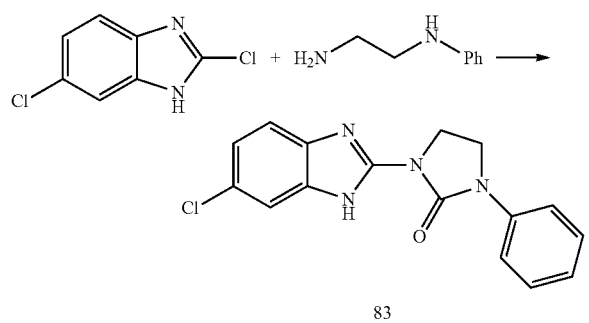

83

A neat mixture of 2,5-dichloro-1H-benzoimidazole (150 mg, 0602 mmol), N-phenyl ethylenediamine (110 mg, 0.808 mmol, 1 eq) and N,N-diisopropylethyl amine (210 mL, 1.21 mmol, 1.5 eq.) in sealed tube was heated overnight at 110° C. The mixture was directly loaded onto a silica gel column and eluted with 5% methanol in dichloromethane to provide 144 mg of N1-(6-chloro-1H-benzo[d]imidazol-2-yl)-N2-phenylethane-1,2-diamine.

A solution of the above product (50 mg, 0.174 mmol), carbonyl diimidazole (37 mg, 0.228 mmol, 1.3 q) in 1 ml THF was heated overnight in sealed tube at 70° C. The mixture was concentrated and purified by preparative chromatography using 5% methanol in dichloromethane to provide 32 mg of 83. MS: m/e=313.2 (MH+)

Examples 84-87

The following compounds were prepared using similar procedure:

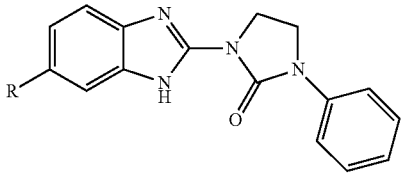

| R | Example | MS m/e (MH+) |
|---|---------|--------------|
| CN | 84 | 304.2 |
| F | 85 | 297.2 |
| CF3 | 86 | 347.2 |
| OMe | 87 | 309.2 |

Example 88-90

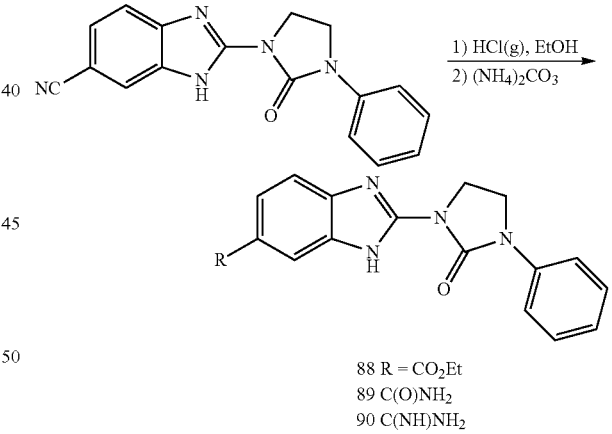

88 R = CO2Et
89 C(O)NH2
90 C(NH)NH2

A solution of example 84 (90 mg) in 5 ml absolute ethanol at 0° C. was bubbled with HCl(g) for 30 min. The flask was stoppered and the mixture was stirred overnight at rt. The solvent was concentrated and diluted with ether. The precipitate was filtered and washed with ether to provide 110 mg of solid. This solid was taken in 5 ml of absolute ethanol and stirred overnight with ammonium carbonate (115 mg, 1.49 mmol, 5 eq.). The mixture was filtered, concentrated to dryness and purified by preparative TLC using 9:1 dichloromethane-7N ammonia in methanol to provide 2 mg of 88 (MS: m/e 351.2 (MH+)), 20 mg of 89 (MS: m/e=322.2 (MH+)) and 47 mg of 90 (MS m/e=321.2 (MH+)).

Example 91

Step 1

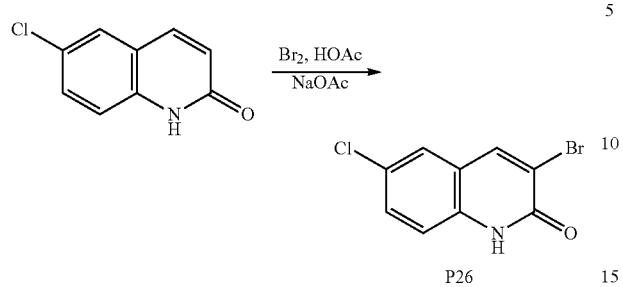

To 1 g of 6-chloro-1H-quinolin-2-one (1) in 100 ml of acetic acid was added 1.43 ml of bromine and 365 mg of sodium acetate. The mixture was heated to 80° C. in a pressure tube for 16 hours then evaporated to dryness. The crude product was triturated in boiling ethanol then filtered providing 1.51 g of P26 as a white solid. MS: m/e=260.1 (MH⁺)

Step 2

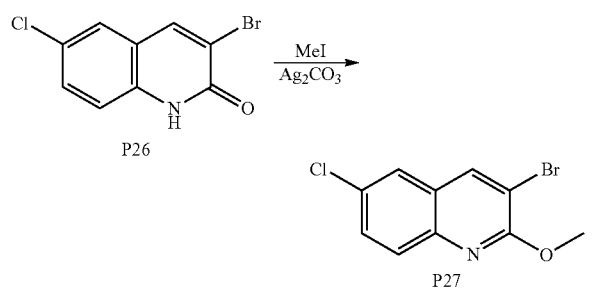

To 450 mg of P26 in toluene was added 433 ul of iodomethane, 960 mg of silver carbonate and the mixture stirred in a flask sealed with a rubber septa and covered with foil. After 14 days the reaction mixture was evaporated to dryness and purified by flash chromatography yielding 269 mg of P27. MS: m/e=274.2 (MH⁺)

Step 3

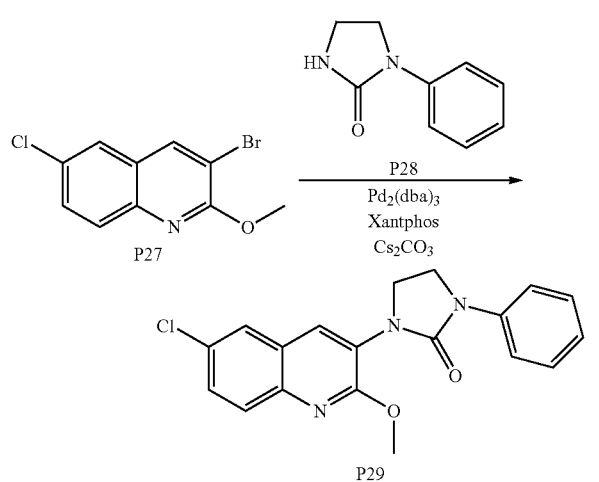

P28 was prepared using the procedures outlined in *Bioorganic and Medicinal Chemistry Letters* 2006, 16, 1486-1490.

To 200 mg of P27 in 2 ml of dry dioxane was added 120 mg of P28, 560 mg of cesium carbonate, 21 mg of Xantphos and 17 mg of Pd₂(dba)₃. After bubbling with argon for one minute, the reaction mixture was heated to 100° C. in a pressure tube for 12 hours. The reaction mixture was poured onto water and extracted with ethyl acetate three times. The combined extracts were washed with brine, dried with MgSO₄, filtered and evaporated to dryness. Purification by flash chromatography yielded 86 mg of P29 as a white solid.
MS: m/e=354.2 (MH⁺)

Step 4

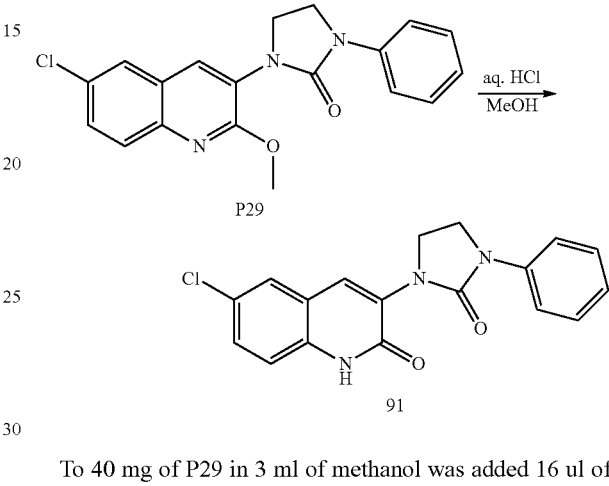

To 40 mg of P29 in 3 ml of methanol was added 16 ul of concentrated aq. HCl and the mixture heated to 70° C. on a pressure tube for 16 hours then evaporated to dryness. The crude product was triturated in boiling isopropanol and 7 mg of 91 was collected by filtration. MS: m/e=340.2 (MH⁺)

Example 92

Step 1

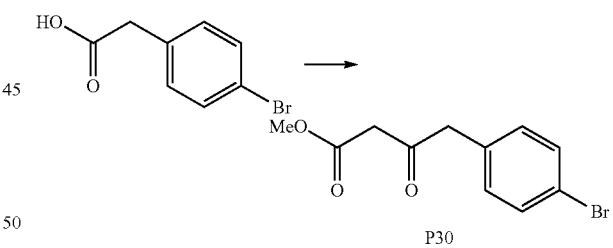

4-Bromophenylacetic acid (7.46 g, 34.7 mmol), EDCI (6.66 g, 1 equiv), and 4-dimethylaminopyridine (1.06 g, 0.25 equiv) were dissolved in CH₂Cl₂ (125 ml) at room temperature under nitrogen. The solution was cooled to 0° C., 2,2-dimethyl-1,3-dioxane-4,6-dione (Meldrum's Acid) (5.00 g, 1 equiv) was added in one portion then warmed to room temperature and let stir overnight. The solution was concentrated under reduced pressure, the residue dissolved in ethyl acetate and washed with 1N HCl (3×), brine (1×), dried (Na₂SO₄) and concentrated under reduced pressure. The residue was dissolved in MeOH (100 mL) and heated at reflux for 16 hours. After cooling to room temperature the solvent was removed under reduced pressure and the residue purified by silica gel chromatography (SGC, 0-50% EtOAc in hexane) to give 5.98 g of P30.

Step 2

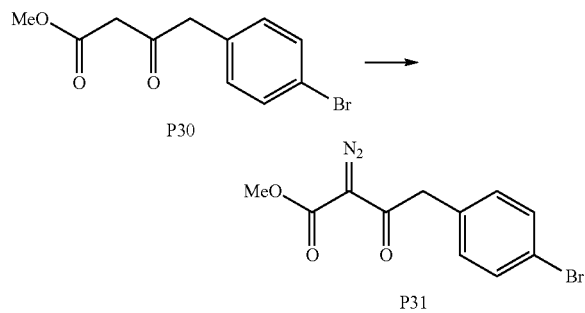

P31 was synthesized using a similar procedure to P2 from P30

Step 3

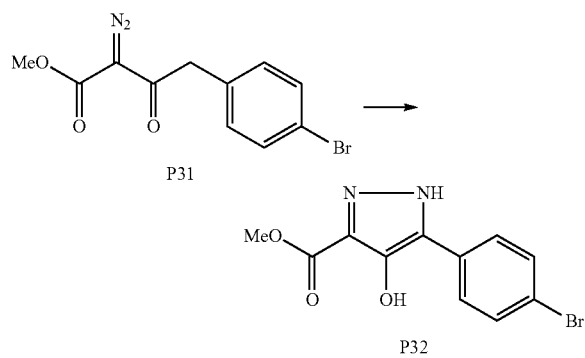

P32 was synthesized using a similar procedure to P3 from P31. MS: (m/z)=399.2 (M+H).

Step 4

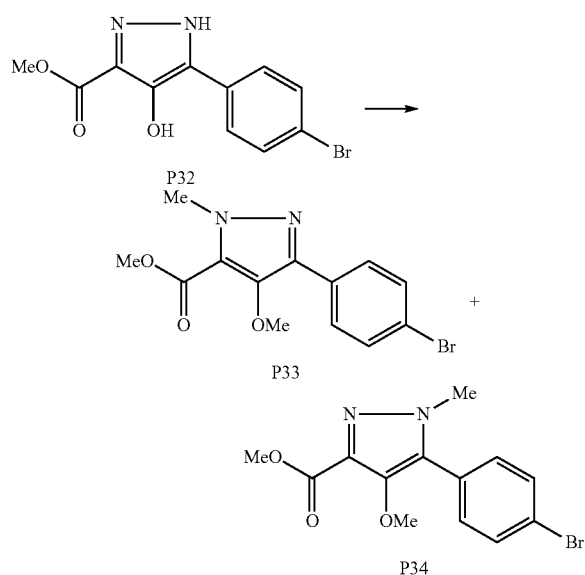

Compounds P33 and P34 were prepared in a similar manner to P4 and P5 substituting methyl iodide for 4-methoxybenzyl bromide. P33: MS: (m/z)=325.2 (M+H) P34: MS: (m/z)=325.2 (M+H)

Step 5

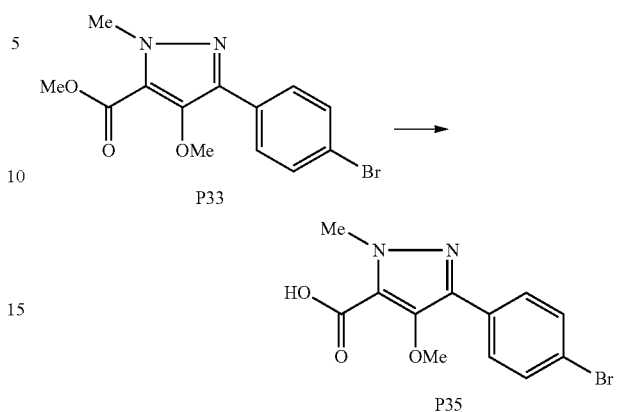

A MeOH (2 mL) solution of P33 (77.0 mg, 0.237 mmol) and LiOH.H$_2$O (84.2, 8.5 equiv) was heated in a microwave at 100° C. for 15 mins. The solution was concentrated under reduced pressure, the residue dissolved in ethyl acetate and washed with 1N HCl (3×), brine (1×), dried (Na$_2$SO$_4$) and concentrated under reduced pressure to provide 71.7 mg of P35 as a white solid. MS: (m/z)=311.2 (M+H).

Step 6

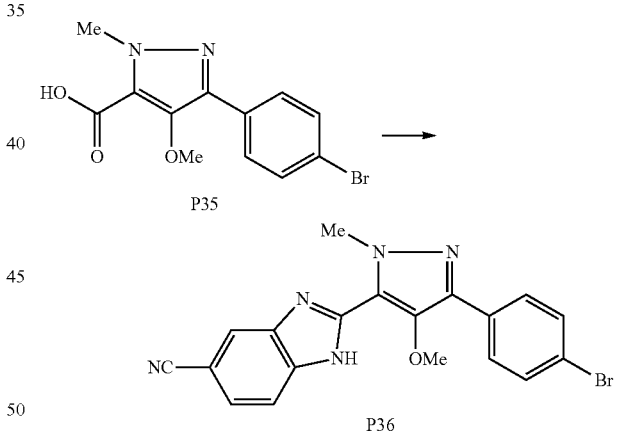

To a DMF (2 mL) solution of P35 (71.7 mg, 0.23 mmol), 3,4-diaminobenzonitrile (34.2 mg, 1.1 equiv) and diisopropylethylamine (84 µL, 2 equiv) at room temperature under nitrogen was added HATU (105.7 mg, 1.2 equiv). After stirring for 16 hours, ethyl acetate and 1N NaOH was added. Let stir for 15 mins, then the two layers were separated and the aqueous layer back extracted with ethyl acetate (2×). The combined organic layers were then washed with water (2×), brine (1×), dried (Na$_2$SO$_4$) and concentrated under reduced pressure to provide the coupled product. The product was then dissolved in acetic acid (3 mL) and heated in a microwave at 150° C. for 45 mins. The solution was then concentrated under reduced pressure to provide 43.5 mg of P36. MS: (m/z)=408.2 (M+H).

Step 7

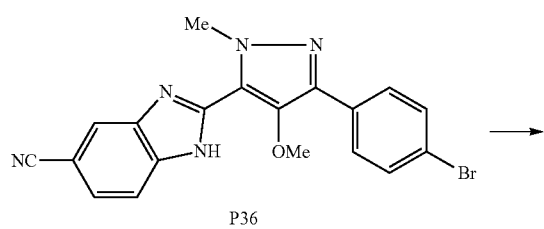

P36

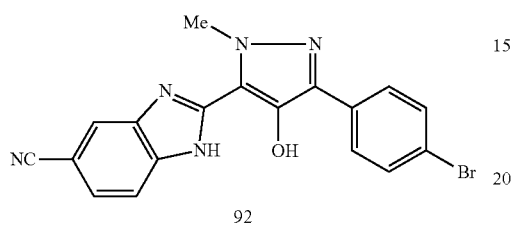

92

92 was synthesized using a similar procedure to example 41 from P36. MS: (m/z): 394.2 (M+H).

Example 93

Step 1

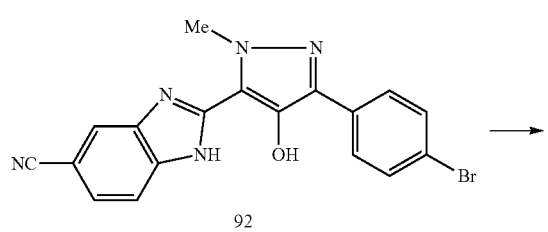

92

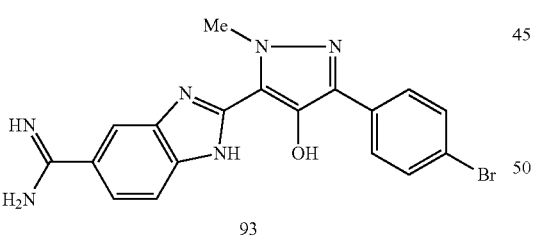

93

Acetyl chloride (1.62 mL, 213 equiv) was added dropwise to an ethanol (2 mL, 320 equiv) suspension of 92 (42 mg, 0.107 mmol) at 0° C. under nitrogen. The reaction was sealed and let stir for 3 days at room temperature. The reaction was concentrated under reduced pressure to give a grey solid which on cooling to 0° C. was treated with 7N ammonia in methanol (3 mL). The reaction was resealed and let stir at room temperature overnight. The solution was then concentrated under reduced pressure. Additional methanol was then added and the solution concentrated under reduced pressure again. This was repeated a total of 3×, then the residue was purified by reverse phase HPLC to obtain 17.6 mg of 93. MS: (m/z): 411.2 (M+H).

Example 94

Step 1

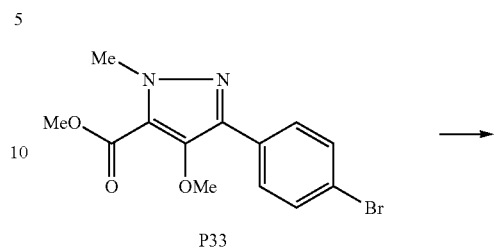

P33

P37

A (10:1) ethanol-water (2.2 mL) suspension of P33 (97.6 mg, 0.300 mmol), phenyl boronic acid (43.9 mg, 1.2 equiv), potassium carbonate (50.2 mg, 1.2 equiv) and polymer bound di(aceto)dicyclohexylphenylphosphine palladium (II) (~5% Pd, 90 mg) was heated in a microwave at 110° C. for 30 mins. Then LiOH H$_2$O (83 mg, 6.6 equiv) was added and the mixture was heated in a microwave at 100° C. for 15 mins. The products were filtered, the solvent removed under reduced pressure and the residue purified by reverse phase HPLC to give 46.1 mg of P37. MS: (m/z): 309.2 (M+H).

Step 2

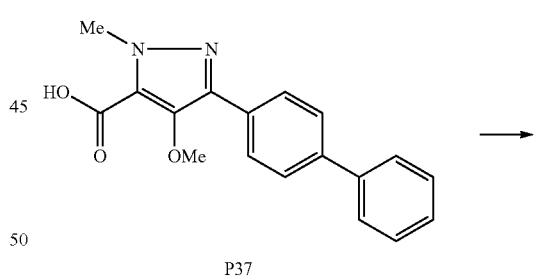

P37

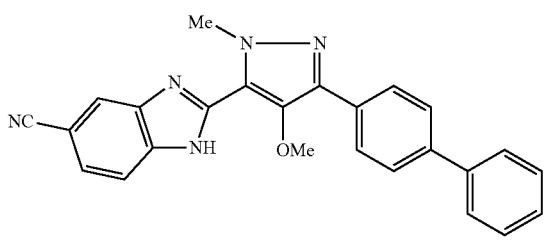

P38

P38 was synthesized using a similar procedure to P36 from P37. MS: (m/z)=406.2 (M+H).

Step 3

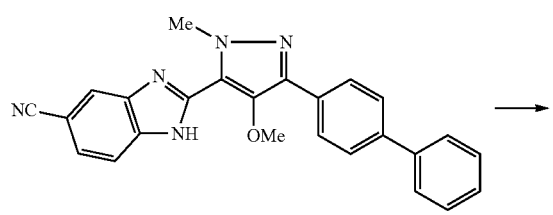

P38

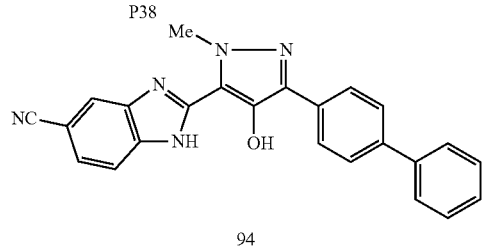

94

94 was synthesized using a similar procedure to example 41 from P38. MS: (m/z): 392.2 (M+H).

Example 95

Step 1

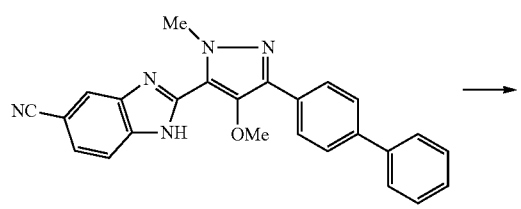

94

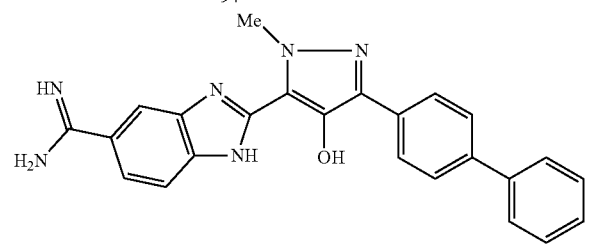

95

95 was synthesized using a similar procedure to example 93 from 94. MS: (m/z): 409.2 (M+H).

Example 96

Step 1

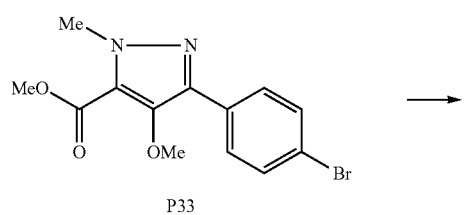

P33

-continued

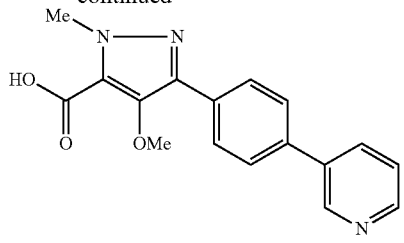

P39

P39 was synthesized using a similar procedure to P37 from P33. MS: (m/z)=310.2 (M+H).

Step 2

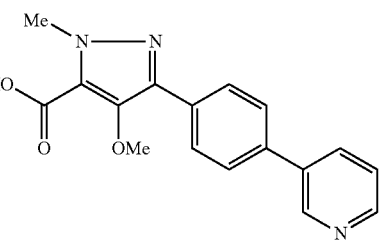

P39

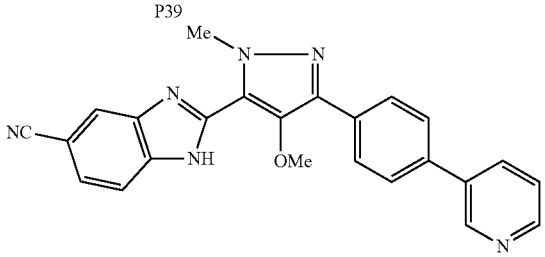

P40

P40 was synthesized using a similar procedure to P36 from P39. MS: (m/z)=407.2 (M+H).

Step 3

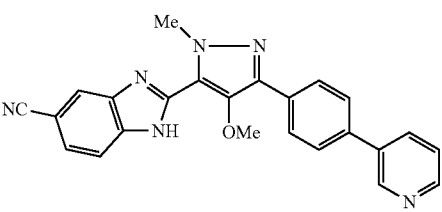

P40

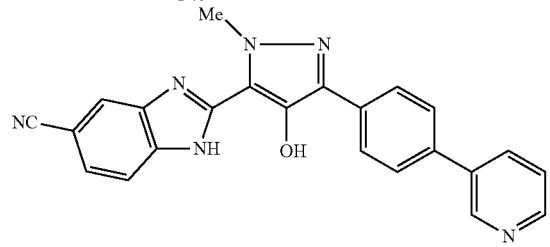

P41

A 1M solution of BBr$_3$ in dichloromethane (0.4 mL, 6 equiv) was added dropwise to a dichloromethane (2.5 mL) solution of P40 (27.0 mg, 0.0665 mmol) at 0° C. under nitrogen. After stirring for 15 mins at 0° C. the suspension was warmed to room temperature and let stir for 2 hrs. The reaction was quenched with water (1 mL) and then concentrated under reduced pressure. The residue was taken up in 2N ammonia in methanol (3 mL) and stirred for 10 mins. The solvent was then concentrated under reduced pressure. The residue was partitioned between ethyl acetate and water. A yellow solid crashed out and this was collected by filtration and found to be P41. The two layers were then separated, with the aqueous layer back extracted with ethyl acetate (2×). The combined organic layers were then dried (Na$_2$SO$_4$) and concentrated under reduced pressure to provide P41. The two batches of P41 were then combined. MS: (m/z): 393.2 (M+H).

Step 4

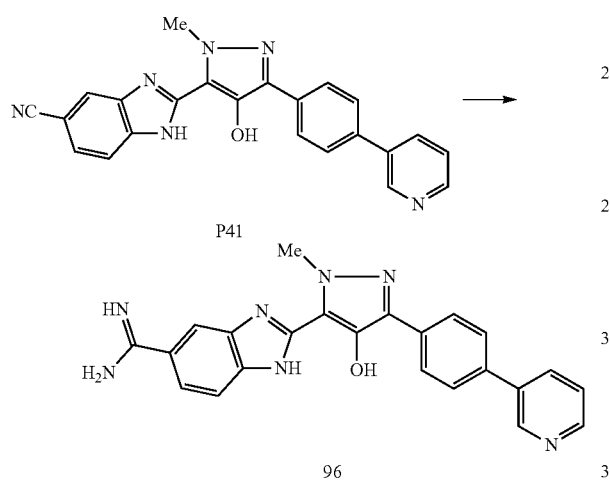

96 was synthesized using a similar procedure to example 93 from P41. MS: (m/z): 410.2 (M+H).

Example 97

Step 1

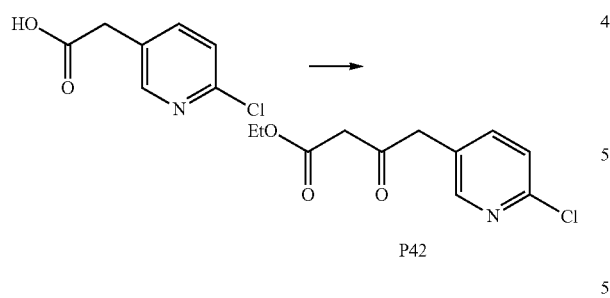

To a THF (250 mL) solution of 2-chloropyridine-5-acetic acid (10.00 g, 58.28 mmol) at room temperature under nitrogen was added N,N-carbonyldiimidazole (10.87 g, 1.15 equiv). The mixture was stirred at room temperature overnight, then magnesium 3-ethoxy-3-oxopropanate (20.04 g, 1.2 equiv) was added and resultant mixture was stirred at room temperature for 3 days. Ethyl acetate and 1N NaOH were added and let stir at room temperature for 15 mins. The two layers were then separated and the aqueous layer back extracted with ethyl acetate (2×). The organic layers were then combined, dried (Na$_2$SO$_4$) and concentrated under reduced pressure. The residue was purified by silica gel chromatography (SGC, 0-5% 2N NH$_3$/MeOH in dichloromethane) to give 11.09 g of P42. MS: (m/z)=242.1 (M+H).

Step 2

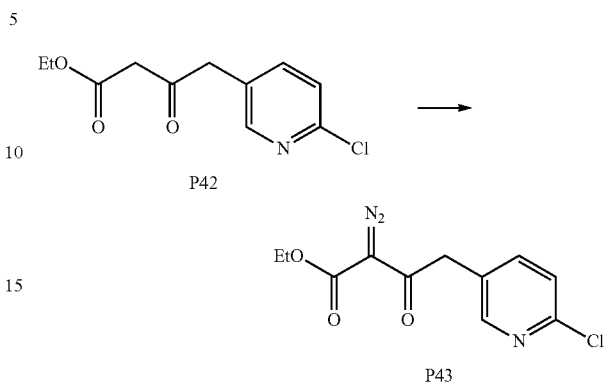

P43 was synthesized using a similar procedure to P2 from P42

Step 3

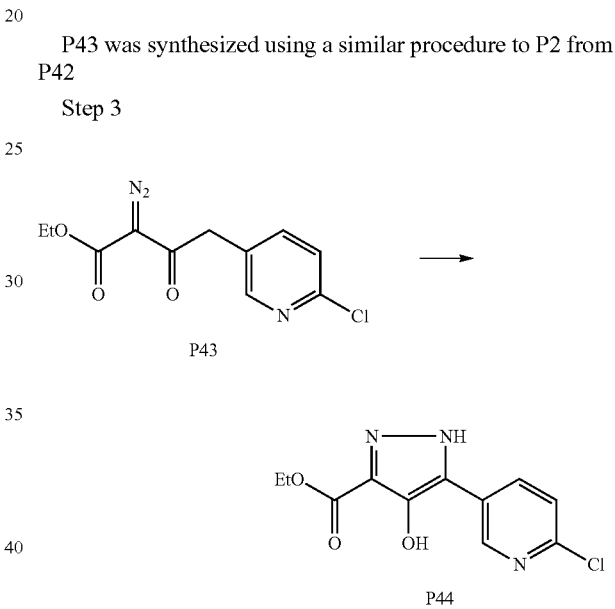

P44 was synthesized using a similar procedure to P3 from P43. MS: (m/z)=268.1 (M+H).

Step 4

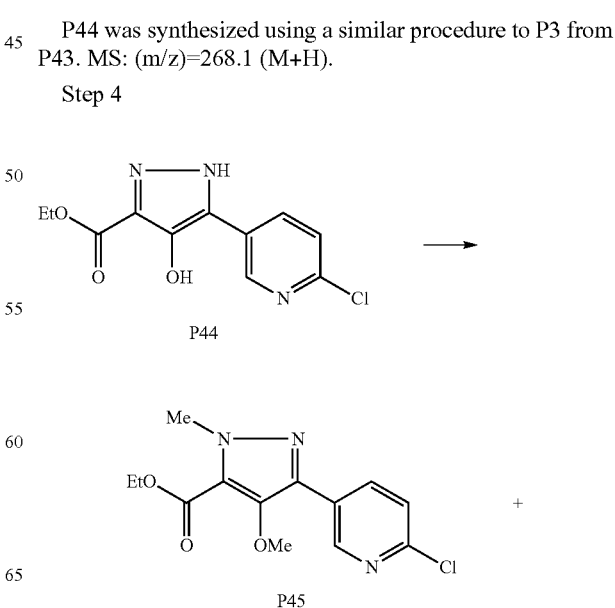

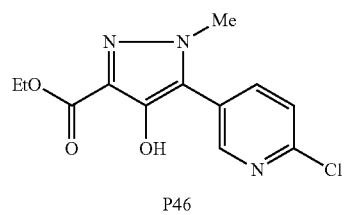

P46

Compounds P45 and P46 were prepared in a similar manner to P4 and P5 substituting methyl iodide for 4-methoxybenzyl bromide. P45: MS: (m/z)=396.2 (M+H)P46: MS: (m/z)=396.2 (M+H)

Step 5

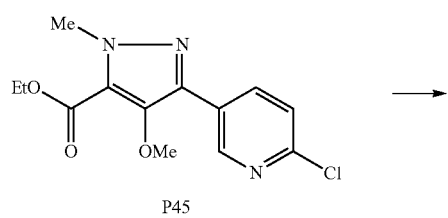

P45

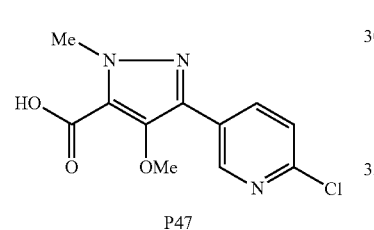

P47

P47 was synthesized using a similar procedure to example P35 from P45. MS: (m/z): 268.1 (M+H).

Step 6

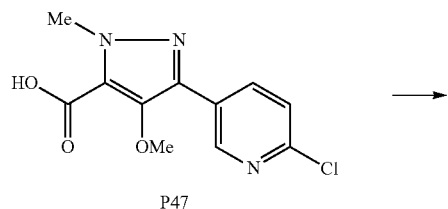

P47

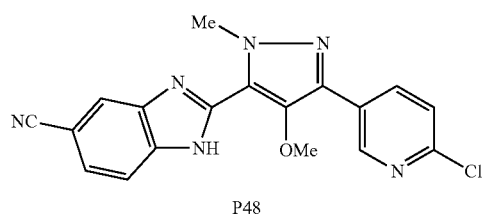

P48

P48 was synthesized using a similar procedure to example P36 from P47. MS: (m/z): 365.2 (M+H).

Step 7

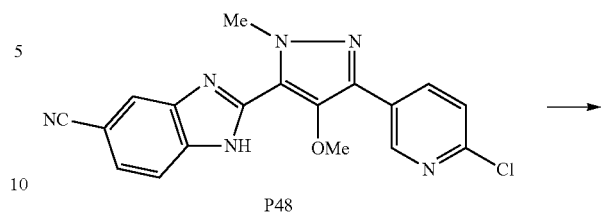

P48

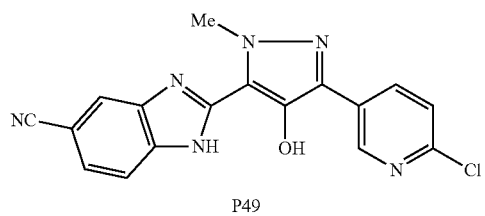

P49

P49 was synthesized using a similar procedure to P41 from P48. MS: (m/z): 351.2 (M+H).

Step 8

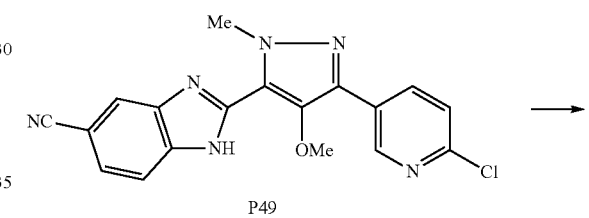

P49

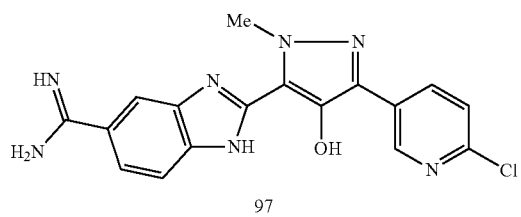

97

97 was synthesized using a similar procedure to example 93 from P49. MS: (m/z): 368.2 (M+H).

Example 98-99

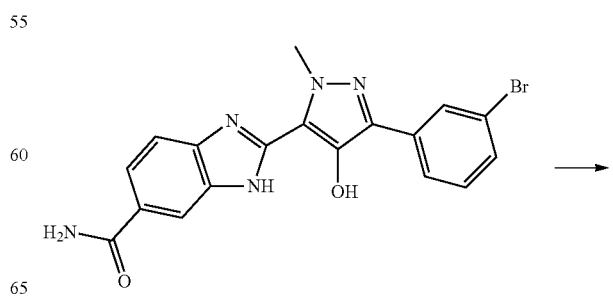

98

-continued

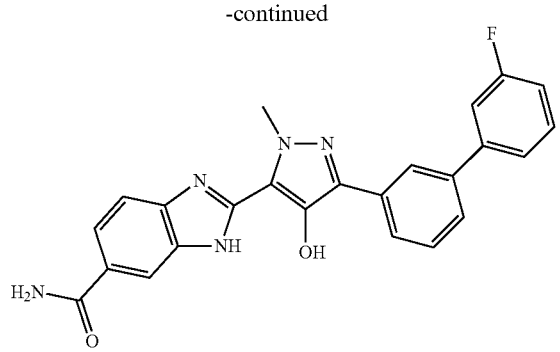

99

To 25 mg of 98 (synthesized in a similar manner to compounds previously described) in 3 mL of 1:1 ethanol/DME was added 11 mg of 3-fluorophenyl boronic acid, 25 mg of cesium carbonate and 25 mg of polymer bound di(acetato) dicyclohexylphenylphosphinepalladium (II). After bubbling with argon for one minute the reaction mixture was heated to 110° C. for 50 minutes in a sealed tube using a microwave reactor. The reaction mixture was filtered through 500 mg of silica gel which was washed with methanol. The filtrate was then evaporated to dryness and the residue purified by reversed phase HPLC yielding 7 mg of 99.

MS: 428.2 (MH$^+$)

Example 100-101

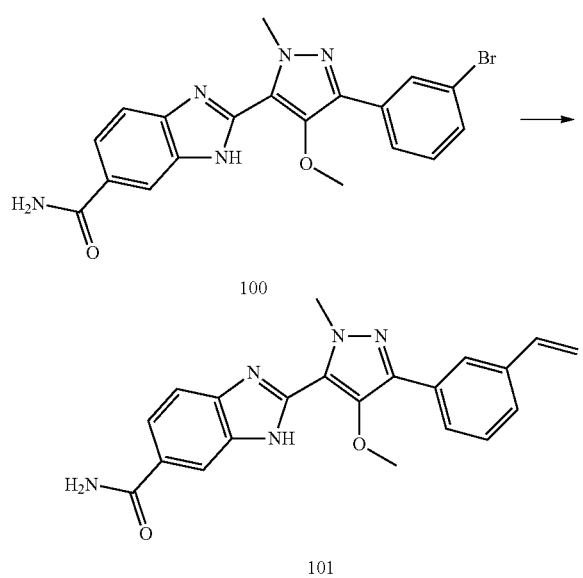

To 100 mg of 100 (synthesized in a similar manner to compounds previously described) in 1.5 mL of DME was added 27 mg of tetrakis(triphenylphosphine)palladium and 103 uL of tributylvinylstannane. After bubbling with argon for one minute the reaction mixture was heated to 100° C. for 60 minutes in a sealed tube using a microwave reactor. The reaction mixture was filtered through 250 mg of C-18 resin which was washed with methanol. The filtrate was then evaporated to dryness and the residue purified by reversed phase HPLC yielding 7 mg of 101.

MS: 374.2 (MH$^+$)

Example 102

Step 1

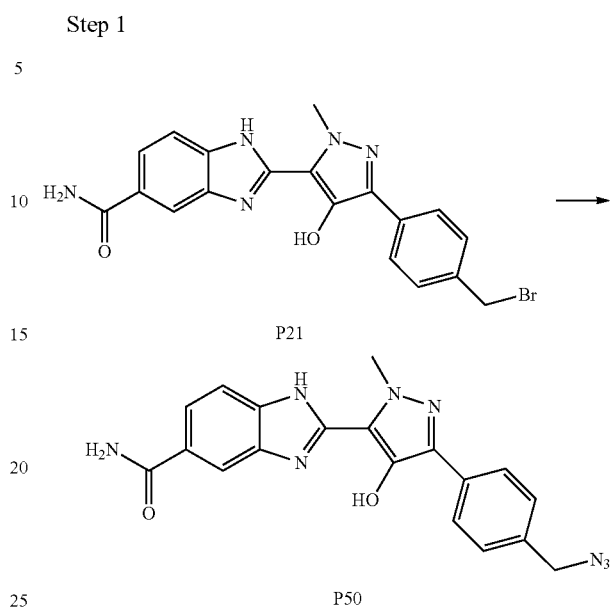

A mixture of P21 (0.98 g, 2.30 mmol) and NaN$_3$ (1.5 g, 23.0 mmol, 10 eq) in 10 ml DMSO was heated at 70° C. for 10 hr. The mixture was diluted with water, extracted 3× with ethyl acetate, the combined organic layer washed brine and evaporated to dryness. The crude product was dry loaded onto silica gel and chromatographed using 0% to 20% MeOH in dichloromethane to provide 310 mg of product P50.

MS: 389.2 (MH$^+$)

Step 2

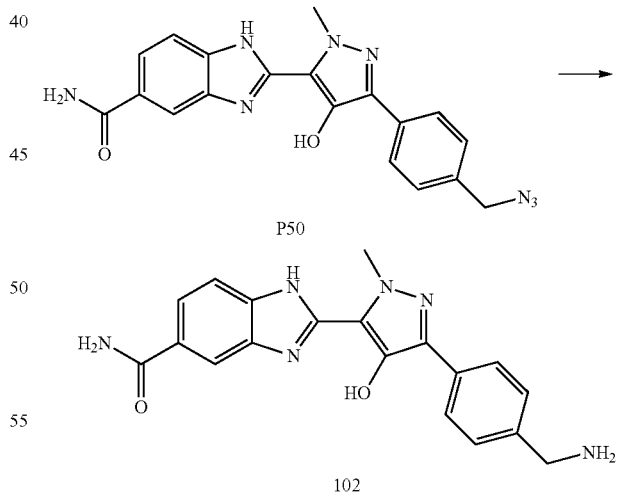

To a solution of P50 (0.88 g, 2.26 mmol) in 20 ml ethyl acetate and 1 ml water was added a 1M solution of trimethyl phosphine in THF (6.8 ml, 6.8 mmol, 3 eq.) and the mixture was stirred overnight at rt. The solvent was evaporated to dryness and the residue was purified by reverse phase HPLC to provide 365 mg of 102.

MS: 363.2 (MH$^+$)

Example 103
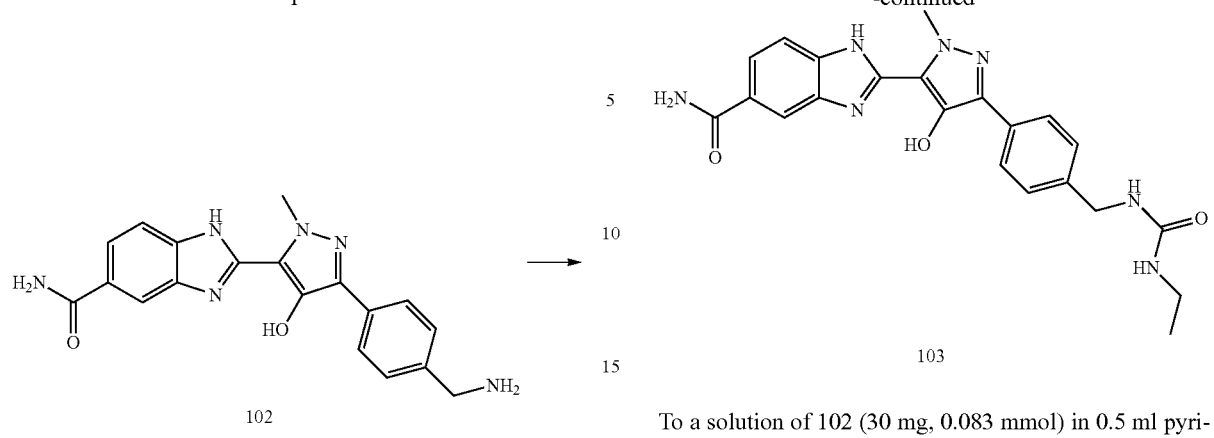
To a solution of 102 (30 mg, 0.083 mmol) in 0.5 ml pyridine at rt was added ethyl isocyanate (8 μL, 0.102 mmol, 1.2 eq). The mixture was stirred at rt for 3 hr, concentrated to dryness and purified by reverse phase HPLC to provide 10 mg of 103.
MS: 434.2 (MH$^+$)
Using a similar procedure to the above, the following compounds were prepared:
| Structure | Example | MS m/e (MH$^+$) |
|---|---|---|
| 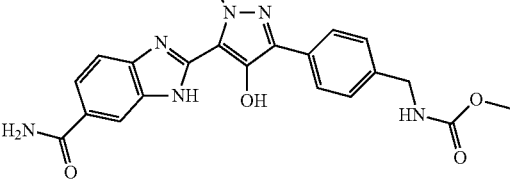 | 104 | 421.2 |
| 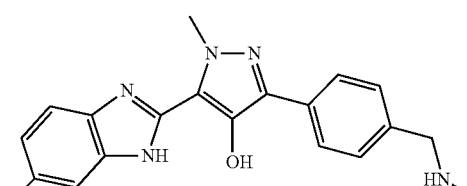 | 105 | 441.2 |
| 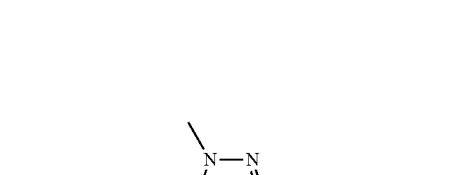 | 106 | 405.2 |

-continued

| Structure | Example | MS m/e (MH+) |
|---|---|---|
| 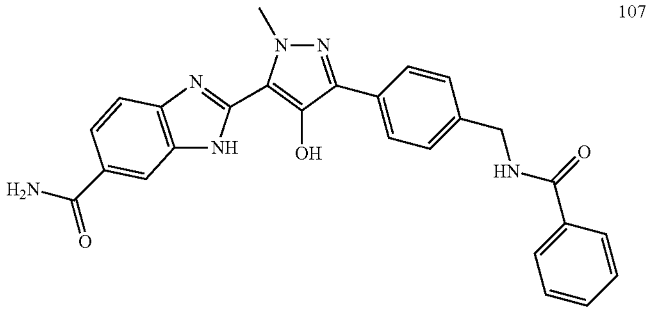 | 107 | 467.3 |
| 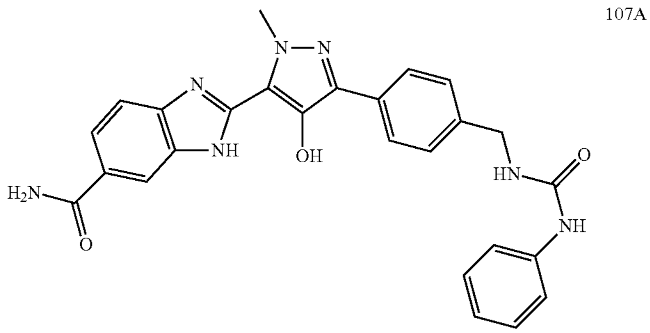 | 107A | 459.3 |

Example 108

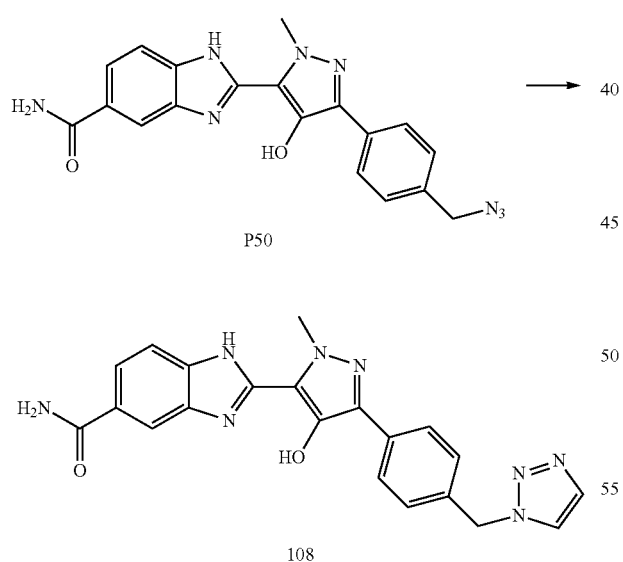

A solution of P50 (250 mg) in 5 ml DMF and 0.5 ml trimethylsilyl acetylene was heated in a sealed tube at 100° C. for about 24 hr. The mixture was diluted with ethyl acetate, washed 3× with water, brine, dried over MgSO$_4$, filtered and dried to give the crude product. The crude product was stirred with 1M solution of TBAF in THF (1.4 ml, 1.4 mmol, 3 eq). The mixture was diluted with ethyl acetate, washed 3× with water, brine, dried, filtered and evaporated to give 100 mg of product 108. The aqueous phase, which contained some insoluble materials, was filtered and the solid dried under vacuum oven to provide another 65 mg of 108.

MS: 415.2 (MH$^+$)

Example 109

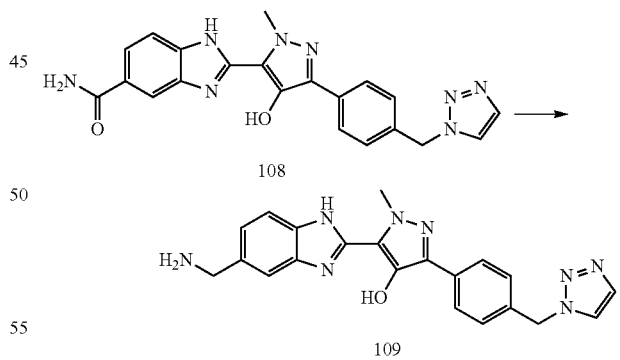

To a solution of 108 (95 mg, 0.229 mmol) in 5 ml THF was added 2M solution of BH$_3$.SMe$_2$ complex in THF (1.15 ml, 2.3 mmol, 10 eq) followed by BF$_3$.OEt$_2$ complex (0.28 ml, 2.27 mmol, 10 eq.). The mixture was heated at reflux for 6 hr, cooled to rt, quenched with MeOH and concentrated to dryness. The residue was heated at reflux with 2 ml of 6N HCl for 1 hr and purified by reverse phase HPLC to provide 47 mg of 109.

MS: 401.2 (MH$^+$)

Examples 110-111

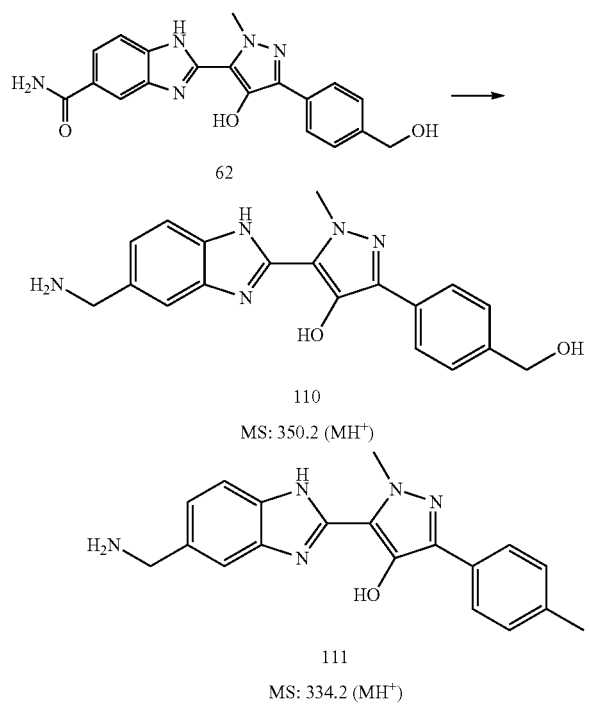

Using the above reduction condition, 90 mg of 62 was reduced to give 14 mg of 110 and 2 mg of 111.

Example 112

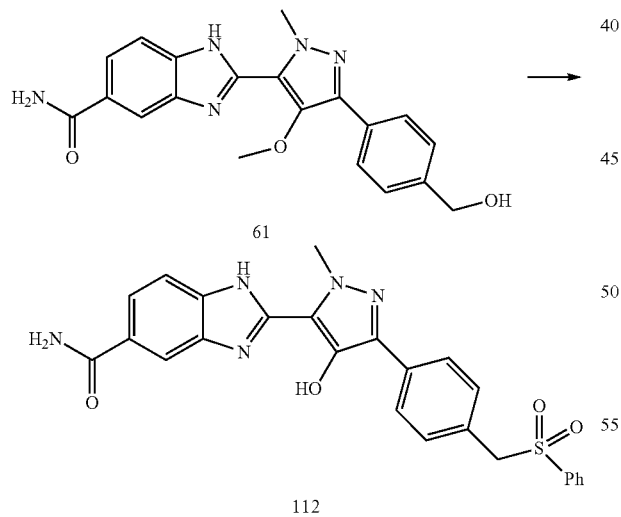

A mixture of 61 (540 mg, 1.43 mmol) and PhSNa (950 mg, 7.12 mmol) in 10 ml DMF was bubbled with argon and heated overnight in a sealed tube at 160° C. The mixture was cooled to rt, stirred with 20 ml of aq. hydrogen peroxide solution for about 2 min and diluted with water. The solution was acidified with 1N HCl, extracted 4× with ethyl acetate, combined organic layer washed with brine, dried over $MgSO_4$, filtered and concentrated. The crude product was initially purified by silica gel chromatography using 0% to 20% 7N $NH_3$/MeOH and dichloromethane followed by purification by reverse phase HPLC to provide 9 mg of 112.

MS: 488.3 (MH$^+$)

The starting compound P51 was synthesized by from P15 using methods described for Example 33 step 2 and Example 41.

Example 113

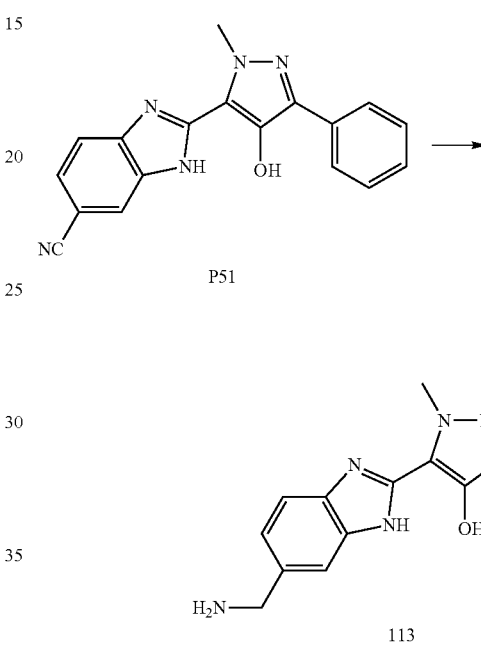

P51 (60 mg, 0.19 mmol) was hydrogenated at 50 psi in the presence of Raney nickel (550 mg) in 6 ml of MeOH/$NH_3$ at ambient temperature. After 2 h the catalyst was filtered and the filtrate concentrated in vacuo. The residue was dissolved in acetonitrile, DMSO and 2 drops of formic acid were added to help make the sample a clear solution for HPLC purification. Reverse phase HPLC (10:90-90:10 MeCN/$H_2O$) to give the 13 mg of 113. ESI-MS (m/z): 320 [M+H]$^+$

Example 114

The starting compound P52 was synthesized from 37 by the method described for Example 41.

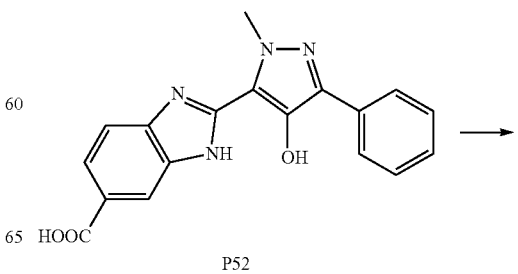

-continued

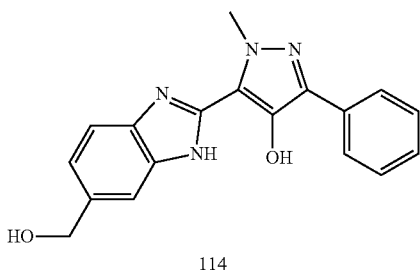

114

P52 (80 mg, 0.239) was added to borane (1.0 M in THF, 0.598 ml, 2.5 equiv.) in 2.0 ml THF at 0° C. The solution was stirred at RT for 2 h and cooled to 0° C. $H_2O$ was added slowly and the resulting solution was concentrated by rotary evaporation. The residue was diluted with EtOAc and the organic phase was washed with dilute sodium hydroxide., the aqueous layer was extracted with $CH_2Cl_2$. The combined extracts were dried over $MgSO_4$ and purified by reverse phase HPLC (10:90-90:10 MeCN/$H_2O$) to give the 7.0 mg of 114. ESI-MS (m/z): 321 [M+H]$^+$ Example 115-116

Step 1

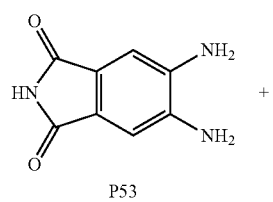

P53

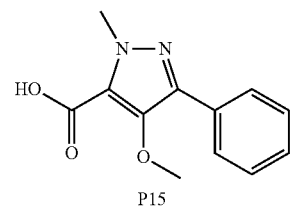

P15

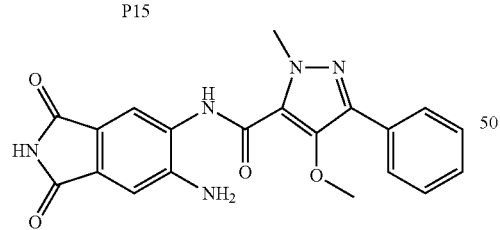

P54

To a solution of P53 (0.5 g, 2.82 mmol) and P15 (0.65 g, 2.80 mmol) in DMF (25 mL) was added HATU (1.30 g, 3.38 mmol) and DIPEA (0.74 mL, 4.23 mmol). The reaction mixture was stirred at room temperature overnight. Solvent was removed under reduced pressure. The crude product was diluted with ethyl acetate. The organic layer was washed with 1 N sodium hydroxide solution and saturated brine. The organic layer was dried over sodium sulfate. Solvent was evaporated under reduced pressure. The crude product was used in the next step without further purification.

Step 2

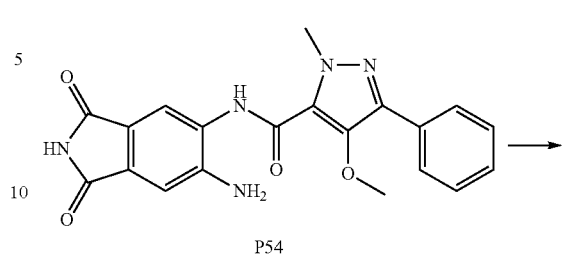

P54

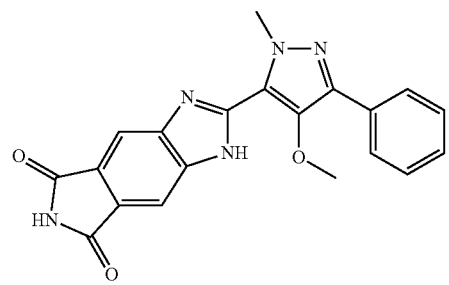

P55

To a sample of P54 (0.56 g, 1.43 mmol) was added acetic acid (30 mL). The reaction mixture was heated in a microwave reactor at 150° C. for 1 hour. The solid crude product was filtered and washed with methanol followed by a solution of methanolic dichloromethane (1:9 v/v). The crude product was used in the next step without further purification.

Step 3

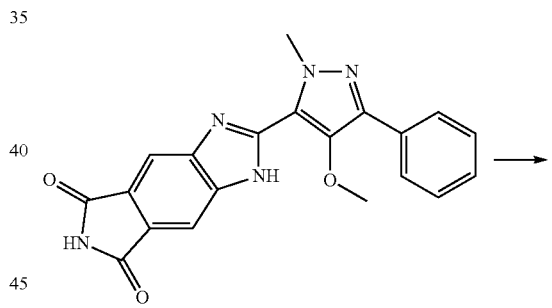

P55

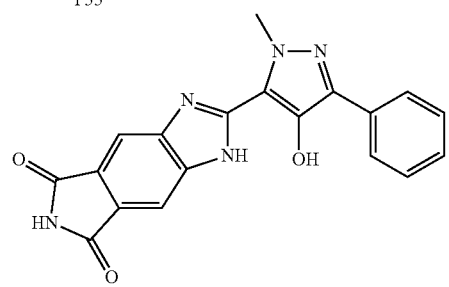

115

To a suspension of P55 (0.23 g, 0.62 mmol) in dichloroethane (30 mL) at 0° C. was added a DCM solution of boron tribromide (1.0 M, 4.8 mL). The reaction mixture was allowed to warm to room temperature. The reaction mixture was heated at 80° C. for 2 hours. Solvent was evaporated under reduced pressure. The crude product was used in the next step without further purification.

Step 4

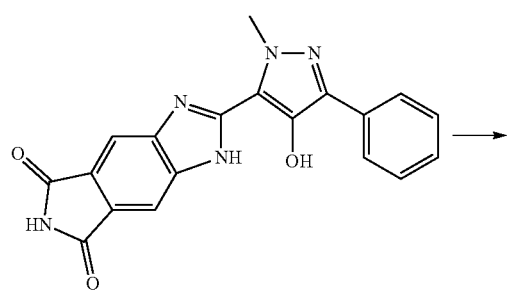

115

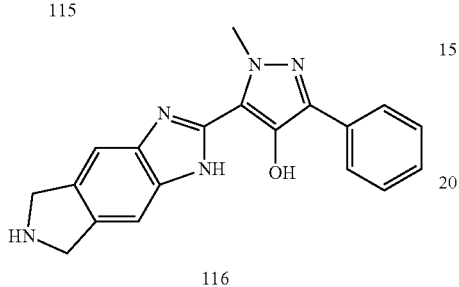

116

To a sample of 115 (0.15 g, 0.42 mmol) in anhydrous THF (2 mL) at 0° C. was added a THF solution of borane-dimethylsulfide (2.0 M, 20 mL). The reaction mixture was allowed to warm to room temperature. The reaction mixture was stirred at room temperature for 2 hours. The reaction mixture was heated at 80° C. for 2 hours. The reaction mixture was allowed to cool to room temperature and methanol (50 mL) was added. The reaction mixture was stirred at room temperature overnight. Hydrochloric acid (12 N, 20 mL) was added. The reaction mixture was heated at 80° C. for 1 hour. Solvent was evaporated under reduced pressure. The crude product was diluted with methanol (50 mL) and dichloromethane (50 mL). The crude product solution was basified with ammonium hydroxide. Solvent was evaporated under reduced pressure. The crude product was purified by RP-HPLC to afford the desired 116 (0.045 g, 0.14 mmol). LCMS MH$^+$=332.2.

The following compounds were synthesized using procedures similar to those outlined previously.

| Structure | Example | MS m/e (MH$^+$) |
|---|---|---|
| 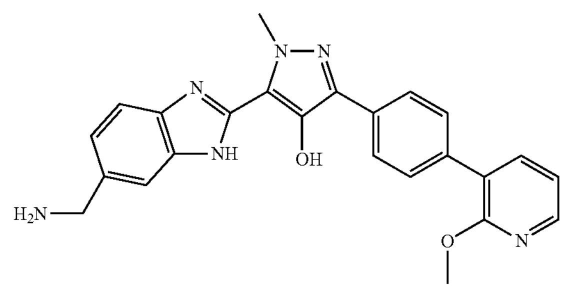 | 117 | 427.2 |
| 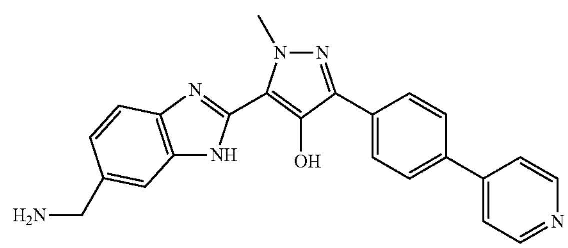 | 118 | 397.2 |
| 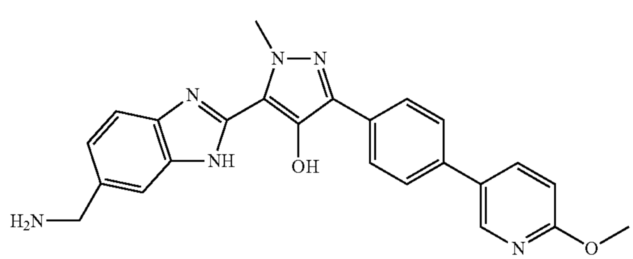 | 119 | 427.2 |

| Structure | Example | MS m/e (MH+) |
|---|---|---|
| 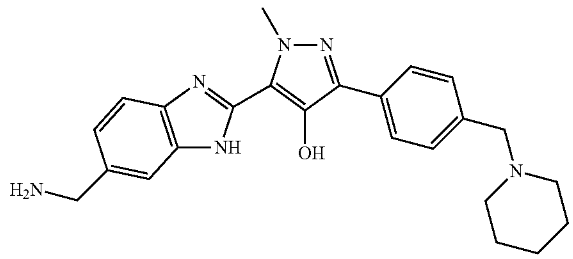 | 120 | 417.2 |

Additional Experimental Details:

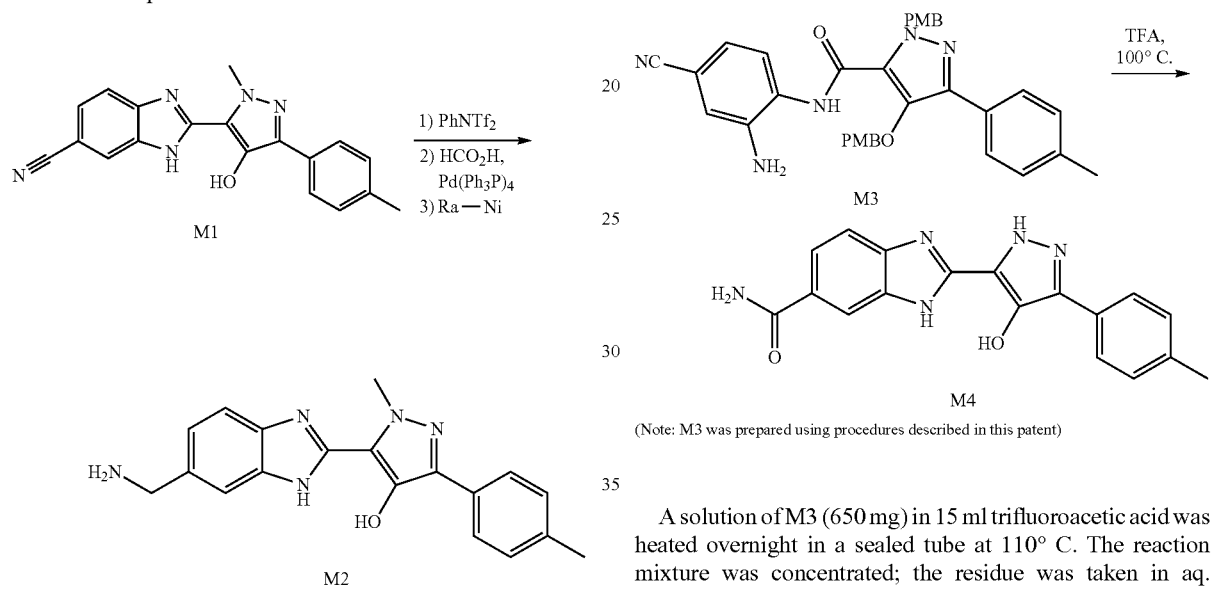

(Note: M1 was prepared using procedures described in this application)

A solution of M1 (100 mg, 0.304 mmol), N-phenylbis(trifluoromethanesulfonimide) (160 mg, 0.448 mmol, 1.5 eq.) and triethyl amine (85 μl, 0.610 mmol, 2 eq.) in 1.5 ml each of dichloromethane and acetonitrile was stirred at rt for 2 days. It was diluted with ethyl acetate, washed 2× with aq. NaHCO₃, brine, dried over MgSO₄, filtered and concentrated. The residue was purified by chromatography using 5% methanol in dichloromethane to provide 70 mg of triflate derivative.

To a solution of above triflate (68 mg, 0.147 mmol) in 1.5 ml DMF in a sealed tube was added formic acid (28 μl, 0.742 mmol, 5 eq.), triethyl amine (103 μl, 0.739 mmol, 5 eq.) and Pd(Ph₃P)₄. The mixture was bubbled with argon, heated overnight at 110° C., diluted with ethyl acetate, washed 2× with water, brine, dried over MgSO₄, filtered, concentrated and purified by preparative TLC using 3% methanol in dichloromethane to provide 31 mg of the reduction product.

The above product was dissolved in 5 ml of 2N NH₃ in methanol and passed through a Ra—Ni cartridge in a H-Cube hydrogenator (60 psi H₂, 50° C., 0.5 ml/min flow rate). The product was purified by RPHPLC to provide 19 mg of M2 as formate salt.

LCMS: 318.2 (MH+)

(Note: M3 was prepared using procedures described in this patent)

A solution of M3 (650 mg) in 15 ml trifluoroacetic acid was heated overnight in a sealed tube at 110° C. The reaction mixture was concentrated; the residue was taken in aq. NaHCO₃ and extracted 3× with ethyl acetate. The combined organic layer was washed with brine, dried over MgSO₄, filtered, concentrated and purified by chromatography using 20% 7N NH₃/MeOH in dichloromethane. The product obtained was repurified by RP-HPLC to provide 110 mg of M4.

LCMS: 34.2 (MH+)

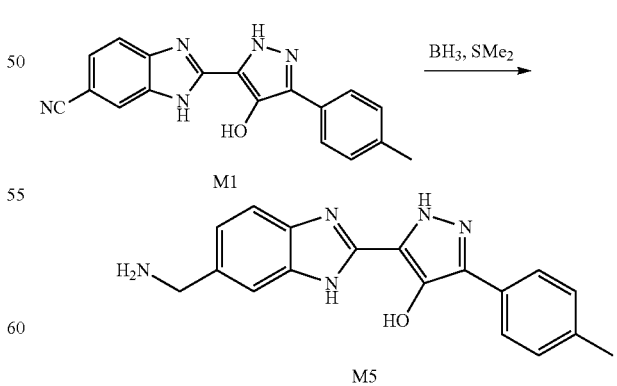

This compound was prepared from M4 using analogous procedure used for the preparation of 109.

LCMS: 334.2 (MH+)

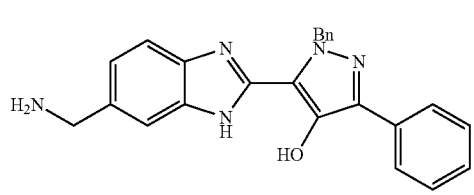

M6

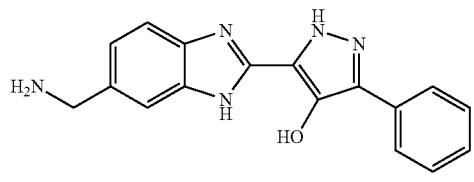

M7

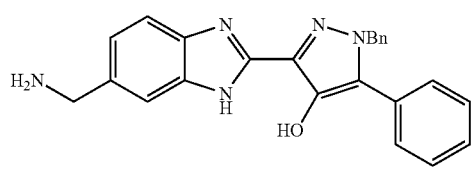

M8

Compound M6 and M7 were obtained as products when compound 26 subjected to the reduction conditions described for the preparation of 109. Similarly M8 was prepared from 48.

LCMS for M6: 396.2 (MH$^+$)

LCMS for M7: 306.2 (MH$^+$)

LCMS for M8: 396.2 (MH$^+$)

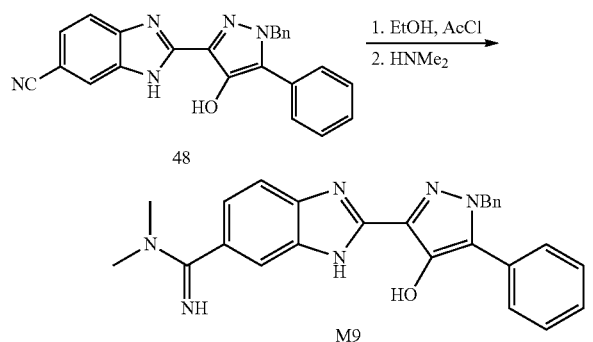

A solution of 26 (100 mg, 0.256 mmol) in ethanol (0.75 ml, 12.85 mmol) in an RB flask was flushed with nitrogen and capped with a septa. The solution was cooled to 0° C., and then acetyl chloride (0.61 ml, 8.58 mmol) was added drop by drop. The mixture was stirred overnight while being allowed to warm to rt. It was concentrated, diluted with ether and the precipitated solid was filtered and dried to provide the ethylimidate derivative. This solid was stirred overnight with 2 ml of a 2M solution of dimethyl amine in THF. The solution was concentrated and purified by RPHPLC to provide 20 mg of M9.

LCMS: 437.2 (MH$^+$)

The following compounds were prepared using a similar procedure:

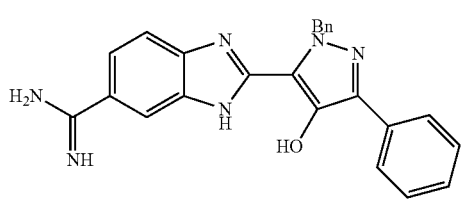

M10

LCMS: 409.2 (MH$^+$)

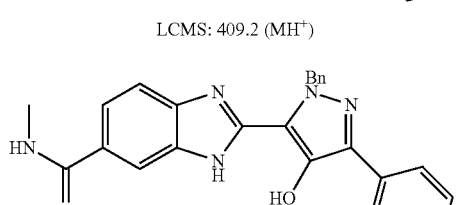

M11

LCMS: 423.2 (MH$^+$)

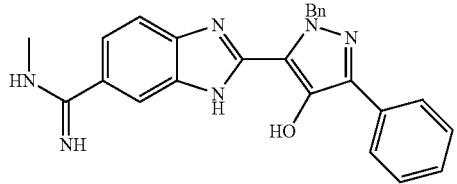

M12

LCMS: 437.2 (MH$^+$)

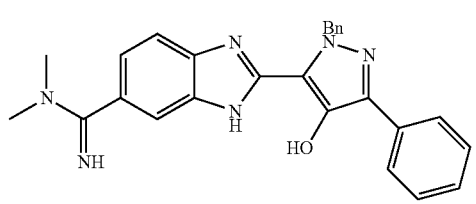

M13

LCMS: 375.2 (MH$^+$)

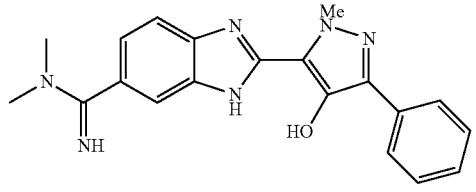

M15

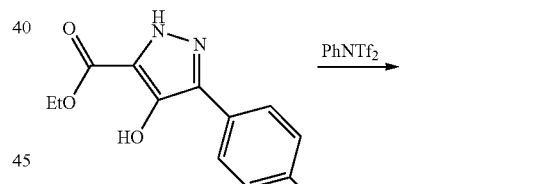

M16

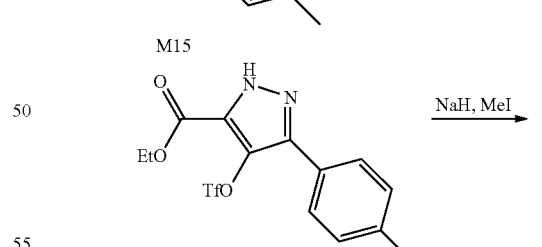

M17

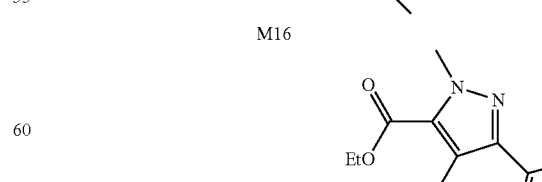

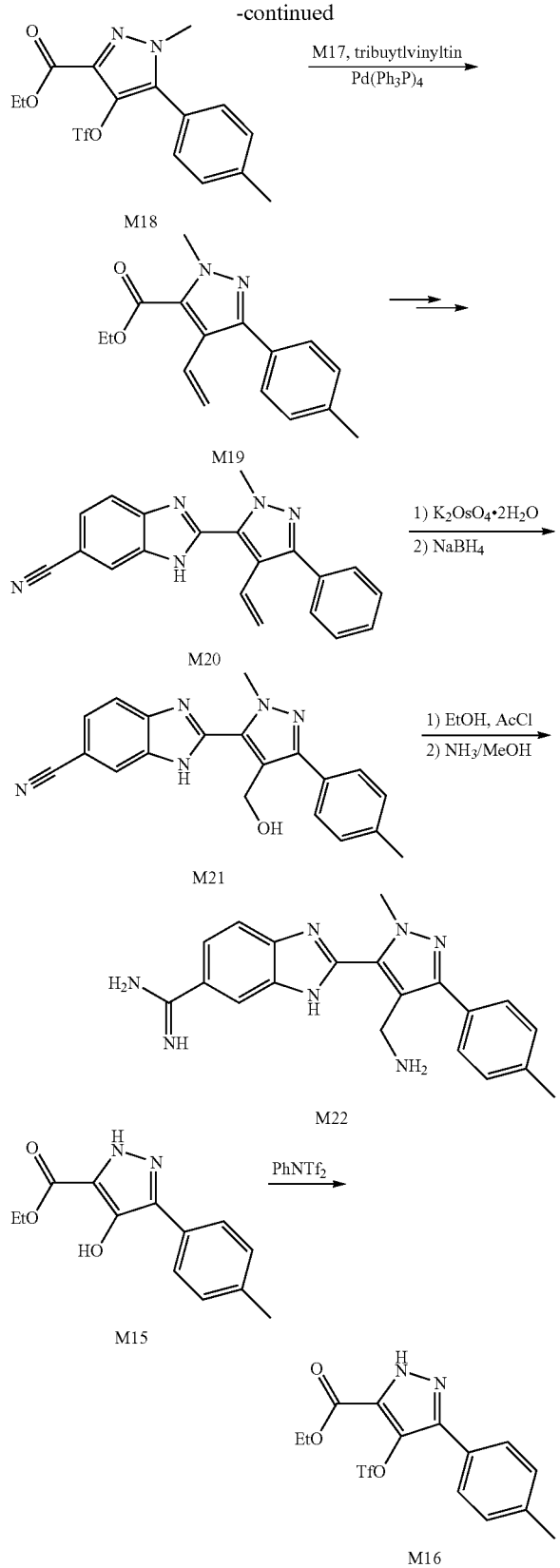

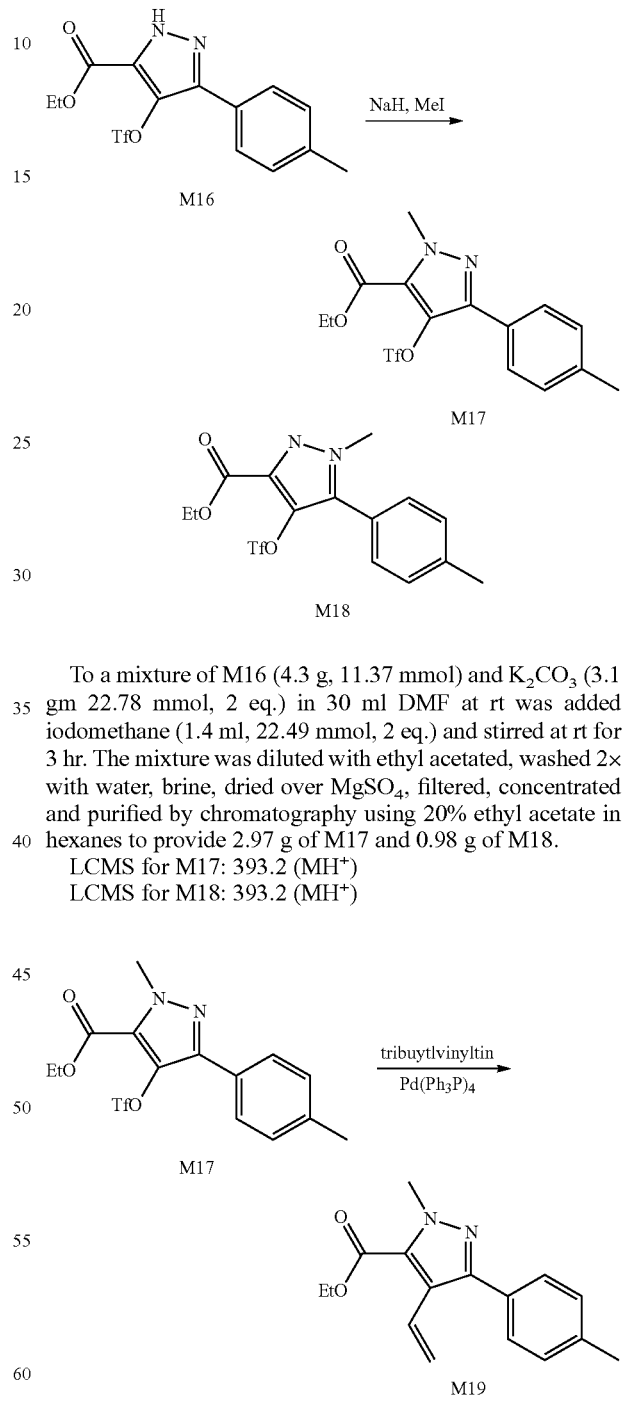

and triethyl amine (3.4 ml, 24.39 mmol). The mixture was stirred overnight at rt, diluted with ethyl acetate, washed 2× with aq. NaHCO$_3$, brine, dried over MgSO$_4$, filtered, concentrated and purified by chromatography eluting with 30% ethyl acetate in hexanes to provide 4.4 g of M16.
LCMS: 379.2 (MH$^+$)

To a mixture of M16 (4.3 g, 11.37 mmol) and K$_2$CO$_3$ (3.1 gm 22.78 mmol, 2 eq.) in 30 ml DMF at rt was added iodomethane (1.4 ml, 22.49 mmol, 2 eq.) and stirred at rt for 3 hr. The mixture was diluted with ethyl acetated, washed 2× with water, brine, dried over MgSO$_4$, filtered, concentrated and purified by chromatography using 20% ethyl acetate in hexanes to provide 2.97 g of M17 and 0.98 g of M18.
LCMS for M17: 393.2 (MH$^+$)
LCMS for M18: 393.2 (MH$^+$)

To a solution of M15 (3.0 g, 12.18 mmol) in 20 ml each of dichloromethane and acetonitrile at rt was added N-phenylbis(trifluoromethanesulfonimide) (5.3 g, 14.8 mmol, 1.2 eq.)

A mixture of M17 (2.0 g, 5.10 mmol), tributylvinyltin (3.0 ml, 10.27 mmol, 2 eq.) and Pd(Ph$_3$P)$_4$ (295 mg, 0.255 mmol, 5 mol %) in 25 ml toluene was bubbled with argon and heated in a sealed tube at 100° C. for 6 hr. After 5 hr added another 295 mg of catalyst and heated overnight. The solution was concentrated and purified by chromatography using 10% ethyl acetate in hexanes to provide 1.02 g of M19.

LCMS: 271.1 (MH+)

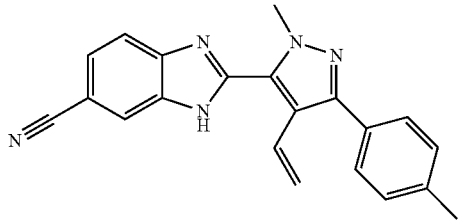
M20

M19 was converted to M20 using procedure described before.

LCMS: 340.2 (MH+)

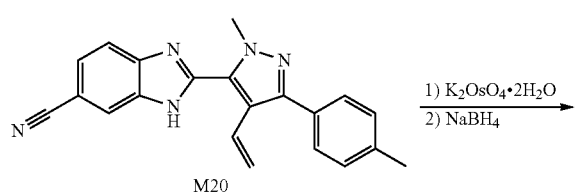

To a solution of M20 (100 mg, 0.295 mmol) in 4 ml of acetone and 3 ml of water at rt was added potassium osmate. To this was added sodium periodate over a period of 1 hr. After 2 hrs of stirring the slurry was filtered and washed with ethyl acetate. The filtrate was washed 2× with water, brine, dried over MgSO4, filtered and concentrated to provide the crude aldehyde. This was taken in 2 ml each of tetrahydrofuran, methanol and water, cooled to 0° C. and treated with excess sodium borohydride. After stirring for 20 min, it was quenched with aq. NH4Cl and extracted 3× with ethyl acetate. The combined organic layers was washed with brine, dried over MgSO4, filtered, concentrated and purified by chromatography using 3% methanol in dichloromethane to provide 74 mg of M21.

LCMS: 344.2 (MH+)

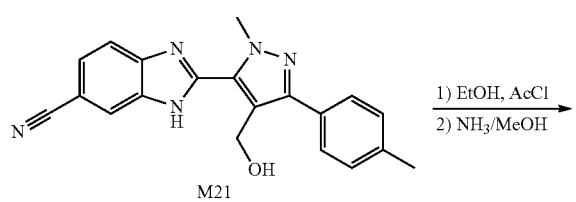

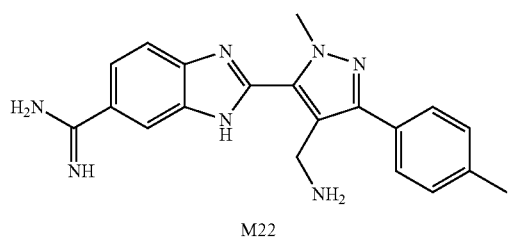
M22

To a solution of M21 (50 mg) in ethanol (1.4 ml) at 0° C. was added acetyl chloride (1.1 ml). The mixture was stirred at 0° C. for 2 hr then at rt for 2 days. It was concentrated and stirred overnight with 3 ml of 7N NH3 solution in methanol. The mixture was concentrated and purified by RPHPLC to provide 3.5 mg of M22.

LCMS: 360.2 (MH+)

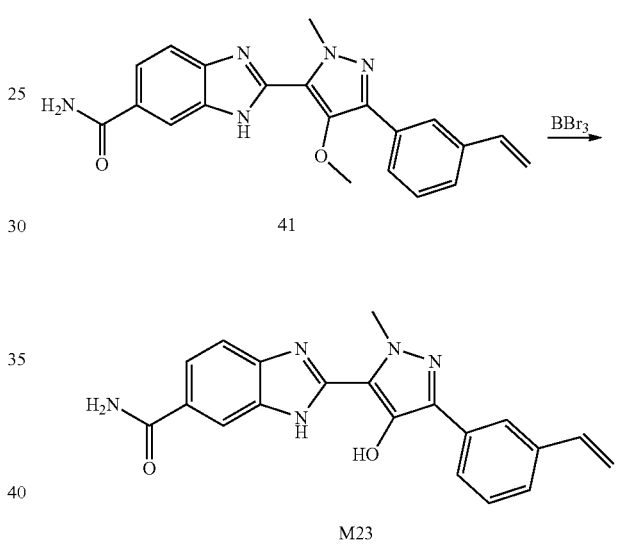

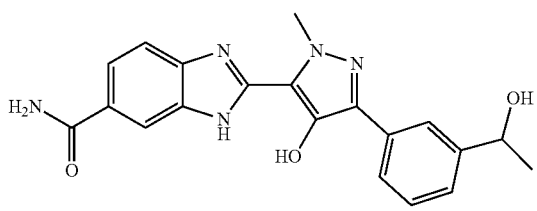
M24

To 60 mg of 41 in 3 mL of dry DCM at 0° C. was added 91 μL (3 eq.) of BBr3 and the mixture stirred under N2 for 10 minutes then warmed to room temperature. After three hours the mixture was cooled to 0° C. and quenched with 10 mL of H2O then stirred at room temperature overnight. DCM was removed by vacuum distillation and the remaining mixture filtered and 49 mg of white solid collected. Purification by RP-HPLC yielded 4 mg of M24 and 16 mg of M23.

LCMS for M24: MH+378.2 (LCMS)

LCMS for M24: MH+360.2 (LCMS)

PX2 and PX3

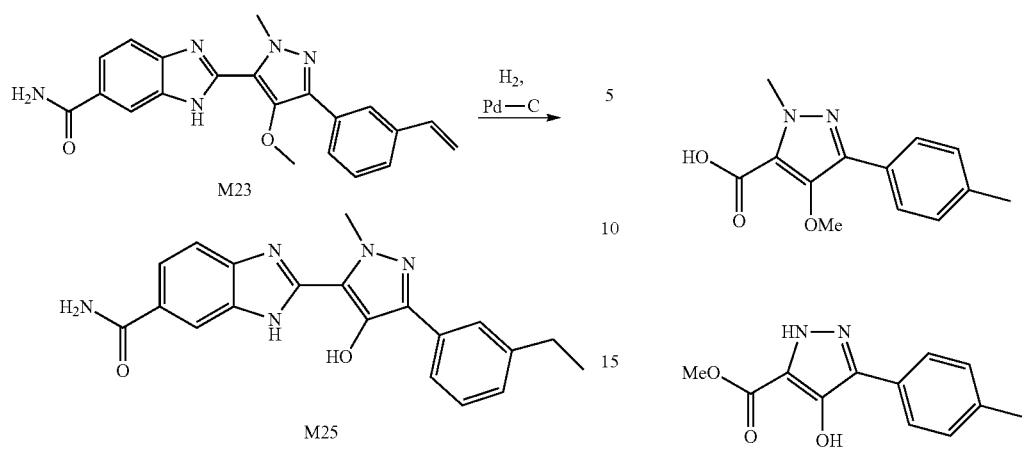

To 15 mg of M23 in 3 mL of methanol was added 15 mg of 10% Pd/C and the mixture stirred under a balloon of H₂ for 30 minutes then filtered through 250 mg of C-18 resin. The filtrate was evaporated to dryness yielding 13.5 mg of M25.

LCMS: 362.2 (MH$^+$)

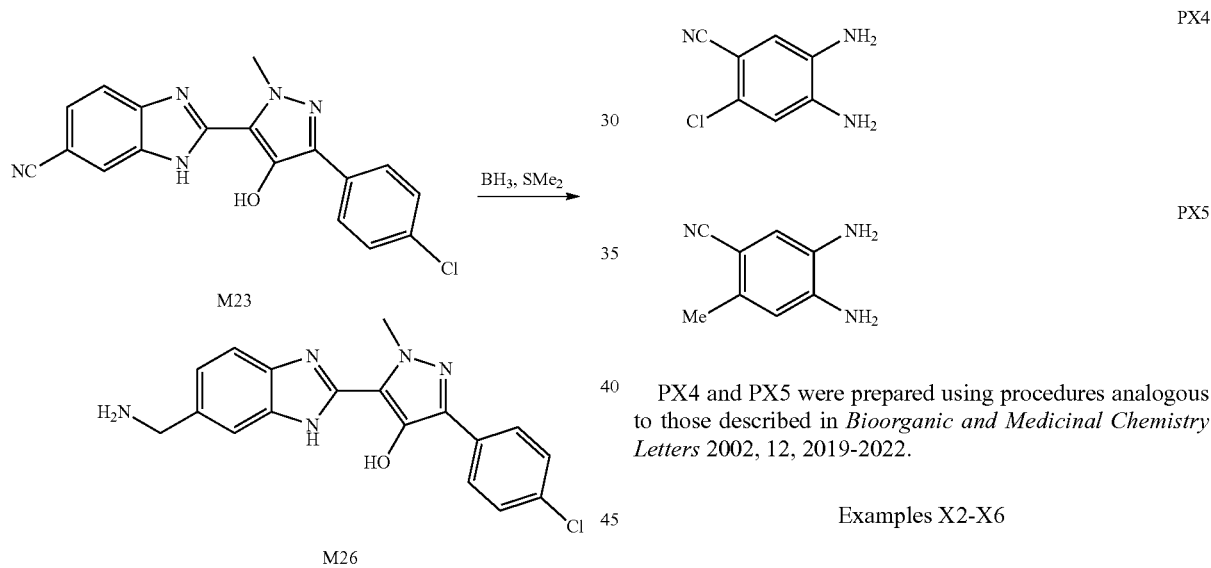

M26 was prepared from 52 using the same procedure used for the preparation of 109.

LCMS: 337.2 (MH$^+$)

Starting Materials

PX1

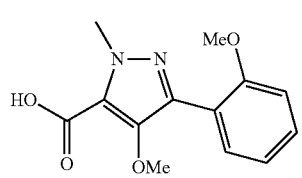

Compound PX1 was synthesized using procedures analogous to compound P12

Compounds PX2 and PX3 was synthesized using procedures analogous to compound P12

PX4 and PX5

PX4 and PX5 were prepared using procedures analogous to those described in *Bioorganic and Medicinal Chemistry Letters* 2002, 12, 2019-2022.

Examples X2-X6

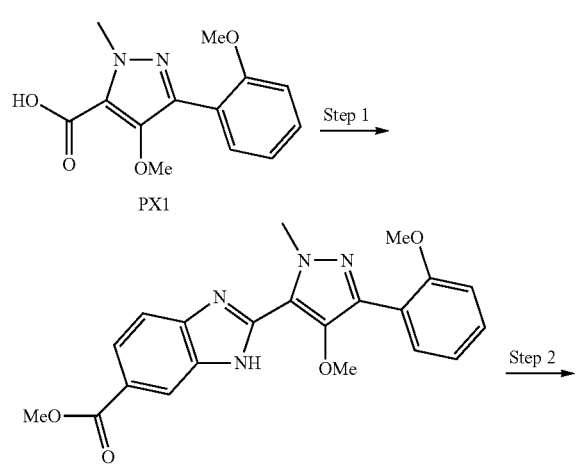

-continued

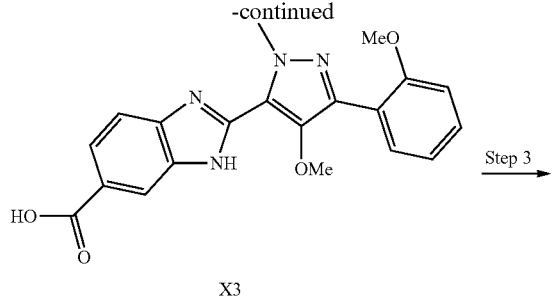

X3

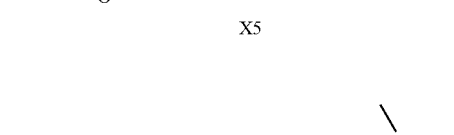

X4

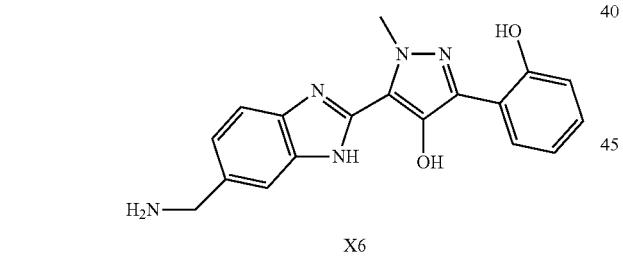

X5, X6

Example X2 (LCMS, MH⁺=393.2) was synthesized from X1 using procedures analogous to compound 33.

Example X3 (LCMS, MH⁺=379.2) was synthesized from X2 using procedures analogous to compound 37.

Example X4 (LCMS, MH⁺=378.2) was synthesized from X3 using procedures analogous to compound 38.

Example X5 (LCMS, MH⁺=350.2) was synthesized from X4 using procedures analogous to compound 41.

Example X6 (LCMS, MH⁺=336.2) was synthesized from X5 using procedures analogous to compound 113.

Example X7

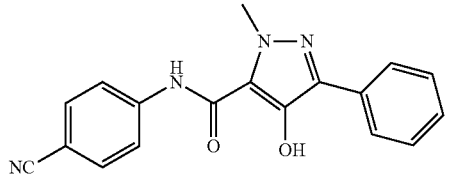

Example X7 (LCMS, MH⁺=319.2) was synthesized from P15 using a procedure analogous to compound 75.

Example X8

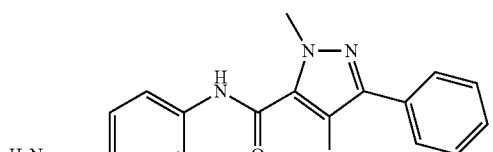

Example X8 (LCMS, MH⁺=306.2 (M−17)) was synthesized from X7 using a procedure analogous to compound 113.

Example X9

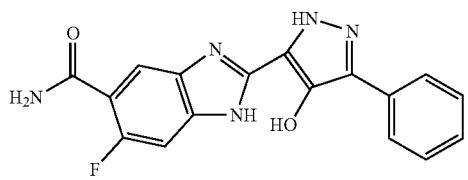

Example X9 (LCMS, MH⁺=338.2) was synthesized from example 12 using the procedure described for example 27.

Example P10-P11

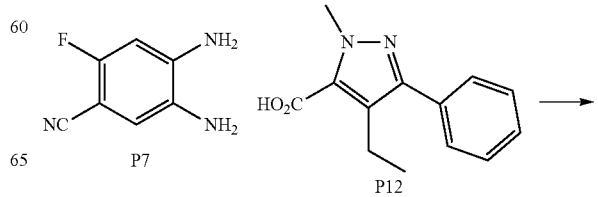

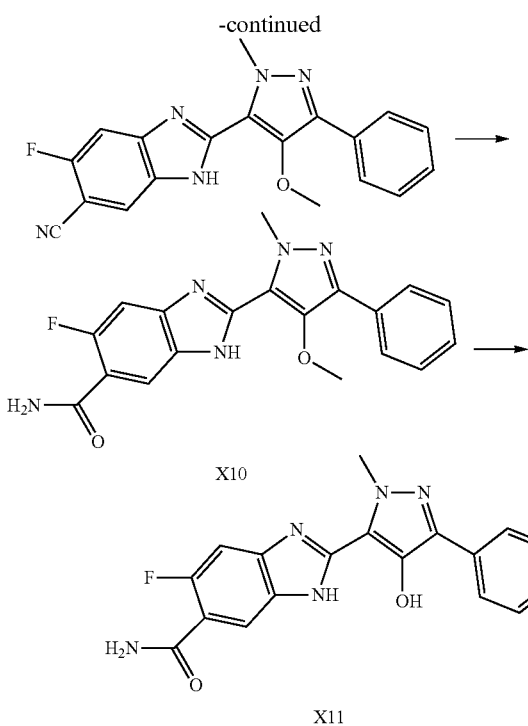

X10

X11

Example X10 (LCMS, MH$^+$=366.2) and example X11 (LCMS, MH$^+$=352.2) were synthesized from P7 and P12 using methods previously outlined herein.

Example X12

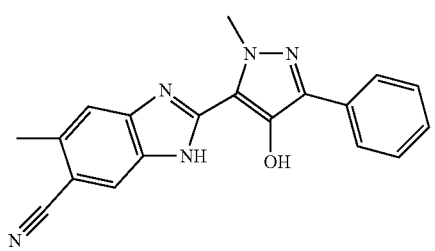

X12

Example X12 (LCMS, MH$^+$=330.2) was synthesized from PX5 and P12 using methods previously outlined herein for example 94.

Example X13

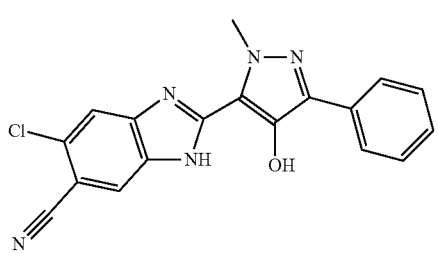

X13

Example X13 (LCMS, MH$^+$=350.2) was synthesized from PX4 and P12 using methods previously outlined herein for example 94.

Example X14

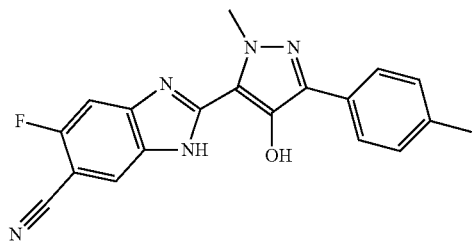

X14

Example X14 (LCMS, MH$^+$=348.2) was synthesized from P7 and PX2 using methods previously outlined herein for example 94.

Example X15

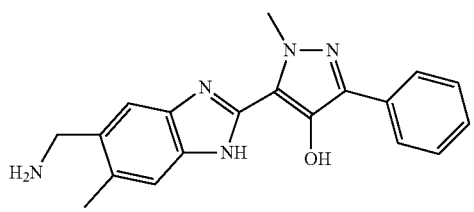

X15

Example X15 (LCMS, MH$^+$=335.2) was synthesized from example X12 using the method previously outlined herein for example 113.

Example X16

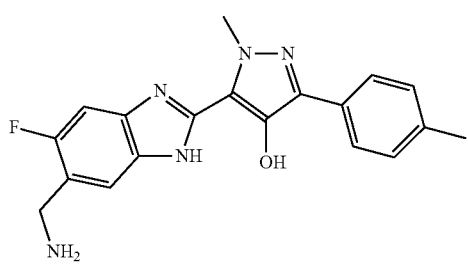

X16

Example X16 (LCMS, MH$^+$=352.2) was synthesized from example X14 using the method previously outlined herein for example 113.

Example X17

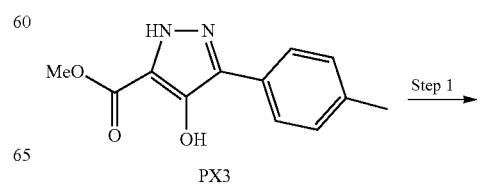

PX3

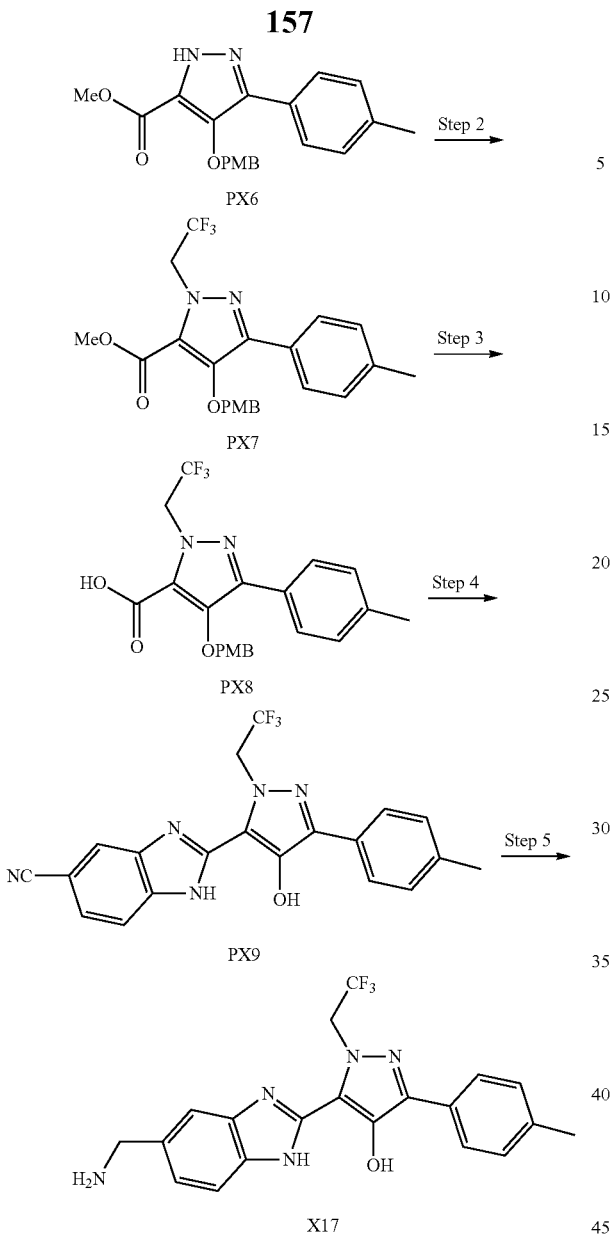

Step 1
PX3 (2 g, 0.0081 mol) was dissolved in DMF (16 ml), LiOH hydrate (0.681 g, 2 eq) was added followed by PMBBr (1.4 ml, 1.2 eq) and the mixture stirred for 50 minutes. Saturated ammonium chloride was added and the mixture was extracted with EtOAc. The extracts were dried and concentrated to give a residue that was purified by silica gel chromatography (0-50% EtOAc/Hexane) to give 2.39 g of PX6.

Step 2
PX6 was dissolved in DMF (16 ml), LiOH—H2O 0.547 g, 2 eq), followed by 2,2,2-trifluoroethyl trifluoromethanesulfonate (1.8 ml, 2 eq) was added stirred for 1 hour. Saturated ammonium chloride was added and the mixture was extracted with EtOAc. The extracts were dried and concentrated to give a residue that was purified by silica gel chromatography (0-30% EtOAc/hexane) to give 1.91 g of PX7.

Step 3
PX7 (0.5 g, 0.0011 mol) was dissolved in MeOH (5.58 ml), 2M KOH (1.95 ml, 3.5 eq) was added and the mixture heated at 70° C. for 3 hours. Cooled to rt, water added and the mixture was acidified to PH3, solid collected by filtration to give 400 mg of PX8.

Step 4
PX 8 (0.3 g, 0.000714 mol) and 3,4-diaminobenzonitrile (0.104 g, 1.1 eq) was dissolved in DMF (3.57 ml), DIPEA (0.249, 2 eq) and HATU (0.353 g, 1.3 eq) added. Stirred for 3 hours. Saturated ammonium chloride was added and the mixture was extracted with $CH_2Cl_2$. The extracts were dried and concentrated to give a residue that was purified by silica gel chromatography (hexane/EtOAc) to give an intermediate that was dissolved in TFA and heated at 90° C. overnight. The mixture was cooled to rt, saturated ammonium chloride was added and the mixture was extracted with EtOAc. The extracts were dried, concentrated, and purified by silica gel chromatography (0-50% EtOAc/Hexane) to give 30 mg of PX 9.

Step 5
Example X17 (LCMS, $MH^+$=402.2) was synthesized from PX9 using the method previously outlined herein for example 113

Preparative Example 1

Preparation of $N^5$,2-bis(2,4-dimethoxybenzyl)isoindoline-5,6-diamine T-04

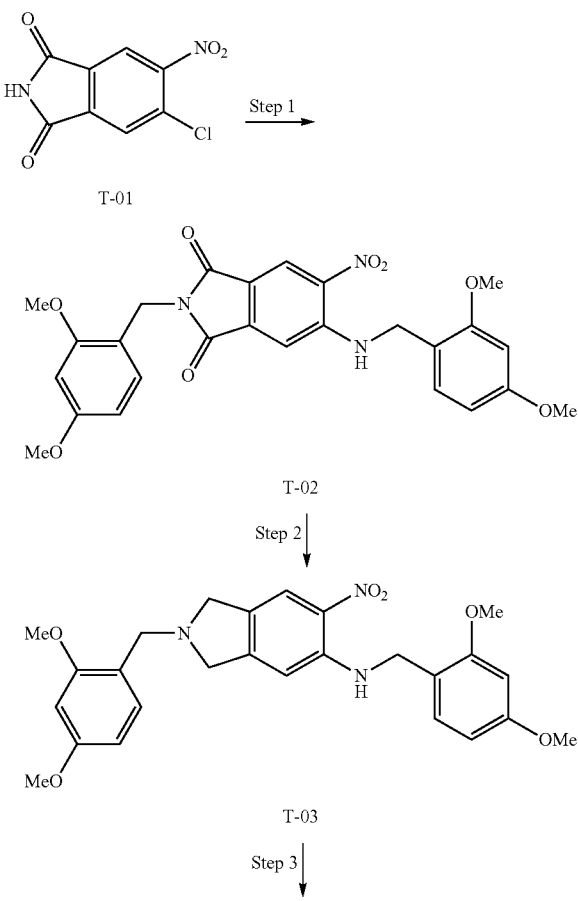

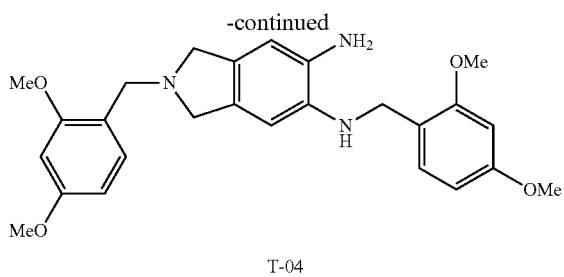

T-04

Step 1

To a solution of 4-chloro-5-nitrophthalimide T-01 (4.8 g, 21 mmol) in anhydrous 1,4-dioxane (80 mL) and trifluoromethylbenzene (16 mL) was added 2,4-dimethoxybenzylamine (7.1 mL, 46 mmol) and diisopropylethylamine (8.0 mL, 46 mmol). The reaction mixture was heated in a microwave reactor at 160° C. for 1 hour. Solvent was removed under reduced pressure. The crude product was diluted with ethyl acetate. The organic layer was washed with a saturated ammonium chloride solution, water and saturated brine. The organic layer was dried over sodium sulfate. Solvent was evaporated under reduced pressure. The crude product was purified by flash chromatography to afford the desired 2-(2,4-dimethoxybenzyl)-5-(2,4-dimethoxybenzylamino)-6-nitroisoindoline-1,3-dione T-02 (6.1 g, 12 mmol).

Step 2

To a solution of 2-(2,4-dimethoxybenzyl)-5-(2,4-dimethoxybenzylamino)-6-nitroisoindoline-1,3-dione T-02 (6.1 g, 12 mmol) in anhydrous tetrahydrofuran (50 mL) cooled in an ice bath was added borane dimethyl sulfide complex (10 M, 36 mL, 360 mmol) in a dropwise manner. The reaction mixture was heated under reflux for 4 hours. The reaction mixture was cooled in an ice bath and methanol (75 mL) was added in a dropwise manner. To the reaction mixture were added triethylamine (6 mL), acetic acid (9 mL) and a solution of iodine (1 g) in anhydrous tetrahydrofuran (5 mL). The reaction mixture was stirred at room temperature overnight. Solvent was removed under reduced pressure. The crude product was diluted with ethyl acetate. The organic layer was washed with 1 N sodium hydroxide solution, water and saturated brine. The organic layer was dried over sodium sulfate. Solvent was evaporated under reduced pressure. The crude product was purified by flash chromatography to afford the desired N,2-bis(2,4-dimethoxybenzyl)-6-nitroisoindolin-5-amine T-03 (2.7 g, 5.6 mmol).

Step 3

To a mixture of N,2-bis(2,4-dimethoxybenzyl)-6-nitroisoindolin-5-amine T-03 (2.7 g, 5.6 mmol) and sodium hydrosulfite (15.6 g, 90 mmol) was added a solution of tetrahydrofuran (40 mL), water (40 mL) and ammonium hydroxide (40 mL). The reaction mixture was stirred at room temperature overnight. The reaction mixture was basified with sodium hydroxide and saturated with sodium chloride. The reaction mixture was filtered and extracted with ethyl acetate. The organic layer was dried over sodium sulfate. Solvent was evaporated under reduced pressure to afford the desired $N^5$,2-bis(2,4-dimethoxybenzyl)isoindoline-5,6-diamine T-04 (2.5 g, 5.6 mmol). The crude product was used in the next step without further purification.

Preparative Example 2

Preparation of 5-(4-(4-hydroxy-1-methyl-5-(1,5,6,7-tetrahydroimidazo[4,5-f]isoindol-2-yl)-1H-pyrazol-3-yl)phenyl)-N-methylpicolinamide T-16

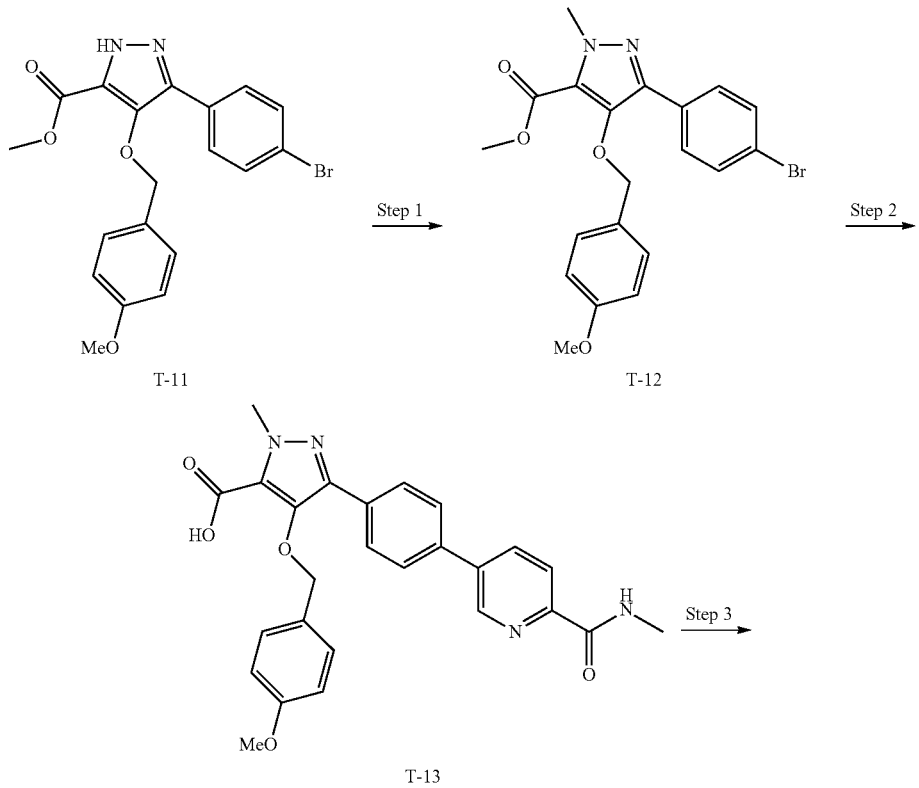

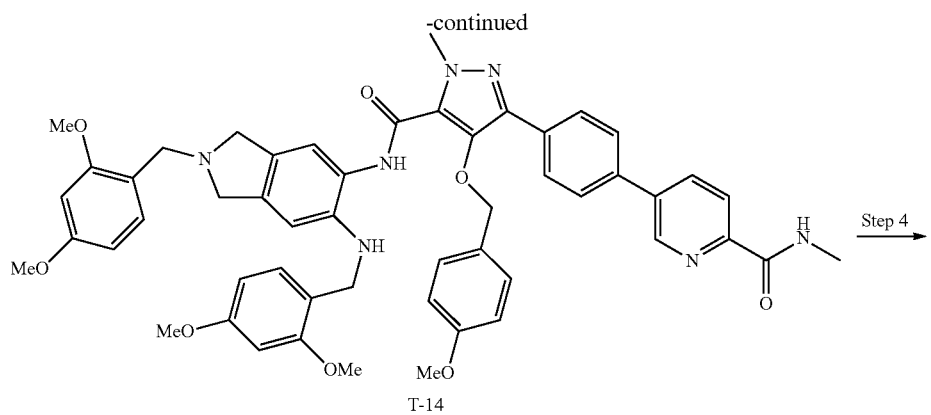

T-14

-continued

T-15

Step 1
To a solution of methyl 3-(4-bromophenyl)-4-(4-methoxybenzyloxy)-1H-pyrazole-5-carboxylate T-11 (10 g, 24 mmol) in anhydrous N,N-dimethylformamide (100 mL) cooled in an ice bath was added lithium hydroxide monohydrate (3 g, 71 mmol) and methyl iodide (10 g, 70 mmol). The reaction mixture was stirred at room temperature for 3 hours. The crude product was diluted with ethyl acetate. The organic layer was washed with water and saturated brine. The organic layer was dried over sodium sulfate. Solvent was evaporated under reduced pressure. The crude solid product was washed with hexane to afford the desired methyl 3-(4-bromophenyl)-4-(4-methoxybenzyloxy)-1-methyl-1H-pyrazole-5-carboxylate T-12 (7 g, 16 mmol).

Step 2
To a solution of 3-(4-bromophenyl)-4-(4-methoxybenzyloxy)-1-methyl-1H-pyrazole-5-carboxylate T-12 (400 mg, 0.96 mmol) in ethanol (10 mL) and water (1 mL) were added 2-(N-methylamidocarboxy)-5-pyridineboronic acid pinacol ester (254 mg, 0.97 mmol), potassium carbonate (138 mg, 1.0 mmol) and polyethylene supported palladium catalyst (Fibre-Cat FC 1007, 3% Pd, 300 mg). The reaction mixture was heated in a microwave reactor at 115° C. for 15 minutes. To the reaction mixture was added lithium hydroxide monohydrate (127 mg, 3.0 mmol). The reaction mixture was heated in a microwave reactor at 115° C. for 20 minutes. The reaction mixture was filtered and the filtrate was evaporated under reduced pressure. The crude product was purified by RP-HPLC to afford the desired 4-(4-methoxybenzyloxy)-1-methyl-3-(4-(6-(methylcarbamoyl)pyridin-3-yl)phenyl)-1H-pyrazole-5-carboxylic acid T-13 (304 mg, 0.64 mmol).

Step 3
To a solution of 4-(4-methoxybenzyloxy)-1-methyl-3-(4-(6-(methylcarbamoyl)pyridin-3-yl)phenyl)-1H-pyrazole-5-carboxylic acid T-13 (304 mg, 0.64 mmol) in N,N-dimethylformamide (4 mL) were added $N^5$,2-bis(2,4-dimethoxybenzyl)isoindoline-5,6-diamine T-04 (347 mg, 0.77 mmol), HATU (318 mg, 0.84 mmol) and diisopropylethylamine (0.34 mL, 2.0 mmol). The reaction mixture was stirred at room temperature for 2 hours. The crude product was diluted with ethyl acetate. The organic layer was washed with water and saturated brine. The organic layer was dried over sodium sulfate. Solvent was evaporated under reduced pressure. The crude product was purified by flash chromatography to afford the desired 5-(4-(5-(2-(2,4-dimethoxybenzyl)-6-(2,4-dimethoxybenzylamino)isoindolin-5-ylcarbamoyl)-4-(4-methoxybenzyloxy)-1-methyl-1H-pyrazol-3-yl)phenyl)-N-methylpicolinamide T-14 (410 mg, 0.45 mmol).

Step 4
A solution of 5-(4-(5-(2-(2,4-dimethoxybenzyl)-6-(2,4-dimethoxybenzylamino)isoindolin-5-ylcarbamoyl)-4-(4-methoxybenzyloxy)-1-methyl-1H-pyrazol-3-yl)phenyl)-N-methylpicolinamide T-14 (410 mg, 0.45 mmol) in acetic acid (4 mL) was heated in a microwave reactor at 150° C. for 50 minutes. Solvent was evaporated under reduced pressure and trifluoroacetic acid (4 mL) was added. The reaction mixture was heated in microwave reactor at 120° C. for 30 minutes. Solvent was evaporated under reduced pressure. The crude product was purified by RP-HPLC to afford the desired 5-(4-(4-hydroxy-1-methyl-5-(1,5,6,7-tetrahydroimidazo[4,5-f]isoindol-2-yl)-1H-pyrazol-3-yl)phenyl)-N-methylpicolinamide T-15 (143 mg, 0.31 mmol).

Preparative Example 3

Preparation of 1-methyl-3-(4-(6-(methylcarbamoyl)pyridin-3-yl)phenyl)-5-(1,5,6,7-tetrahydroimidazo[4,5-f]isoindol-2-yl)-1H-pyrazol-4-yl diethylcarbamate T-17

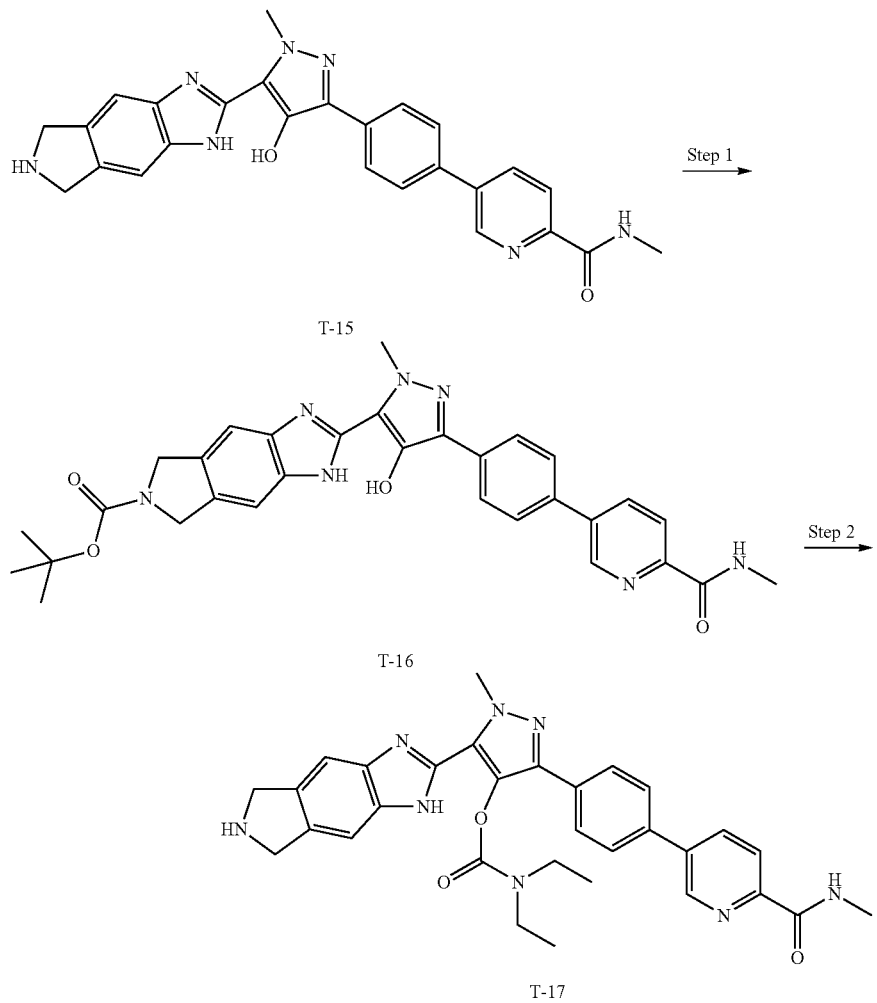

Step 1

To a solution of 5-(4-(4-hydroxy-1-methyl-5-(1,5,6,7-tetrahydroimidazo[4,5-f]isoindol-2-yl)-1H-pyrazol-3-yl)phenyl)-N-methylpicolinamide T-15 (113 mg, 0.24 mmol) in anhydrous N,N-dimethylformamide (3 mL) was added di-tert-butyl dicarbonate (106 mg, 0.48 mmol) and diisopropylethylamine (0.1 mL, 0.6 mmol). The reaction mixture was stirred at room temperature for 2 hours. The reaction mixture was diluted with ethyl acetate. The organic layer was washed with water and saturated brine. The organic layer was dried over sodium sulfate. Solvent was evaporated under reduced pressure. The residual solid was dissolved in methanol (4 mL) and sodium hydroxide (30 mg, 0.75 mmol) was added. The reaction mixture was stirred at room temperature for 2 hours. The reaction mixture was diluted with ethyl acetate. The organic layer was washed with water and saturated brine. The organic layer was dried over sodium sulfate. Solvent was evaporated under reduced pressure. The crude product was purified by RP-HPLC to afford the desired tert-butyl 2-(4-hydroxy-1-methyl-3-(4-(6-(methylcarbamoyl)pyridin-3-yl)phenyl)-1H-pyrazol-5-yl)-5,7-dihydroimidazo[4,5-f]isoindole-6(1H)-carboxylate T-16 (63 mg, 0.11 mmol).

Step 2

To a solution of 2-(4-hydroxy-1-methyl-3-(4-(6-(methylcarbamoyl)pyridin-3-yl)phenyl)-1H-pyrazol-5-yl)-5,7-dihydroimidazo[4,5-f]isoindole-6(1H)-carboxylate 1-16 (63 mg, 0.11 mmol) in anhydrous N,N-dimethylformamide (2 mL) was added potassium tert-butoxide (25 mg, 0.22 mmol) and diethylcarbamoyl chloride (21 mg, 0.15 mmol). The reaction mixture was stirred at room temperature for 4 hours. The reaction mixture was diluted with ethyl acetate. The organic layer was washed with water and saturated brine. The organic layer was dried over sodium sulfate. Solvent was evaporated under reduced pressure. To the residue was added a 30% solution of trifluoroacetic acid in dichloromethane (4 mL). The reaction mixture was stirred at room temperature for 2 hours. Solvent was evaporated under reduced pressure. The crude product was purified by RP-HPLC to afford the desired 1-methyl-3-(4-(6-(methylcarbamoyl)pyridin-3-yl)phenyl)-5-(1,5,6,7-tetrahydroimidazo[4,5-f]isoindol-2-yl)-1H-pyrazol-4-yl diethylcarbamate T-17 (48 mg, 0.085 mmol).

Preparative Example 4

Preparation of 2-(4-hydroxy-1-methyl-3-(4-(2-oxopiperidin-1-yl)phenyl)-1H-pyrazol-5-yl)-1H-benzo[d]imidazole-5-carboximidamide T-24

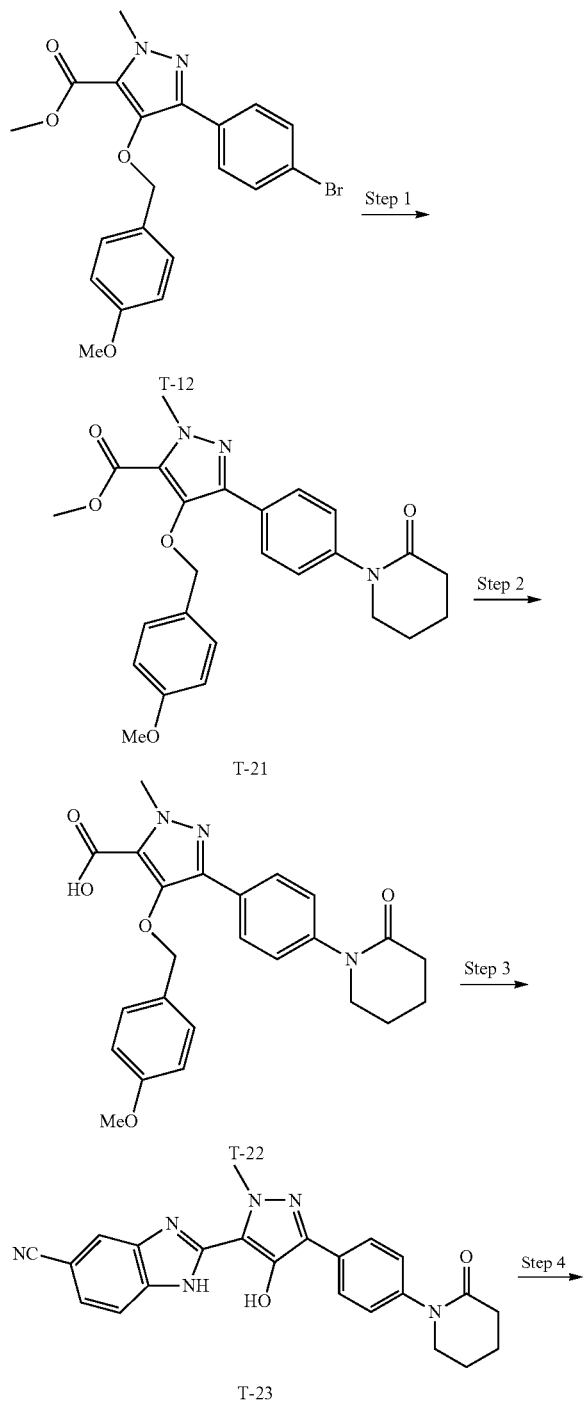

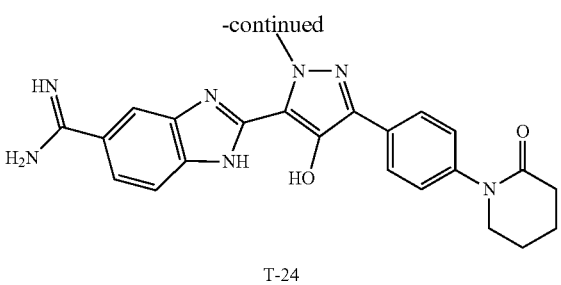

Step 1

To a solution of 3-(4-bromophenyl)-4-(4-methoxybenzyloxy)-1-methyl-1H-pyrazole-5-carboxylate T-12 (0.5 g, 1.2 mmol) in anhydrous 1,4-dioxane (10 mL) under nitrogen were added 2-piperidone (0.17 g, 1.7 mmol), cesium carbonate (0.755 g, 2.3 mmol), Xantphos (0.15 g, 0.26 mmol) and $Pd_2dba_3$ (0.05 g, 0.055 mmol). The reaction mixture was heated in a microwave reactor at 120° C. for 1 hour. The reaction mixture was filtered and washed with dichloromethane and ethyl acetate. The filtrate was evaporated under reduced pressure. The residue was diluted with ethyl acetate. The organic layer was washed with water and saturated brine. The organic layer was dried over sodium sulfate. Solvent was evaporated under reduced pressure. The crude product was purified by flash chromatography to afford the desired methyl 4-(4-methoxybenzyloxy)-1-methyl-3-(4-(2-oxopiperidin-1-yl)phenyl)-1H-pyrazole-5-carboxylate T-21 (0.44 g, 1.0 mmol).

Step 2

To a solution of methyl 4-(4-methoxybenzyloxy)-1-methyl-3-(4-(2-oxopiperidin-1-yl)phenyl)-1H-pyrazole-5-carboxylate T-21 (440 mg, 1.0 mmol) in methanol (10 mL) was added lithium hydroxide monohydrate (124 mg, 3.0 mmol). The reaction mixture was heated in a microwave reactor at 120° C. for 20 minutes. Solvent was removed under reduced pressure. Ethyl acetate and 0.1 N hydrochloric acid were added. The organic layer was washed with saturated brine. The organic layer was dried over sodium sulfate. Solvent was evaporated under reduced pressure. The crude product was purified by RP-HPLC to afford the desired 4-(4-methoxybenzyloxy)-1-methyl-3-(4-(2-oxopiperidin-1-yl)phenyl)-1H-pyrazole-5-carboxylic acid T-22 (100 mg, 0.23 mmol).

Step 3

To a solution of 4-(4-methoxybenzyloxy)-1-methyl-3-(4-(2-oxopiperidin-1-yl)phenyl)-1H-pyrazole-5-carboxylic acid T-22 (180 mg, 0.42 mmol) in N,N-dimethylformamide (4 mL) were added 3,4-diaminobenzonitrile (66 mg, 0.5 mmol), HATU (204 mg, 0.54 mmol) and diisopropylethylamine (0.22 mL, 1.3 mmol). The reaction mixture was stirred at room temperature overnight. The reaction mixture was diluted with ethyl acetate. The organic layer was washed with water and saturated brine. The organic layer was dried over sodium sulfate. Solvent was evaporated under reduced pressure. The residue was purified by flash chromatography. To the purified fraction (155 mg, 0.28 mmol) was added acetic acid (4 mL). The reaction mixture was heated in a microwave reactor at 150° C. for 55 minutes. Solvent was evaporated under reduced pressure. To the residue was added trifluoroacetic acid (4 mL). The reaction mixture was heated in a microwave reactor at 120° C. for 30 minutes. Solvent was evaporated under reduced pressure. The crude product was purified by flash chromatography to afford the desired 2-(4-hydroxy-1-methyl-3-(4-(2-oxopiperidin-1-yl)phenyl)-1H-pyrazol-5-yl)-1H-benzo[d]imidazole-5-carbonitrile T-23 (110 mg, 0.27 mmol).

Step 4

To a suspension of 2-(4-hydroxy-1-methyl-3-(4-(2-oxopiperidin-1-yl)phenyl)-1H-pyrazol-5-yl)-1H-benzo[d]imidazole-5-carbonitrile T-23 (110 mg, 0.27 mmol) in ethanol (5 mL) cooled in an ice bath was added acetyl chloride (4.0 mL) in a dropwise manner. The reaction mixture was stirred at room temperature overnight. Solvent was evaporated under reduced pressure. To the residue was added a 7 N solution of ammonia in methanol (20 mL). The reaction mixture was stirred at room temperature overnight. Solvent was evaporated under reduced pressure. The crude product was purified by RP-HPLC to afford the desired 2-(4-hydroxy-1-methyl-3-(4-(2-oxopiperidin-1-yl)phenyl)-1H-pyrazol-5-yl)-1H-benzo[d]imidazole-5-carboximidamide T-24 (37 mg, 0.086 mmol).

The following compounds also were synthesized using procedures similar to those outlined previously. The synthesis of some of the compounds in the table below has been shown separately above.

| Structure | MS m/e (MH+) |
|---|---|
| 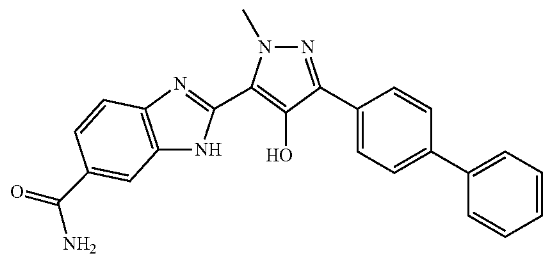 | 410.2 |
| 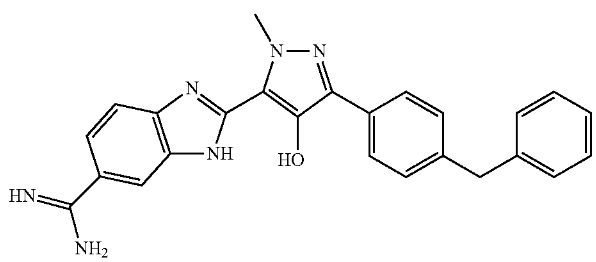 | 423.2 |
| 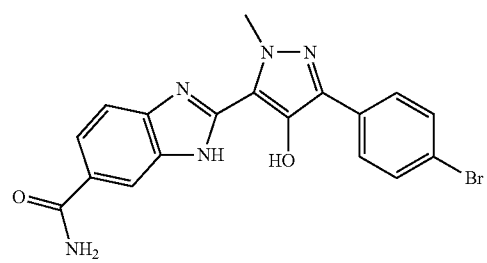 | 412.2 |
| 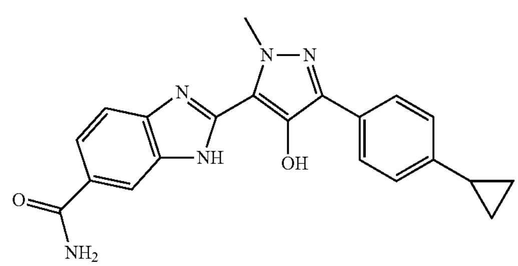 | 374.2 |
| 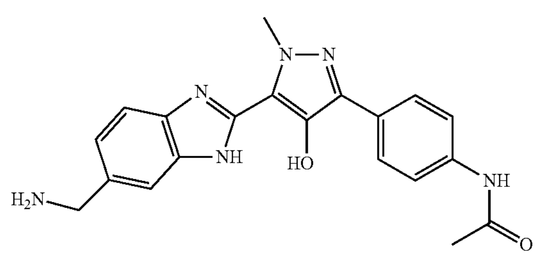 | 377.2 |

-continued

| Structure | MS m/e (MH+) |
|---|---|
| 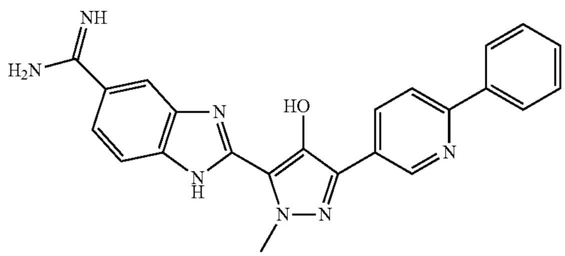 | 410.2 |
| 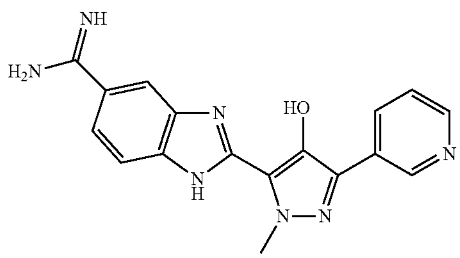 | 334.2 |
| 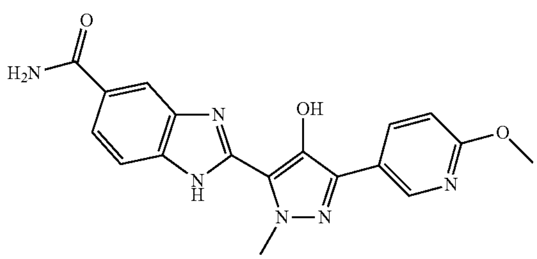 | 365.2 |
| 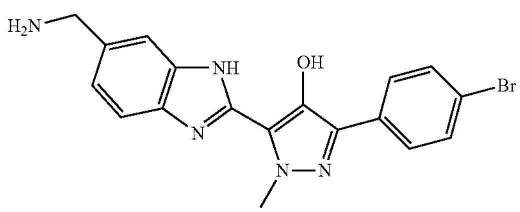 | 398.2 |
| 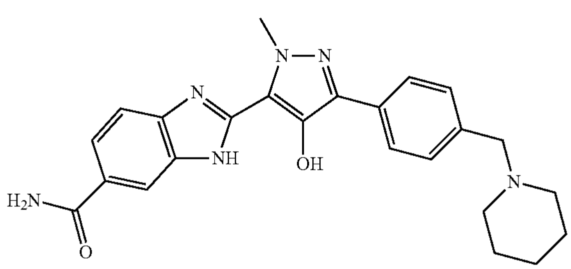 | 431.2 |
| 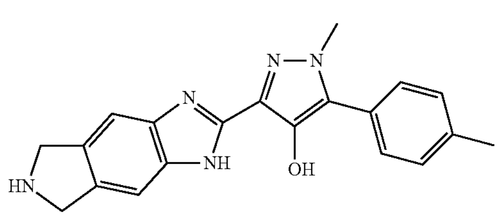 | 346.2 |

-continued

| Structure | MS m/e (MH+) |
|---|---|
| 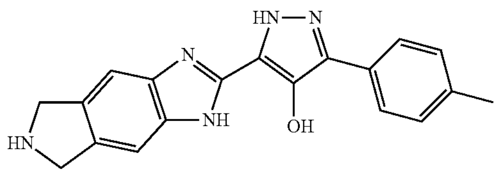 | 332.2 |
| 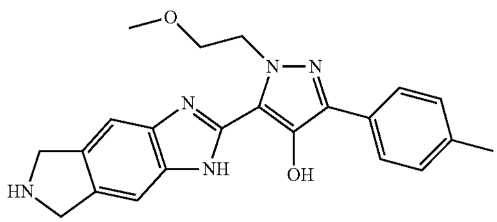 | 390.2 |
| | 404.2 |
| | 404.2 |
| 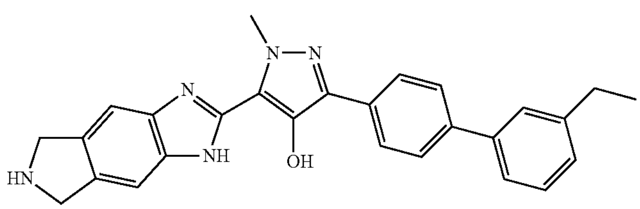 | 436.2 |
| 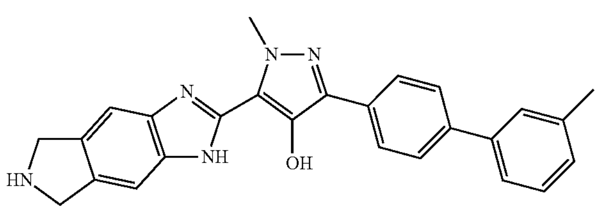 | 422.2 |
| 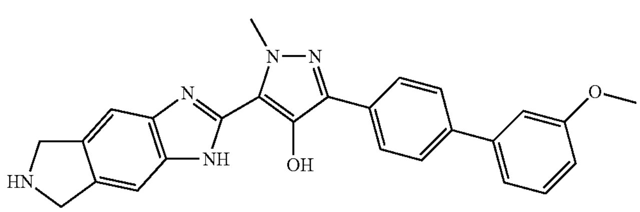 | 438.2 |

-continued

| Structure | MS m/e (MH+) |
|---|---|
| 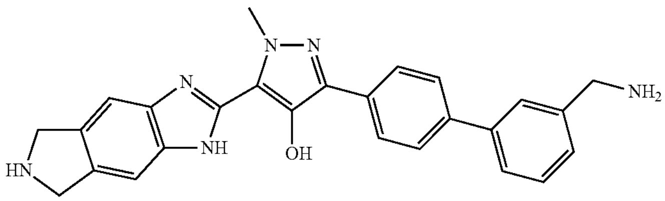 | 437.2 |
| 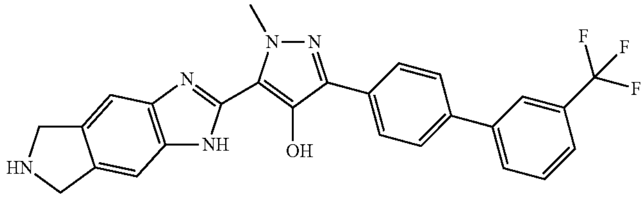 | 476.3 |
| 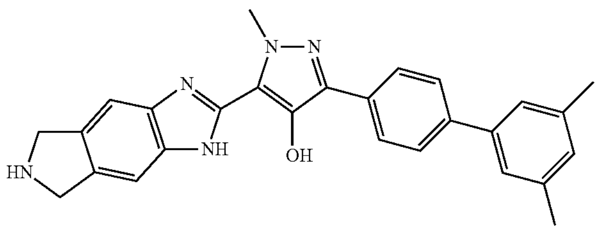 | 422.2 |
| 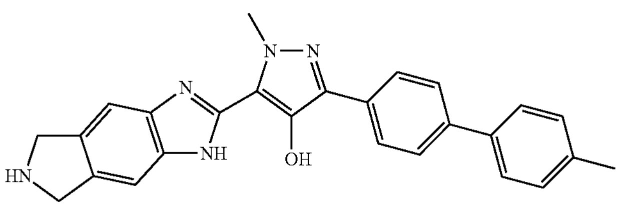 | 462.3 |
| | 442.2 |
| | 442.2 |
| 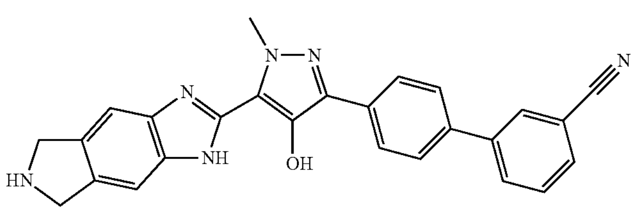 | 433.2 |

-continued
| Structure | MS m/e (MH+) |
|---|---|
| 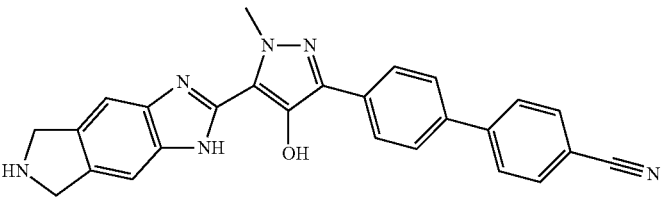 | 433.2 |
| 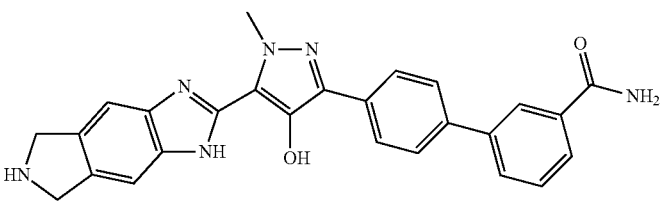 | 451.2 |
| 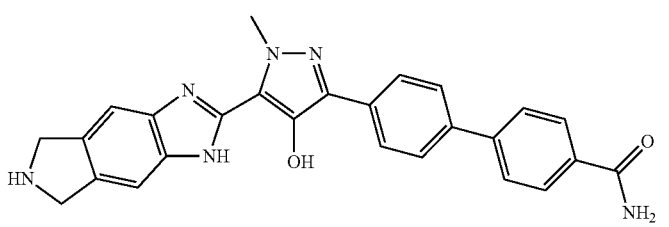 | 451.2 |
| 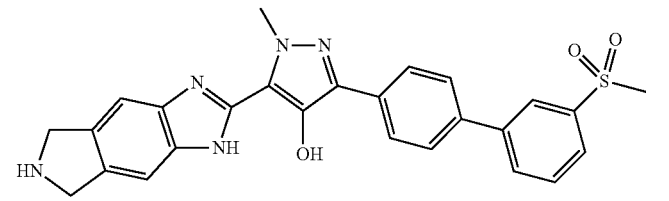 | 486.3 |
| 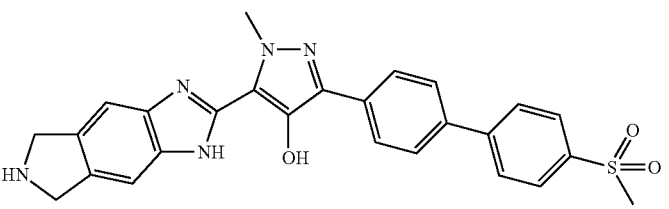 | 486.3 |
| 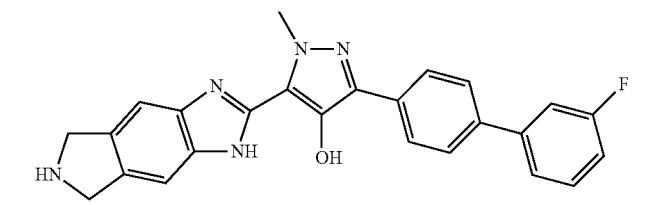 | 426.2 |
| 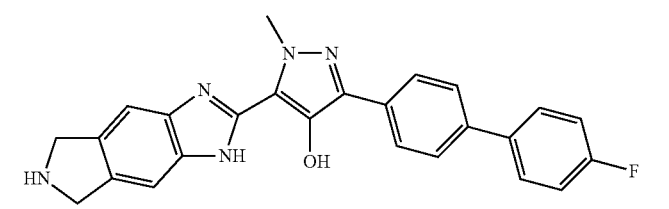 | 426.2 |

-continued
| Structure | MS m/e (MH+) |
|---|---|
| 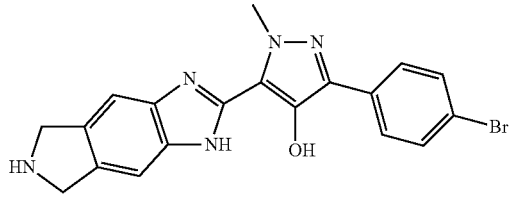 | 410.2 |
| 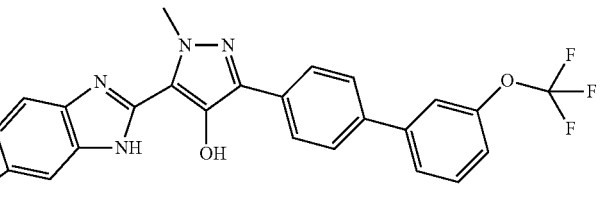 | 492.3 |
| 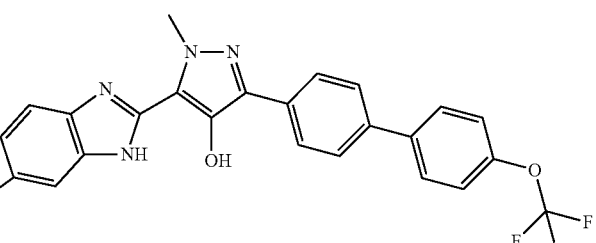 | 492.3 |
| 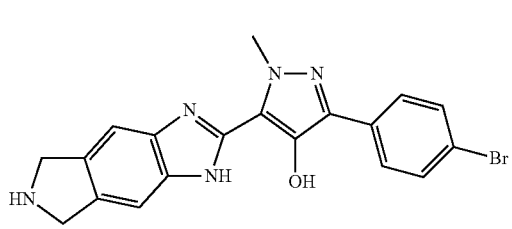 | 410.2 |
| 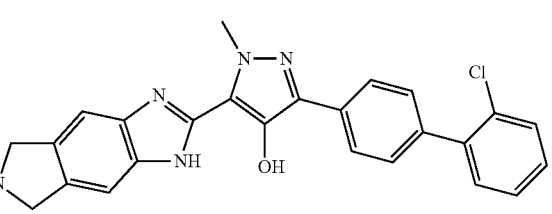 | 442.2 |
| 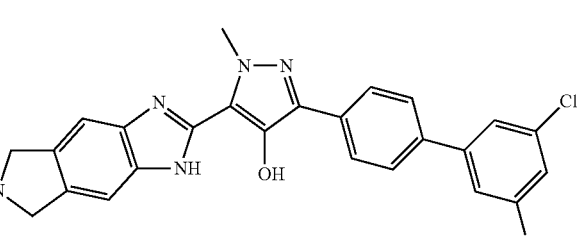 | 476.3 |
| 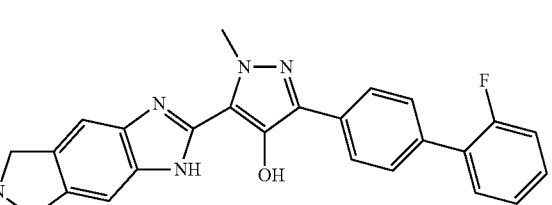 | 426.2 |

| Structure | MS m/e (MH+) |
|---|---|
| 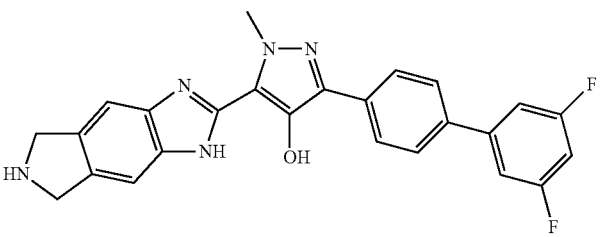 | 444.2 |
| 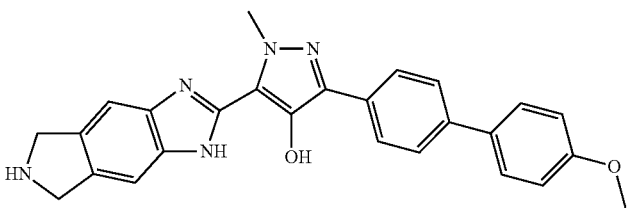 | 438.2 |
| 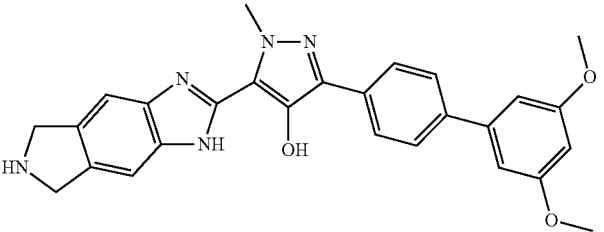 | 468.3 |
| 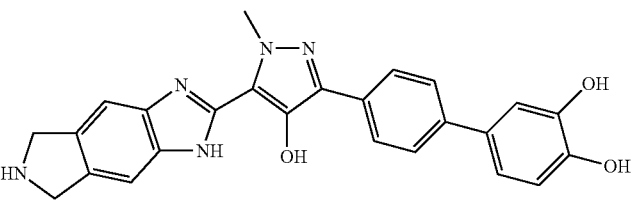 | 440.2 |
| 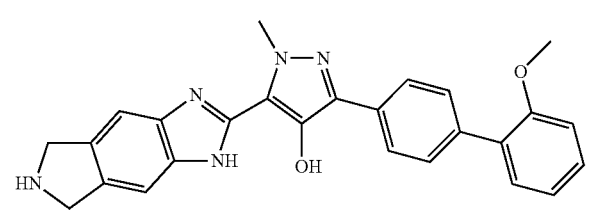 | 438.2 |
| 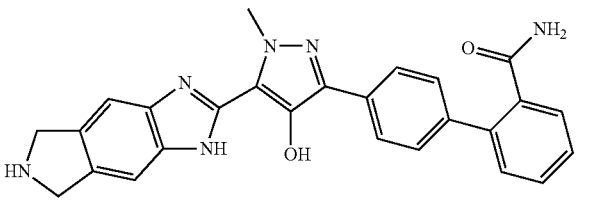 | 451.2 |
| 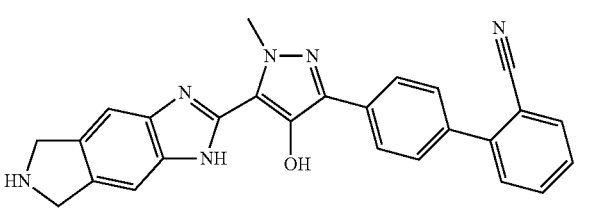 | 433.2 |

-continued

| Structure | MS m/e (MH+) |
|---|---|
| 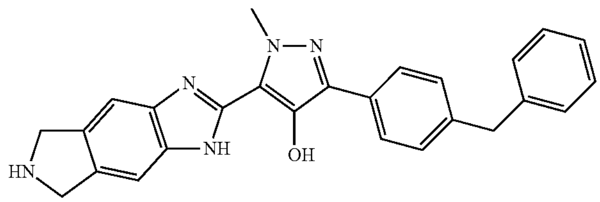 | 422.2 |
| 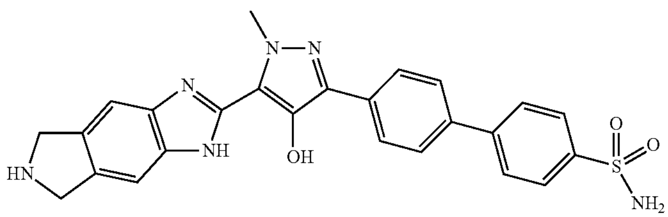 | 487.3 |
| 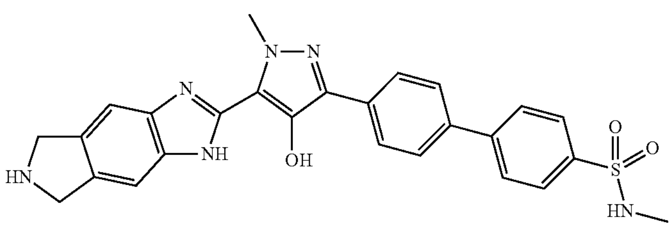 | 501.3 |
| 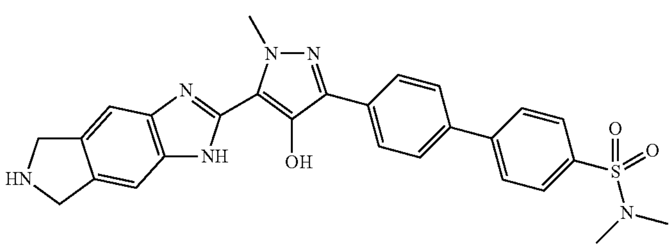 | 515.3 |
| 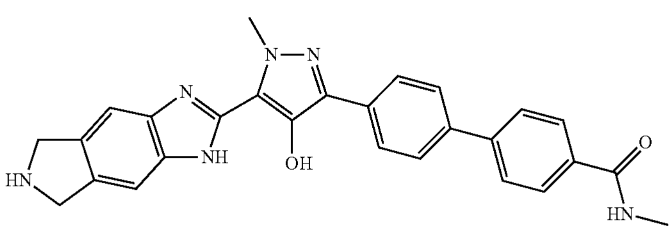 | 465.3 |
| 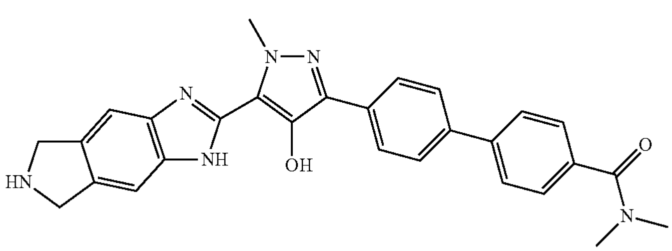 | 479.3 |

| Structure | MS m/e (MH+) |
|---|---|
| 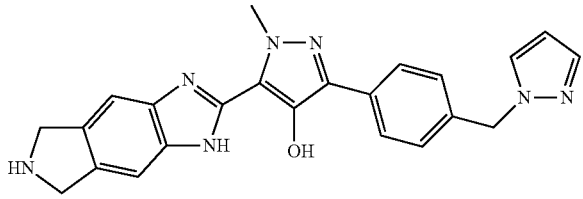 | 412.2 |
| 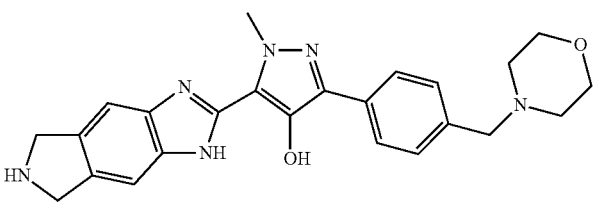 | 431.2 |
| 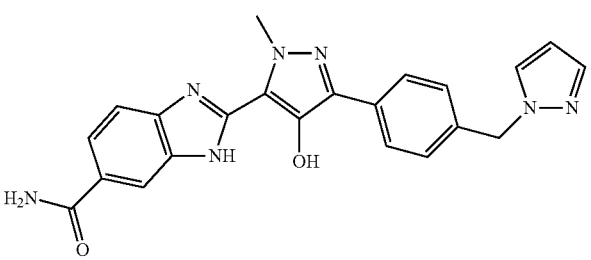 | 414.2 |
| 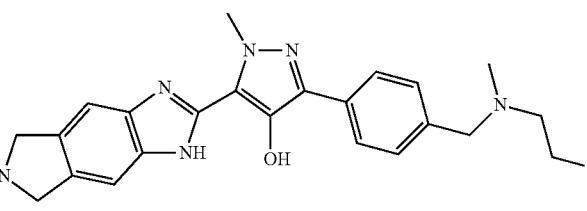 | 432.2 |
| 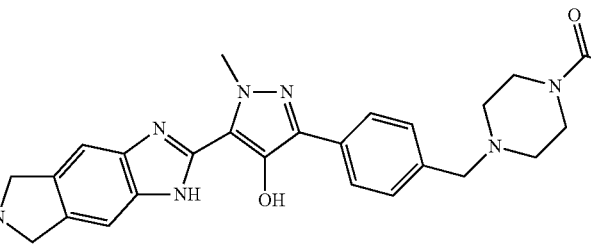 | 472.3 |
| 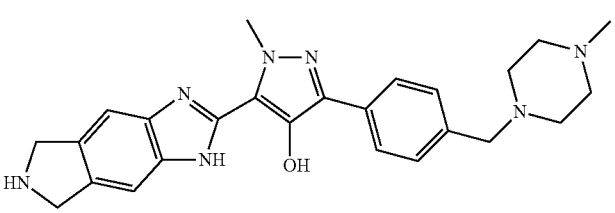 | 444.2 |

| Structure | MS m/e (MH+) |
|---|---|
| 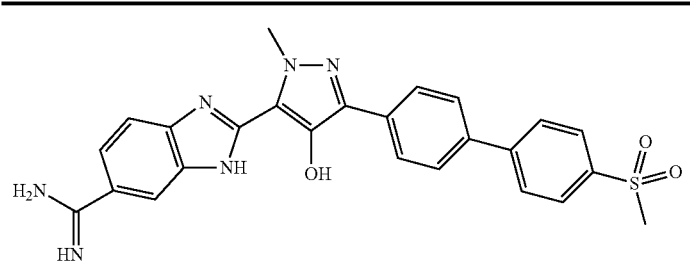 | 487.3 |
| 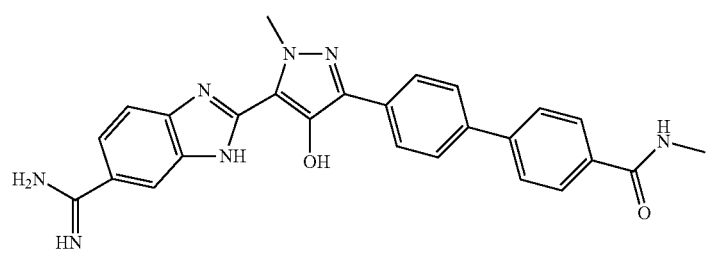 | 466.3 |
| 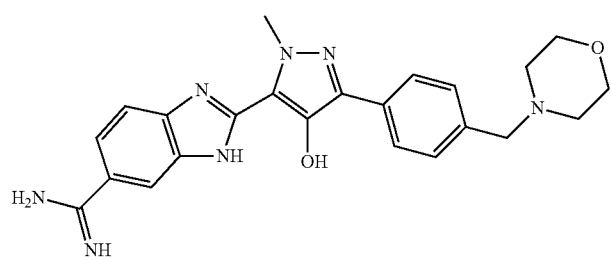 | 432.2 |
| 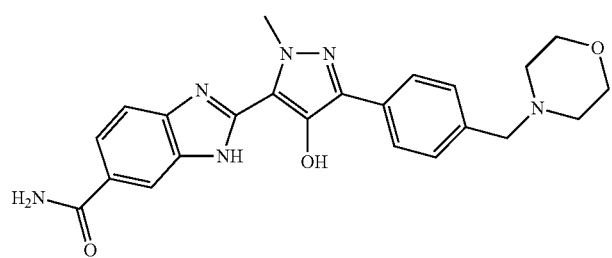 | 433.2 |
| 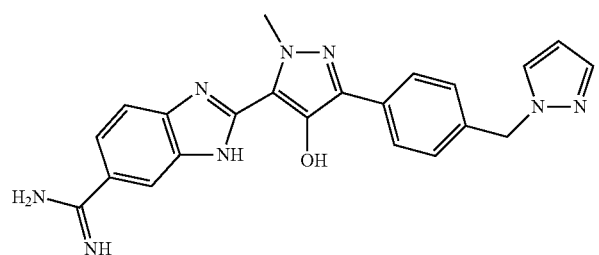 | 413.2 |

| Structure | MS m/e (MH+) |
|---|---|
| 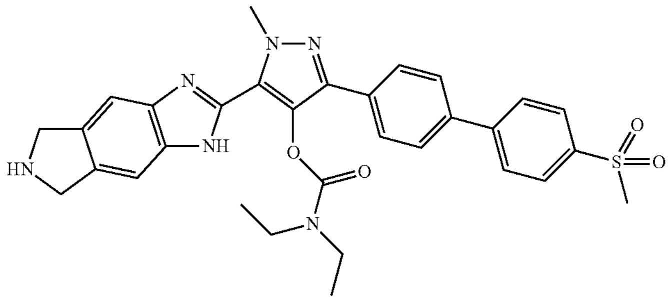 | 585.3 |
| 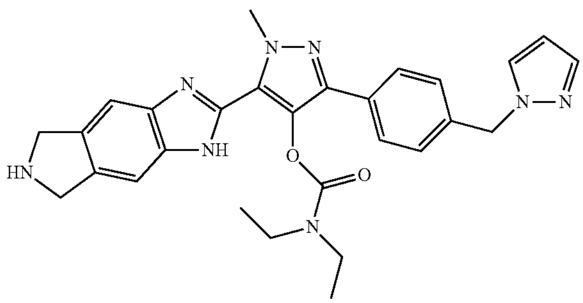 | 511.3 |
| 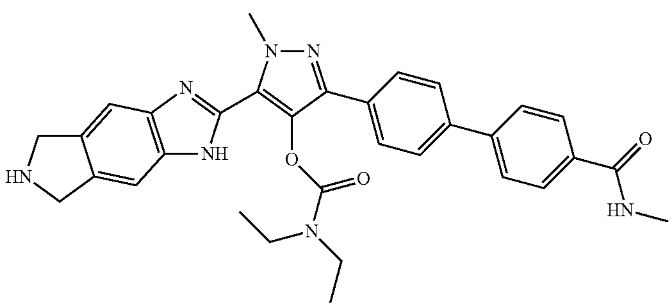 | 564.3 |
| 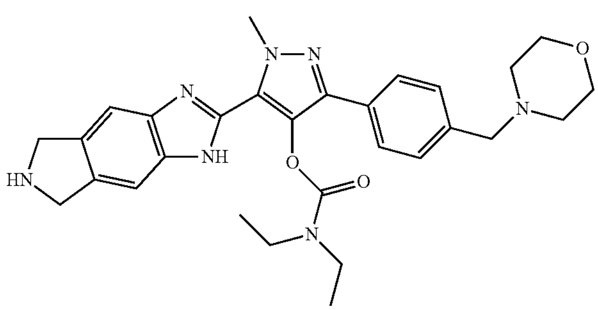 | 530.3 |
| 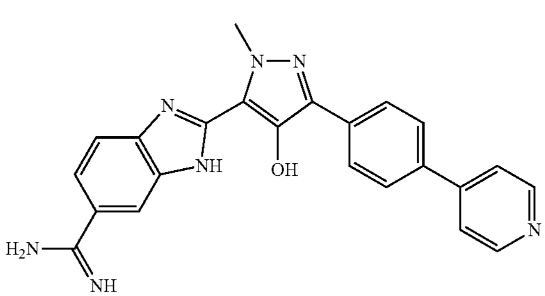 | 410.2 |

| Structure | MS m/e (MH+) |
|---|---|
| (structure) | 437.2 |
| (structure) | 410.2 |
| (structure) | 440.2 |
| (structure) | 370.2 |
| (structure) | 382.2 |
| (structure) | 411.2 |

| Structure | MS m/e (MH+) |
|---|---|
| 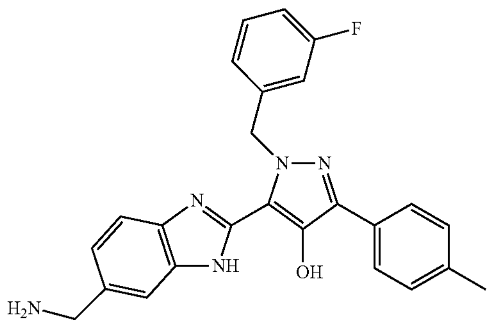 | 428.2 |
| 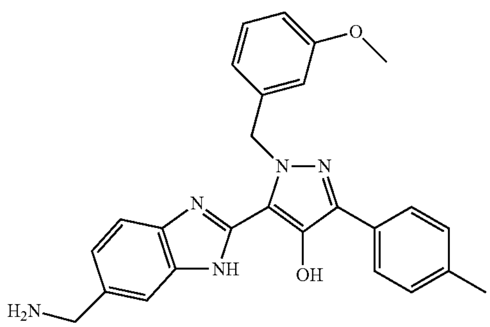 | 440.2 |
| 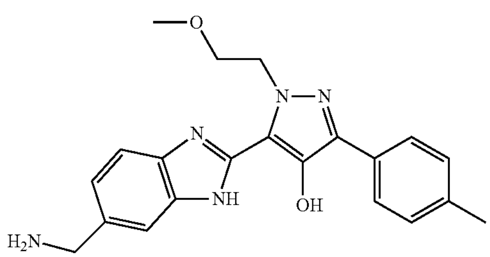 | 378.2 |
| 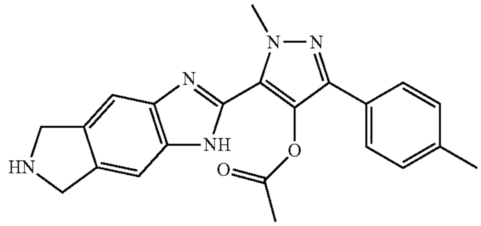 | 388.2 |
| 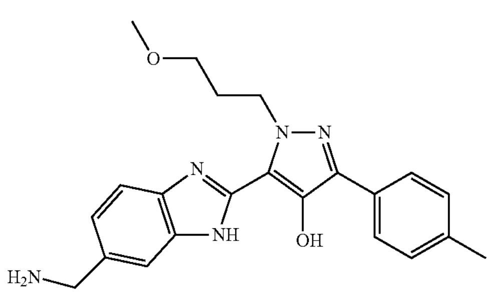 | 392.2 |

| Structure | MS m/e (MH+) |
|---|---|
| 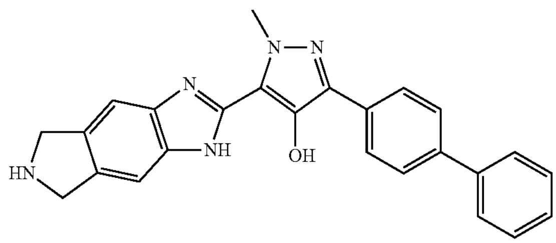 | 408.2 |
| 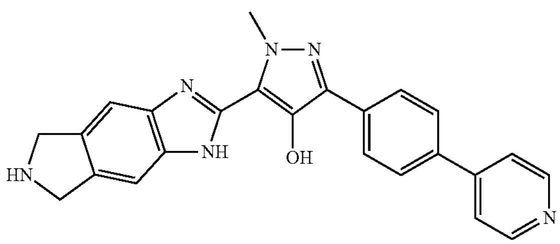 | 409.2 |
| 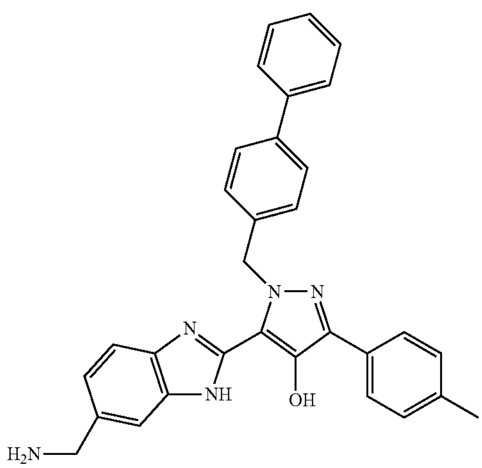 | 486.3 |
| 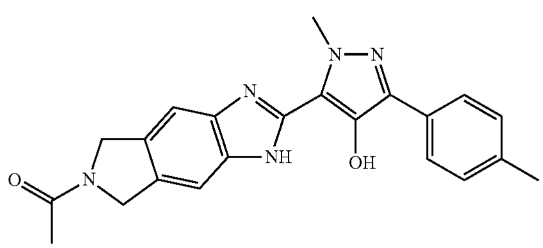 | 388.2 |
| 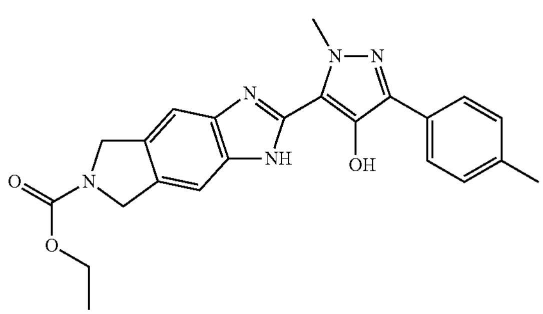 | 418.2 |

| Structure | MS m/e (MH+) |
|---|---|
| 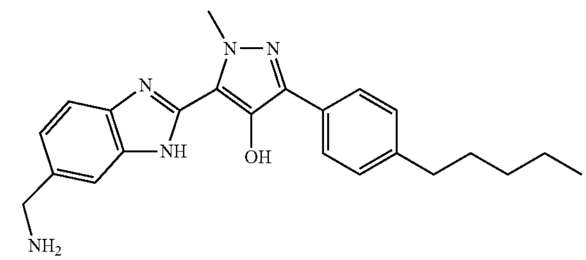 | 390.2 |
| 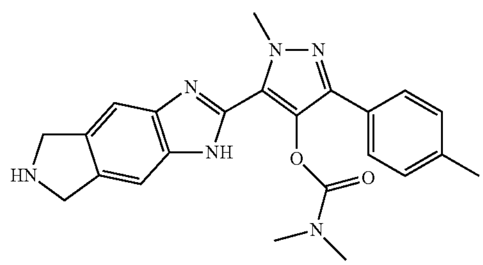 | 417.2 |
| 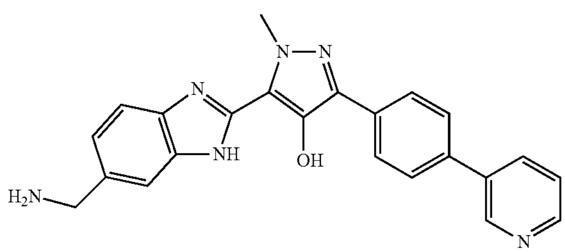 | 397.2 |
| 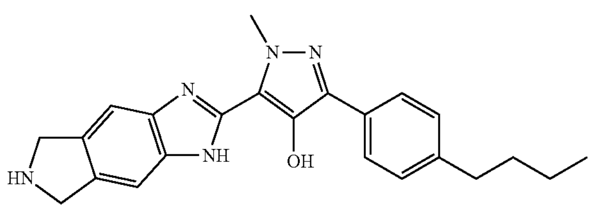 | 388.2 |
| 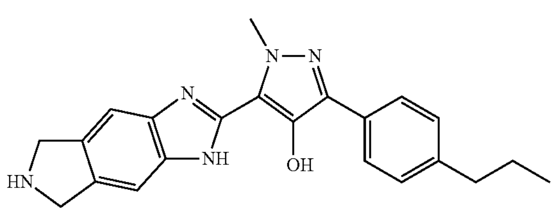 | 374.2 |
| 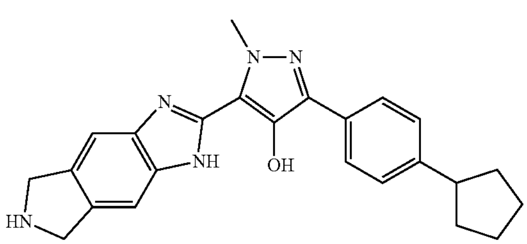 | 400.2 |

-continued

| Structure | MS m/e (MH+) |
|---|---|
| 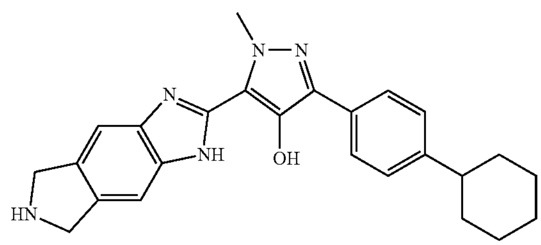 | 414.2 |
| 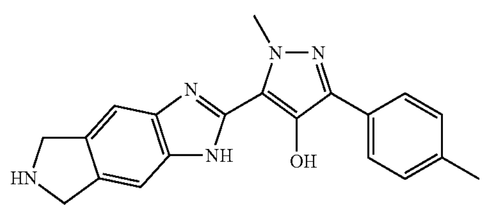 | 346.2 |
| 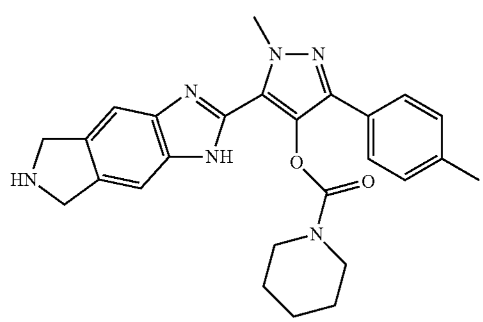 | 457.3 |
| 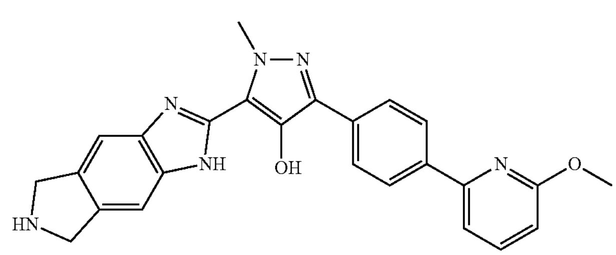 | 439.2 |
| 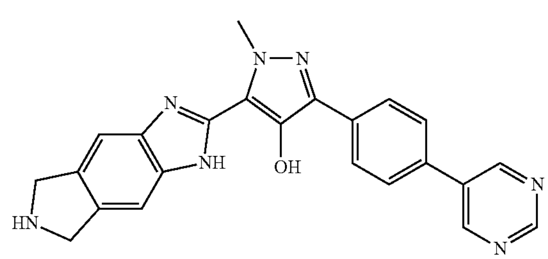 | 410.2 |

-continued
| Structure | MS m/e (MH+) |
|---|---|
| 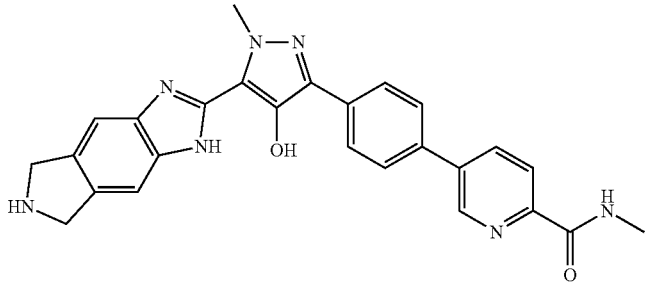 | 466.3 |
| 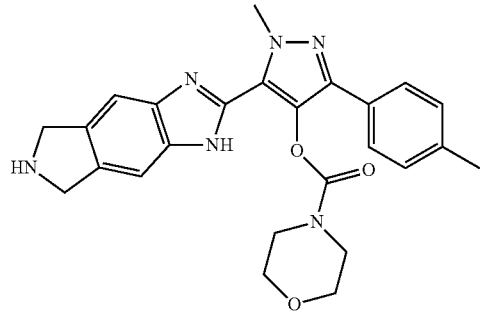 | 459.3 |
| 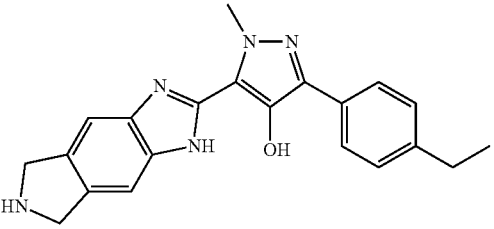 | 360.2 |
| 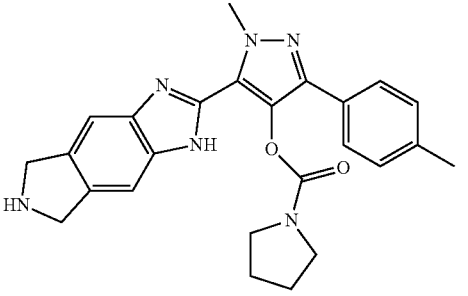 | 443.2 |
| 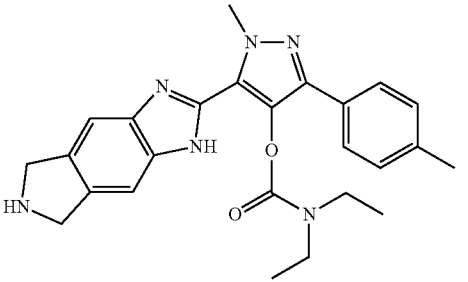 | 445.2 |

| Structure | MS m/e (MH+) |
|---|---|
| 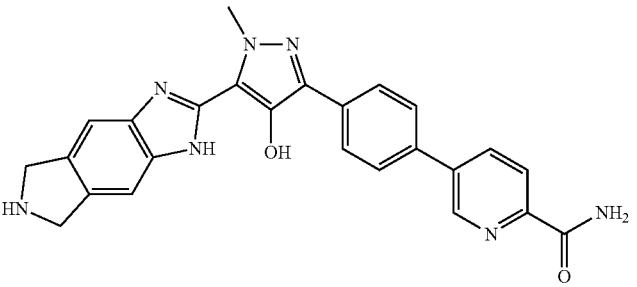 | 452.2 |
| 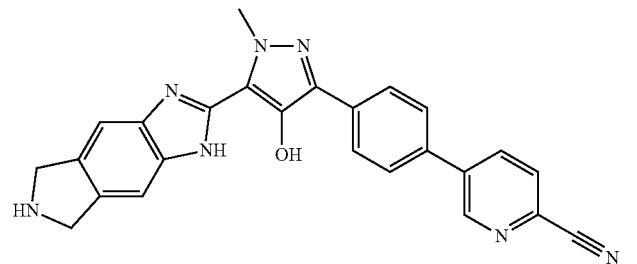 | 434.2 |
| 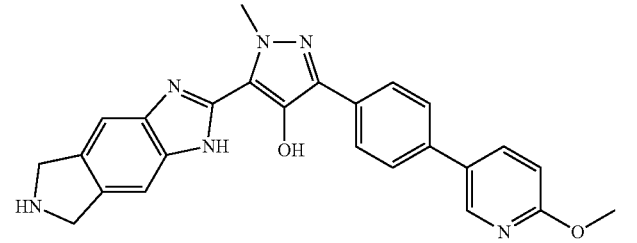 | 439.2 |
| 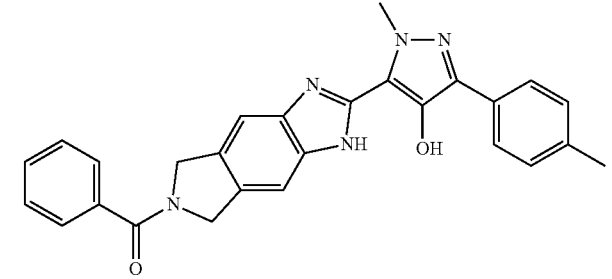 | 450.2 |
| 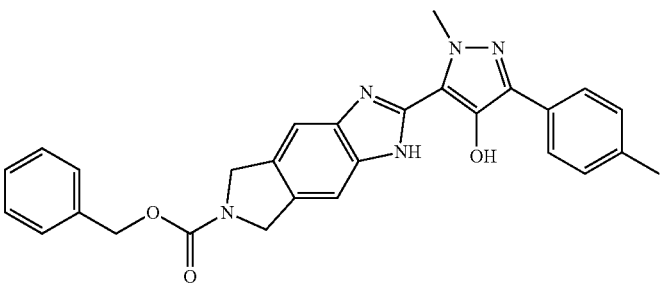 | 480.3 |

-continued
| Structure | MS m/e (MH+) |
|---|---|
| 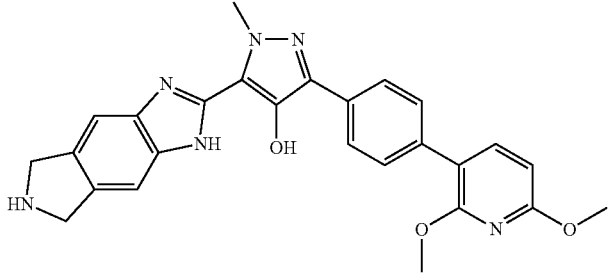 | 469.3 |
| 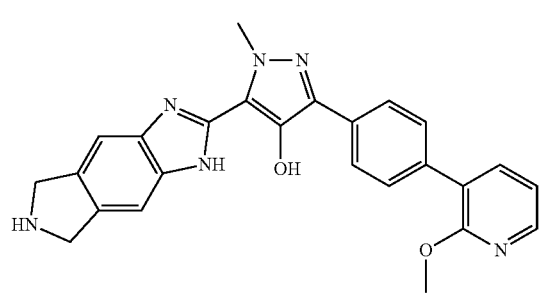 | 439.2 |
| 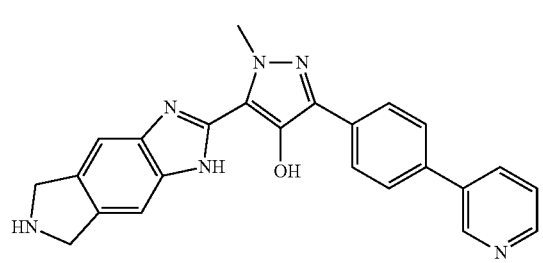 | 409.2 |
| 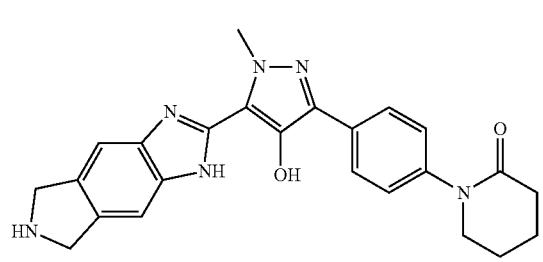 | 429.2 |
| 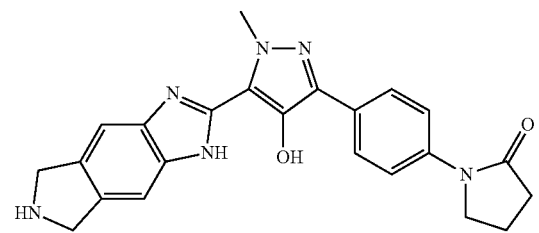 | 415.2 |

-continued
| Structure | MS m/e (MH+) |
|---|---|
| 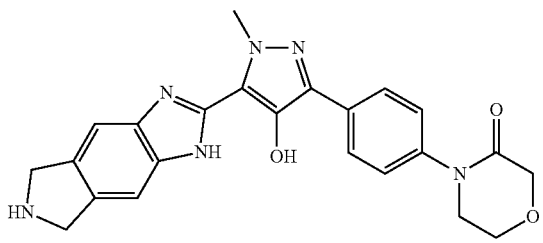 | 431.2 |
| 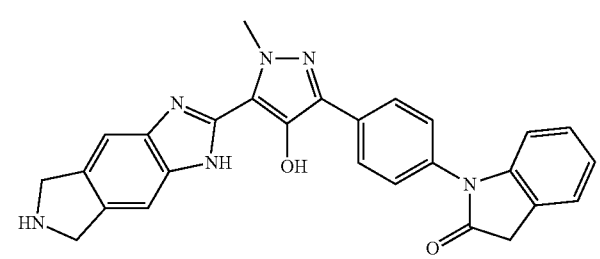 | 463.3 |
| 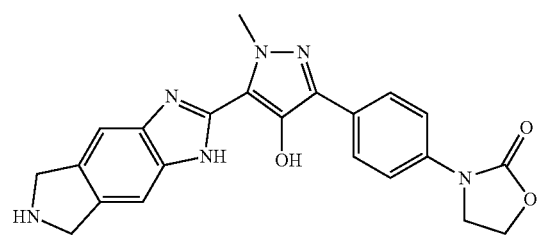 | 417.2 |
| 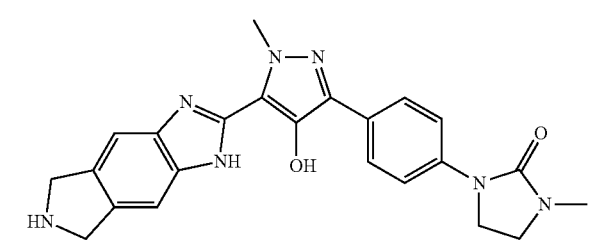 | 430.2 |
| 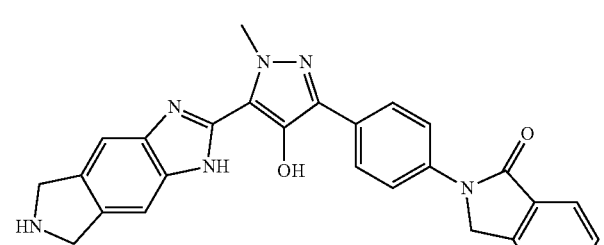 | 463.3 |
| 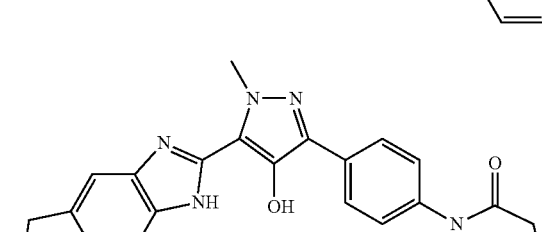 | 443.2 |

-continued
| Structure | MS m/e (MH+) |
|---|---|
| 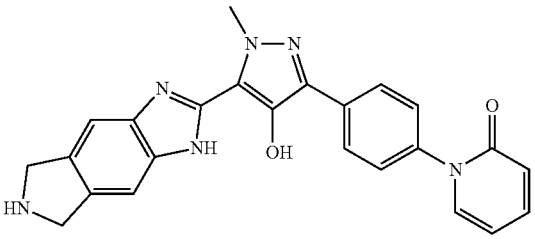 | 425.2 |
| 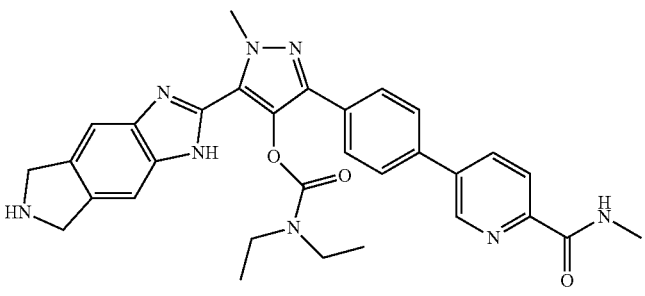 | 565.3 |
| 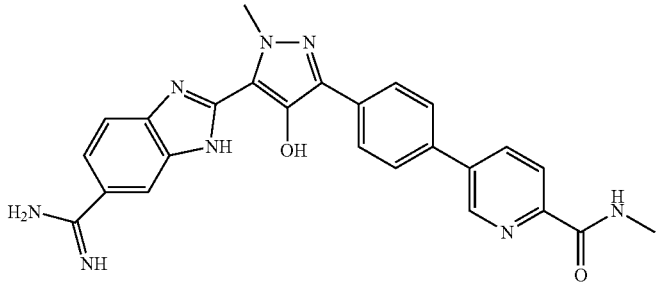 | 467.3 |
| 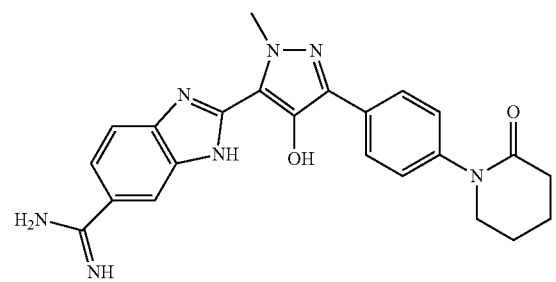 | 430.2 |
| 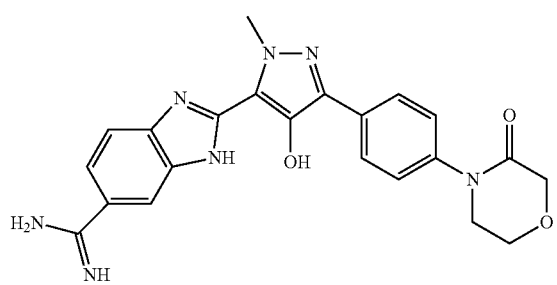 | 432.2 |

-continued

| Structure | MS m/e (MH+) |
|---|---|
| 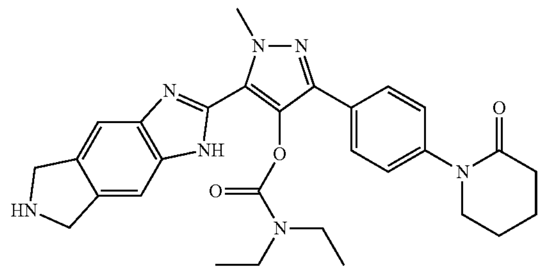 | 528.3 |
| 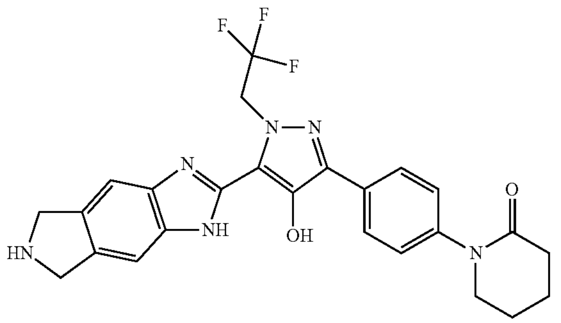 | 497.3 |
| 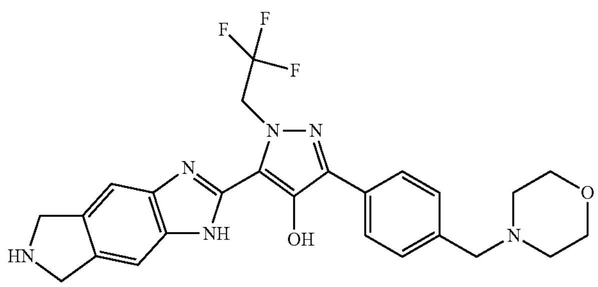 | 499.3 |
| 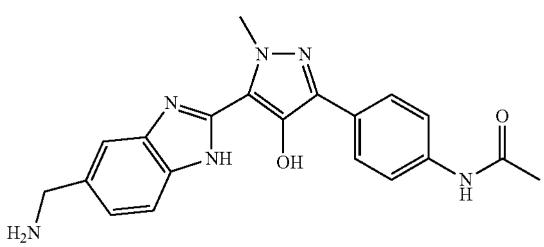 | M + H 377.2 |
| 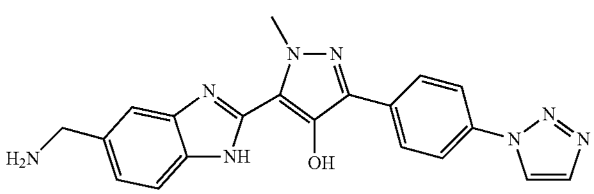 | M + H 387.2 |
| 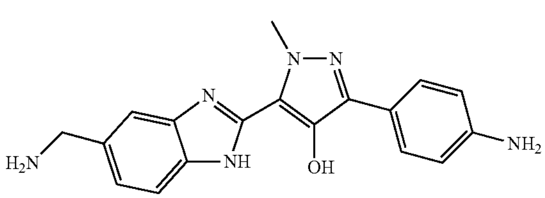 | M + H 335.2 |

-continued
| Structure | MS m/e (MH+) |
|---|---|
| 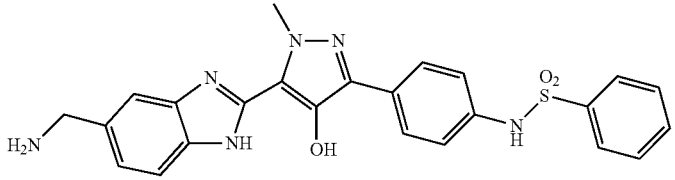 | M + H 475.3 |
| 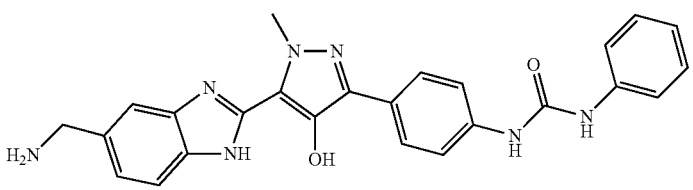 | M + H 454.2 |
| 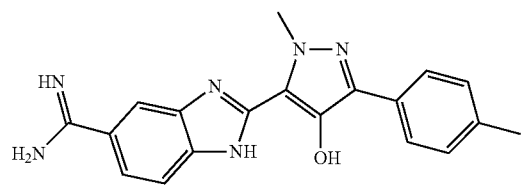 | M + H 347.2 |
| 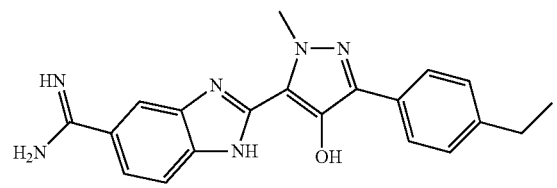 | M + H 361.2 |
| 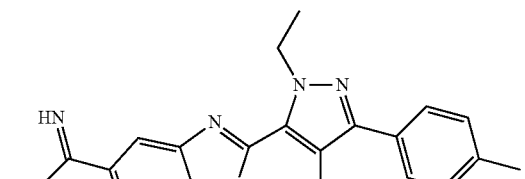 | M + H 361.2 |
| 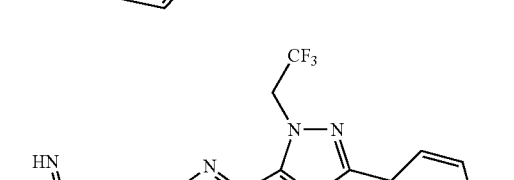 | M + H 435.2 |
| 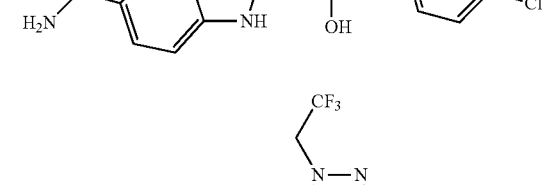 | M + H 451.2 |

-continued
| Structure | MS m/e (MH+) |
|---|---|
| 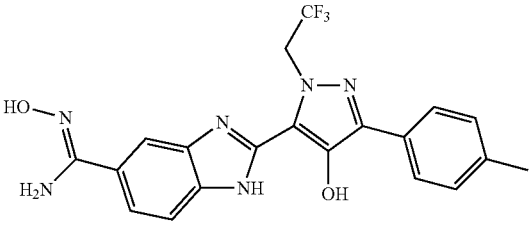 | M + H 431.2 |
| 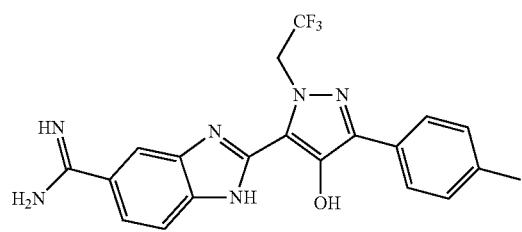 | M + H 415.2 |
| 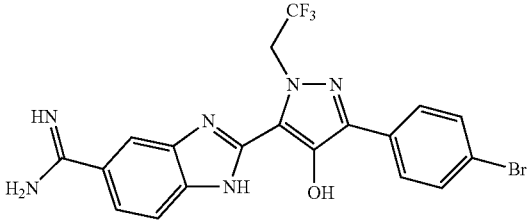 | M + H 479.3 |
| 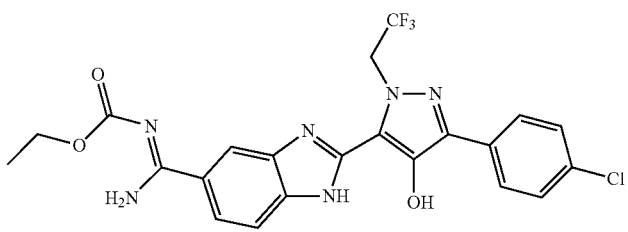 | M + H 507.3 |
| 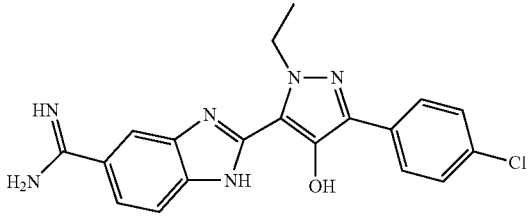 | M + H 381.2 |
| 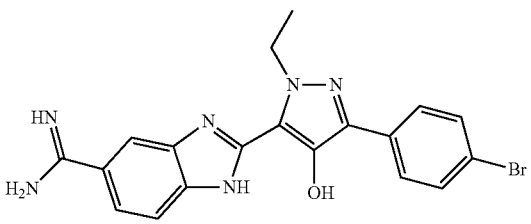 | M + H 425.2 |

| Structure | MS m/e (MH+) |
|---|---|
| 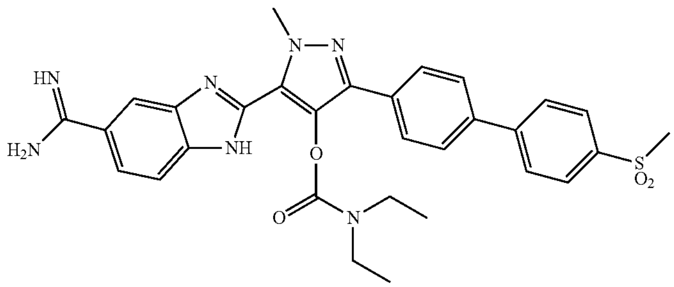 | M + H 586.3 |
| 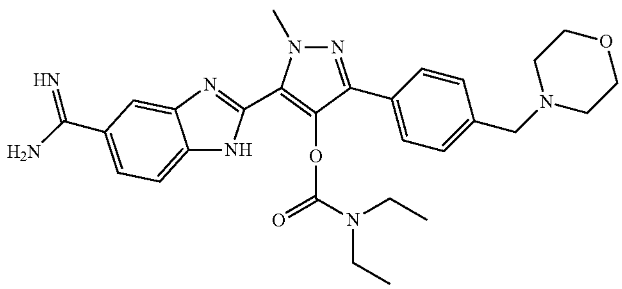 | M + H 531.3 |
| 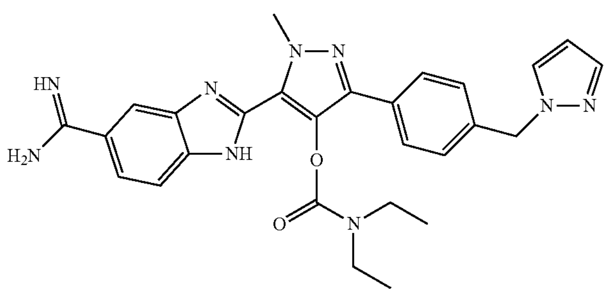 | M + H 512.3 |
| 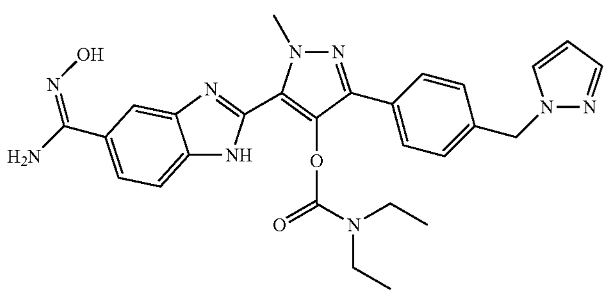 | M + H 528.3 |

Utility

The compounds of this invention are inhibitors of factor IXa and are useful as anticoagulants for the treatment or prevention of thromboembolic disorders in mammals (i.e., factor IXa-associated disorders). In general, a thromboembolic disorder is a circulatory disease caused by blood clots (i.e., diseases involving fibrin formation, platelet activation, and/or platelet aggregation).

The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory distress syndrome, hereditary angioedema or other inherited or acquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations can be made in 50 mM HEPES buffer at pH 7.4 containing 145 mM NaCl, 5 mM KCl, and 0.1% PEG 8000 (polyethylene glycol; JT Baker or Fisher Scientific). Determinations can be made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. Compounds tested in the Factor XIa assay are considered to be active if they exhibit a $K_i$ of equal to or less than 15 µM. Preferred compounds of the present invention have $K_i$'s of equal to or less than 1 µM. More preferred compounds of the present invention have $K_i$'s of equal to or less than 0.1 µM. Even more preferred compounds of the present invention have $K_i$'s of equal to or less than 0.01 µM.

Factor VIIa determinations can be made in 0.005 M calcium chloride, 0.15 M sodium chloride, 0.05 M HEPES buffer containing 0.5% PEG 8000 at a pH of 7.4. Determinations can be made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. Compounds tested in the Factor VIIa assay are considered to be active if they exhibit a K of equal to or less than 15 µM.

Factor IXa determinations were made according to the following assay procedure:
Buffer:
50 mM Tris pH 8.0
5 mM $CaCl_2.2H_2O$
100 mM NaCl
15% vol/vol Ethylene Glycol
Enzyme:
 Human plasma factor IXa. (American Diagnostica Inc. product)
 Enzyme is diluted 1:800 in buffer to achieve 0.0057 ug/ml working stock for use in assay. Mix by inversion.
Substrate:
 Spectrozyme factor IXa Fluorogenic substrate (American Diagnostica Inc.) The substrate (10 umoles lyophilized) is reconstituted with 1 ml water to give a 10 mM stock. The substrate is then further diluted to 300 uM in buffer for use in assay. Mix by inversion.
Procedure in 384 well plate:
Add 10 ul vehicle or compound
Add 10 ul Factor IXa enzyme.
Add 10 ul Fluorogenic substrate.
Incubate reaction at room temperature for 2 h.
Quench with 5 ul 50% acetic acid.
Read Fluorescence-Absorbance 360 nm; Emission 440 nm
 Factor Xa determinations are made according to the following assay procedure:
Buffer:
20 mM Tris pH 8.0
2.5 mM $CaCl_2.2H_2O$
200 mM NaCl
Enzyme:
Human plasma factor Xa. (American Diagnostica Inc.)
Resuspend enzyme in water to 80 ug/ml.
Enzyme is diluted to 0.133 ug/ml in buffer. Mix by inversion.
Substrate:
 Spectrozyme factor IXa Fluorogenic substrate (American Diagnostica Inc.) Reconstitute with 1 ml water to give a 10 mM stock. The substrate is then further diluted to 300 uM in buffer for use in assay. Mix by inversion.
Procedure in 384 well plate:
Add 10 ul vehicle or compound
Add 10 ul Factor Xa enzyme.
Add 10 ul Fluorogenic substrate.
Incubate reaction at room temperature for 2 h.
Quench with 5 ul 50% acetic acid.
Read Fluorescence-Absorbance 360 nm; Emission 440 nm
 IC50 determinations for factor IXa and Xa were made for the present compounds as described below
IC50 calculation
Compounds were tested at multiple concentrations beginning at 100 uM and decreasing at half log intervals. IC50 values for compounds at each coagulation factor were then generated using nonlinear curvefit software within ActivityBase (IDBS software). Each compound that was tested was tested in at least 2 separate assays (4 replicates per experiment). The final IC50 values obtained represent the average of all determinations.

In one embodiment, the compounds of the present invention have factor IXa IC50 (μM; micromolar) values ranging from less than 0.1 (<0.1 μM) to greater than 100 (>100 μM). In another embodiment, for some of the compounds, the values range from less than 0.1 μM (<0.1 μM) to 50 μM, and in another embodiment from less than 0.1 μM to 30 μM and in another embodiment from less than 0.1 μM to 20 μM, and in another embodiment from less than 0.1 μM to 10 μM, and in another embodiment from less than 0.1 μM to 5 μM.

In another embodiment, the compounds of the present invention have factor Xa IC50 (μM; micromolar) values ranging from less than 1 (1 μM) to greater than 100 (>100 μM). In another embodiment, for some of the compounds, the values range from less than 1 μM (<1 μM) to 50 μM, and in another embodiment from less than 1 μM to 30 μM and in another embodiment from less than 1 μM to 20 μM, and in another embodiment from less than 1 μM to 10 μM, and in another embodiment from less than 1 μM to less than 10 μM.

In one embodiment, the compounds of the present invention are selective factor IXa inhibitors, i.e., selective for factor IXa over other coagulation factors, such as factor Xa.

Selectivity Calculation

Selectivity for Factor IXa activity over Factor Xa activity can be determined by the following calculation.: (IC50 Factor Xa)/(IC50 Factor IXa). Similar calculations can be made for selectivity of compounds for Factor IX compared to other coagulation factors.

Plasma kallikrein determinations can be made in 0.1 M sodium phosphate buffer at a pH of 7.4 containing 0.2 M sodium chloride and 0.5% PEG 8000. Determinations can be made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value useful for calculation of $K_i$ is 0.00005 to 0.00007 M. Compounds tested in the plasma kallikrein assay are considered to be active if they exhibit a $K_i$ of equal to or less than 15 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM.

Thrombin determinations can be made in 0.1 M sodium phosphate buffer at a pH of 7.4 containing 0.2 M sodium chloride and 0.5% PEG 8000. Determinations are made using purified human alpha thrombin (Haematologic Technologies or Enzyme Research Laboratories) at a final assay concentration of 200-250 μM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 15 μM.

Compounds of the present invention are useful as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease can be determined at 25° C. using the method of Lineweaver and Burk. Values of $K_i$ are determined by allowing the protease to react with the substrate in the presence of the inhibitor. Reactions are allowed to go for periods of 20-180 minutes (depending on the protease) and the velocities (rate of absorbance or fluorescence change versus time) are measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and
$K_i=IC_{50}/(1+S/K_m)$ for a competitive inhibitor where:

$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model: The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model: The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg in.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANOX®), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art. Factor IXa inhibitors different from the compounds of Formulae I-III include monoclonal antibodies, synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulents. *Arterioscler Thromb Vasc Biol.* 2007; 27: 722-727.)

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof. The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and WO 01/96330 and 10/271,715.

Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamili nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor IXa in serum samples could be determined by careful titration of protease activity in the presence of the relevant chromogenic substrate, S2366, with a potent and selective Factor IXa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound of formula IA or IB

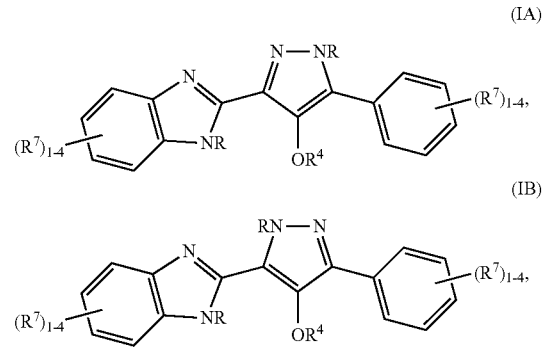

or a pharmaceutically acceptable salt, or ester thereof; wherein each $R^7$ is independently selected from the group consisting of hydrogen, halo, alkyl, aminoalkyl, hydroxyalkyl, haloalkyl, alkoxy, -alkyl-O-hydroxyalkyl, haloalkoxy, cyano, hydroxy, —C(O)NR$^5$R$^6$, —C(=NOR$^5$)N(R$^6$)$_2$, —C(O)OR$^4$, -alkyl-NR$^5$C(=O)OR$^4$, -alkyl-S(=O)$_2$-aryl, -alkyl-NR$^5$S(=O)$_2$-alkyl, —alkyl-NR$^5$C(=O)NR$^5$-alkyl, -alkyl-heteraryl, -alkyl-heterocyclyl, -alkyl-NR$^5$C(=O)alkyl, -alkyl -NR$^5$C(=O)aryl, alkoxyalkyl, aryl, heteroaryl, cycloalkyl, heterocycylyl, —NR$^5$R$^6$, —SR$^4$, and —C(O)NR$^5$R$^6$, each R independently is H, alkyl, haloalkyl, cycloalkyl, heterocyclyl, aryl, heteroaryl, or -(CR$^5$R$^6$)$_n$W, wherein W is selected from the group consisting of cycloalkyl, heterocyclyl,aryl, heteroaryl, —C(=O)NR$^5$R$^6$, C(=O)OR$^4$, —OR$^4$, —NR$^5$R$^6$;

each R$^4$ independently is selected from the group consisting of H, alkyl, —C(=O)-heterocyclyl, —C(=O)NHalkyl, and —C(=O)N(alkyl)$_2$;

each R$^5$ and R$^6$ is independently selected from the group consisting of H alkyl, —C(=O)alkyl, and —C(=O)Oalkyl.

2. The compound of claim 1 selected from the group consisting of:

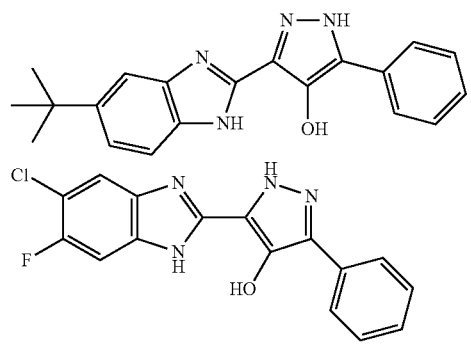

-continued
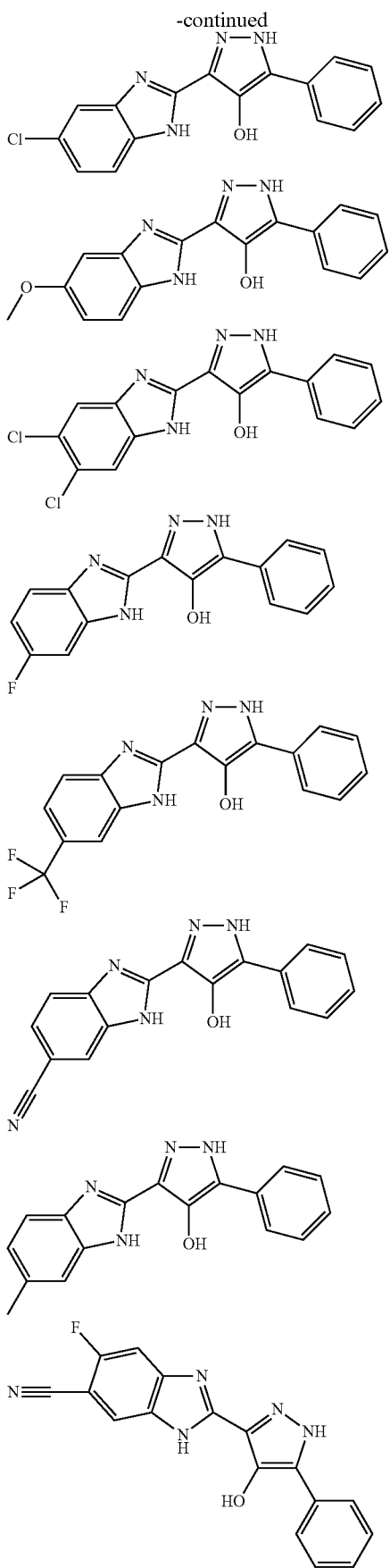
-continued
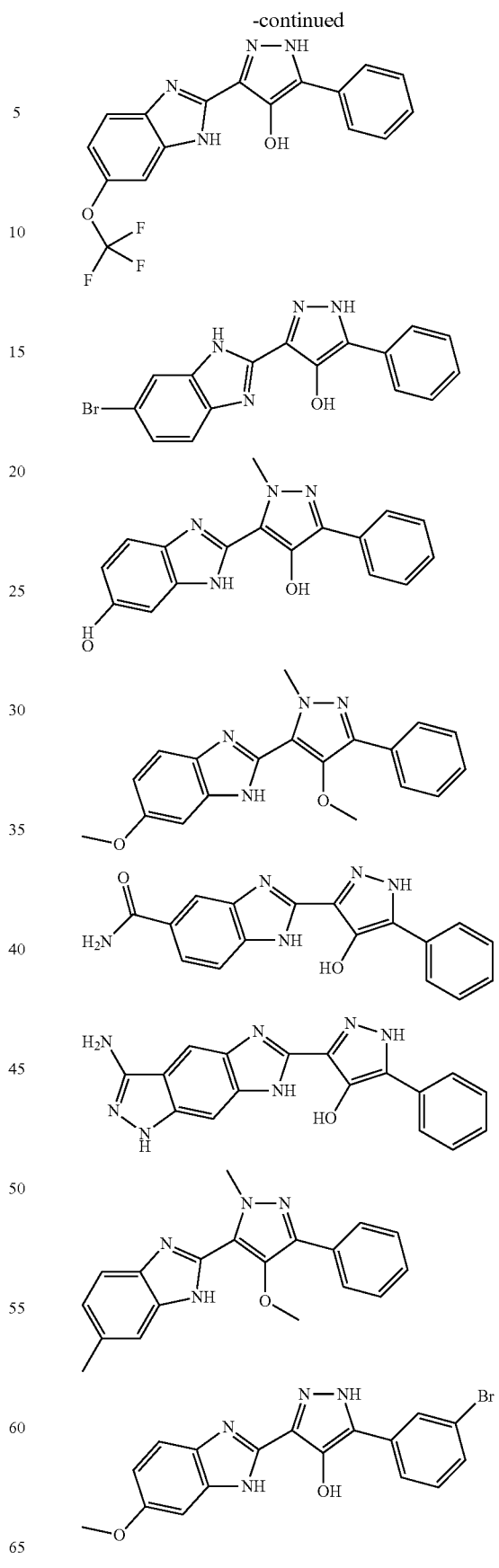

233
-continued
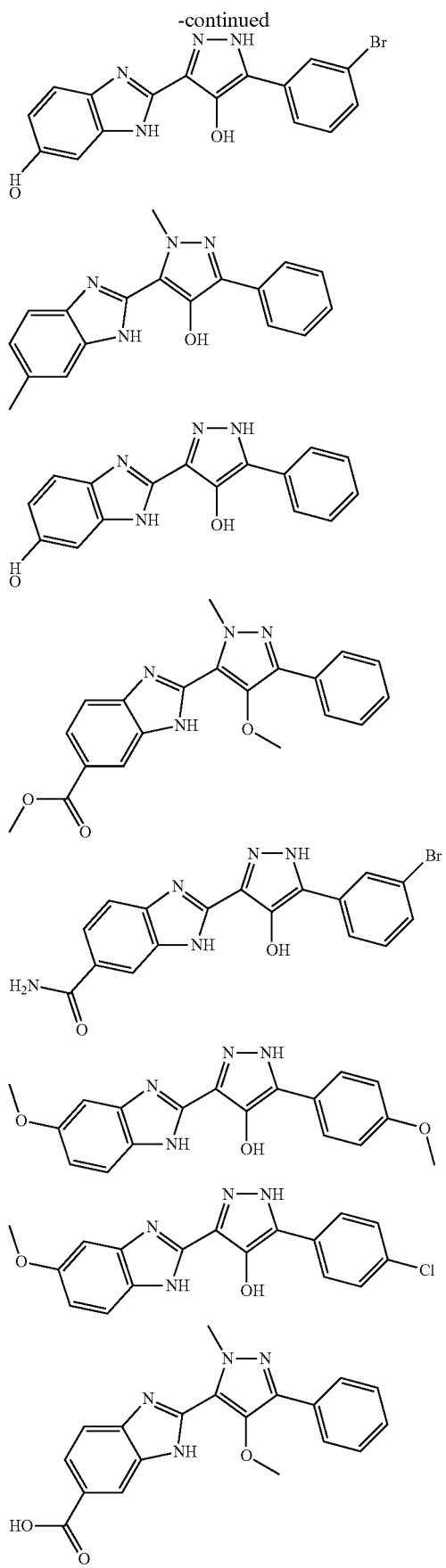
234
-continued
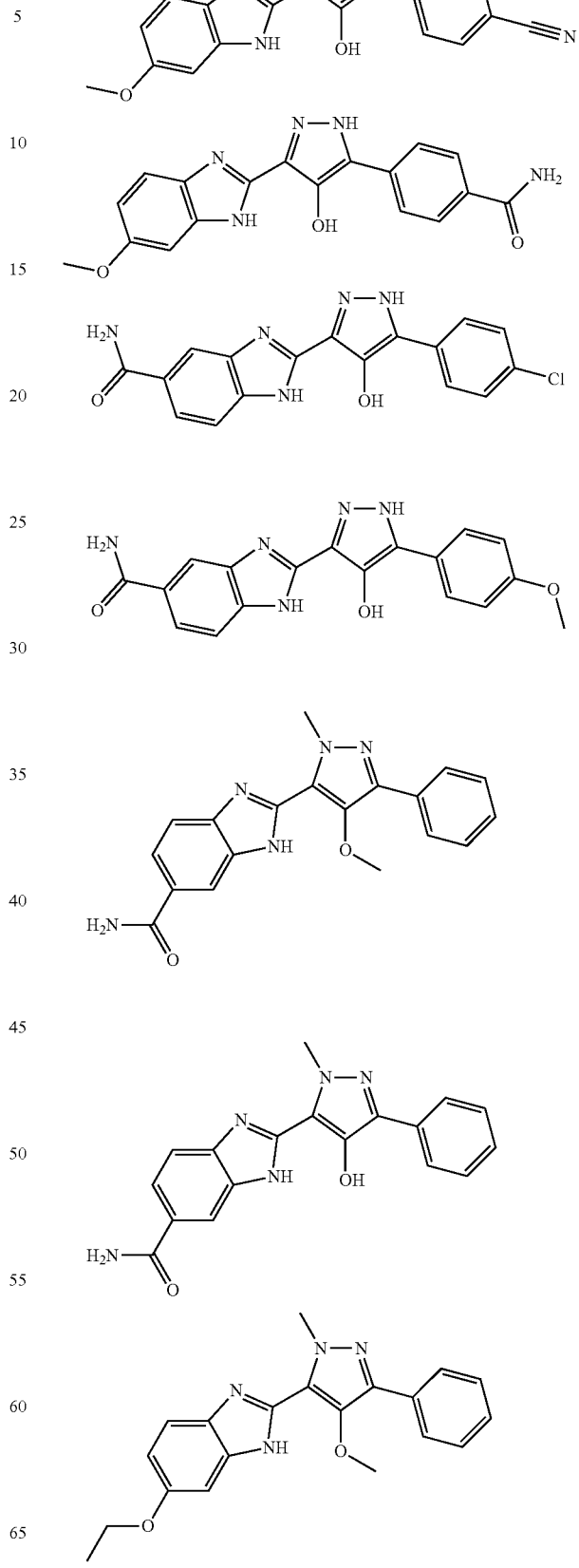

235
-continued
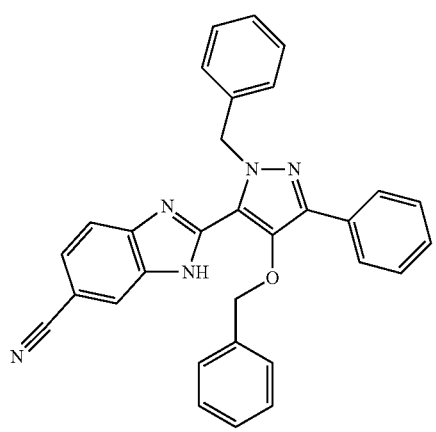
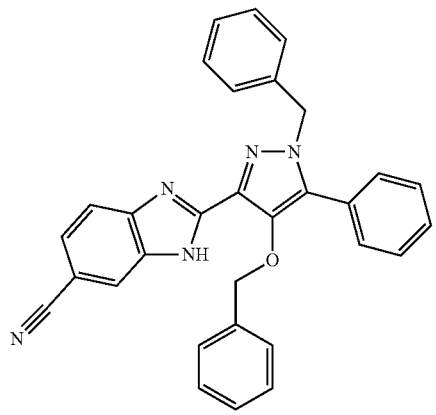
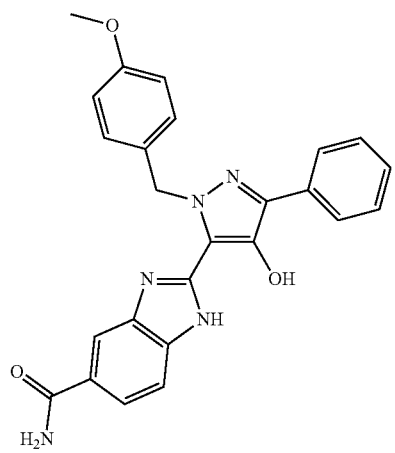
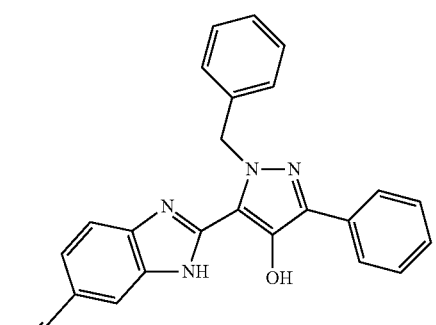
236
-continued
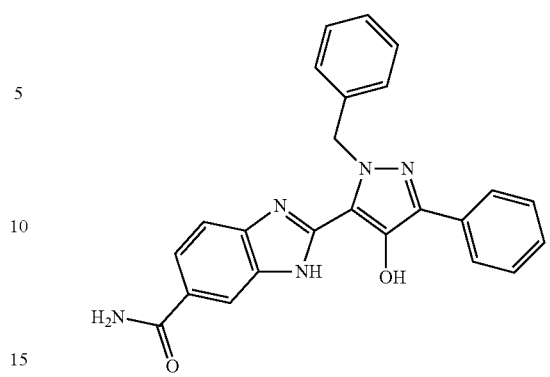
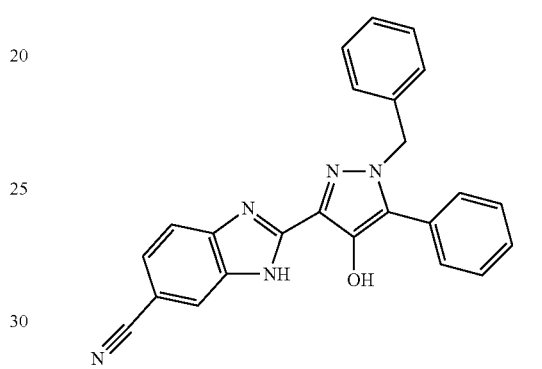
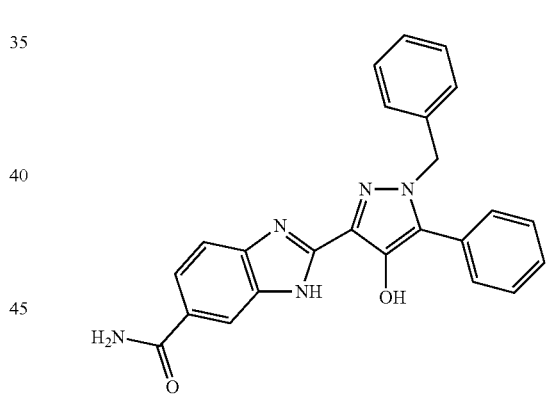
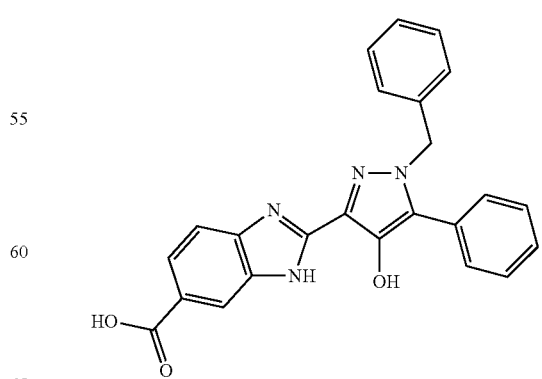

237
-continued
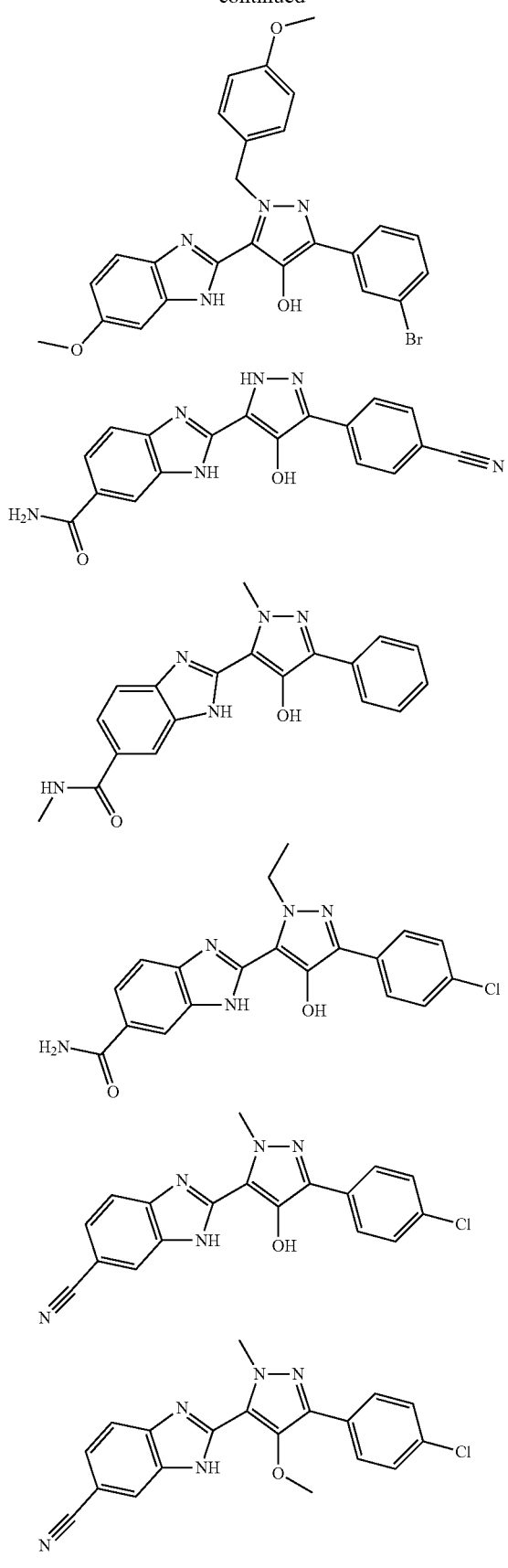
238
-continued
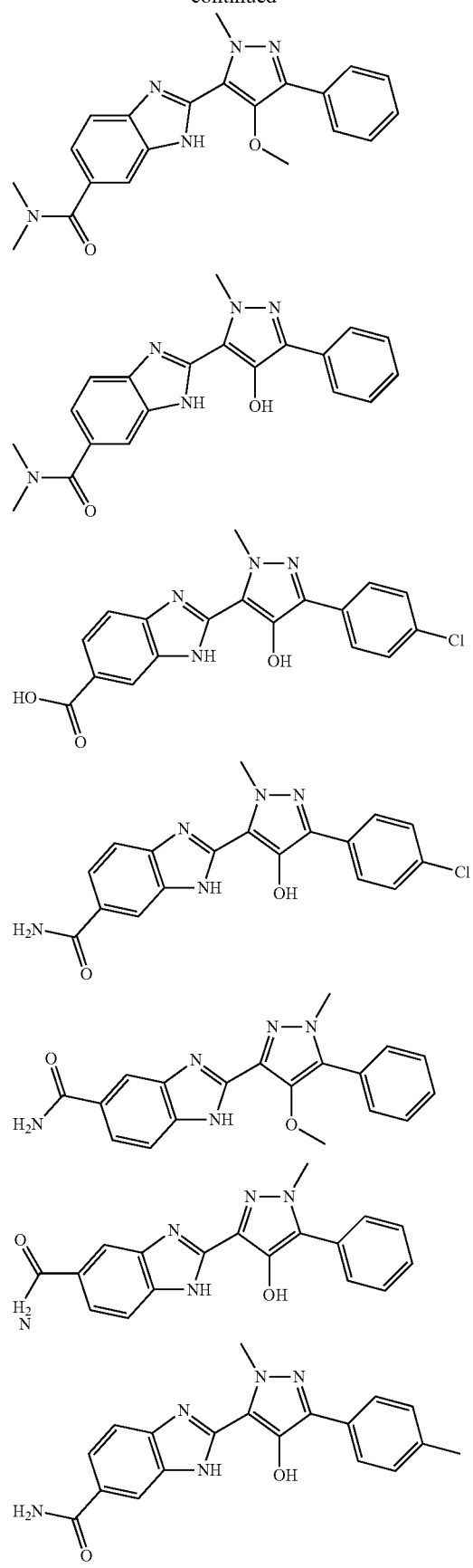

239
-continued
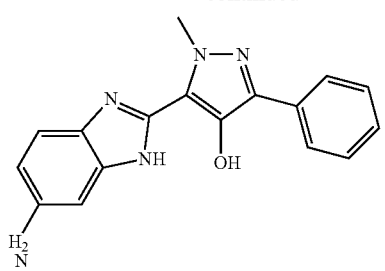
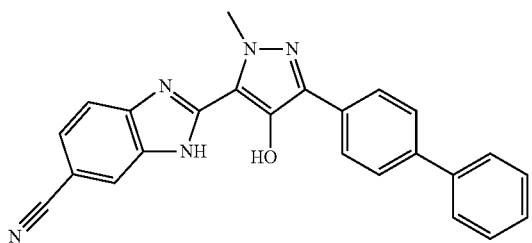
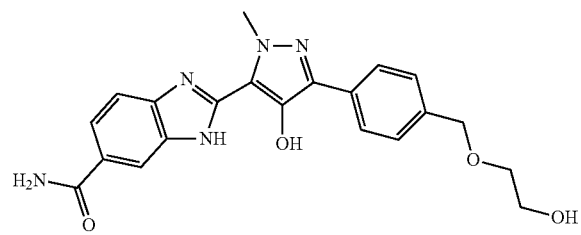
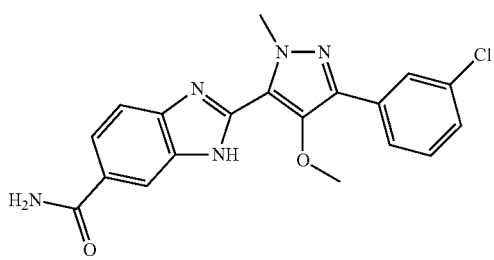
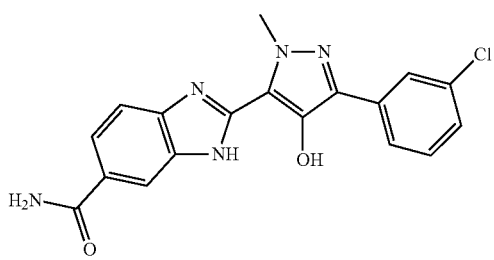
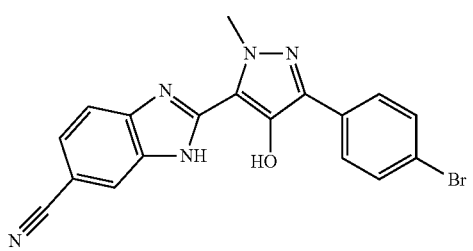
240
-continued
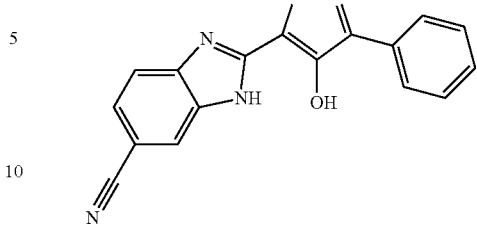
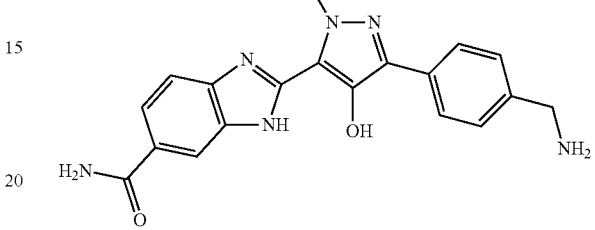
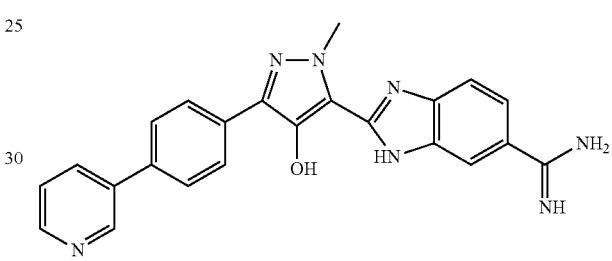
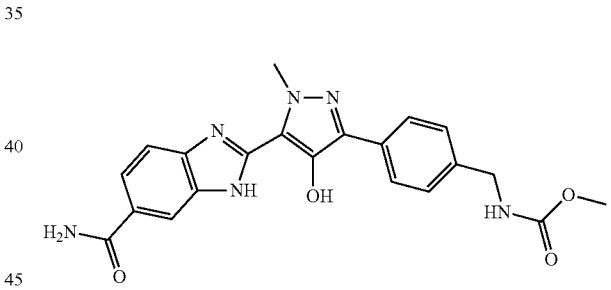
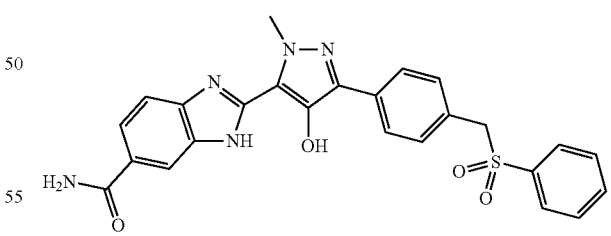
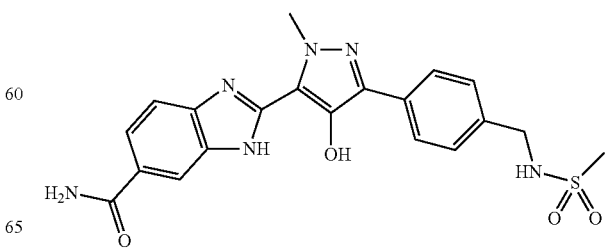

241
-continued
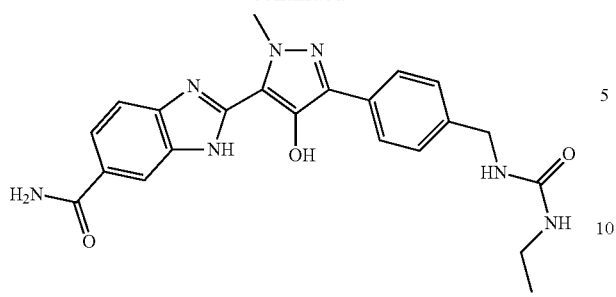
242
-continued
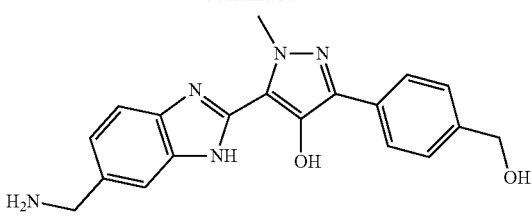
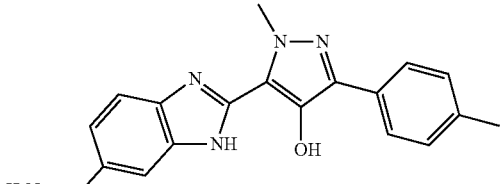
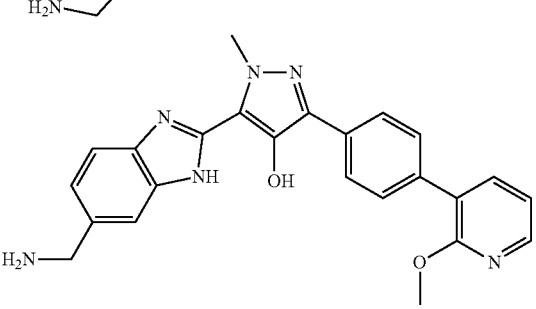
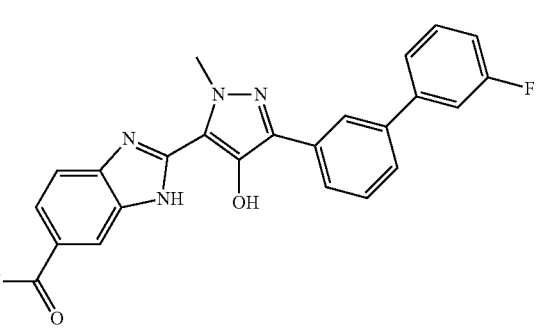
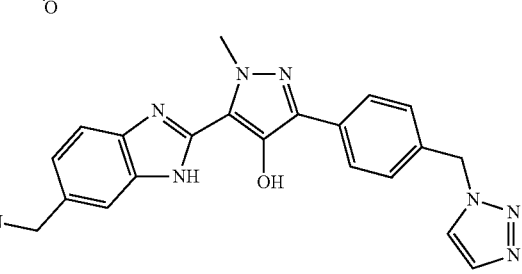
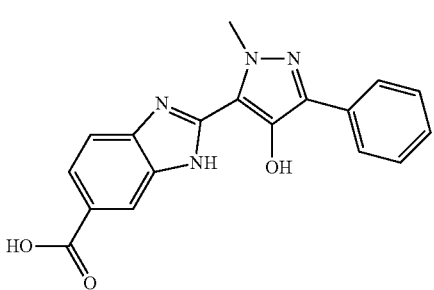

243
-continued
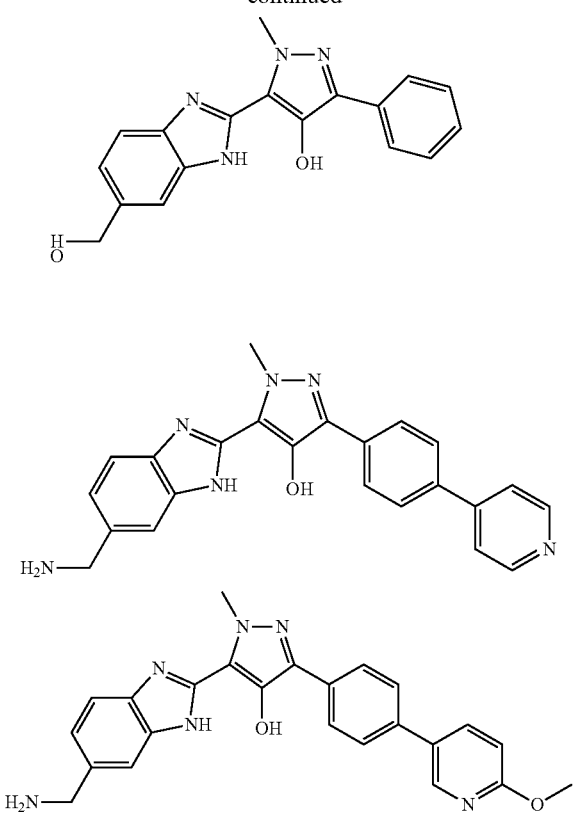
244
-continued
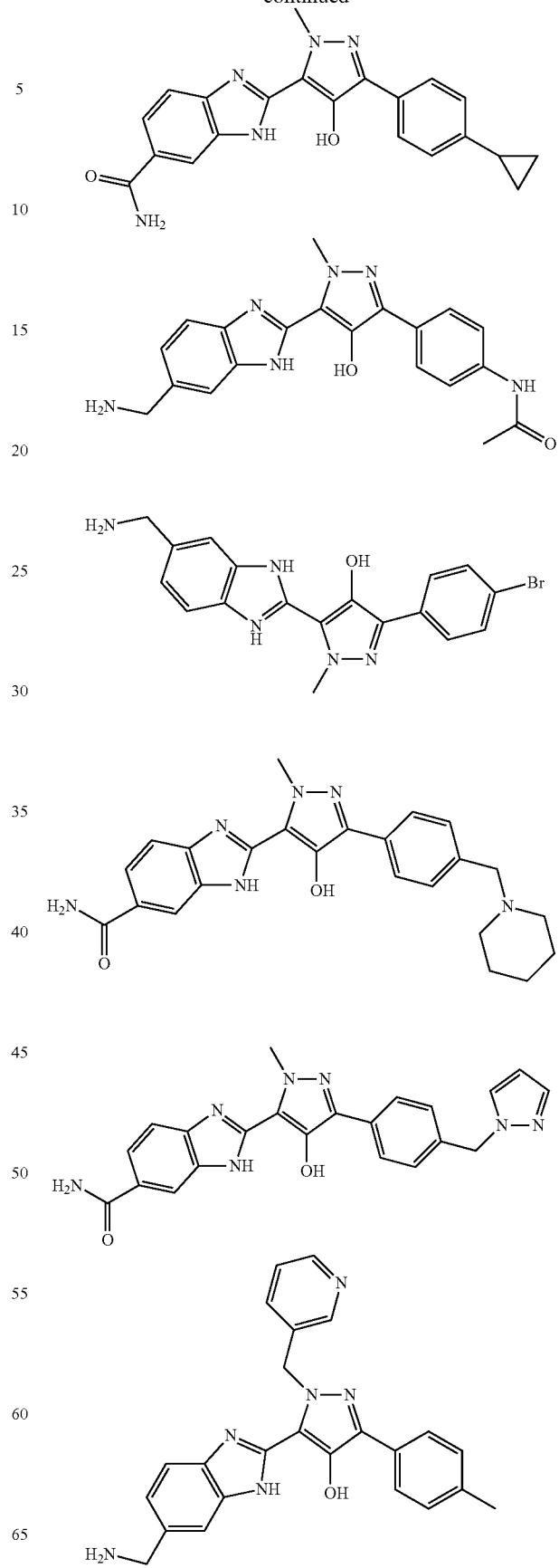

245
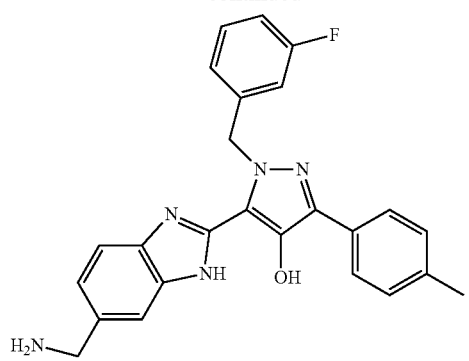
246
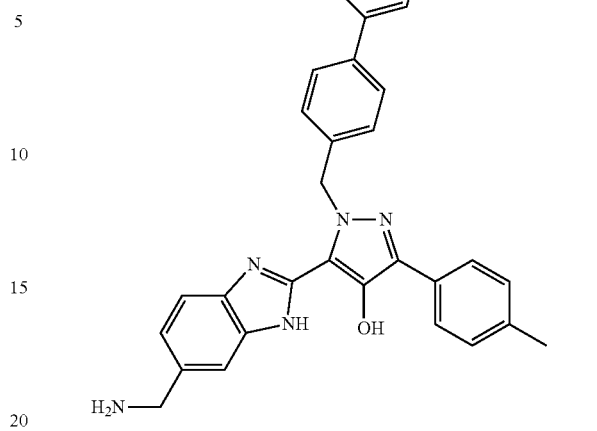
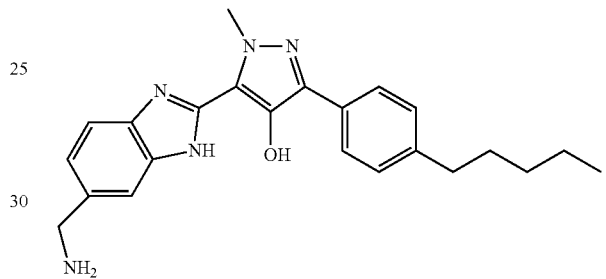
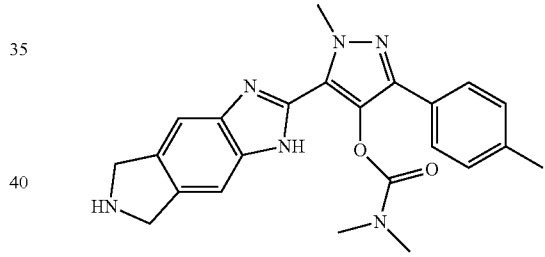
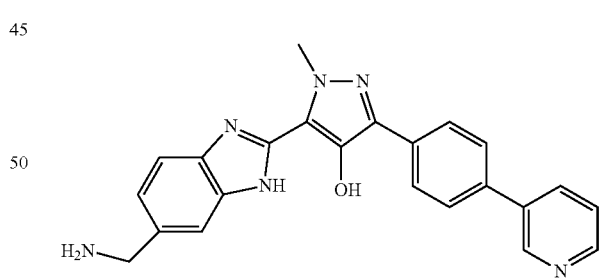
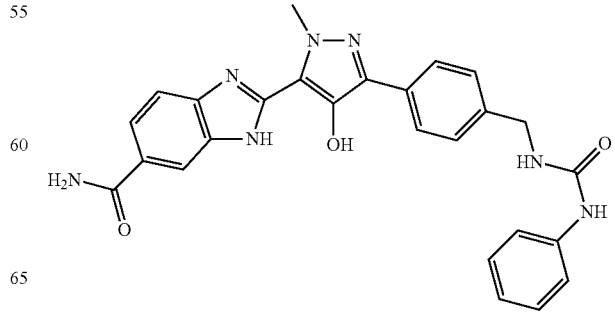

247
-continued
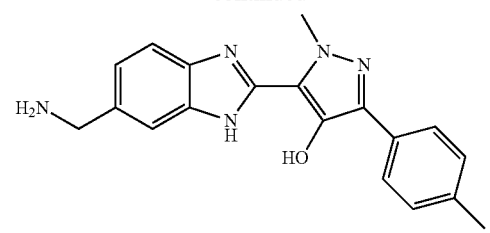
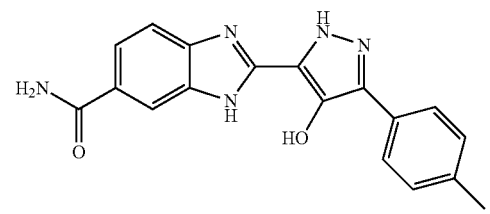
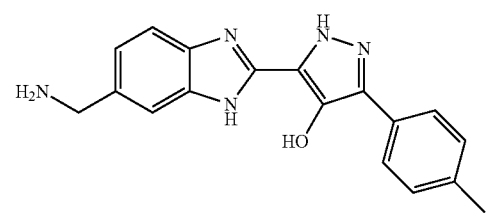
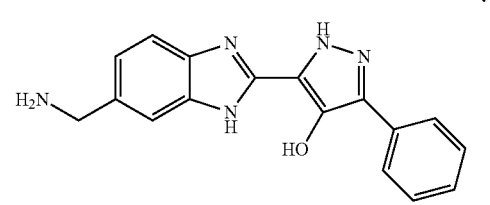
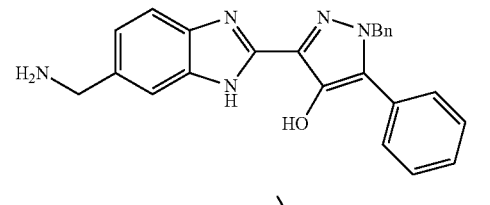
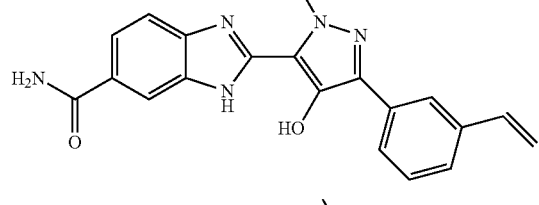
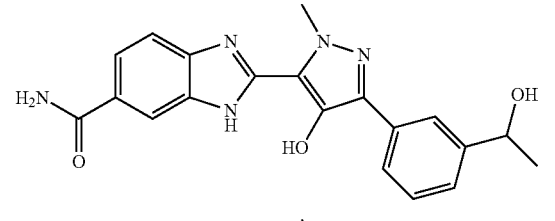
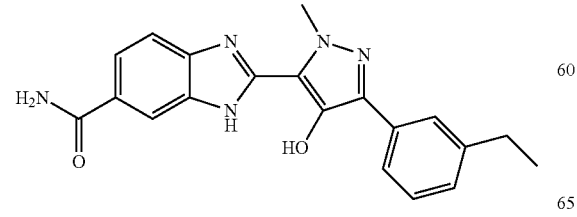
248
-continued
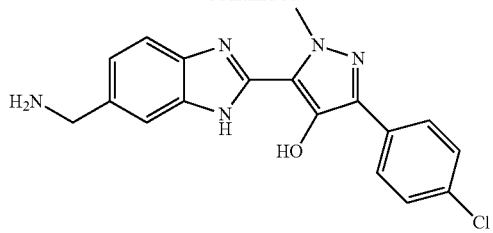
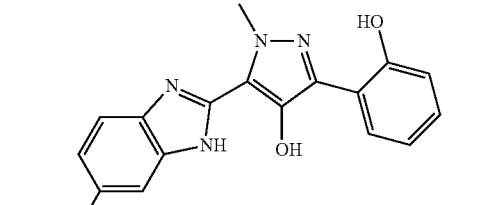
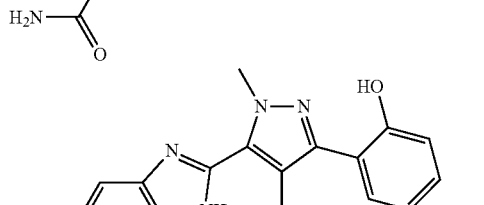
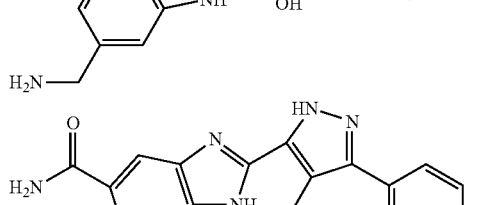
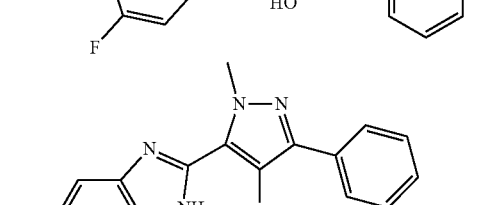
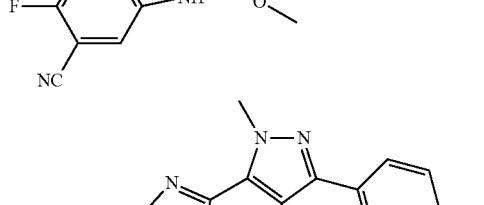
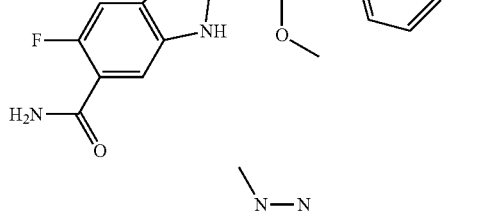
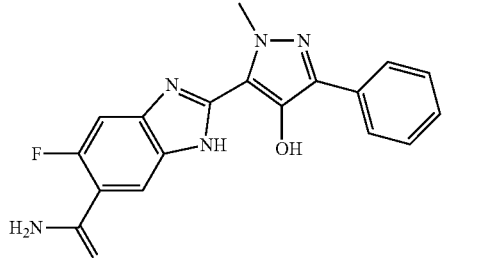

-continued

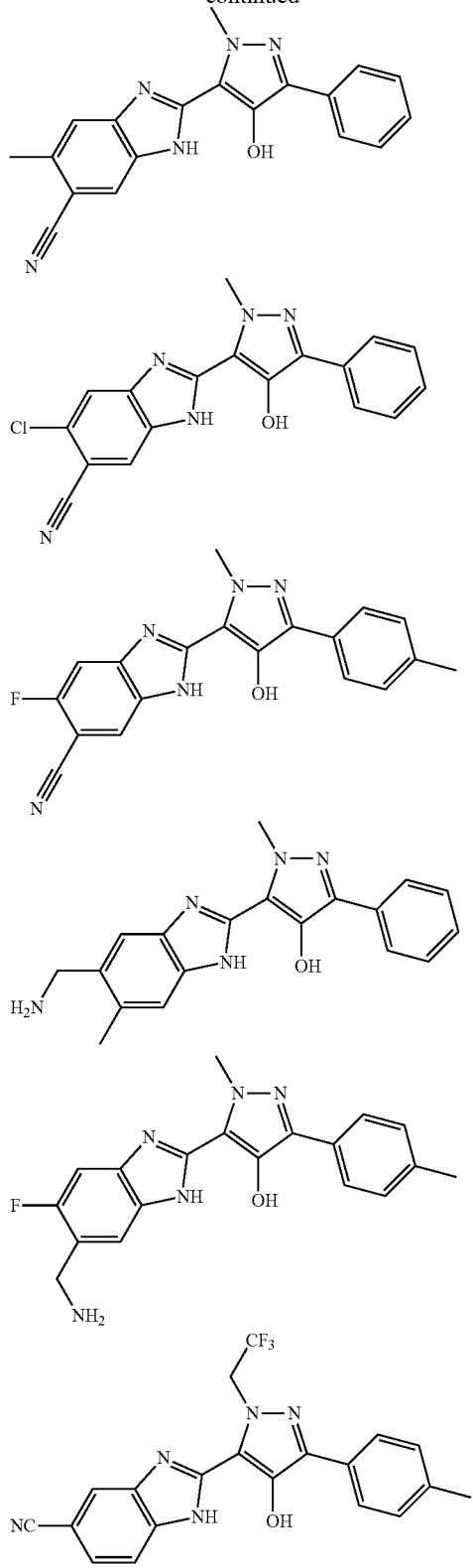

-continued

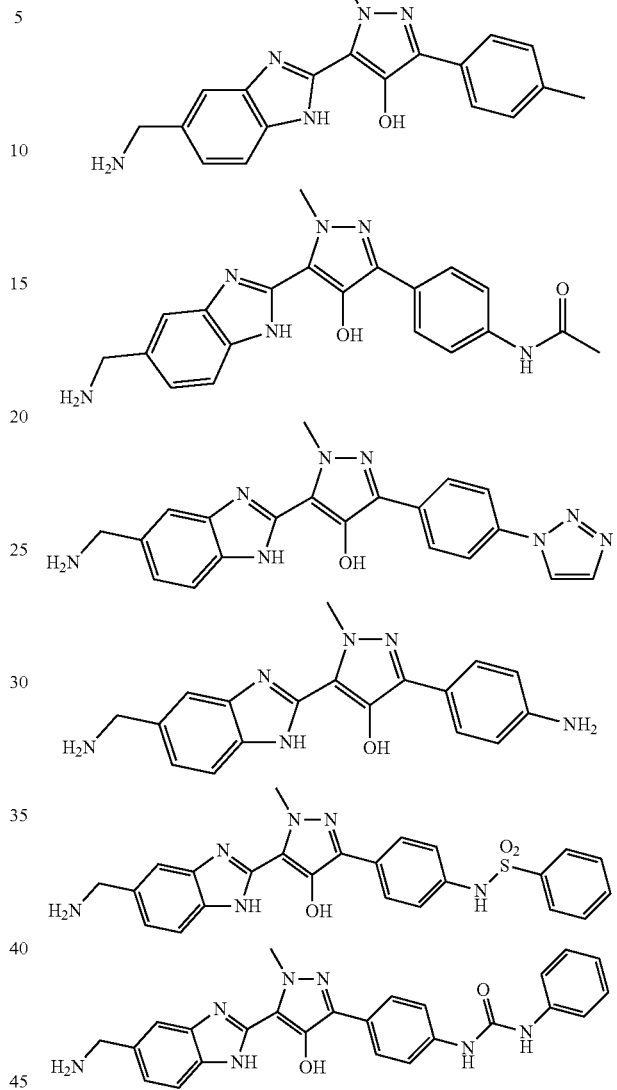

or a pharmaceutically acceptable salt, or ester thereof, wherein Bn=benzyl.

3. A pharmaceutical composition comprising at least one compound of claim 1, or a pharmaceutically acceptable salt, or ester thereof and at least one pharmaceutically acceptable carrier.

4. A method of treating blood coagulation, comprising administering to a patient in need thereof a therapeutically effective amount of a compound of claim 1 or a pharmaceutically acceptable salt, solvate, or ester thereof.

* * * * *